(12) United States Patent
Kim et al.

(10) Patent No.: US 11,377,496 B2
(45) Date of Patent: Jul. 5, 2022

(54) TARGETING AGENT ANTIBODY CONJUGATES AND USES THEREOF

(71) Applicant: The Scripps Research Institute, La Jolla, CA (US)

(72) Inventors: Chanhyuk Kim, Daejeon (KR); Jun Y. Axup, San Diego, CA (US); Hwayoung Yun, Daejeon (KR); Peter G. Schultz, La Jolla, CA (US); Jennifer Ma, La Jolla, CA (US); Jiayin Shen, San Diego, CA (US); Pengyu Yang, San Diego, CA (US)

(73) Assignee: THE SCRIPPS RESEARCH INSTITUTE, La Jolla, CA (US)

( * ) Notice: Subject to any disclaimer, the term of this patent is extended or adjusted under 35 U.S.C. 154(b) by 350 days.

(21) Appl. No.: 16/420,062

(22) Filed: May 22, 2019

(65) Prior Publication Data

US 2019/0315863 A1    Oct. 17, 2019

Related U.S. Application Data

(62) Division of application No. 14/774,647, filed as application No. PCT/US2014/029379 on Mar. 14, 2014, now Pat. No. 10,351,626.

(60) Provisional application No. 61/783,426, filed on Mar. 14, 2013, provisional application No. 61/839,330, filed on Jun. 25, 2013.

(51) Int. Cl.
| | |
|---|---|
| *C07K 16/28* | (2006.01) |
| *A61K 47/54* | (2017.01) |
| *C07K 16/32* | (2006.01) |
| *C07K 16/46* | (2006.01) |
| *A61K 39/395* | (2006.01) |
| *C07C 275/16* | (2006.01) |
| *C07C 275/24* | (2006.01) |
| *C07D 249/04* | (2006.01) |
| *C07K 16/30* | (2006.01) |
| *A61K 39/00* | (2006.01) |

(52) U.S. Cl.
CPC ...... *C07K 16/2809* (2013.01); *A61K 39/3955* (2013.01); *A61K 39/39558* (2013.01); *A61K 47/542* (2017.08); *C07C 275/16* (2013.01); *C07C 275/24* (2013.01); *C07D 249/04* (2013.01); *C07K 16/2803* (2013.01); *C07K 16/2806* (2013.01); *C07K 16/2851* (2013.01); *C07K 16/2863* (2013.01); *C07K 16/2887* (2013.01); *C07K 16/2896* (2013.01); *C07K 16/3069* (2013.01); *C07K 16/32* (2013.01); *C07K 16/468* (2013.01); *A61K 2039/505* (2013.01); *C07K 2317/31* (2013.01); *C07K 2317/33* (2013.01); *C07K 2317/35* (2013.01); *C07K 2317/52* (2013.01); *C07K 2317/55* (2013.01); *C07K 2317/56* (2013.01); *C07K 2317/73* (2013.01); *C07K 2317/92* (2013.01); *C07K 2317/94* (2013.01); *Y02A 50/30* (2018.01)

(58) Field of Classification Search
CPC ............ C07K 16/2809; C07K 16/2803; C07K 16/2806; C07K 16/2851; C07K 16/2863; C07K 16/2887; C07K 16/2896; C07K 16/3069; C07K 16/32; C07K 16/468; C07K 2317/31; C07K 2317/33; C07K 2317/35; C07K 2317/52; C07K 2317/55; C07K 2317/56; C07K 2317/73; C07K 2317/92; C07K 2317/94; A61K 39/3955; A61K 39/39558; A61K 47/542; A61K 2039/505; C07C 275/16; C07C 275/24; C07D 249/04; Y02A 50/30; A61P 17/00; A61P 35/00; A61P 35/02
See application file for complete search history.

(56) References Cited

U.S. PATENT DOCUMENTS

| | | | |
|---|---|---|---|
| 5,258,498 A | 11/1993 | Huston et al. | |
| 5,766,886 A | 6/1998 | Studnicka et al. | |
| 5,821,337 A | 10/1998 | Carter et al. | |
| 6,982,321 B2 | 1/2006 | Winter | |
| 7,087,409 B2 | 8/2006 | Barbas et al. | |
| 7,416,541 B2 | 8/2008 | Yuzhakov et al. | |
| 7,527,791 B2 | 5/2009 | Adams et al. | |
| 8,236,308 B2 | 8/2012 | Kischel et al. | |
| 9,493,563 B2 | 11/2016 | Blein et al. | |
| 10,351,626 B2 * | 7/2019 | Kim ...................... | A61P 35/00 |
| 2004/0044177 A1 | 3/2004 | Macke et al. | |

(Continued)

FOREIGN PATENT DOCUMENTS

| | | |
|---|---|---|
| JP | 2002534441 A | 10/2002 |
| JP | 2005505580 A | 2/2005 |

(Continued)

OTHER PUBLICATIONS

Strop et al., Chemistry and Biology 20: 161-167 (Year: 2013).*

(Continued)

*Primary Examiner* — Phuong Huynh
(74) *Attorney, Agent, or Firm* — Wilson Sonsini Goodrich & Rosati

(57) ABSTRACT

Methods, compositions and uses are provided for bispecific antibodies comprising one or more unnatural amino acids. The bispecific antibodies may bind to two or more different receptors, co-receptors, antigens, or cell markers on one or more cells. The bispecific antibodies may be used to treat a disease or condition (e.g., cancer, autoimmune disease, pathogenic infection, inflammatory disease). The bispecific antibodies may be used to modulate (e.g., stimulate or suppress) an immune response.

1 Claim, 29 Drawing Sheets

Specification includes a Sequence Listing.

(56) References Cited

U.S. PATENT DOCUMENTS

| | | | |
|---|---|---|---|
| 2009/0140214 | A1 | 6/2009 | Sonobe et al. |
| 2010/0285037 | A1 | 11/2010 | Abo et al. |
| 2010/0324008 | A1 | 12/2010 | Low et al. |
| 2012/0189621 | A1 | 7/2012 | Dean et al. |
| 2013/0171095 | A1 | 7/2013 | Bernett et al. |
| 2014/0099318 | A1 | 4/2014 | Huang et al. |
| 2014/0120096 | A1 | 5/2014 | Bakker et al. |
| 2014/0242080 | A1 | 8/2014 | Jaeger et al. |
| 2014/0294823 | A1 | 10/2014 | Moore et al. |
| 2014/0377270 | A1 | 12/2014 | Moore et al. |
| 2015/0166661 | A1 | 6/2015 | Chen et al. |
| 2016/0017058 | A1 | 1/2016 | Kim et al. |
| 2017/0002076 | A1 | 1/2017 | Kim |

FOREIGN PATENT DOCUMENTS

| | | | |
|---|---|---|---|
| JP | 2011523639 A | | 8/2011 |
| WO | WO-03028527 A2 | | 4/2003 |
| WO | WO-2004106380 A2 | | 12/2004 |
| WO | WO-2007058725 A2 | | 5/2007 |
| WO | WO-2007059312 A2 | | 5/2007 |
| WO | WO-2007070659 A2 | | 6/2007 |
| WO | WO-2007079130 A2 | | 7/2007 |
| WO | WO-2007094916 A2 | | 8/2007 |
| WO | WO-2007042261 A3 | | 12/2007 |
| WO | WO-2008077079 A1 | | 6/2008 |
| WO | WO-2008083346 A1 | | 7/2008 |
| WO | WO-2009070642 A1 | | 6/2009 |
| WO | WO-2009139863 A2 | | 11/2009 |
| WO | WO-2010037062 A1 | | 4/2010 |
| WO | WO-2011028195 A2 | | 3/2011 |
| WO | WO-2012142659 A1 | | 10/2012 |
| WO | WO-2012166559 A1 | | 12/2012 |
| WO | WO-2012166560 A1 | | 12/2012 |
| WO | WO-2013093809 A1 | | 6/2013 |
| WO | WO-2014056783 A1 | | 4/2014 |
| WO | WO-2014059213 A1 | | 4/2014 |
| WO | WO-2014153002 A1 | | 9/2014 |
| WO | WO-2014153164 A1 | | 9/2014 |
| WO | WO-2014185985 A1 | | 11/2014 |
| WO | WO-2014195888 A1 | | 12/2014 |
| WO | WO-2015057852 A1 | | 4/2015 |
| WO | WO-2015184203 A1 | | 12/2015 |
| WO | WO-2016014974 A3 | | 3/2016 |
| WO | WO-2016168773 A2 | | 10/2016 |
| WO | WO-2017136659 A2 | | 8/2017 |

OTHER PUBLICATIONS

Aggarwal et al. Comparative study of PSMA expression in the prostate of mouse, dog, monkey, and human. Prostate 66:903-10 (2006).

Agten et al. Oxime conjugation in protein chemistry: from carbonyl incorporation to nucleophilic catalysis. J Pept Sci 22:271-9 (2016).

Almagro and Fransson, Humanization of antibodies, Front. Biosci. vol. 13, pp. 1619-1633, 2008.

Austin et al. Endocytosis and sorting of ErbB2 and the site of action of cancer therapeutics trastuzumab and geldanamycin. Mol Biol Cell 15(12):5268-82 (2004).

Axup et al. Synthesis of site-specific antibody-drug conjugates using unnatural amino acids. PNAS vol. 109, No. 40, pp. 16101-16106, Oct. 2, 2012.

Baeuerle et al. Bispecific T-cell engaging antibodies for cancer therapy. Cancer Res 69:4941-4944 (2009).

Barrett et al. First-in-man evaluation of 2 high-affinity PSMA-avid small molecules for imaging prostate cancer. J Nucl Med 54:380-7 (2013).

Bendig, M.M. Humanization of rodent monoclonal antibodies by CDR grafting. Methods: A Companion to Methods in Enzymology, 8; 83-93 (1995).

Borst et al. Target antigen of monoclonal reagent S5.7: comparison with T3 antigen. Hybridoma 2:265-74 (1983).

Brockman et al. Nomogram Predicting Prostate Cancer-specific Mortality for Men with Biochemical Recurrence After Radical Prostatectomy. Eur Urol 67:1160-67 (2015).

Casset et al. A peptide mimetic of an anti-CD4 monoclonal antibody by rational design. Biochemical and Biophysical Research Communication 307:198-205 (2003).

Chatterjee et al. A Versatile Platform for Single- and Multiple Unnatural Amino Acid Mutagenesis in *Escherichia coli*, Biochemistry, Mar. 12, 2013, vol. 52, No. 10.

Conrad et al. TCR and CD3 antibody cross-reactivity in 44 species. Cytometry A 71:925-33 (2007).

Coutrot, Federic et al. A New pH-Switchable Dimannosyl[c2]Daisy Chain Molecular Machine, Org. Lett. vol. 10, No. 17, pp. 3741-3744, Jul. 31, 2008.

Cui et al. Chemically Programmed Bispecific Antibodies That Recruit and Activate T Cells. The Journal of Biological Chemistry vol. 287, No. 34, pp. 28206-28214, Aug. 17, 2012.

Denmeade et al. Engineering a prostate-specific membrane antigen-activated tumor endothelial cell prodrug for cancer therapy. Sci Transl Med 4:140ra86 (2012).

Doods, Hn et al. BIBP 3226, the first selective neuropeptide Y1 receptor antagonist: A review of its pharmacological properties. Regulatory Peptides, 65(1):71-77 (Aug. 27, 1996).

Dubrovska, Anna, et al. A Chemically Induced Vaccine Strategy for Prostate Cancer. ACS Chem. Biol., 6(11):1223-1231 (2011).

Facchini et al. Very Early PSA Response to Abiraterone in mCRPC Patients: A Novel Prognostic Factor Predicting Overall Survival. Front Pharmacol 7:123 (2016).

FDA. Immunogenicity Assessment for Therapeutic Protein Products, Guidance for Industry (39 pgs) (2014).

Friedrich, M. Regression of Human Prostate Cancer Xenografts in Mice by AMG 212/BAY2010112, a Novel PSMA/CD3-Bispecific BiTE Antibody Cross-Reactive with Non-Human Primate Antigens. Mol. Cancer Ther. 11(12):2664-2673 (Dec. 2012).

GENBANK Accession No. AB064051: Homo spaiens IGK mRNA for immunoglobulin kappa light chain VLJ region.partial cds, clone:K10. Jul. 2, 2012.

Gharbi, R. et al. Condensation D'Alcenes Aromatiques Avec L'Acetaldehyde Catalysee Par Des Resines Echangeuses D'Ions—II, Tetrahedron, 39(18); 2953-2963 (1983).

Gicquiaux, H. et al. Rapid Internalization and Recycling of the Human Neuropeptide Y Y1 Receptor. The Journal of Biological Chemistry, 277(8):6645-6655 (Feb. 2002).

Hernandez-Hoyos et al. MOR209/ES414, a Novel Bispecific Antibody Targeting PSMA for the Treatment of Metastatic Castration-Resistant Prostate Cancer. Mol Cancer Ther 15:2155-65 (2016).

Humblet, Valerie et al. Multivalent Scaffolds for Affinity Maturation of Small Molecule Cell Surface Binders and Their Application to Prostate Tumor Targeting, J. Med. Chem, vol. 52, No. 2, pp. 544-550, 2009.

Hutchins et al. Site-specific coupling and sterically controlled formation of multimeric antibody fab fragments with unnatural amino acids. J. Mol. Biol., vol. 406, No. 4, pp. 595-603, Mar. 4, 2011.

International Application No. PCT/US2014/028612 International Preliminary Report on Patentability and Written Opinion dated Sep. 24, 2015.

International Application No. PCT/US2014/028612 International Search Report and Written Opinion dated Jul. 1, 2014.

International Application No. PCT/US2014/029379 International Preliminary Report on Patentability and Written Opinion dated Sep. 24, 2015.

International Application No. PCT/US2014/029379 International Search Report and Written Opinion dated Aug. 26, 2014.

International Application No. PCT/US2017/016407 International Search Report and Written Opinion dated Jul. 26, 2017.

Janthur, W.D. Drug Conjugates Such as Antibody Drug Conjugates (ADCs), Immunotoxins and Immunoliposomes Challenge Daily Clinical Practice. Int J Mol Sci. Nov. 28, 2012;13(12):16020-45.

Johnson, David et al. RF1 Knockout Allows Ribosomal Incorporation of Unnatural Amino Acids at Multiple Sites, Nat Chem Biol., vol. 7, No. 11, pp. 779-86, Sep. 18, 2011.

(56) References Cited

OTHER PUBLICATIONS

Kashmiri et al., SDR grafting—a new approach to antibody humanization, Methods vol. 36, No. 1, pp. 25-34, May 2005.
Kazane, Stephanie et al. Self-Assembled Antibody Multimers through Peptide Nucleic Acid Conjugation, J. Am. Chem. Soc. vol. 135, No. 1, pp. 340-346, Jan. 9, 2013.
Kiess et al. Prostate-specific membrane antigen as a target for cancer imaging and therapy. Q J Nucl Med Mol Imaging 59:241-68 (2015).
Kim et al. Bispecific small molecule—antibody conjugate targeting prostate cancer. PNAS USA 110:17796-801 (2013).
Kim et al. Protein conjugation with genetically encoded unnatural amino acids. Current Opinion in Chemical Biology, vol. 17, No. 3, pp. 412-419, May 9, 2013.
Kim et al., Synthesis of bispecific antibodies using genetically encoded unnatural amino acids. Journal of the American Chemical Society. 134(24): 9918-9921 (2012).
Kinoshita et al. Expression of prostate-specific membrane antigen in normal and malignant human tissues. World J Surg 30:628-36 (2006).
Klimka et al., Human anti-CD30 recombinant antibodies by guided phage antibody selection using cell panning, Br. J. Cancer, 83:252-260 (2000).
Kularatne et al. Prostate-specific membrane antigen targeted imaging and therapy of prostate cancer using a PSMA inhibitor as a homing ligand. Mol Pharm 6:780-9 (2009).
Kularatne et al. Recruiting Cytotoxic T Cells to Folate-Receptor-Positive Cancer Cells. Angew Chem Int Ed Engl. 52:12101-12104 (2013).
Kularatne, S. et al. Folate Receptor-Targeted T cells for Cancer Immunotherapy. Angew Chem. Int. Ed. Engl. 52(46):12101-12104 (Nov. 11, 2013).
Lang et al., Genetic encoding of bicyclononynes and trans-cyclooctenes for site-specific protein labeling in vitro and in live mammalian cells via rapid fluorogenic Diels-Alder Reactions. Journal of the American Chemical Society, vol. 134, No. 25, pp. 10317-10320(2012).
Lin et al. Transglutaminase-Catalyzed Site-Specific Conjugation of Small-Molecules to Proteins in Vitro and on the Surface of Living Cells. Journal of American Chemical Society 128(14):4542-4543 (2006).
Liu, Ma et al. Hormone conjugated with antibody to CD3 mediates cytotoxic T cell lysis of human melanoma cells. Science. Jan. 22, 1988;239(4838):395-8.
Liu, et al. Adding new chemistries to the genetic code Annu. Rev. Biochem, vol. 79, pp. 413-444, Jul. 2010.
Lutje et al. PSMA Ligands for Radionuclide Imaging and Therapy of Prostate Cancer: Clinical Status. Theranostics 5:1388-401 (2015).
MacCallum, R.M. et al. Antibody-antigen interactions: Contact analysis and binding site topography. Journal of Molecular Biology 262:732-745 (1998).
Maindron, Nicolas et al. Synthesis and luminescence properties of new red-shifted absorption lanthanide(III) chelates suitable for peptide and protein labelling, Organic & Biomolecular Chemistry, vol. 9, No. 7, Apr. 7, 2011.
Malik, Noeen et al. Radiosynthesis of a new PSMA targeting ligand ([18F]FPy-DUPA-Pep), Applied Radiation and Isotopes 69;1014-1018 (Apr. 8, 2011).
McNeel et al. The Society for Immunotherapy of Cancer consensus statement on immunotherapy for the treatment of prostate carcinoma. J Immunother Cancer 4:92 (2016).
Meller et al. Alterations in androgen deprivation enhanced prostate-specific membrane antigen (PSMA) expression in prostate cancer cells as a target for diagnostics and therapy. EJNMMI Res 5:66 (2015).
Molema et al. CD3 directed bispecific antibodies induce increased lymphocyte-endothelial cell interactions in vitro. Br J Cancer 82:472-9 (2000).
Paul, W.E., Fundamental Immunology, 3rd Edition, p. 292-295, 1993.

Queen C., et al., "A humanized antibody that binds to the interleukin 2 receptor," Dec. 1989, Proceedings of the National Academy of Sciences, National Academy of Sciences, vol. 86, No. 24, pp. 10029-10033, XP002614478.
Reubi, J.C. et al. Co-expressed peptide receptors in breast cancer as a molecular basis for in vivo multireceptor tumour targeting. European Journal of Nuclear Medicine, 29(7):855-862 (Jul. 2002).
Riechmann et al. Reshaping human antibodies for therapy, Nature vol. 332, pp. 323-329, 1988.
Ristau et al. The prostate-specific membrane antigen: lessons and current clinical implications from 20 years of research. Urol Oncol 32:272-9 (2014).
Roberts et al. Chemistry for peptide and protein PEGylation. Adv Drug Deliv Rev 54: 459-476 (2002).
Saber et al. An FDA oncology analysis of CD3 bispecific constructs and first-in-human dose selection. Regul Toxicol Pharmacol 90:144-52 (2017).
Schraa, Astrid J. et al. RGD-Modified Anti-CD3 Antibodies Redirect Cytolytic Capacity of Cytotoxic T Lumphocytes Toward $\alpha v \beta 3$-Expressing Endothelial Cells, International Journal of Cancer, 112; 279-285 (2004).
Sigma-Aldrich Co. LLC, Monoclonal Anti-CD3, clone UCHT-1, Catalog No. C7048. (2012).
Silver et al. Prostate-specific membrane antigen expression in normal and malignant human tissues. Clin Cancer Res 3:81-5 (1997).
Sokoloff et al. A dual-monoclonal sandwich assay for prostate-specific membrane antigen: levels in tissues, seminal fluid and urine. Prostate 43:150-7 (2000).
Sweat et al. Prostate-specific membrane antigen expression is greatest in prostate adenocarcinoma and lymph node metastases. Urology 52:637-40 (1998).
Tai et al. Development of a peptide-drug conjugate for prostate cancer therapy. Molecular Pharmaceutics, vol. 8, No. 3, pp. 901-912, Jun. 6, 2011.
Takehisa et al. Natural infection of wild-born mandrills (Mandrillus sphinx) with two different types of simian immunodeficiency virus. AIDS Res Hum Retroviruses 17:1143-54 (2001).
Thomas, et al. Application of strain-promoted azide-alkyne cycloaddition and tetrazine ligation to targeted Fc-drug conjugates. Bioconjugate Chemistry, vol. 23, No. 10, pp. 2007-2013 (2012).
Thomson, S. et al. The construction and in vitro testing of photo-activatable cancer targeting folated anti-CD3 conjugates, Biochemical and Biophysical Research Communications 366;526-531 (2008).
Troyer et al. Detection and characterization of the prostate-specific membrane antigen (PSMA) in tissue extracts and body fluids. Int J Cancer 62:552-8 (1995).
U.S. Appl. No. 14/774,647 Final Office Action dated Sep. 11, 2018.
U.S. Appl. No. 14/774,647 Non-Final Office Action dated Feb. 8, 2018.
U.S. Appl. No. 14/774,649 Restriction Requirement dated Apr. 27, 2016.
U.S. Appl. No. 15/268,389 Non-Final Office Action dated Sep. 27, 2018.
U.S. Appl. No. 14/774,647 Restriction Requirement dated Aug. 24, 2017.
U.S. Appl. No. 14/774,647 Notice of Allowance dated Feb. 26, 2019.
U.S. Appl. No. 14/774,647 Notice of Allowance dated Jan. 10, 2019.
U.S. Appl. No. 15/268,389 Restriction Requirement dated Jun. 12, 2018.
Wang, Lei and Schultz, Peter. Expanding the Genetic Code. Angewandte Chemie Int. Ed, vol. 44, pp. 34-66, 2005.
Wright et al. Upregulation of prostate-specific membrane antigen after androgen-deprivation therapy. Urology 48:326-34 (1996).
Yang et al. Engineering a long-acting, potent GLP-1 analog for microstructure-based transdermal delivery. PNAS 113(15):4140-4145 (2016).
Young et al. Beyond the canonical 20 amino acids: expanding the genetic lexicon. J Biol Chem 285:11039-44 (2010).
Zhang et al. A remote arene-binding site on prostate specific membrane antigen revealed by antibody-recruiting small molecules. J Am Chem Soc. 132(36):12711-12716 (2010).

(56) References Cited

OTHER PUBLICATIONS

Co-pending U.S. Appl. No. 16/074,600, inventors Kim; Chanhyuk et al., filed on Aug. 1, 2018.

* cited by examiner pAcF, 1

GnRH

CCK2 antagonist

Bombesin

Pentagastrin cRGD

Octreotide

TARGETING AGENT ANTIBODY CONJUGATES AND USES THEREOF

CROSS-REFERENCE

This application is a divisional application of U.S. application Ser. No. 14/774,647 filed Sep. 10, 2015, now U.S. Pat. No. 10,351,626, which is a U.S. National Stage Entry of International Application No. PCT/US2014/029379 filed Mar. 14, 2014, which claims the benefit of priority from U.S. provisional application Ser. No. 61/783,426, filed Mar. 14, 2013 and U.S. provisional application Ser. No. 61/839,330, filed Jun. 25, 2013; all of which are incorporated by reference in their entirety.

STATEMENT AS TO FEDERALLY SPONSORED RESEARCH

This invention was made with government support under GM062159 and GM097206 awarded by the National Institutes of Health (NIH). The government has certain rights in the invention.

SEQUENCE LISTING

The instant application contains a Sequence Listing which has been submitted electronically in ASCII format and is hereby incorporated by reference in its entirety. Said ASCII copy, created on Apr. 7, 2014, is named 41135-720.601_SL.txt and is 20,561 bytes in size.

FIELD OF THE INVENTION

Described herein are targeting agent antibody conjugates comprising one or more unnatural amino acids, methods of making such constructs, pharmaceutical compositions and medicaments comprising such constructs, and methods of using such constructs and compositions to prevent, inhibit, and/or treat a disease or condition in a subject.

BACKGROUND OF THE INVENTION

Antibodies are natural proteins that the vertebrate immune system forms in response to foreign substances (antigens), primarily for defense against infection. For over a century, antibodies have been induced in animals under artificial conditions and harvested for use in therapy or diagnosis of disease conditions, or for biological research. Each individual antibody producing cell produces a single type of antibody with a chemically defined composition, however, antibodies obtained directly from animal serum in response to antigen inoculation actually comprise an ensemble of non-identical molecules (e.g., polyclonal antibodies) made from an ensemble of individual antibody producing cells.

Some antibody conjugates, such as bispecific antibodies, may bind to two or more different antigens. A number of recombinant strategies have been developed to synthesize bispecific antibodies, which include single chain variable fragment (scFv)-derived formats such as diabodies, tandem diabodies, BiTes (bispecific T-cell engager), and DARTs (Dual Affinity Re-Targeting), as well as immunoglobulin G (IgG)-based formats such as Triomab, DVD-Ig (Dual Variable Domain antibodies), and two-in-one antibodies. However, bispecific antibodies can have poor pharmacokinetics and physical properties, such as immunogenicity and manufacturing challenges. Therefore, there is a need for an improvement or alternative to such existing technology. In addition, precise control over geometry in such a targeting moiety is desirable because the geometry can alter binding affinity and specificity. Disclosed herein are targeting agent antibody conjugates, and methods for producing such conjugates, with specific geometries for optimal therapeutic efficacy and target specificity by the site-specifically coupling of an antibody or antibody fragment to a targeting agent.

SUMMARY OF THE INVENTION

Disclosed herein are targeting agent antibody conjugates comprising: a targeting agent that binds to a target cell, wherein the targeting agent is not an antibody or antibody fragment; and an antibody or antibody fragment that does not bind to the target cell; and one or more linkers, wherein the antibody or antibody fragment is linked to the targeting agent by the one or more linkers and wherein the antibody or antibody fragment binds an antigen on a cytotoxic effector cell. The antibody or antibody fragment may comprise one or more unnatural amino acids. The targeting agent may be site-specifically linked by the one or more linkers to the one or more unnatural amino acids of the antibody or antibody fragment.

The targeting agent antibody conjugate may be of Formula I: X-L1-Y or Formula IA: Y-L1-X, wherein: X comprises the antibody or antibody fragment; L1 comprises the one or more linkers; and Y comprises the targeting agent.

At least a portion of the antibody may be based on or derived from a human, humanized, human engineered or fully human antibody. The antibody may be a chimeric antibody. The antibody or antibody fragment may bind an antigen on a cytotoxic effector cell and the targeting agent binds a cell surface protein or a cell surface marker on a target cell. The cytotoxic effector cell may be capable of mounting an immune response. At least a portion of the antibody or antibody fragment may bind at least a portion of a receptor on the cytotoxic effector cell. At least a portion of the antibody or antibody fragment may bind at least a portion of a co-receptor on the cytotoxic effector cell. The receptor may be a T-cell receptor (TCR). The co-receptor may comprise a T-cell co-receptor. The co-receptor may be a CD3 T-cell co-receptor. The cytotoxic effector cell may be a hematopoietic cell. The hematopoietic cell may be selected from a macrophage, a neutrophil, an eosinophil, a natural killer cell, a B-cell, or a T-cell. The cytotoxic effector cell may be a cytotoxic T cell. The antibody fragment may comprise a Fab fragment. The Fab fragment may comprise an anti-CD3 Fab fragment. The anti-CD3 Fab fragment may be UCHT1. The antibody fragment may be encoded by a sequence selected from SEQ ID NOs: 1 and 2.

The targeting agent may be selected from a small molecule, a cell-targeting molecule, a ligand, a protein, a peptide, a peptoid, a DNA aptamer, a peptide nucleic acid, a vitamin a substrate or a substrate analog. The targeting agent may not comprise an antibody or an antibody fragment. The cell surface protein or cell surface marker may be selected from an antigen, a receptor, a co-receptor, a trans-membrane protein or a cell marker on the target cell. The cell surface protein may be selected from a cholecystokinin B receptor, a gonadotropin-releasing hormone receptor, a somatostatin receptor 2, an avb3 integrin, a gastrin-releasing peptide receptor, a neurokinin 1 receptor, a melanocortin 1 receptor, a neurotensin receptor, neuropeptide Y receptor and C-type lectin like molecule 1. The antigen may comprise a prostate specific membrane antigen. The targeting agent may comprise an octreotide. The targeting agent may comprise an octreotate. The targeting agent may comprise a somatostatin analog. The targeting agent may comprise a CD38 NAD+ glycohydrolase inhibitor. The targeting agent may comprise a pentagastrin. The targeting agent may comprise a gonadotropin releasing hormone. The targeting agent may comprise a CCKB antagonist. The targeting agent may comprise a cRGD. The targeting agent may comprise a bombesin. The targeting agent may comprise 2-[3-(1,3-dicarboxypropy) ureidol] pentanedioic acid (DUPA). The targeting agent may be sufficiently small to penetrate a tumor. The targeting agent may be encoded by a sequence selected from SEQ ID NOs: 3-40. The targeting agent antibody conjugate may further comprise a second targeting agent. The targeting agent antibody conjugate may comprise 1, 2, 3, 4, or more targeting agents.

The antibody or antibody fragment may bind an antigen on a cytotoxic effector cell and the targeting agent may bind a cell surface protein or a cell surface marker on a target cell. The target cell may be a cancerous cell. The cancerous cell may be derived from a prostate cancer. The cancerous cell may be derived from an epithelial cancer. The cancerous cell may be derived from a breast cancer. The cancerous cell may be derived from a kidney cancer. The cancerous cell may be derived from a lung cancer. The cancerous cell may be derived from a colon cancer. The cancerous cell may be derived from a colorectal cancer. The cancerous cell may be derived from a gastric cancer. The cancerous cell may be derived from a brain cancer. The cancerous cell may be derived from a glioblastoma. The cancerous cell may be derived from a pancreatic cancer. The cancerous cell may be derived from a myeloid leukemia. The cancerous cell may be derived from a cervical cancer. The cancerous cell may be derived from a medullary thyroid carcinoma. The cancerous cell may be derived from a stromal ovarian cancer. The cancerous cell may be derived from an astrocytoma. The cancerous cell may be derived from an endometrial cancer. The cancerous cell may be derived from a neuroendocrine cancer. The cancerous cell may be derived from a gastroenteropancreatic tumor. The cancerous cell may be derived from a non-Hodgkin's lymphoma. The cancerous cell may be derived from an exocrine pancreatic cancer. The cancerous cell may be derived from an Ewing's sarcoma. The cancerous cell may be derived from a skin cancer. The skin cancer may be a melanoma. The skin cancer may be a neoangiogenic skin cancer. The lung cancer may be a small cell lung cancer.

X may be coupled to L1. Y may be coupled to L1. X may be coupled to L1 by an oxime. Y may be coupled to L1 by an oxime. X may be coupled to L1 by a covalent bond, ionic bond, or non-covalent bond. Y may be coupled to L1 by a covalent bond, ionic bond, or non-covalent bond. L1 may provide between about 10 and about 100 angstrom (Å) distance between X and Y. L1 may provide equal to or less than about 50 angstrom (Å) distance between X and Y. L1 may provide equal to or less than about 45 angstrom (Å) distance between X and Y. L1 may provide equal to or less than about 40 angstrom (Å) distance between X and Y. L1 may provide equal to or less than about 30 angstrom (Å) distance between X and Y. L1 may provide equal to or greater than about 5 angstrom (Å) distance between X and Y. L1 may provide equal to or greater than about 10 angstrom (Å) distance between X and Y. L1 may provide equal to or greater than about 15 angstrom (Å) distance between X and Y. L1 may provide equal to or greater than about 20 angstrom (Å) distance between X and Y. L1 may provide a distance between X and Y including and between about 10 to about 100 angstrom (Å).

The one or more unnatural amino acids of the antibody or antibody fragment comprises a p-acetylphenylalanine (pAcF). The one or more unnatural amino acids of the antibody or antibody fragment comprises a selenocysteine. The one or more unnatural amino acids may comprise (a) various substituted tyrosine and phenylalanine analogues such as O-methyl-L-tyrosine, p-amino-L-phenylalanine, 3-nitro-L-tyrosine, p-nitro-L-phenylalanine, m-methoxy-L-phenylalanine and p-isopropyl-L-phenylalanine; (b) amino acids with aryl azide and benzophenone groups that may be photo-cross-linked; (c) amino acids that have unique chemical reactivity including acetyl-L-phenylalanine and m-acetyl-L-phenylalanine, O-allyl-L-tyrosine, O-(2-propynyl)-L-tyrosine, p-ethylthiocarbonyl-L-phenylalanine and p-(3-oxobutanoyl)-L-phenylalanine; (d) heavy-atom-containing amino acids for phasing in X-ray crystallography including p-iodo and p-bromo-L-phenylalanine; (e) the redox-active amino acid dihydroxy-L-phenylalanine; (f) glycosylated amino acids including b-N-acetylglucosamine-O-serine and a-N-acetylgalactosamine-O-threonine; (g) fluorescent amino acids with naphthyl, dansyl, and 7-aminocoumarin side chains; (h) photocleavable and photoisomerizable amino acids with azobenzene and nitrobenzyl Cys, Ser, and Tyr side chains; (i) the phosphotyrosine mimetic p-carboxymethyl-L-phenylalanine; (j) the glutamine homologue homoglutamine; (k) 2-aminooctanoic acid; (l) or a combination of (a)-(k). The one or more unnatural amino may comprise at least one oxime, carbonyl, dicarbonyl, hydroxylamine, cyclooctyne, aryl/alkyl azides, norbornene, cyclopropene, trans-cyclooctene, and tetrazine group. The one or more unnatural amino acids may be genetically encoded. The one or more unnatural amino acids may be incorporated into the antibody or antibody fragment. The one or more unnatural amino acids may be site-specifically incorporated the antibody or antibody fragment. The targeting agent antibody conjugate may comprise two or more unnatural amino acids. The targeting agent antibody conjugate may comprise three or more unnatural amino acids. The targeting agent antibody conjugate may comprise four or more unnatural amino acids. The one or more unnatural amino acids may replace one or more amino acid residues in the antibody or antibody fragment. The one or more unnatural amino acids may replace an amino acid residue in a heavy chain of the antibody or antibody fragment. The one or more unnatural amino acids of the antibody or antibody fragment replace an amino acid residue in a light chain of the antibody or antibody fragment. The one or more unnatural amino acids of the antibody or antibody fragment replace an amino acid residue in a variable region of the antibody or antibody fragment.

Further disclosed herein are pharmaceutical compositions comprising a targeting agent antibody conjugate comprising: an antibody or antibody fragment; a targeting agent, wherein the targeting agent is not an antibody or antibody fragment; and one or more linkers, wherein the antibody or antibody fragment is linked to the targeting agent by the one or more linkers. The antibody or antibody fragment and the targeting agent may be site-specifically linked. The antibody or antibody fragment may comprise one or more unnatural amino acids. The pharmaceutical composition may further comprise a pharmaceutically acceptable diluent. The pharmaceutical composition may further comprise a pharmaceutically acceptable excipient. The pharmaceutical composition may further comprise a pharmaceutically acceptable carrier.

Disclosed herein are methods for treating a disease or condition in a subject in need thereof, comprising administering a targeting agent antibody conjugate comprising an antibody or antibody fragment; a targeting agent, wherein the targeting agent is not an antibody or antibody fragment; and one or more linkers, wherein the antibody or antibody fragment is linked to the targeting agent by the one or more linkers. The antibody or antibody fragment and the targeting agent may be site-specifically linked. The antibody or antibody fragment may comprise one or more unnatural amino acids. The disease or condition may be a pathogenic infection. The pathogenic infection may be a bacterial infection. The pathogenic infection may be a viral infection. The disease or condition may be an inflammatory disease. The disease or condition may be an autoimmune disease. The autoimmune disease may be diabetes. The disease or condition may be a cancer. The disease or condition may be a prostate cancer. The disease or condition may be an epithelial cancer. The disease or condition may be a kidney cancer. The disease or condition may be lung cancer. The disease or condition may be a colon cancer. The disease or condition may be a colorectal cancer. The disease or condition may be a gastric cancer. The disease or condition may be a brain cancer. The disease or condition may be a glioblastoma. The disease or condition may be a pancreatic cancer. The disease or condition may be a myeloid leukemia. The disease or condition may be a cervical cancer. The disease or condition may be a medullary thyroid carcinoma. The disease or condition may be a breast cancer. The disease or condition may be an ovarian cancer. The disease or condition may be an astrocytoma. The disease or condition may be an endometrial cancer. The disease or condition may be a neuroendocrine cancer. The disease or condition may be a gastroenteropancreatic tumor. The disease or condition may be a non-Hodgkin's lymphoma. The disease or condition may be an exocrine pancreatic cancer. The disease or condition may be an Ewing's sarcoma. The disease or condition may be a skin cancer. The skin cancer may be a melanoma. The skin cancer may be a neoangiogenic skin cancer. The lung cancer may be a small cell lung cancer. Administering the targeting agent antibody conjugate or pharmaceutical composition may comprise an intravenous administration, a subcutaneous administration, an intraperitoneal administration, an intramuscular administration, an intravascular administration, an intrathecal administration, an intravitreal administration, a topical administration or an infusion. Administering may comprise oral administration. Administering may comprise intranasal administration. Administering may comprise use of a microneedle device.

Disclosed herein are targeting agent antibody conjugates comprising: an antibody or antibody fragment; one or more DUPA molecules; and one or more linkers, wherein the antibody or antibody fragment is linked to the one or more DUPA molecules by the one or more linkers. The antibody or antibody fragment may be site-specifically linked to the one or more DUPA molecules by the one or more linkers. The antibody or antibody fragment may comprise one or more unnatural amino acids. The antibody or antibody fragment may be linked to the one or more DUPA molecules by the one or more linkers to the one or more unnatural amino acids. The antibody or antibody fragment may alternatively be linked to the one or more DUPA molecules by the one or more linkers to a natural amino acid. The antibody or antibody fragment may be an anti-CD3 Fab.

Disclosed herein are targeting agent antibody conjugates comprising: an anti-CD3 Fab; one or more DUPA molecules; and one or more linkers, wherein the anti-CD3 Fab is linked to the one or more DUPA molecules by the one or more linkers. The anti-CD3 Fab may comprise one or more unnatural amino acids. The one or more unnatural amino acids may replace a natural amino acid of the anti-CD3 Fab. The one or more unnatural amino acids may replace a natural amino acid of the anti-CD3 Fab, wherein the natural amino acid is selected from Lysine 138 (Lys 138) of a heavy chain of the anti-CD3 Fab, Alanine 123 (Ala 123) of a heavy chain of the anti-CD3 Fab, Threonine 109 (Thr 109) of a heavy chain of the anti-CD3 Fab and Serine 202 (Ser 202) of a heavy chain of the anti-CD3 Fab. A first DUPA molecule and a second DUPA molecule may be site-specifically linked to a first unnatural amino acid and a second unnatural amino acid of the anti-CD3 Fab a first linker and a second linker. The targeting agent antibody conjugate may be of Formula I: X-L-Y or Formula IA: Y-L-X, wherein: X comprises the anti-CD3 Fab; L comprises the one or more linkers; and Y comprises one or more DUPA molecules.

The targeting agent antibody conjugate may comprise a compound selected from Formula V, Formula VI, Formula VII or Formula VIII:

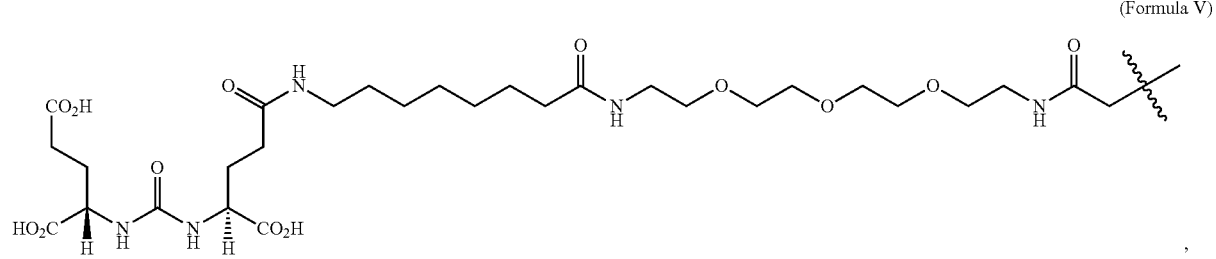

(Formula V)

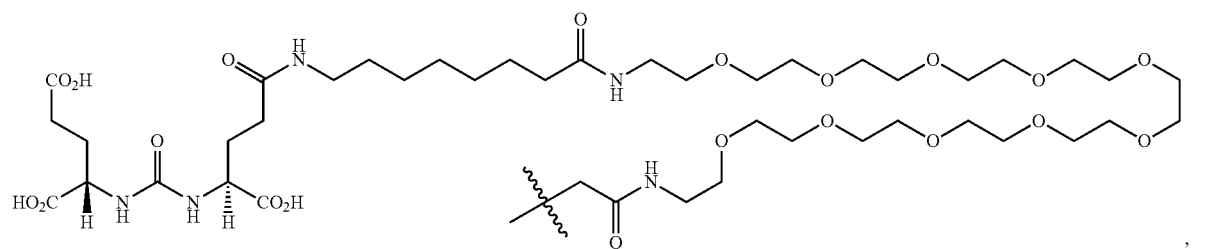

(Formula VI)

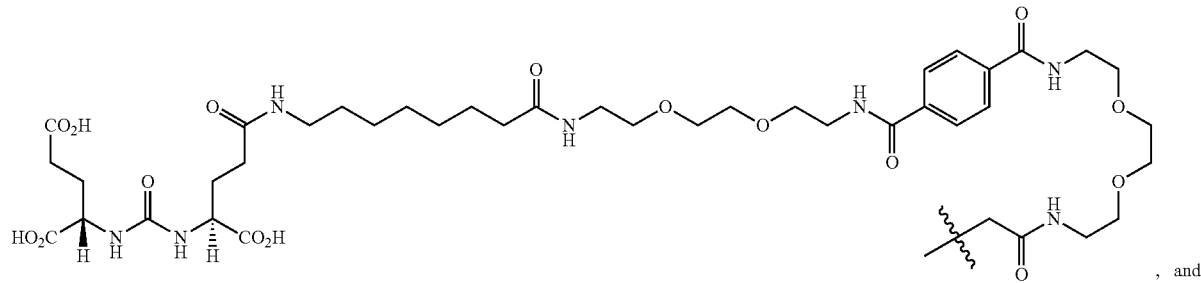
(Formula VII)
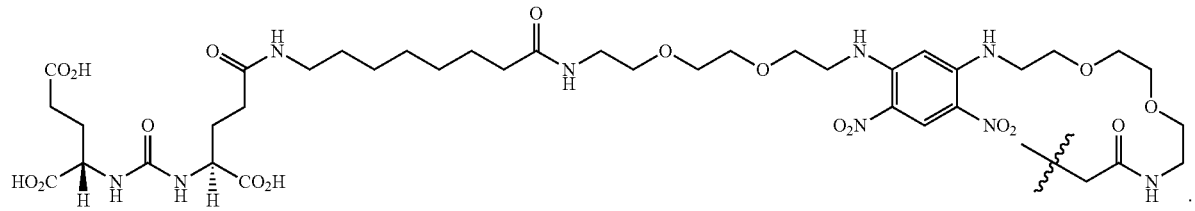
(Formula VIII)
The targeting agent antibody conjugate may comprise a compound of Formula IX:
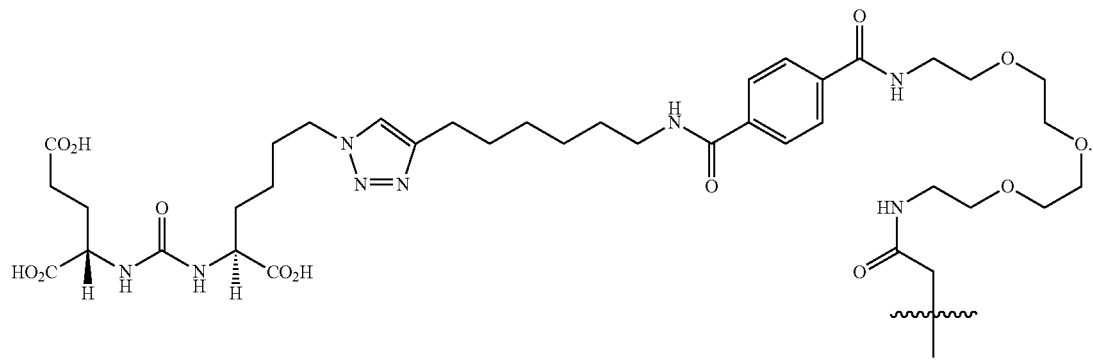
(Formula IX)
The targeting agent antibody conjugate may comprise a compound of Formula X:
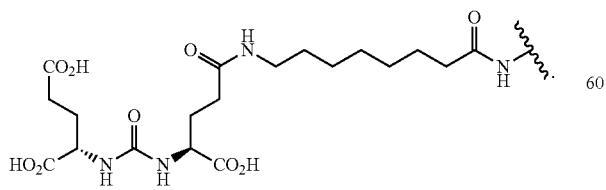
(Formula X)
The targeting agent antibody conjugate may comprise a compound of Formula XI:

(Formula XI)

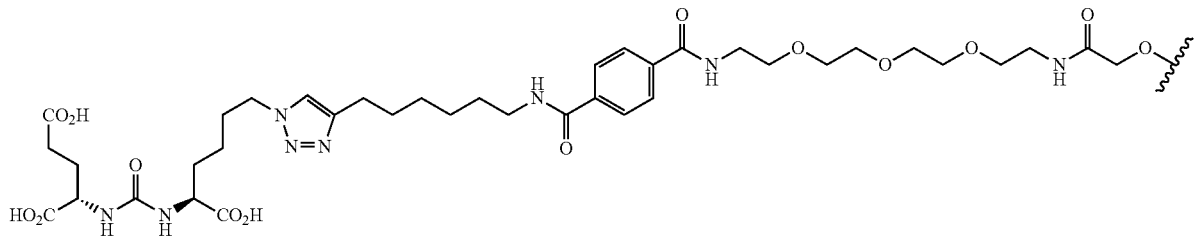

In another aspect, provided herein are compounds of Formula XII:

Y-L-A$^1$-L$^1$-A$^2$-L$^2$-A$^3$-L$^3$-X$^2$ (Formula XII)

wherein:

Y is a ligand of prostate specific membrane antigen (PSMA);

L is

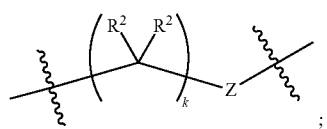

A$^1$ is selected from the group consisting of an aryl, a 5- to 6-membered heteroaryl, —C(O)—, —N(R$^1$)—, —O—, —C(O)N(R$^1$)—, —N(R$^1$)C(O)—, —S(O)$_{1,2}$N(R$^1$)—, and —N(R$^1$)S(O)$_{1,2}$—;

L$^1$ is

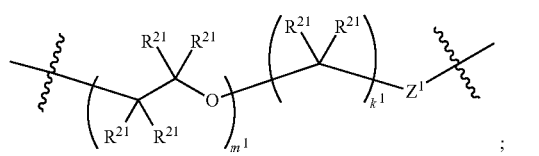

A$^2$ is selected from the group consisting of a bond, —C(O)—, —N(R$^1$)—, —O—, —C(O)N(R$^1$)—, —N(R$^1$)C(O)—, —S(O)$_{1,2}$N(R$^1$)—, and —N(R$^1$)S(O)$_{1,2}$—;

L$^2$ is

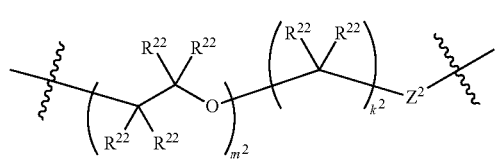

A$^3$ is a bond,

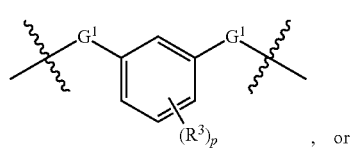, or

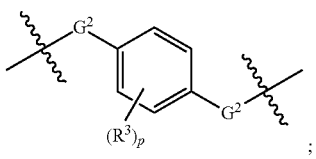;

L$^3$ is

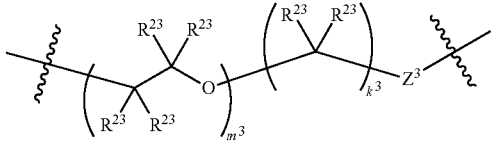;

X$^2$ is a linker bound to a functional group that reacts with an amino acid, or a linker bound to a modified amino acid, wherein the modified amino acid is part of X, wherein X is a modified therapeutic peptide, protein, or antibody;

each R$^1$ is independently selected from H, alkyl, or haloalkyl;

each R$^2$, R$^{21}$, R$^{22}$, and R$^{23}$ is independently selected from H, halo, —OR$^1$, —CN, —SR$^1$, alkyl, cycloalkyl, haloalkyl, arylalkyl, or heteroarylalkyl;

each R$^3$ is independently selected from halo, —OR$^1$, —CN, —SR$^1$, alkyl, cycloalkyl, haloalkyl, arylalkyl, or heteroarylalkyl, —NO$_2$, and NR$^1$R$^1$;

each G$^1$ and G$^2$ is independently selected from the group consisting of a bond, —C(O)—, —N(R$^1$)—, —O—, —C(O)N(R$^1$)—, —N(R$^1$)C(O)—, —S(O)$_{1,2}$N(R$^1$)—, and —N(R$^1$)S(O)$_{1,2}$—;

each Z, Z$^1$, Z$^2$, and Z$^3$ is independently selected from the group consisting of a bond, —O—, and —N(R$^1$)—;

k, k$^1$, k$^2$ and k$^3$ are each independently selected from 0, 1, 2, 3, 4, 5, 6, 7, 8, 9, and 10;

m$^1$, m$^2$ and m$^3$ are each independently selected from 0, 1, 2, 3, 4, 5, 6, 7, 8, 9, and 10; and p is 0, 1, 2, 3 or 4;

or a stereoisomer thereof.

In some embodiments described above or below of a compound of Formula XII, the compound is of Formula XIIa:

(Formula XIIa)

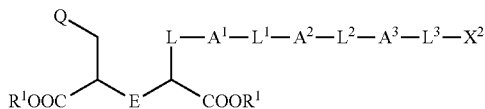

wherein:
Q is selected from the group consisting of:

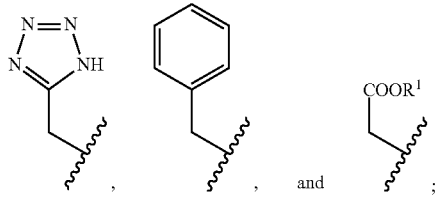

and
E is selected from the group consisting of:

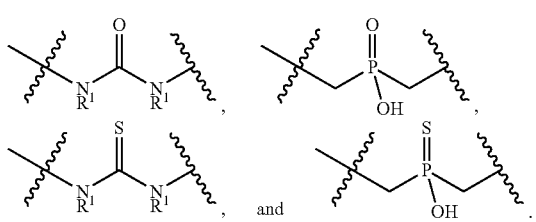

In some embodiments described above or below of a compound of Formula XII, the compound is of Formula XIIb:

(Formula XIIb)

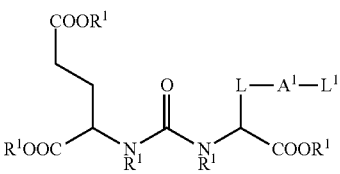

In further embodiments described above or below of a compound of Formula XII, the compound is of Formula XIIc:

(Formula XIIc)

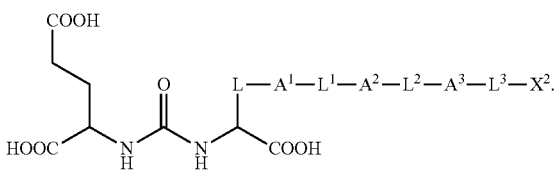

In some embodiments described above or below of a compound of Formula XII, the compound is of Formula XIId:

(Formula XIId)

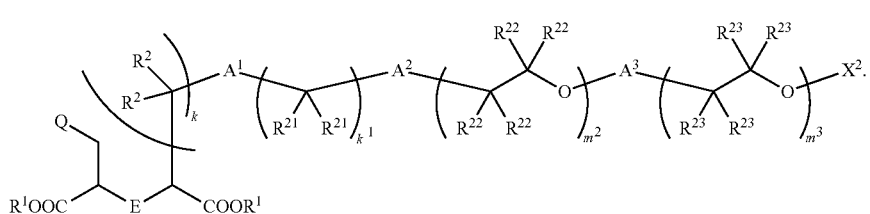

In further embodiments described above or below of a compound of Formula XII, the compound is of Formula XIIe:

(Formula XIIe)

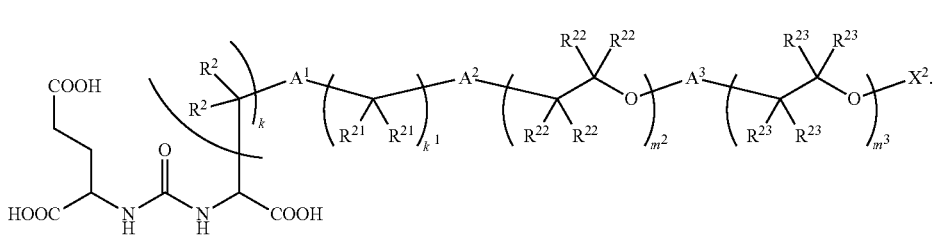

In still further embodiments described above or below of a compound of Formula XII, the compound is of Formula XIIf:

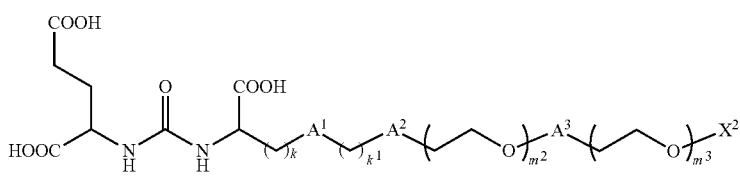

(Formula XIIf)

In some embodiments described above or below of a compound of Formula XII, $A^1$ is —C(O)N(H)—. In some embodiments described above or below of a compound of Formula XII, $A^1$ is

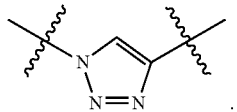 [SMILES: *c1cn(*)nn1 ; "."]

In some embodiments described above or below of a compound of Formula XII, $A^3$ is

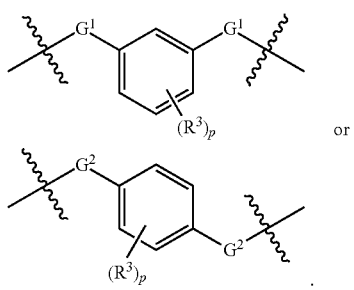

In further embodiments described above or below of a compound of Formula XII, $A^3$ is

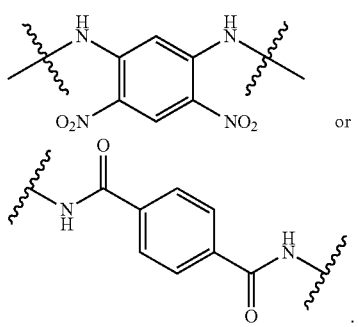

In some embodiments described above or below of a compound of Formula XII, each $R^2$, $R^{21}$, $R^{22}$, $R^{23}$, and $R^{24}$ is independently selected from H, F, —CH$_3$, or —CF$_3$. In some embodiments described above or below of a compound of Formula XII, each $R^2$, $R^{21}$, $R^{22}$, $R^{23}$, and $R^{24}$ is H.

In some embodiments described above or below of a compound of Formula XII, $X^2$ is

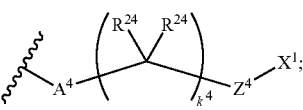

wherein:
$A^4$ is selected from the group consisting of a bond, —C(O)—, —N(R$^1$)—, —O—, —C(O)N(R$^1$)—, —N(R$^1$)C(O)—, —S(O)$_{1,2}$N(R$^1$)—, and —N(R$^1$)S(O)$_{1,2}$—;
each $R^{24}$ is independently selected from H, halo, —OR$^1$, —CN, —SR$^1$, alkyl, cycloalkyl, haloalkyl, arylalkyl, or heteroarylalkyl;
$k^4$ is selected from 0, 1, 2, 3, 4, 5, 6, 7, 8, 9, and 10;
$Z^4$ is selected from a bond, aryl, and a 5- to 6-membered heteroaryl; and
$X^1$ is —ONH$_2$,

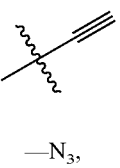

—N$_3$,

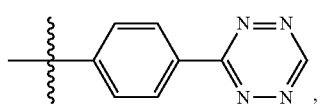

—N(H)NH$_2$, or —SH.

In some embodiments described above or below of a compound of Formula XII, $X^2$ is

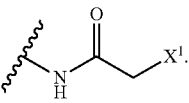

In further embodiments described above or below of a compound of Formula XII, $X^2$ is

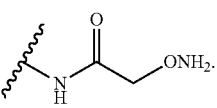

In some embodiments described above or below of a compound of Formula XII, the compound is selected from:
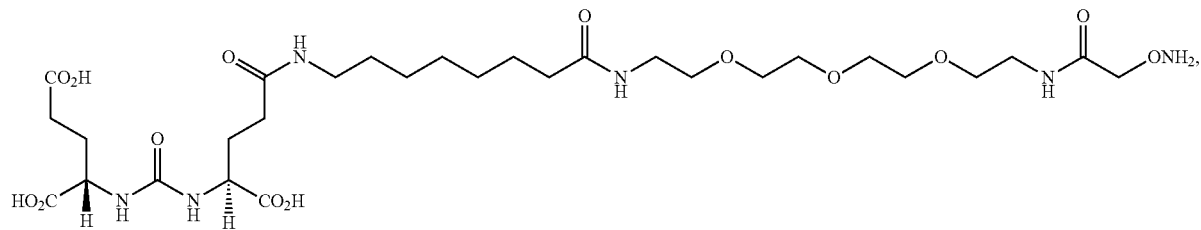
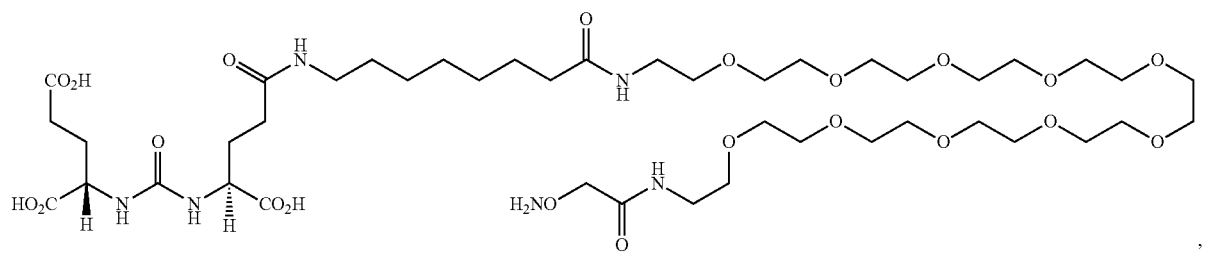
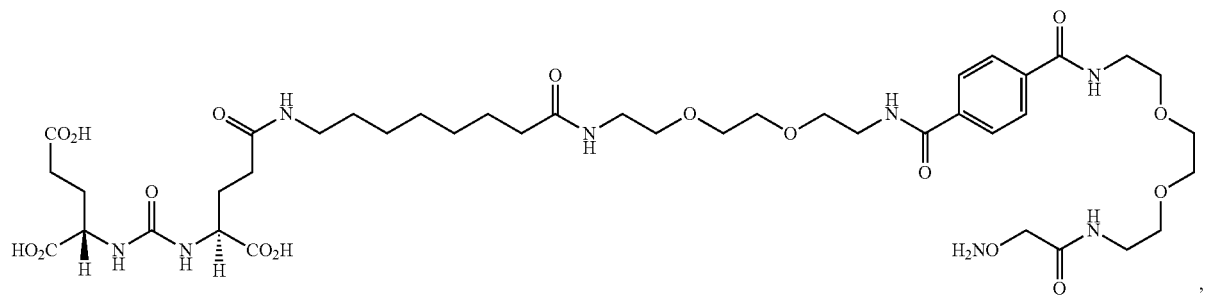
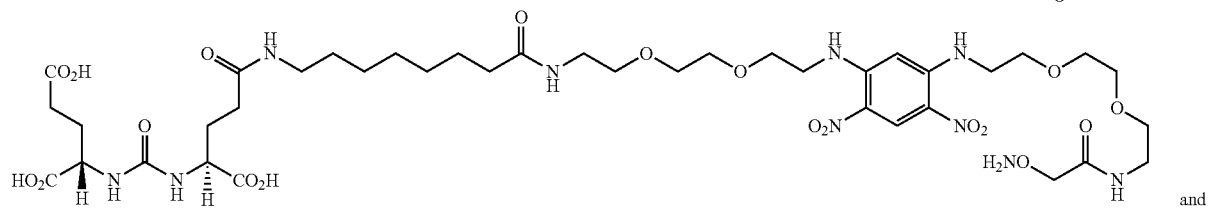
and
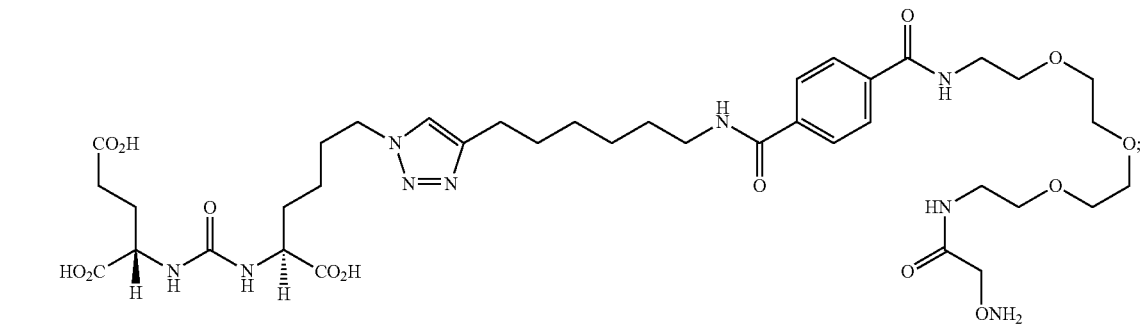
or a stereoisomer thereof.

In some embodiments described above or below of a compound of Formula XII,
$X^2$ is

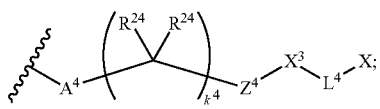

wherein:
$A^4$ is selected from the group consisting of a bond, —C(O)—, —N($R^1$)—, —O—, —C(O)N($R^1$)—, —N($R^1$)C(O)—, —S(O)$_{1,2}$N($R^1$)—, and —N($R^1$)S(O)$_{1,2}$—;
each $R^{24}$ is independently selected from H, halo, —O$R^1$, —CN, —S$R^1$, alkyl, cycloalkyl, haloalkyl, arylalkyl, or heteroarylalkyl;
$k^4$ is selected from 0, 1, 2, 3, 4, 5, 6, 7, 8, 9, and 10;
$Z^4$ is selected from a bond, aryl, and a 5- to 6-membered heteroaryl; and
$X^3$ is

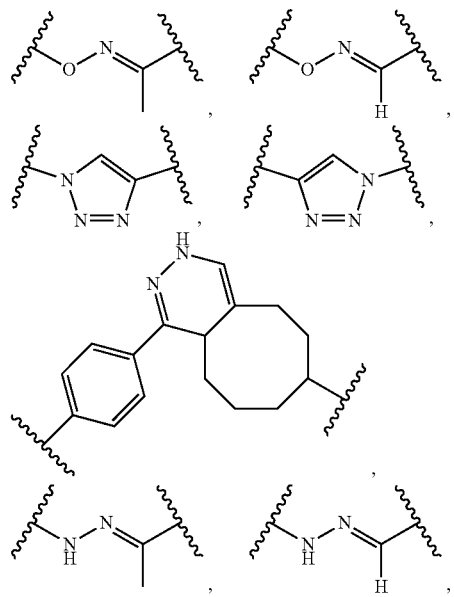

or —S—;
X is a modified therapeutic peptide, protein, or antibody;
$L^4$ is a bond directly attached to a modified amino acid, or a linker bound to a modified amino acid, wherein the modified amino acid is part of X.

In some embodiments described above or below of a compound of Formula XII, the amino acid is an unnatural amino acid.

In some embodiments described above or below of a compound of Formula XII, k is 1, 2, or 3; and Z is a bond.

In some embodiments described above or below of a compound of Formula XII, $A^1$ is —C(O)N($R^1$)—, 6-membered aryl, or 5-membered heteroaryl.

In some embodiments described above or below of a compound of Formula XII, $m^1$ is 0; $k^1$ is 6 or 7; and $Z^1$ is a bond.

In some embodiments described above or below of a compound of Formula XII, $A^2$ is a bond; $m^2$ and $k^2$ are 0; and $Z^2$ is a bond.

In some embodiments described above or below of a compound of Formula XII, $A^2$ is —C(O)N(H)—; $m^2$ is 2; $k^2$ is 2; and $Z^2$ is a bond. In some embodiments described above or below of a compound of Formula XII, $A^2$ is —C(O)N(H)—; $m^2$ is 3; $k^2$ is 2; and $Z^2$ is a bond. In some embodiments described above or below of a compound of Formula XII, $A^2$ is —C(O)N(H)—; $m^2$ is 10; $k^2$ is 2; and $Z^2$ is a bond.

In some embodiments described above or below of a compound of Formula XII, $R^3$ is —NO$_2$; and p is 2.

In some embodiments described above or below of a compound of Formula XII, each $GX^1$ and $GX^2$ are independently selected from the group consisting of —N(H)—, —C(O)N(H)—, and —N(H)C(O)—.

In some embodiments described above or below of a compound of Formula XII, $m^3$ is 3; $k^3$ is 2; and $Z^3$ is a bond. In some embodiments described above or below of a compound of Formula XII,
$m^3$ is 2; $k^3$ is 2; and $Z^3$ is a bond.

In some embodiments described above or below of a compound of Formula XII, $A^3$ is a bond; $m^3$ and $k^3$ are 0; and $Z^3$ is a bond.

Further disclosed herein are compositions comprising a targeting agent antibody conjugate comprising an antibody or antibody fragment; one or more linkers; and a targeting agent wherein the purity of the targeting agent antibody conjugate or the compound is at least 90%. The targeting agent antibody construct may comprise an unnatural amino acid. The antibody or antibody fragment and the targeting agent may be site specifically linked.

Further disclosed herein are compounds comprising a Formula selected from Formulas XII or XIIa-f, wherein the purity of the compound is at least 90%.

Disclosed herein are targeting agent antibody conjugates comprising: an antibody or antibody fragment; one or more linkers; and a targeting agent, wherein the antibody or antibody fragment binds to or interacts with a receptor, co-receptor, antigen or cell marker on a first cell; and the targeting agent binds to or interacts with a receptor, co-receptor, antigen or cell marker on a second cell.

Further disclosed herein are targeting agent antibody conjugates comprising an antibody or antibody fragment; one or more linkers; and a targeting agent, wherein the antibody or antibody fragment binds to or interacts with a receptor, co-receptor, antigen or cell marker on a first cell; the targeting agent binds to or interacts with a receptor, co-receptor, antigen or cell marker on a second cell; and the one or more linkers links the antibody or antibody fragment and the targeting agent site-specifically.

BRIEF DESCRIPTION OF THE DRAWINGS

The foregoing summary, as well as the following detailed description of the disclosure, may be better understood when read in conjunction with the appended figures. For the purpose of illustrating the disclosure, shown in the figures are embodiments which are presently preferred. It should be understood, however, that the disclosure is not limited to the precise arrangements, examples and instrumentalities shown.

The invention may be best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures.

DETAILED DESCRIPTION OF THE INVENTION

Figure 1:
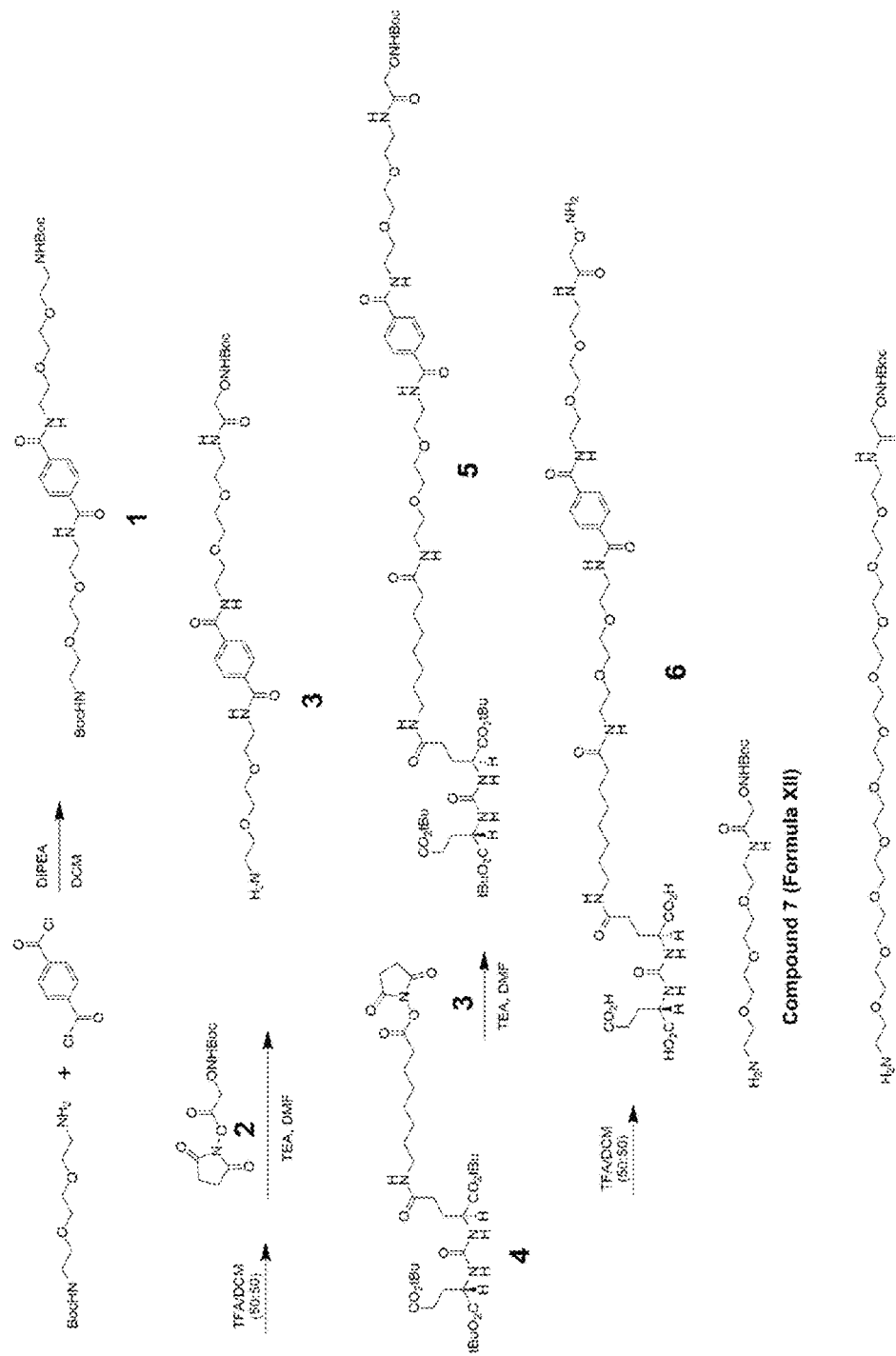
FIG. 1 depicts a scheme for synthesizing a PSMA binding targeting agent-linker compound.
Figure 2:
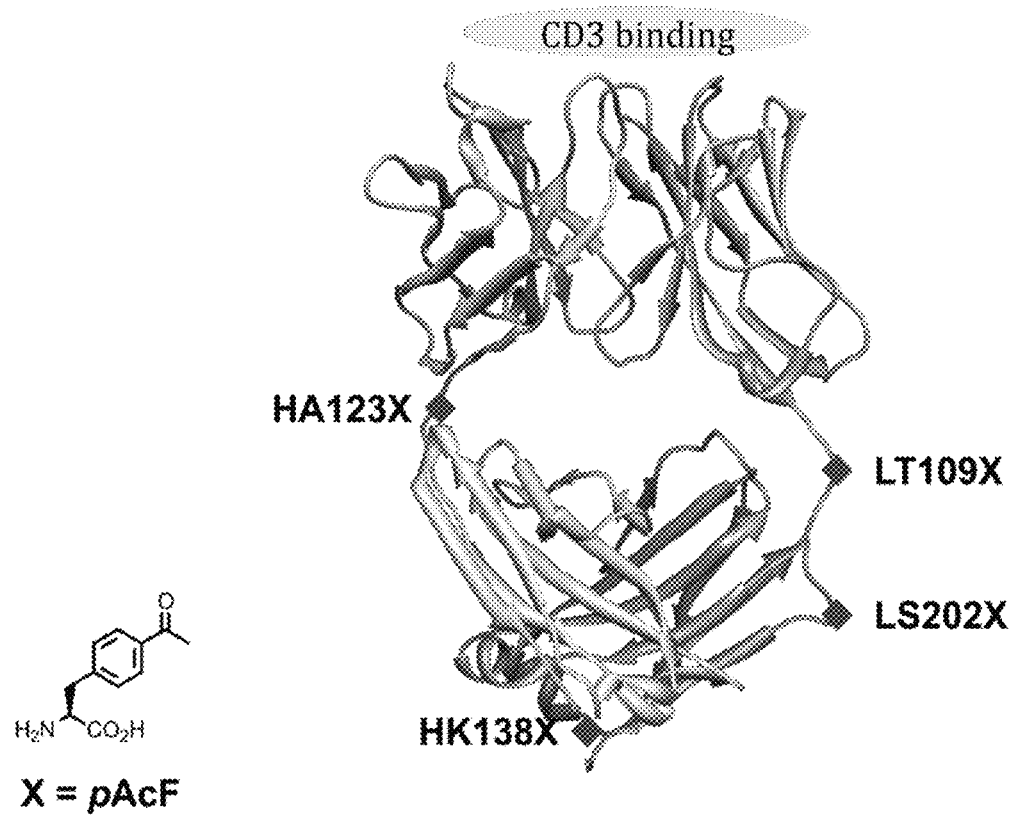
FIG. 2 depicts a ribbon diagram of a UCHT1-Fab fragment.
Figure 3A:
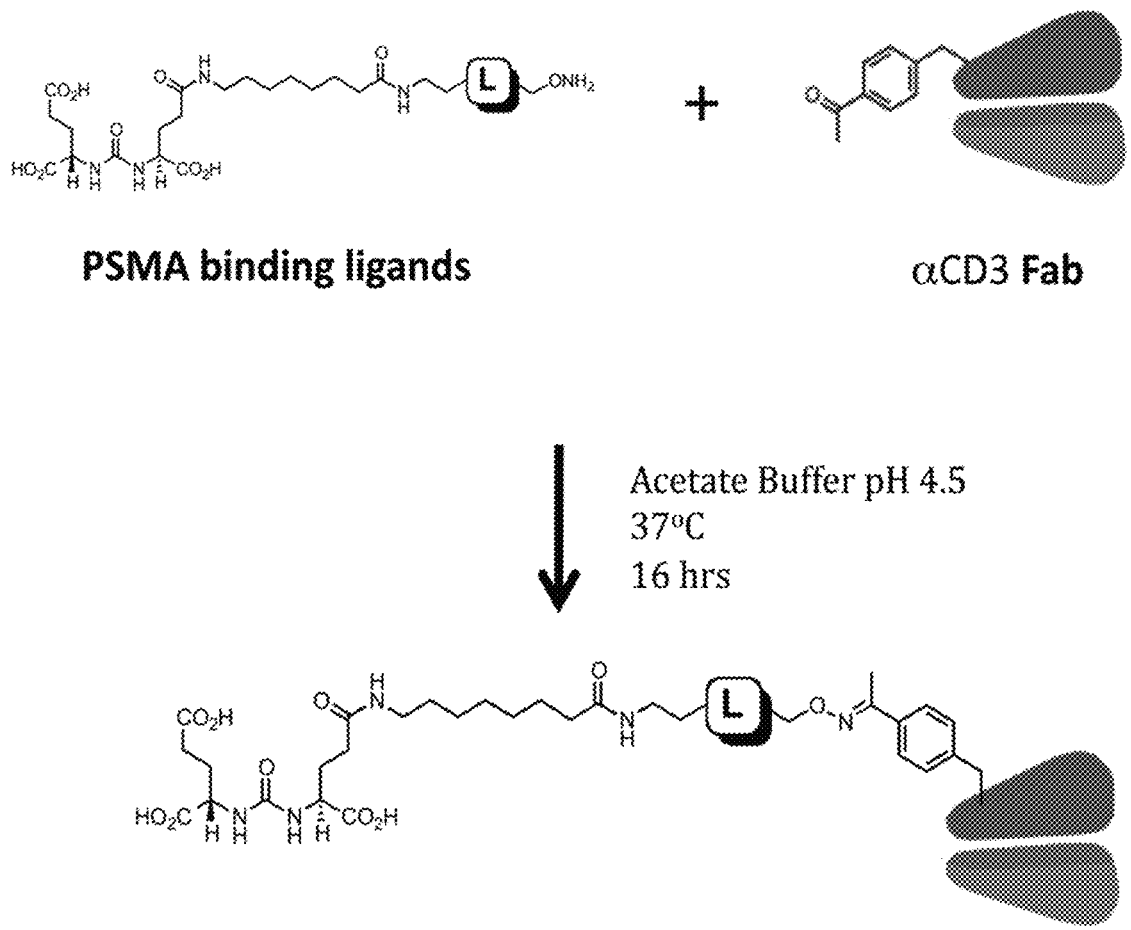
FIG. 3A depicts a scheme for linking a PSMA binding targeting agent-linker compound to a linker-conjugated Fab fragment.
Figure 3B:
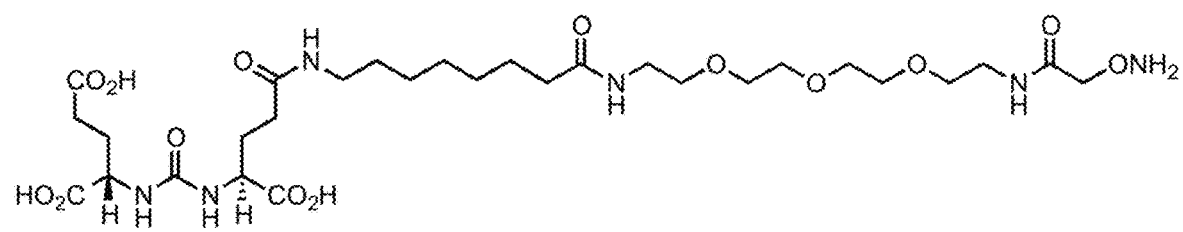
FIG. 3B-3E shows examples of linkers.
Figure 3C:
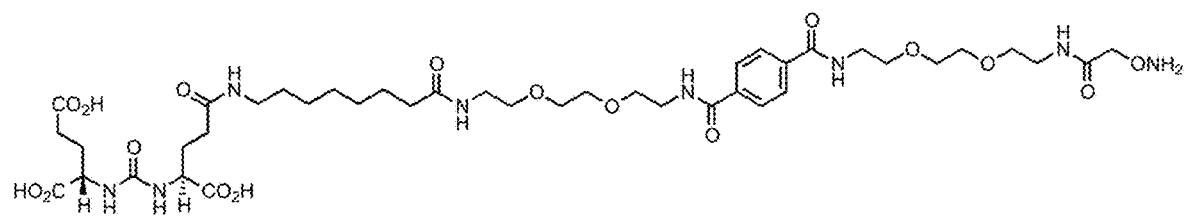
Figure 3D:
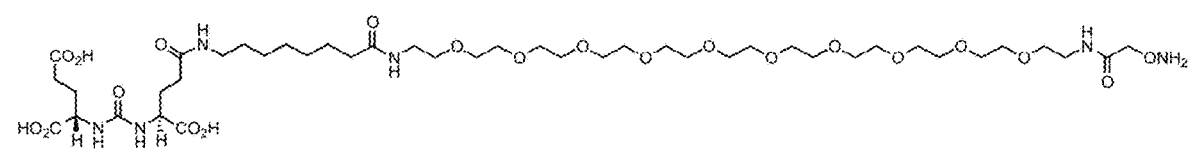
Figure 3E:
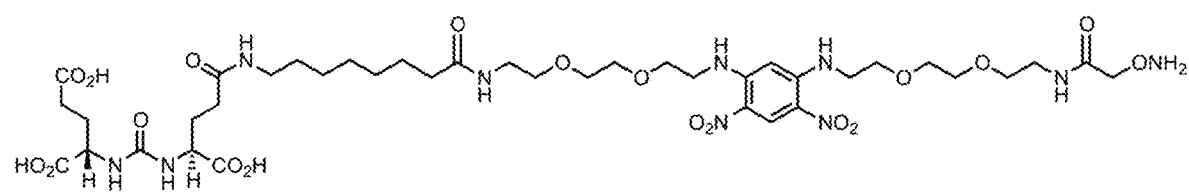
Figure 4A:
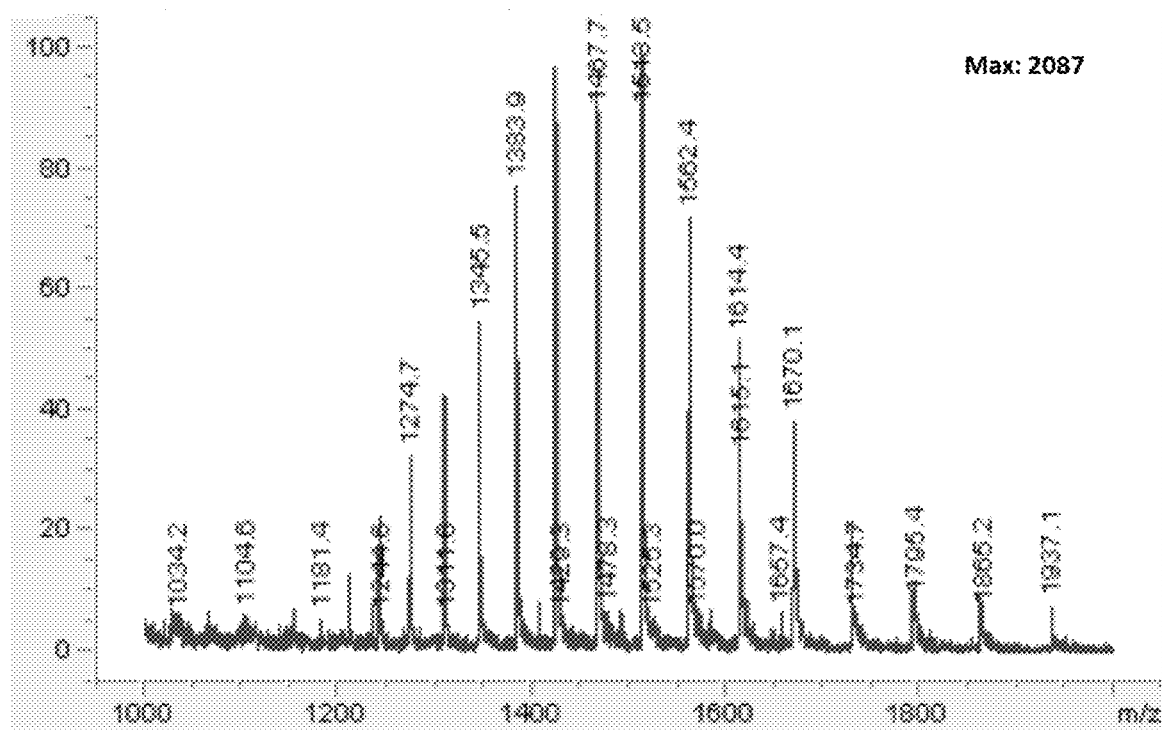
FIGS. 4A and 4C depict ESI-MS analysis of Fab fragments before and after linker conjugation.
Figure 4B:
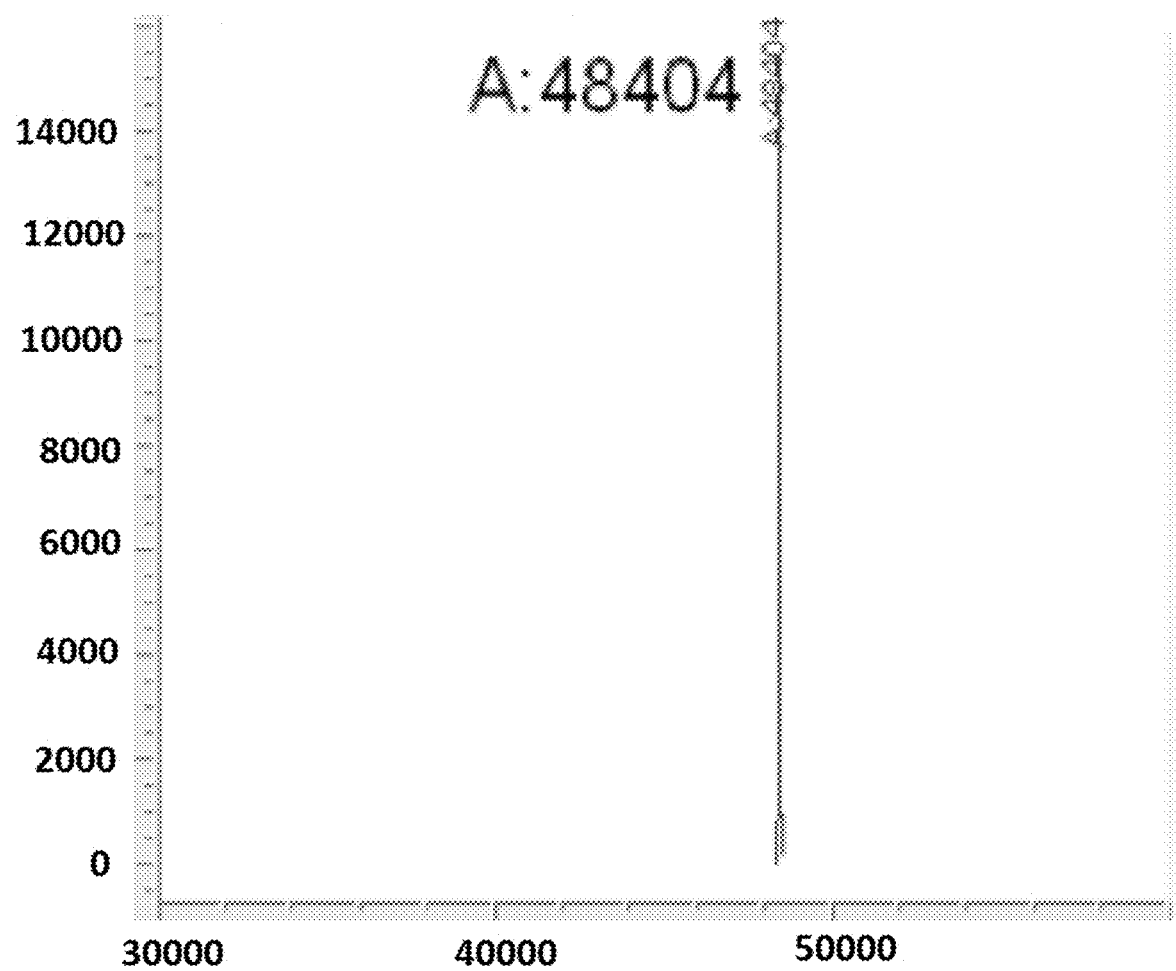
FIGS. 4B and 4D depict deconvoluted mass spectrum of Fab fragments before and after linker conjugation.
Figure 4C:
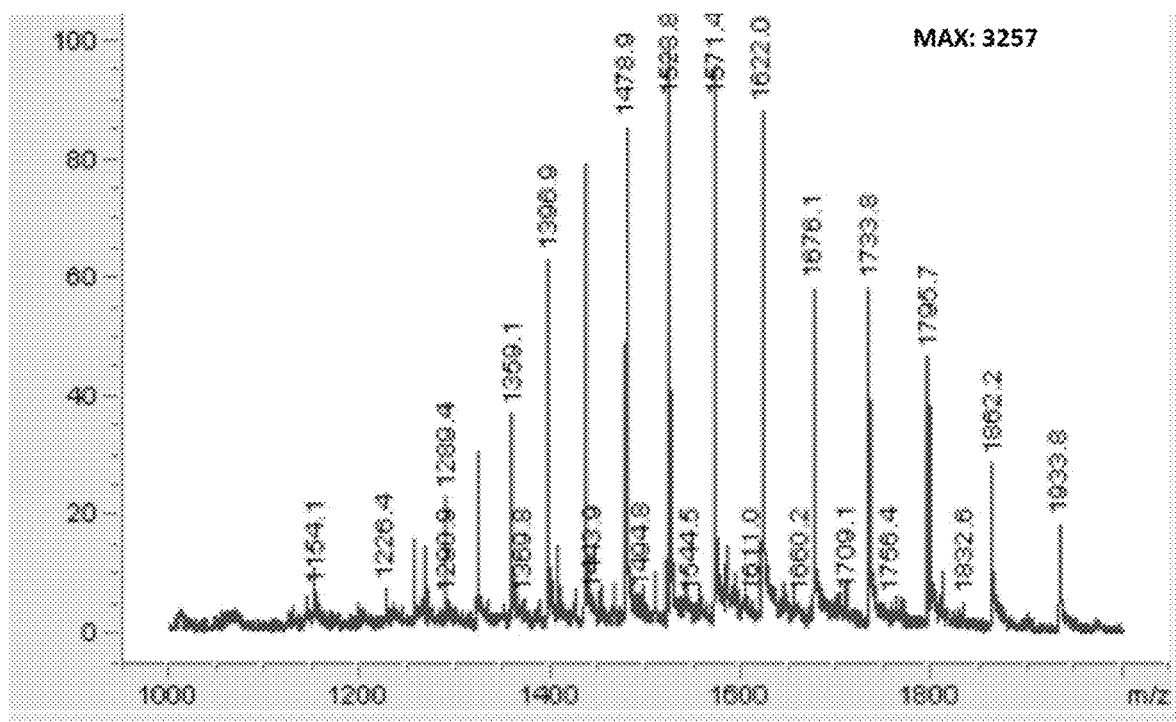
Figure 4D:
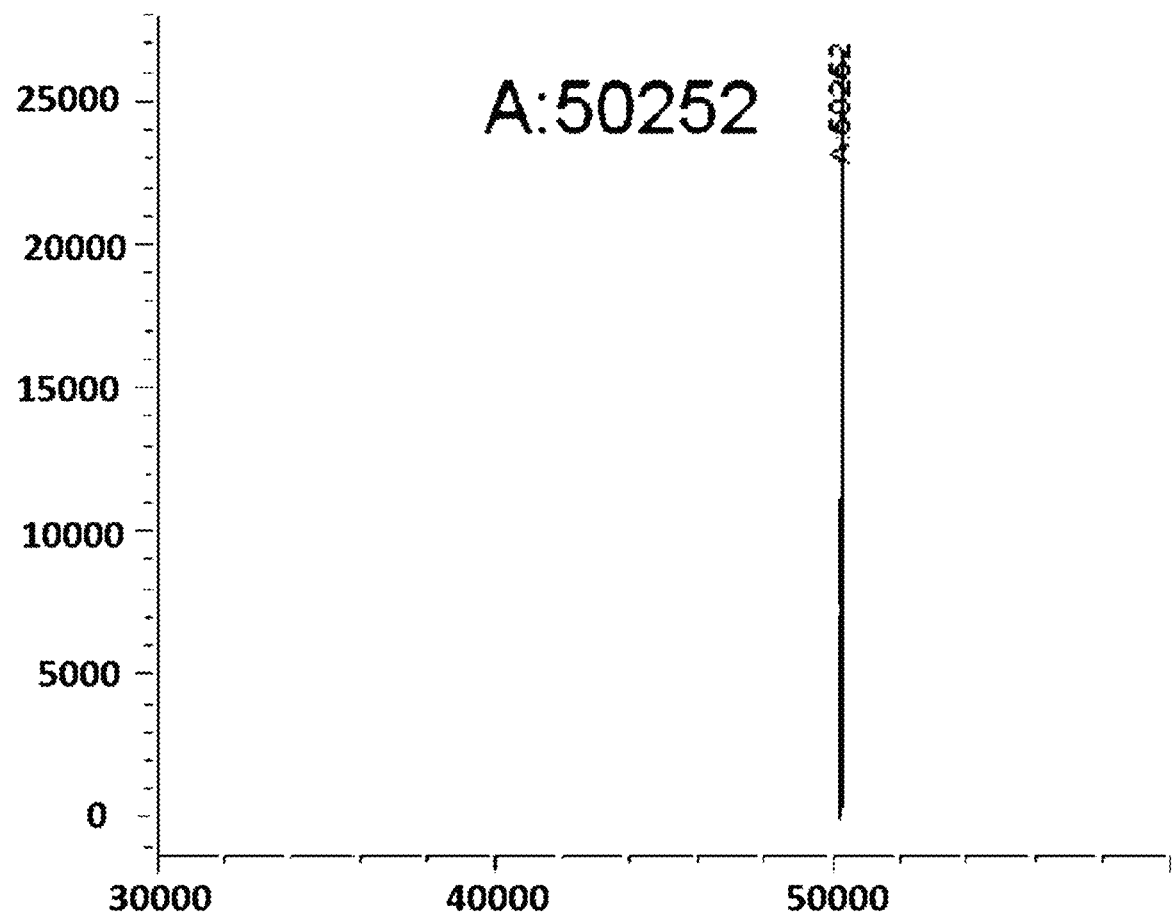
Figure 5A:
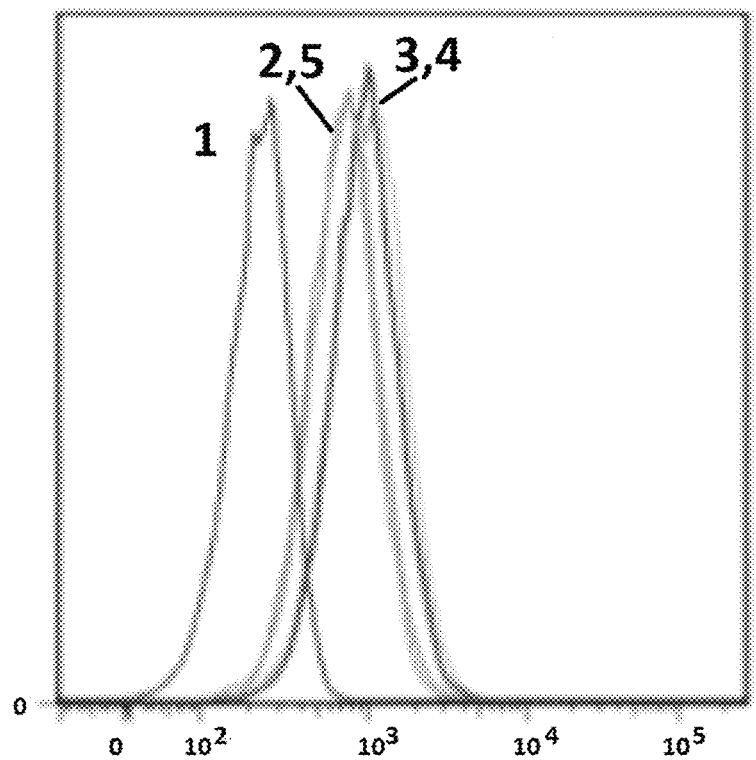
FIG. 5A-5B depicts flow cytometry analysis of Jurkat cells (FIG. 5A) and C4-2 cells (FIG. 5B) incubated with targeting agent antibody conjugates.
Figure 5B:
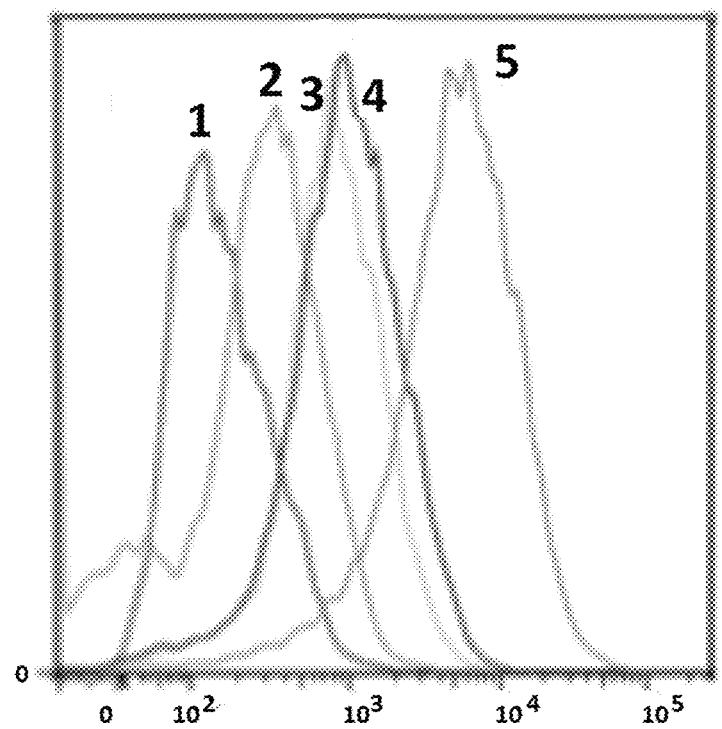
Figure 5C:
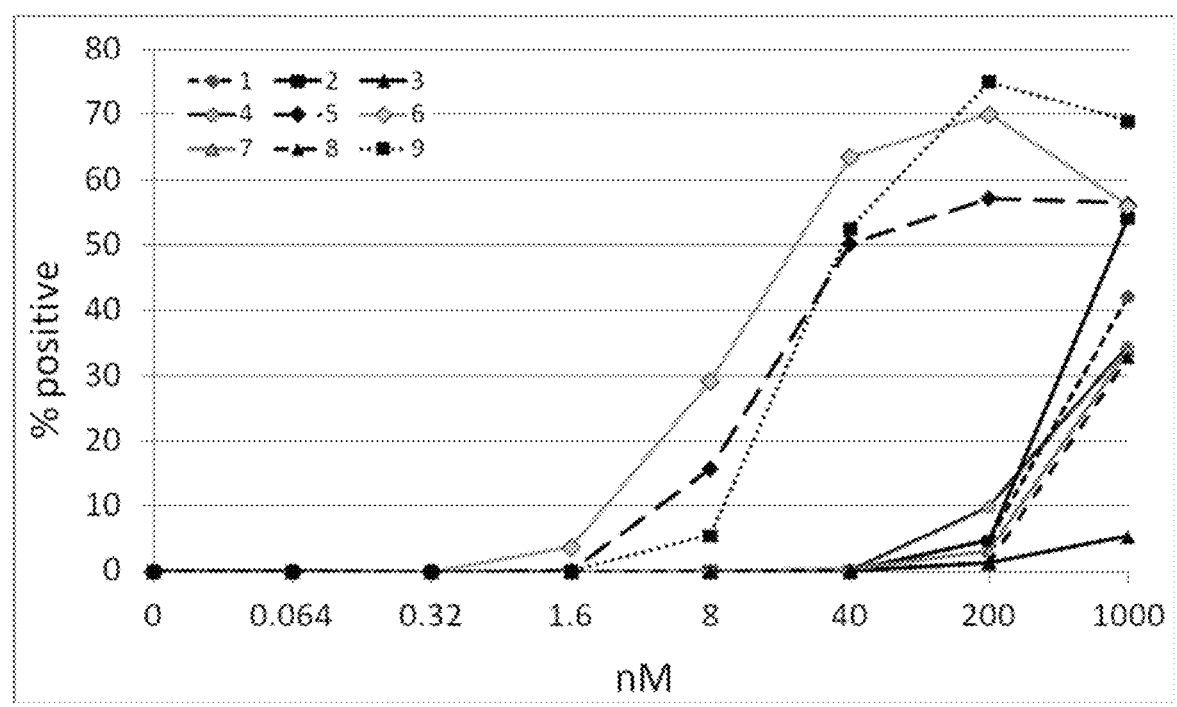
FIG. 5C depicts FACS-based binding assay of different Fabs to C4-2 cells.
Figure 6A:
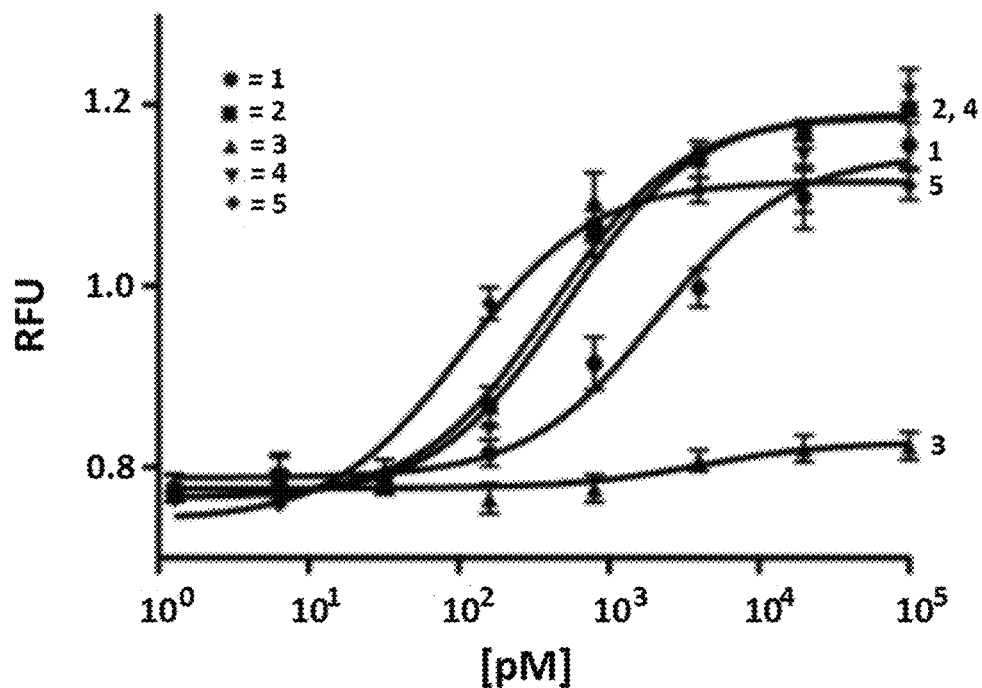
FIG. 6A depicts the relative fluorescence of C4-2 cells treated with different concentrations of conjugated and unconjugated Fabs in C4-2 cells.
Figure 6B:
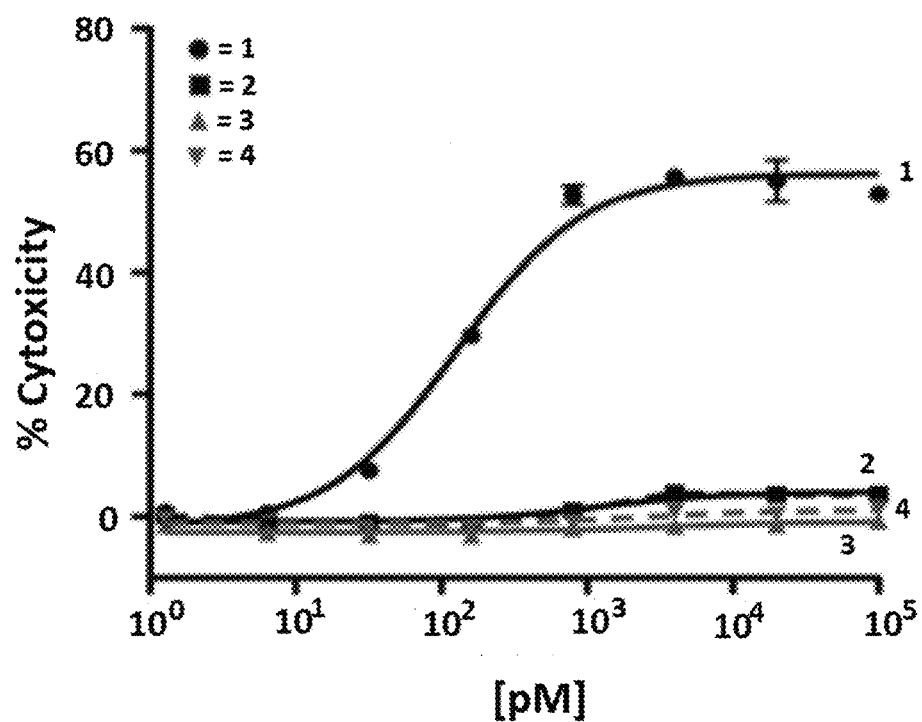
FIG. 6B depicts the percent cytotoxicity of C4-2 or DU145 cells incubated with double-Phthal or a mixture.
Figure 6C:
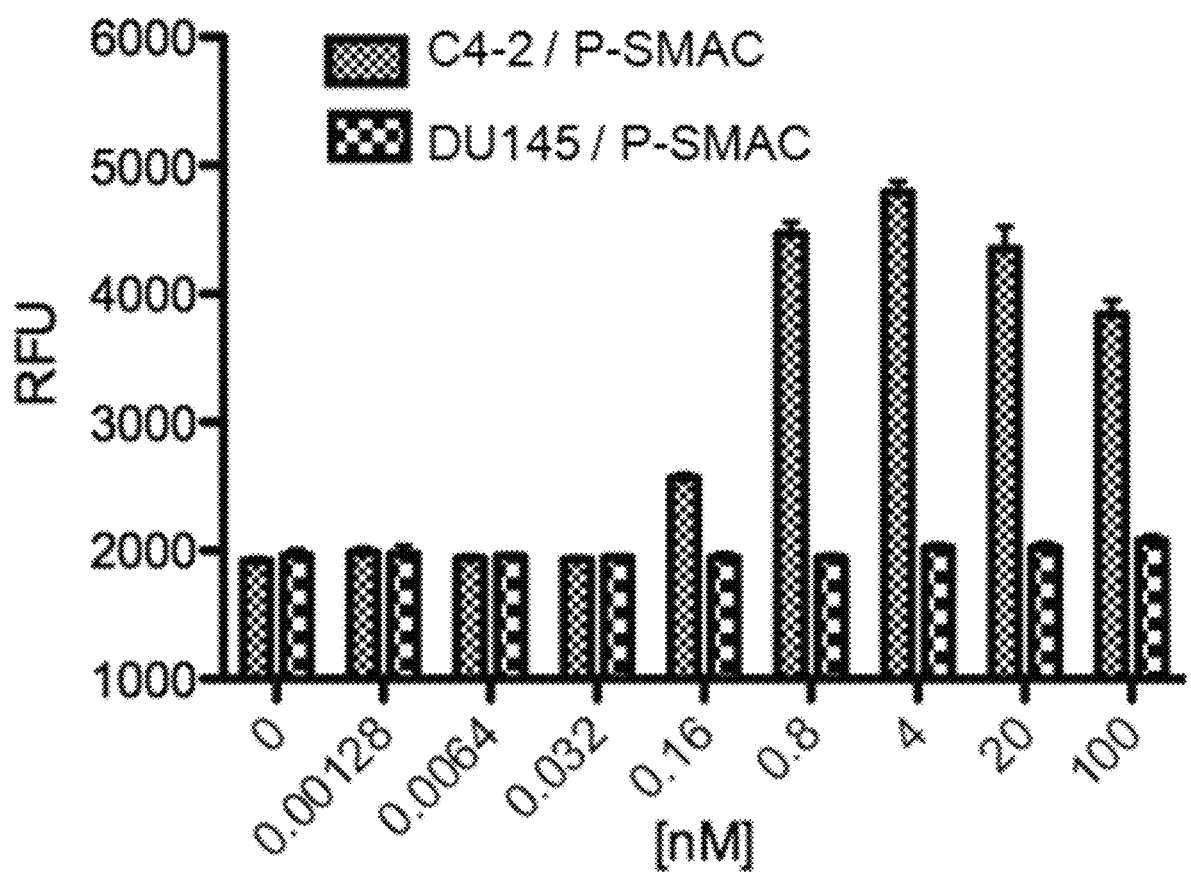
FIG. 6C depicts Proinflamatory cytokine TNF-alpha levels in the supernatant from the cytotoxicity assay. Dose-dependent TNF-alpha signals were detected only in the presence of PSMA-positive C4-2 cells by ELISA assay (R&D systems).
Figure 7A:
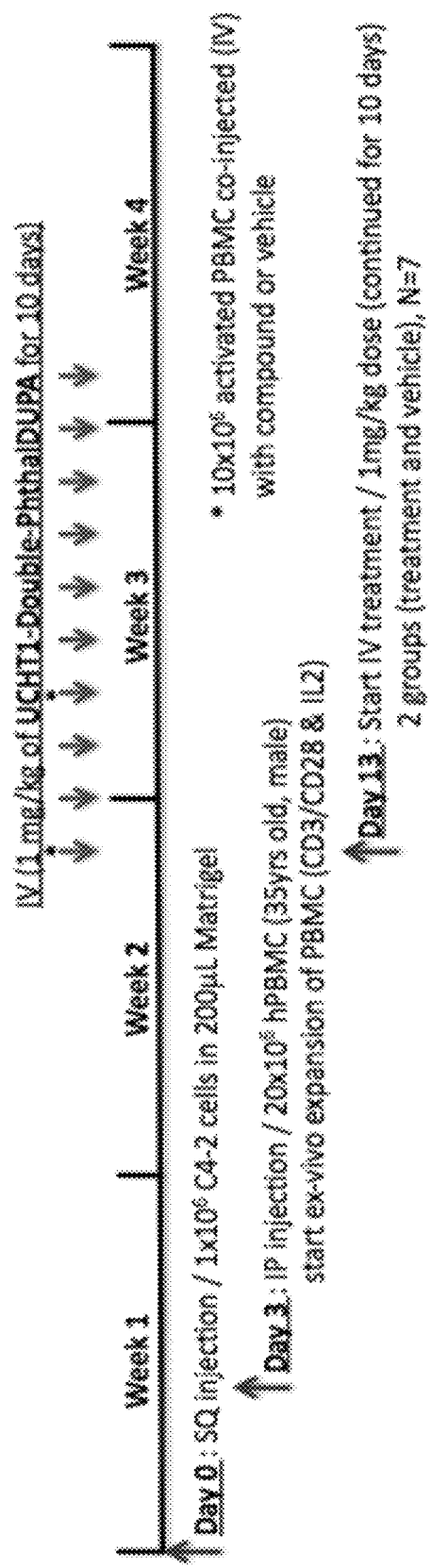
FIG. 7A depicts a schematic of an in vivo xenograft model experiment
Figure 7B:
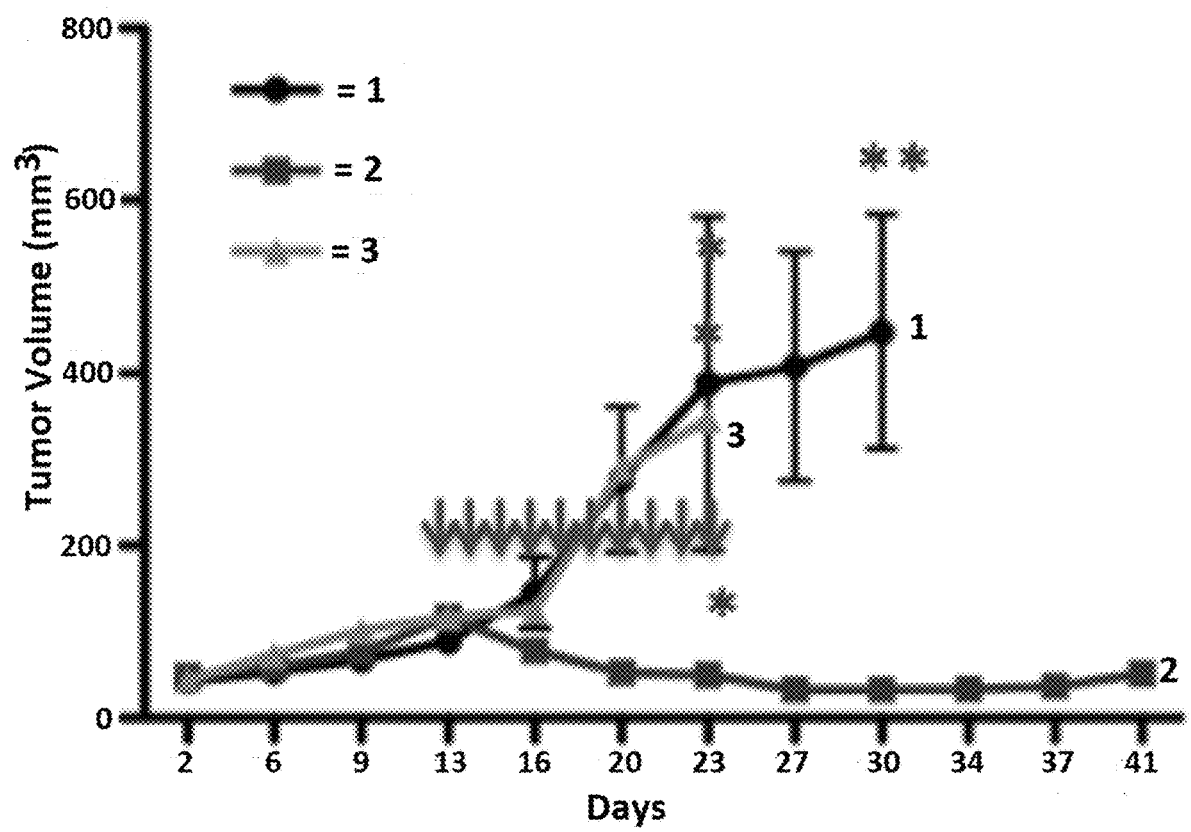
FIG. 7B depicts the tumor volume of C4-2 cells implanted in mice treated with PBS, conjugated Fab and PBMC, or conjugated Fab (no PBMC).
Figure 8:
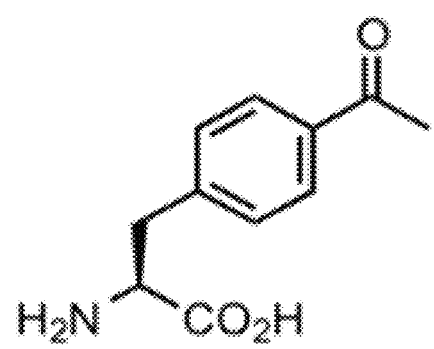
FIG. 8 depicts the structure of p-acetylphenylaline.

Before the present methods and compositions are described, it is to be understood that this invention is not limited to particular method or composition described, as such may, of course, vary. It is also to be understood that the terminology used herein is for the purpose of describing particular embodiments only, and is not intended to be limiting. Examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein may be used in the practice or testing of the present invention, some potential and preferred methods and materials are now described. All publications mentioned herein are incorporated herein by reference to disclose and describe the methods and/or materials in connection with which the publications are cited. It is understood that the present disclosure supersedes any disclosure of an incorporated publication to the extent there is a contradiction.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method may be carried out in the order of events recited or in any other order which is logically possible.

It must be noted that as used herein and in the appended claims, the singular forms "a", "an", and "the" include plural referents unless the context clearly dictates otherwise. Thus, for example, reference to "a cell" includes a plurality of such cells and reference to "the peptide" includes reference to one or more peptides and equivalents thereof, e.g. polypeptides, known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Disclosed herein are targeting agent antibody conjugates comprising: a targeting agent that binds to a target cell, wherein the targeting agent is not an antibody or antibody fragment; and an antibody or antibody fragment that does not bind to the target cell; and one or more linkers, wherein the antibody or antibody fragment is linked to the targeting agent by the one or more linkers and wherein the antibody or antibody fragment binds an antigen on a cytotoxic effector cell. The antibody or antibody fragment may comprise one or more unnatural amino acids. The targeting agent may be site-specifically linked by the one or more linkers to the one or more unnatural amino acids of the antibody or antibody fragment.

Further disclosed herein are targeting agent antibody conjugates. The targeting agent antibody conjugate may comprise Formula I: X-L1-Y or Formula IA: Y-L1-X, wherein (a) X comprises at least a portion of antibody or antibody fragment; (b) L1 comprises one or more linkers; and (c) Y comprises a targeting agent, wherein the antibody or antibody fragment is linked to the targeting agent by the one or more linkers. The antibody or antibody fragment and the targeting agent may be site-specifically linked. Generally X binds a cytotoxic effector cell and Y binds a target cell. For example, X may bind an antigen on a cytotoxic T cell and Y may bind a receptor or cell surface marker on a cancer cell. Another example is a cytotoxic effector cell may be a macrophage and the target cell may be a pathogen.

Disclosed herein are targeting agent antibody conjugates. The targeting agent antibody conjugate may comprise Formula I: X-L1-Y or Formula IA: Y-L1-X, wherein (a) X comprises at least a portion of antibody or antibody fragment; (b) $L^1$ comprises one or more linkers; and (c) Y comprises a targeting agent, wherein the antibody or antibody fragment is linked to the targeting agent by the one or more linkers and wherein the antibody or antibody fragment and the targeting agent are site-specifically linked. Generally, the targeting agent antibody conjugate comprises one or more unnatural amino acids. Generally, the antibody or antibody fragment comprises the one or more unnatural amino acids.

Further disclosed herein are targeting antibody conjugates of the Formula I: X-L1-Y or Formula IA: Y-L1-X, wherein X comprises more than one antibody or antibody fragment. X may comprise 1, 2, 3, 4 or more antibodies or antibody fragments. X may comprise two antibodies or antibody fragments. Two or more antibodies or antibody fragments may be linked by a peptide. The peptide may be about 2, 3, 4, 5, 6, 7, 8, 9 or 10 amino acids in length. The peptide may be about five amino acids in length. X may comprise one or more single chain variable fragments (scFvs). X may comprise one or more Fabs. X may comprise 1, 2, 3, 4 or more scFvs. X may comprise 1, 2, 3, 4 or more Fabs. X may comprise a monovalent Fab. X may comprise a bivalent Fab. X may comprise a trivalent Fab. X may comprise a tetravalent Fab. X may comprise a monovalent scFv. X may comprise a bivalent scFv. X may comprise a trivalent scFv. X may comprise a tetravalent scFv. One or more Fabs may be the same. One or more Fabs may be different. One or more scFvs may be the same. One or more scFvs may be different.

Further disclosed herein are targeting antibody conjugates of the Formula I: X-L1-Y or Formula IA: Y-L1-X, wherein X comprises more than one antibody or antibody fragment and Y comprises one or more targeting agents. Y may comprise 1, 2, 3, 4 or more targeting agents. The one or more targeting agents may be the same. The one or more targeting agents may be different. The targeting antibody conjugate may comprise a second linker wherein the first linker links one targeting agent to the first antibody or antibody fragment and the second linker links the second targeting agent to the second antibody or antibody fragment. The targeting agent may comprise 2, 3, 4 or more linkers wherein each linker links each targeting agent to an antibody or antibody fragment of the targeting antibody conjugate.

Further disclosed herein are targeting antibody conjugates of the Formula I: $X-L^1-Y$ or Formula IA: Y-L1-X, wherein X comprises one antibody or antibody fragment and wherein Y comprises one or more targeting agents. Y may comprise 1, 2, 3, 4, 5, 6 or more targeting agents. The one or more targeting agents may be the same. The one or more targeting agents may be different. The targeting antibody conjugate may comprise 1, 2, 3, 4, 5, 6 or more linkers wherein each linker links a targeting agent to the antibody or antibody fragment.

The efficacy of the targeting antibody conjugates may be optimized by modifying linker structure, linker length, relative binding orientation and stoichiometry of the targeting agent. Conventional chemical approaches that use lysine or cysteine chemistry to link antigen-binding moieties tend to yield heterogeneous products which likely differ in their ability to accommodate productive geometries for the formation of immunological synapses and/or have reduced stability or half-life in vivo. Circumventing these challenges, are targeting antigen antibody conjugates disclosed herein that incorporate unnatural amino acids which allow for precise control of linker moiety placement and thus precise control over targeting agent antibody conjugate geometry as well as generation of homogenous pools of targeting agent antibody conjugates.

Disclosed herein is a targeting agent antibody conjugate comprising an anti-CD3 antibody or antibody fragment; one or more linkers; and a targeting agent that binds a prostate specific membrane antigen (PSMA). The targeting agent may be DUPA. The antibody fragment may be an anti-CD3

Fab. The anti-CD3 Fab may be UCHT1. The linker may be a P-TriA linker. The linker may be a P-Und linker. The linker may be a P-Tet linker. The linker may be a P-Phthal linker. The linker may be a P-DNP linker. The targeting agent antibody conjugate may further comprise a second anti-CD3 Fab. The targeting agent antibody conjugate may further comprise a second, third, or fourth targeting agent that binds a prostate specific membrane antigen. The second, third, or fourth targeting agent that binds a prostate specific membrane antigen may comprise DUPA. The targeting agent antibody conjugate may comprise a bivalent anti-CD3 Fab and four DUPAs, wherein a first and a second DUPA are linked by a first linker and a second linker to a first Fab of the anti-CD3 Fab and a third and a fourth DUPA are linked by a third linker and a fourth linker to a second Fab of the anti-CD3 Fab. The anti-CD3 antibody or antibody fragment may comprise one or more unnatural amino acids. The anti-CD3 antibody or antibody fragment may comprise one or more unnatural amino acids, wherein the unnatural amino acid is site-specifically incorporated. The anti-CD3 antibody or antibody fragment may be site-specifically linked to DUPA. DUPA may be site-specifically linked to the anti-CD3 antibody or antibody fragment at the unnatural amino acid of the anti-CD3 antibody or antibody fragment.

Disclosed herein is a targeting agent antibody conjugate comprising an anti-CD3 antibody or antibody fragment; one or more linkers; and a targeting agent that binds a c-type lectin-like molecule. The anti-CD3 antibody or antibody fragment may comprise one or more unnatural amino acids. The anti-CD3 antibody or antibody fragment may comprise one or more unnatural amino acids, wherein the unnatural amino acid is site-specifically incorporated. The anti-CD3 antibody or antibody fragment may be site-specifically linked to the targeting agent that binds the c-type lectin-like molecule. The targeting agent that binds c-type lectin-like molecule may be site-specifically linked to the anti-CD3 antibody or antibody fragment at the unnatural amino acid of the anti-CD3 antibody or antibody fragment.

Disclosed herein is a targeting agent antibody conjugate comprising an anti-CD3 antibody or antibody fragment; one or more linkers; and a targeting agent that binds a cholecystokinin B receptor (CCKBR). The targeting agent that binds the cholecystokinin B receptor may comprise pentagastrin. The targeting agent that binds the cholecystokinin B receptor may comprise a CCKBR antagonist. The anti-CD3 antibody or antibody fragment may comprise one or more unnatural amino acids. The anti-CD3 antibody or antibody fragment may comprise one or more unnatural amino acids, wherein the unnatural amino acid is site-specifically incorporated. The anti-CD3 antibody or antibody fragment may be site-specifically linked to pentagastrin. The anti-CD3 antibody or antibody fragment may be site-specifically linked to the CCKBR antagonist. The CCKBR antagonist may be site-specifically linked to the anti-CD3 antibody or antibody fragment at the unnatural amino acid of the anti-CD3 antibody or antibody fragment. Pentagastrin may be site-specifically linked to the anti-CD3 antibody or antibody fragment at the unnatural amino acid of the anti-CD3 antibody or antibody fragment.

Disclosed herein is a targeting agent antibody conjugate comprising an anti-CD3 antibody or antibody fragment; one or more linkers; and a targeting agent that binds a gonadotropin releasing hormone receptor (GnRHR). The targeting agent that binds the GnRHR receptor may comprise gonadotropin releasing hormone (GnRH). The anti-CD3 antibody or antibody fragment may comprise one or more unnatural amino acids. The anti-CD3 antibody or antibody fragment may comprise one or more unnatural amino acids, wherein the unnatural amino acid is site-specifically incorporated. The anti-CD3 antibody or antibody fragment may be site-specifically linked to GnRH. GnRH may be site-specifically linked to the anti-CD3 antibody or antibody fragment at the unnatural amino acid of the anti-CD3 antibody or antibody fragment Disclosed herein is a targeting agent antibody conjugate comprising an anti-CD3 antibody or antibody fragment; one or more linkers; and a targeting agent that binds a somatostatin receptor 2 (SST2). The targeting agent that binds the somatostatin receptor 2 may comprise octreotide. The targeting agent that binds the somatostatin receptor 2 may comprise octreotate. The targeting agent that binds the somatostatin receptor 2 may comprise a somatostatin analog. The anti-CD3 antibody or antibody fragment may comprise one or more unnatural amino acids. The anti-CD3 antibody or antibody fragment may comprise one or more unnatural amino acids, wherein the unnatural amino acid is site-specifically incorporated. The anti-CD3 antibody or antibody fragment may be site-specifically linked to octreotide, octreotate or the somatostatin analog. The octreotide, octreotate or somatostatin analog may be site-specifically linked to the anti-CD3 antibody or antibody fragment at the unnatural amino acid of the anti-CD3 antibody or antibody fragment.

Disclosed herein is a targeting agent antibody conjugate comprising an anti-CD3 antibody or antibody fragment; one or more linkers; and a targeting agent that binds an avb3 integrin. The targeting agent that binds the avb3 integrin may comprise a cyclic Arginine-Glycine-Aspartic Acid peptide (cRGD). The anti-CD3 antibody or antibody fragment may comprise one or more unnatural amino acids. The anti-CD3 antibody or antibody fragment may comprise one or more unnatural amino acids, wherein the unnatural amino acid is site-specifically incorporated. The anti-CD3 antibody or antibody fragment may be site-specifically linked to cRGD. The cRGD may be site-specifically linked to the anti-CD3 antibody or antibody fragment at the unnatural amino acid of the anti-CD3 antibody or antibody fragment.

Disclosed herein is a targeting agent antibody conjugate comprising an anti-CD3 antibody or antibody fragment; one or more linkers; and a targeting agent that binds a gastrin releasing peptide receptor. The targeting agent that binds the gastrin releasing peptide receptor may comprise a bombesin. The anti-CD3 antibody or antibody fragment may comprise one or more unnatural amino acids. The anti-CD3 antibody or antibody fragment may comprise one or more unnatural amino acids, wherein the unnatural amino acid is site-specifically incorporated. The anti-CD3 antibody or antibody fragment may be site-specifically linked to bombesin. The bombesin may be site-specifically linked to the anti-CD3 antibody or antibody fragment at the unnatural amino acid of the anti-CD3 antibody or antibody fragment.

Disclosed herein is a targeting agent antibody conjugate comprising an anti-CD3 antibody or antibody fragment; one or more linkers; and a targeting agent that binds neurokinin 1 receptor. The anti-CD3 antibody or antibody fragment may comprise one or more unnatural amino acids. The anti-CD3 antibody or antibody fragment may comprise one or more unnatural amino acids, wherein the unnatural amino acid is site-specifically incorporated. The anti-CD3 antibody or antibody fragment may be site-specifically linked to the targeting agent that binds the neurokinin 1 receptor. The targeting agent that binds neurokinin 1 receptor may be site-specifically linked to the anti-CD3 antibody or antibody fragment at the unnatural amino acid of the anti-CD3 antibody or antibody fragment.

Disclosed herein is a targeting agent antibody conjugate comprising an anti-CD3 antibody or antibody fragment; one or more linkers; and a targeting agent that binds melanocortin 1 receptor. The anti-CD3 antibody or antibody fragment may comprise one or more unnatural amino acids. The anti-CD3 antibody or antibody fragment may comprise one or more unnatural amino acids, wherein the unnatural amino acid is site-specifically incorporated. The anti-CD3 antibody or antibody fragment may be site-specifically linked to the targeting agent that binds the melanocortin 1 receptor. The targeting agent that binds melanocortin 1 receptor may be site-specifically linked to the anti-CD3 antibody or antibody fragment at the unnatural amino acid of the anti-CD3 antibody or antibody fragment.

Disclosed herein is a targeting agent antibody conjugate comprising an anti-CD3 antibody or antibody fragment; one or more linkers; and a targeting agent that binds neurotensin receptor. The anti-CD3 antibody or antibody fragment may comprise one or more unnatural amino acids. The anti-CD3 antibody or antibody fragment may comprise one or more unnatural amino acids, wherein the unnatural amino acid is site-specifically incorporated. The anti-CD3 antibody or antibody fragment may be site-specifically linked to the targeting agent that binds the neurotensin receptor. The targeting agent that binds neurotensin receptor may be site-specifically linked to the anti-CD3 antibody or antibody fragment at the unnatural amino acid of the anti-CD3 antibody or antibody fragment.

Disclosed herein is a targeting agent antibody conjugate comprising an anti-CD3 antibody or antibody fragment; one or more linkers; and a targeting agent that binds neuropeptide Y receptor. The anti-CD3 antibody or antibody fragment may comprise one or more unnatural amino acids. The anti-CD3 antibody or antibody fragment may comprise one or more unnatural amino acids, wherein the unnatural amino acid is site-specifically incorporated. The anti-CD3 antibody or antibody fragment may be site-specifically linked to the targeting agent that binds the neuropeptide Y receptor. The targeting agent that binds neuropeptide Y receptor may be site-specifically linked to the anti-CD3 antibody or antibody fragment at the unnatural amino acid of the anti-CD3 antibody or antibody fragment.

Relative to bispecific antibodies with similar binding targets, the targeting agent antibody conjugates disclosed herein, may show an improved serum half-life, selectivity and potency.

Further disclosed herein are methods of producing targeting agent antibody conjugates, These methods allow for facile generation of various targeting agent antibody conjugates with different relative geometries.

I. Antibodies, Antibody Fragments, and Targeting Agents

The targeting agent antibody conjugate may comprise an Ig-targeting agent construct, wherein X comprises an immunoglobulin and Y comprises a targeting agent. The targeting agent antibody conjugate may comprise a Fab-targeting agent construct, wherein X comprises a Fab fragment and Y comprises a targeting agent. X and Y may be linked by one or more linkers (e.g., $L^1$, $L^2$). As used herein, the term "antibody fragment" refers to any form of an antibody other than the full-length form. Antibody fragments herein include antibodies that are smaller components that exist within full-length antibodies, and antibodies that have been engineered. Antibody fragments include, but are not limited to, Fv, Fc, Fab, and (Fab')2, single chain Fv (scFv), diabodies, triabodies, tetrabodies, bifunctional hybrid antibodies, CDR1, CDR2, CDR3, combinations of CDRs, variable regions, framework regions, constant regions, heavy chains, light chains, alternative scaffold non-antibody molecules, and bispecific antibodies. Unless specifically noted otherwise, statements and claims that use the term "antibody" or "antibodies" may specifically include "antibody fragment" and "antibody fragments."

The antibodies disclosed herein may be human, fully human, humanized, human engineered, non-human, and/or chimeric antibody. For example, the antibody of Formula I may be a humanized antibody. In another example, the antibody of Formula I is a chimeric antibody. The antibodies disclosed herein may be based on or derived from human, fully human, humanized, human engineered, non-human and/or chimeric antibodies. For example, X of Formula IA may be based on or derived from a human engineered antibody. Alternatively, X of Formula IA may be based on or derived from a non-human antibody. The non-human antibody may be humanized to reduce immunogenicity to humans, while retaining the specificity and affinity of the parental non-human antibody. Generally, a humanized antibody comprises one or more variable domains in which CDRs (or portions thereof) are derived from a non-human antibody, and FRs (or portions thereof) are derived from human antibody sequences. A humanized antibody optionally also comprises at least a portion of a human constant region. In some embodiments, some FR residues in a humanized antibody are substituted with corresponding residues from a non-human antibody (e.g., the antibody from which the CDR residues are derived), e.g., to restore or improve antibody specificity or affinity.

Humanized antibodies and methods of making them are reviewed, e.g., in Almagro and Fransson, Front. Biosci. 13:1619-1633 (2008), and are further described, e.g., in Riechmann et al., Nature 332:323-329 (1988); Queen et al., Proc. Nat'l Acad. Sci. USA 86:10029-10033 (1989); U.S. Pat. Nos. 5,821,337, 7,527,791, 6,982,321, and 7,087,409; Kashmiri et al., Methods 36:25-34 (2005) (describing SDR (a-CDR) grafting); Padlan, Mol. Immunol. 28:489-498 (1991) (describing "resurfacing"); Dall'Acqua et al., Methods 36:43-60 (2005) (describing "FR shuffling"); and Osbourn et al., Methods 36:61-68 (2005); Klimka et al., Br. J. Cancer, 83:252-260 (2000) (describing the "guided selection" approach to FR shuffling); and Studnicka et al., U.S. Pat. No. 5,766,886.

Chimeric antibodies may refer to antibodies created through the joining of two or more antibody genes which originally encoded for separate antibodies. A chimeric antibody may comprise at least one amino acid from a first antibody and at least one amino acid from a second antibody, wherein the first and second antibodies are different. X (e.g., antibody of Formula I, IA, II) may be a chimeric antibody. At least a portion of the antibody or antibody fragment may be from a bovine species, a human species, or a murine species. At least a portion of the antibody or antibody fragment may be from a cow. At least a portion of the antibody or antibody fragment may be from a rat, a goat, a guinea pig or a rabbit. At least a portion of the antibody or antibody fragment may be from a human. At least a portion of the antibody or antibody fragment antibody may be from cynomolgus monkey.

The antibodies disclosed herein may be based on or derived from an antibody or antibody fragment from a mammal, bird, fish, amphibian, reptile. Mammals include, but are not limited to, carnivores, rodents, elephants, marsupials, rabbits, bats, primates, seals, anteaters, cetaceans, odd-toed ungulates and even-toed ungulates. The mammal may be a human, non-human primate, mouse, sheep, cat, dog, cow, horse, goat, or pig.

Birds include, but are not limited to, albatrosses, hummingbirds, eagles, ostriches, cardinals, kiwis, and penguins. Fish may be cartilaginous fishes, ray-finned fishes, or lobe-fined fishes. Amphibians may include, but are not limited to, newts, salamanders, frogs and toads. Examples of reptiles include, but are not limited to, turtles, squamates, crocodiles and tuataras. Squamates may include amphisbaenas, lizards and snakes.

The antibodies disclosed herein may be cross-species reactive. For example, an antibody may recognize a human antigen and a cynomogolus monkey antigen (e.g. human/cyno antibody.

The antibody or antibody fragment may comprise at least a portion of a sequence selected from SEQ ID NOs: 1-2. The antibody or antibody fragment may comprise a sequence that is at least 50% identical to a sequence selected from SEQ ID NOs: 1-2. The antibody or antibody fragment may comprise a sequence that is at least 60% identical to a sequence selected from SEQ ID NOs: 1-2. The antibody or antibody fragment may comprise a sequence that is at least 70% identical to a sequence selected from SEQ ID NOs: 1-2. The antibody or antibody fragment may comprise a sequence that is at least 80% identical to a sequence selected from SEQ ID NOs: 1-2. The antibody or antibody fragment may comprise a sequence that is at least 50% identical to a sequence selected from SEQ ID NOs: 1-2. The antibody or antibody fragment may comprise a sequence that is at least 85% identical to a sequence selected from SEQ ID NOs: 1-2. The antibody or antibody fragment may comprise a sequence that is at least 90% identical to a sequence selected from SEQ ID NOs: 1-2. The antibody or antibody fragment may comprise a sequence that is at least 95% identical to a sequence selected from SEQ ID NOs: 1-2. The antibody or antibody fragment may comprise a sequence that is at least 97% identical to a sequence selected from SEQ ID NOs: 1-2.

The antibody or antibody fragment may comprise a sequence comprising five or more amino acids based on or derived from a sequence selected from SEQ ID NOs: 1-2. The antibody or antibody fragment may comprise a sequence comprising 6, 7, 8, 9, 10 or more amino acids based on or derived from a sequence selected from SEQ ID NOs: 1-2. The antibody or antibody fragment may comprise a sequence comprising 15, 16, 17, 18, 19, 20 or more amino acids based on or derived from a sequence selected from SEQ ID NOs: 1-2. The antibody or antibody fragment may comprise a sequence comprising 25, 30, 35, 40, 45, 50 or more amino acids based on or derived from a sequence selected from SEQ ID NOs: 1-2. The antibody or antibody fragment may comprise a sequence comprising 55, 60, 65, 70, 75, 80, 85, 90, 95, 100 or more amino acids based on or derived from a sequence selected from SEQ ID NOs: 1-2. The amino acids may be consecutive. The amino acids may be non-consecutive.

IA. Antibody or Antibody Fragments of X

The antibodies disclosed herein may comprise X, wherein X comprises at least a portion of an antibody or antibody fragment. The antibody or antibody fragment may comprise one or more unnatural amino acids. X may comprise an entire antibody. X may comprise at least a portion of antibody. X may comprise at least a portion of a monoclonal antibody. X may comprise at least a portion of a polyclonal antibody. X may comprise at least a portion of a multivalent antibody.

X may comprise at least a portion of an antibody. The portion of the antibody may comprise an antibody fragment. The portion of the antibody may be an immunoglublulin (Ig). The immunoglobulin may selected from an IgG, an IgA, an IgD, an IgE, an IgM, a fragment thereof or a modification thereof. The immunoglobulin may be IgG. The IgG may be IgG1. The IgG may be IgG2. The IgG may have Fc mutations for reduced FcR binding. The Fc mutations in the IgG1 may be L234A and L235A. The Fc mutations in the IgG1 may be L234A and L235E. The Fc mutation in the IgG1 may be N297A. The Fc mutation in the IgG2 may be V234A and V237A. Antibody fragments include, but are not limited to, Fv, Fc, Fab, and (Fab')2, single chain Fv (scFv), diabodies, triabodies, tetrabodies, bifunctional hybrid antibodies, CDR1, CDR2, CDR3, combinations of CDR's, variable regions, framework regions, constant regions, heavy chains, light chains, alternative scaffold non-antibody molecules, and bispecific antibodies. X may comprise a Fab fragment. X may comprise at least a portion of a heavy chain (HC) of an antibody. X may comprise at least a portion of a light chain (LC) of an antibody. X may comprise at least a portion of a variable region of an antibody. X may comprise at least a portion of a constant region of an antibody.

X may comprise at least a portion of a sequence selected from SEQ ID NOs: 1-2. X may comprise a sequence that is at least 50% identical to a sequence selected from SEQ ID NOs: 1-2. X may comprise a sequence that is at least 60% identical to a sequence selected from SEQ ID NOs: 1-2. X may comprise a sequence that is at least 70% identical to a sequence selected from SEQ ID NOs: 1-2. X may comprise a sequence that is at least 80% identical to a sequence selected from SEQ ID NOs: 1-2. X may comprise a sequence that is at least 50% identical to a sequence selected from SEQ ID NOs: 1-2. X may comprise a sequence that is at least 85% identical to a sequence selected from SEQ ID NOs: 1-2. X may comprise a sequence that is at least 90% identical to a sequence selected from SEQ ID NOs: 1-2. X may comprise a sequence that is at least 95% identical to a sequence selected from SEQ ID NOs: 1-2. X may comprise a sequence that is at least 97% identical to a sequence selected from SEQ ID NOs: 1-2.

X may comprise a sequence comprising five or more amino acids based on or derived from a sequence selected from SEQ ID NOs: 1-2. X may comprise a sequence comprising 6, 7, 8, 9, 10 or more amino acids based on or derived from a sequence selected from SEQ ID NOs: 1-2. X may comprise a sequence comprising 15, 16, 17, 18, 19, 20 or more amino acids based on or derived from a sequence selected from SEQ ID NOs: 1-2. X may comprise a sequence comprising 25, 30, 35, 40, 45, 50 or more amino acids based on or derived from a sequence selected from SEQ ID NOs: 1-2. X may comprise a sequence comprising 55, 60, 65, 70, 75, 80, 85, 90, 95, 100 or more amino acids based on or derived from a sequence selected from SEQ ID NOs: 1-2. The amino acids may be consecutive. The amino acids may be non-consecutive.

X may comprise an antibody or antibody fragment that binds to at least a portion of a receptor on a cell. X may comprise an antibody or antibody fragment that binds to at least a portion of a co-receptor on a cell. X may comprise an antibody or antibody fragment that binds to at least a portion of an antigen or cell surface marker on a cell. The cell may be a hematopoietic cell. The hematopoietic cell may be a myeloid cell. The myeloid cell may be an erythrocyte, thrombocyte, monocyte, eosinophil, basophil, or mast cell. The hematopoietic cell may be a lymphoid cell. The hematopoietic cell may be a macrophage. The hematopoietic cell may be a neutrophil. The lymphoid cell may be a B-cell, T-cell, or NK-cell. The hematopoietic cell may be a leukocyte. The hematopoietic cell may be a lymphocyte. The T-cell may be a cytotoxic T-cell, a helper T-cell, a regulatory T-cell, a memory T cell or a natural killer T-cell. The T-cell may be a cytotoxic T-cell. The T-cell may be a killer T-cell. X may comprise at least a portion of an anti-T cell receptor antibody. X may comprise at least a portion of an anti-T cell co-receptor antibody. X may comprise at least a portion of an antibody that binds to an antigen on a T cell. X may comprise at least a portion of an antibody that binds to a cell surface protein on a T cell. X may comprise at least a portion of an antibody that binds to a cell surface marker on a T cell. X may comprise at least a portion of an antibody that binds to a cluster of differentiation protein on a T cell. X may comprise at least a portion of an anti-CD3 antibody. X may comprise an anti-CD3 antibody. The anti-CD3 antibody may be UCHT1. X may comprise at least a portion of a Fab fragment of an anti-CD3 antibody. X may comprise an antibody fragment of an anti-CD3 antibody. X may comprise a human/cynomolgus cross-reactive antiCD3 Fab (e.g. SP34).

X may comprise an antibody or antibody fragment that binds to at least a portion of a receptor on a cell. X may comprise an antibody or antibody fragment that binds to at least a portion of a co-receptor on a cell. X may comprise an antibody or antibody fragment that binds to at least a portion of an antigen or cell surface marker on a cell. The cell may be an immune cell. The cell may be a hematopoietic cell. The hematopoietic cell may be a myeloid cell. The myeloid cell may be an erythrocyte, thrombocyte, neutrophil, monocyte, macrophage, eosinophil, basophil, or mast cell. The hematopoietic cell may be a lymphoid cell. The lymphoid cell may be a B-cell, T-cell, or NK-cell. The hematopoietic cell may be a leukocyte. The hematopoietic cell may be a lymphocyte. The cell may be a genetically modified cell. The cell may be genetically modified to have cytotoxic activity. The cell may be genetically modified to have enhanced cytotoxic activity. The cell may be modified to have decreased cytotoxic activity.

X may comprise an antibody or antibody fragment that binds to at least a portion of a receptor on a T-cell. The receptor may be a T-cell receptor (TCR). The TCR may comprise TCR alpha, TCR beta, TCR gamma and/or TCR delta. The receptor may be a T-cell receptor zeta.

X may comprise an antibody or antibody fragment that binds to at least a portion of a receptor on a lymphocyte, B-cell, macrophage, monocytes, neutrophils and/or NK cells. The receptor may be an Fc receptor. The Fc receptor may be an Fc-gamma receptor, Fc-alpha receptor and/or Fc-epsilon receptor. Fc-gamma receptors include, but are not limited to, FcγRI (CD64), FcγRIIA (CD32), FcγRIIB (CD32), FcγRIIIA (CD16a) and FcγRIIIB (CD16b). Fc-alpha receptors include, but are not limited to, FcaRI. Fc-epsilon receptors include, but are not limited to, FccRI and FccRII. The receptor may be CD89 (Fc fragment of IgA receptor or FCAR). The targeting agent antibody conjugate may bind specifically to pathogenic bacteria or fungi when the targeting agent antibody conjugate comprises a Fc receptor-binding antibody.

X may comprise an antibody or antibody fragment that binds at least a portion of a co-receptor on a T-cell. The co-receptor may be a CD3, CD4, and/or CD8. X may comprise an antibody fragment that binds to a CD3 co-receptor. The CD3 co-receptor may comprise CD3-gamma, CD3-delta and/or CD3-epsilon. CD8 may comprise CD8-alpha and/or CD8-beta chains.

X may comprise an antibody or at least a portion of an antibody that is a human, fully human, humanized, human engineered, non-human, or chimeric antibody. X may comprise an antibody or at least a portion of an antibody that is a mammalian antibody. X may comprise an antibody or at least a portion of an antibody that is a non-mammalian antibody.

X may comprise a sequence based on or derived from one or more antibodies and/or antibody fragment sequences. X may comprise a sequence that is at least about 50%, 55%, 60%, 65%, 70%, 75%, 80%, 85%, 90%, 92%, 95%, 97%, 98%, 99% or more homologous to a sequence based on or derived from one or more antibodies and/or antibody fragments. X may comprise a sequence that is at least about 70% homologous to a sequence based on or derived from one or more antibodies and/or antibody fragments. X may comprise a sequence that is at least about 80% homologous to a sequence based on or derived from one or more antibodies and/or antibody fragments. X may comprise a sequence that is at least about 90% homologous to a sequence based on or derived from one or more antibodies and/or antibody fragments. X may comprise a sequence that is at least about 95% homologous to a sequence based on or derived from one or more antibodies and/or antibody fragments. The sequence may be a peptide sequence. Alternatively, the sequence is a nucleotide sequence.

X may comprise a peptide sequence that differs from a peptide sequence based on or derived from one or more antibodies and/or antibody fragments by less than or equal to about 20, 17, 15, 12, 10, 8, 6, 5, 4 or fewer amino acids. X may comprise a peptide sequence that differs from a peptide sequence based on or derived from one or more antibodies and/or antibody fragments by less than or equal to about 4 or fewer amino acids. X may comprise a peptide sequence that differs from a peptide sequence based on or derived from one or more antibodies and/or antibody fragments by less than or equal to about 3 or fewer amino acids. X may comprise a peptide sequence that differs from a peptide sequence based on or derived from one or more antibodies and/or antibody fragments by less than or equal to about 2 or fewer amino acids. X may comprise a peptide sequence that differs from a peptide sequence based on or derived from one or more antibodies and/or antibody fragments by less than or equal to about 1 or fewer amino acids. The amino acids may be consecutive, nonconsecutive, or a combination thereof. For example, X may comprise a peptide sequence that differs from a peptide sequence based on or derived from one or more antibodies and/or antibody fragments by less than about 3 consecutive amino acids. Alternatively, or additionally, X may comprise a peptide sequence that differs from a peptide sequence based on or derived from one or more antibodies and/or antibody fragments by less than about 2 non-consecutive amino acids. In another example, X may comprise a peptide sequence that differs from a peptide sequence based on or derived from one or more antibodies and/or antibody fragments by less than about 5 amino acids, wherein 2 of the amino acids are consecutive and 2 of the amino acids are non-consecutive.

X may comprise a nucleotide sequence that differs from a nucleotide sequence based on or derived from one or more antibodies and/or antibody fragments by less than or equal to about 30, 25, 20, 19, 18, 17, 16, 15, 14, 13, 12, 11, 10, 9, 8, 7, 6, 5, 4 or fewer nucleotides or base pairs. X may comprise a nucleotide sequence that differs from a nucleotide sequence based on or derived from one or more antibodies and/or antibody fragments by less than or equal to about 15 or fewer nucleotides or base pairs. X may comprise a nucleotide sequence that differs from a nucleotide sequence based on or derived from one or more antibodies and/or antibody fragments by less than or equal to about 12 or fewer nucleotides or base pairs. X may comprise a nucleotide sequence that differs from a nucleotide sequence based on or derived from one or more antibodies and/or antibody fragments by less than or equal to about 9 or fewer nucleotides or base pairs. X may comprise a nucleotide sequence that differs from a nucleotide sequence based on or derived from one or more antibodies and/or antibody fragments by less than or equal to about 6 or fewer nucleotides or base pairs. X may comprise a nucleotide sequence that differs from a nucleotide sequence based on or derived from one or more antibodies and/or antibody fragments by less than or equal to about 4 or fewer nucleotides or base pairs. X may comprise a nucleotide sequence that differs from a nucleotide sequence based on or derived from one or more antibodies and/or antibody fragments by less than or equal to about 3 or fewer nucleotides or base pairs. X may comprise a nucleotide sequence that differs from a nucleotide sequence based on or derived from one or more antibodies and/or antibody fragments by less than or equal to about 2 or fewer nucleotides or base pairs. X may comprise a nucleotide sequence that differs from a nucleotide sequence based on or derived from one or more antibodies and/or antibody fragments by less than or equal to about 1 or fewer nucleotides or base pairs. The nucleotides or base pairs may be consecutive, nonconsecutive, or a combination thereof. For example, X may comprise a nucleotide sequence that differs from a nucleotide sequence based on or derived from one or more antibodies and/or antibody fragments by less than about 3 consecutive nucleotides or base pairs. Alternatively, or additionally, X may comprise a nucleotide sequence that differs from a nucleotide sequence based on or derived from one or more antibodies and/or antibody fragments by less than about 2 non-consecutive nucleotides or base pairs. In another example, X may comprise a nucleotide sequence that differs from a nucleotide sequence based on or derived from one or more antibodies and/or antibody fragments by less than about 5 nucleotides or base pairs, wherein 2 of the nucleotides or base pairs are consecutive and 2 of the nucleotides or base pairs are non-consecutive.

The peptide sequence of X may differ from the peptide sequence of the antibody or antibody fragment that it is based on and/or derived from by one or more amino acid substitutions. The peptide sequence of X may differ from the peptide sequence of the antibody or antibody fragment that it is based on and/or derived from by two or more amino acid substitutions. The peptide sequence of X may differ from the peptide sequence of the antibody or antibody fragment that it is based on and/or derived from by three or more amino acid substitutions. The peptide sequence of X may differ from the peptide sequence of the antibody or antibody fragment that it is based on and/or derived from by four or more amino acid substitutions. The peptide sequence of X may differ from the peptide sequence of the antibody or antibody fragment that it is based on and/or derived from by five or more amino acid substitutions. The peptide sequence of X may differ from the peptide sequence of the antibody or antibody fragment that it is based on and/or derived from by six or more amino acid substitutions. The peptide sequence of X may differ from the peptide sequence of the antibody or antibody fragment that it is based on and/or derived from by 1, 2, 3, 4, 5, 6, 7, 8, 9, 10, 12, 14, 15, 17, 20, 25 or more amino acid substitutions.

The nucleotide sequence of X may differ from the nucleotide sequence of the antibody or antibody fragment that it is based on and/or derived from by one or more nucleotide and/or base pair substitutions. The nucleotide sequence of X may differ from the nucleotide sequence of the antibody or antibody fragment that it is based on and/or derived from by two or more nucleotide and/or base pair substitutions. The nucleotide sequence of X may differ from the nucleotide sequence of the antibody or antibody fragment that it is based on and/or derived from by three or more nucleotide and/or base pair substitutions. The nucleotide sequence of X may differ from the nucleotide sequence of the antibody or antibody fragment that it is based on and/or derived from by four or more nucleotide and/or base pair substitutions. The nucleotide sequence of X may differ from the nucleotide sequence of the antibody or antibody fragment that it is based on and/or derived from by five or more nucleotide and/or base pair substitutions. The nucleotide sequence of X may differ from the nucleotide sequence of the antibody or antibody fragment that it is based on and/or derived from by six or more nucleotide and/or base pair substitutions. The nucleotide sequence of X may differ from the nucleotide sequence of the antibody or antibody fragment that it is based on and/or derived from by nine or more nucleotide and/or base pair substitutions. The nucleotide sequence of X may differ from the nucleotide sequence of the antibody or antibody fragment that it is based on and/or derived from by twelve or more nucleotide and/or base pair substitutions. The nucleotide sequence of X may differ from the nucleotide sequence of the antibody or antibody fragment that it is based on and/or derived from by fifteen or more nucleotide and/or base pair substitutions. The nucleotide sequence of X may differ from the nucleotide sequence of the antibody or antibody fragment that it is based on and/or derived from by eighteen or more nucleotide and/or base pair substitutions. The nucleotide sequence of X may differ from the nucleotide sequence of the antibody or antibody fragment that it is based on and/or derived from by 20, 22, 24, 25, 27, 30 or more nucleotide and/or base pair substitutions.

X may comprise one or more unnatural amino acids. X may comprise two or more unnatural amino acids. X may comprise three or more unnatural amino acids. X may comprise four or more unnatural amino acids. X may comprise 5, 6, 7, 8, 9, 10 or more unnatural amino acids. X may comprise one or more antibodies or antibody fragments, wherein one or more of the antibodies or antibody fragments comprises one or more unnatural amino acids. X may comprise one or more unnatural amino acids, wherein one amino acid replaces Lysine 138 of a heavy chain of the antibody or antibody fragment. X may comprise one or more unnatural amino acids distal to the antigen binding site of the antibody or antibody fragment. X may comprise one or more unnatural amino acids near the antigen binding site of the antibody or antibody fragment. X may comprise one or more unnatural amino acids in the antigen binding site of the antibody or antibody fragment.

X may be coupled to one or more linkers. X may be linked to Y by one or more linkers. X may be linked to Y by two or more linkers. X may be linked to Y by three or more linkers.

IB. Targeting Agents of Y

Y may comprise a targeting agent. Y may not be an antibody or an antibody fragment. Y may be selected from a small molecule, a cell-targeting molecule, a ligand, a protein, a peptide, a peptoid, a DNA aptamer, a peptide nucleic acid (PNA), a vitamin, a substrate or a substrate analog. The peptide may comprise a cyclic a peptide or a linear peptide. Y may comprise a ligand. Y may comprise at least a portion of a ligand. The ligand may be a chemical ligand. The ligand may be a hormonal ligand. The ligand may be a peptide ligand. The ligand may be a protein ligand. Y may be chemically modified. Y may be derivatized (e.g. with a naturally occurring protein or peptide). Y may be a small molecule. Y may be sufficiently small to penetrate a tissue. Y may be sufficiently small to penetrate a tumor. Y may comprise a small molecule, thus producing a small molecule antibody conjugate (SMAC) when conjugated to X. The SMAC may be sufficiently small to penetrate a tissue. The SMAC may be sufficiently small to penetrate a tumor. The small molecule may be amenable to extensive chemical modification. The small molecule may be derivatized easily with other molecules, including proteins.

The targeting agent may bind a target cell. The targeting agent may bind a cell surface protein or a cell surface marker on a cell. The targeting agent may bind a protein, a peptide, or a biomolecule, wherein the protein, the peptide or the biomolecule is not bound to a cell. The protein, peptide or biomolecule may be circulating in a bloodstream. The protein, peptide or biomolecule may be a component of extracellular matrix. The protein may be an enzyme. The enzyme may have enzymatic activity. A biomolecule, by non-limiting example, may be selected from a fiber, a biopolymer (e.g. collagen), a glycan, a proteoglycan, a lipid, a sterol, a carbohydrate, a nucleic acid and a cellular fragment.

The targeting agent of the targeting agent antibody conjugate may have a therapeutic effect because it brings a cytotoxic effector cell in proximity of a target cell. The therapeutic effect on the intended indication of the targeting agent antibody construct may be due to the targeting agent antibody conjugate recruiting a cytotoxic effector cell to the target cell. The therapeutic effect on the intended indication of the targeting agent antibody construct may be wholly due to the targeting agent antibody conjugate recruiting a cytotoxic effector cell to the target cell. The therapeutic effect on the intended indication of the targeting agent antibody construct may be predominantly due to the targeting agent antibody conjugate recruiting a cytotoxic effector cell to the target cell.

The therapeutic effect of the intended indication may be due to the targeting agent antibody conjugate recruiting a protein, peptide or biomolecule to the target cell. The therapeutic effect of the intended indication may wholly due to the targeting agent antibody conjugate recruiting a protein, peptide or biomolecule to the target cell. The therapeutic effect on the intended indication may be at least partially due to the targeting agent antibody conjugate recruiting a protein, peptide or biomolecule to the target cell.

The targeting agent alone may not have any therapeutic effect. The targeting agent alone may not have any therapeutic effect towards an intended indication of the targeting agent antibody conjugate. The targeting agent may not have a therapeutic effect towards the intended indication of the targeting agent antibody conjugate without being conjugated to the anti-CD3 antibody or antibody fragment. The dose of the therapeutic agent when administered as part of the targeting agent antibody conjugate to provide a therapeutic effect may not have a therapeutic effect when the therapeutic agent is administered alone at that dose. The targeting agent of the targeting agent antibody conjugate may not be intended to have any therapeutic effect besides recruiting the cytotoxic effector cell to the target cell. The targeting agent of the targeting agent antibody conjugate may have a therapeutic effect on the target cell, wherein the therapeutic effect is negligible relative to the therapeutic effect of recruiting the cytotoxic effector cell, protein, peptide or biomolecule to the target cell. The targeting agent of the targeting agent antibody conjugate may have a therapeutic effect on the target cell, wherein the therapeutic effect is less than the therapeutic effect of recruiting the cytotoxic effector cell, protein, peptide or biomolecule to the target cell. The binding of the targeting agent to the target cell may induce an unintentional response from the target cell. The binding of the targeting agent to the target cell may induce an unintentional therapeutic effect in addition to the therapeutic effect of recruiting the cytotoxic effector cell, protein, peptide or biomolecule to the target cell.

The targeting agent may possess a mass between about 0.1 kDa and about 60 kDa. The targeting agent may posses a mass between about 0.1 kDa and about 55 kDa. The targeting agent may posses a mass between about 0.1 kDa and about 50 kDa. The targeting agent may posses a mass between about 0.3 kDa and about 50 kDa. The targeting agent may posses a mass of about 0.1 kDa, about 0.2 kDa, about 0.3 kDa, about 0.4 kDa, about 0.5 kDa, about 0.6 kDa, about 0.7 kDa, about 0.8 kDa, about 0.9 kDa or about 1 kDa. The targeting agent may comprise a mass of about 20 kDa, about 25 kDa, about 30 kDa, about 35 kDa, about 40 kDa, about 45 kDa, about 50 kDa or about 55 kDa.

The small molecule targeting agent may comprise a prostate specific membrane antigen (PSMA) inhibitor. PSMA is also known as glutamate carboxypeptidase II and N-acetyl-L-aspartyl-L-glutamate peptidase I. The PSMA inhibitor may be 2-[3-(1,3-dicarboxypropy)ureidol]pentanedioic acid (DUPA) or a derivative thereof. The targeting agent antibody conjugate may comprise an anti-CD3 Fab and two DUPAs, wherein a first of the two DUPAs is linked by a first linker to the anti-CD3 Fab and a second of the two DUPAs is linked by a second linker to the anti-CD3 Fab.

Y may comprise a ligand that binds to at least a portion of a receptor on a cell. Y may comprise a ligand that binds to at least a portion of a co-receptor on a cell. Y may comprise a ligand that binds to at least a portion of an antigen or cell surface marker on a cell. The cell may be a hematopoietic cell. The hematopoietic cell may be a myeloid cell. The myeloid cell may be an erythrocyte, thrombocyte, neutrophil, monocyte, macrophage, eosinophil, basophil, or mast cell. The hematopoietic cell may be a lymphoid cell. The lymphoid cell may be a B-cell, T-cell, or NK-cell. The hematopoietic cell may be a leukocyte. The hematopoietic cell may be a lymphocyte. The cell may be a prostate cell. The cell may be a breast cell. The cell may be a liver cell, kidney cell, lung cell, cardiac cell, muscle cell, nerve cell, neuron, brain cell, epithelial cell, esophageal cell. The cell may be a tumor cell. The cell may be a non-tumor cell. The cell may be an inflammatory cell. The inflammatory cell may be a macrophage. The macrophage may be pro-inflammatory. The macrophage may be anti-inflammatory. The cell may produce a cytokine. The cell may produce a chemokine.

The cell may be a cancer cell. The cancer cell may be derived from a prostate gland, a breast, an ovary, a cervix, a lung, a kidney, a colon, a rectum, a brain, a thyroid gland, a pancreas, a gastrointestinal tract or a stomach. The cancer cell may be derived from an epithelial tissue, a stromal tissue or an endometrial tissue.

Y may comprise a ligand that binds to a receptor on a cell. The receptor may be a G-protein coupled receptor (GPCR), a tyrosine kinase receptor, a cytokine receptor or an integrin. The receptor may be a growth factor receptor. The growth factor receptor may be an epidermal growth factor receptor (EGFR), platelet derived growth factor receptor (PDGFR) or fibroblast growth factor receptor (FGFR). The EGFR may be EGFR1. The EGFR may be Her2. The receptor may be a cholecystokinin B receptor. The receptor may be a gonadotropin-releasing hormone receptor. The receptor may be a somatostatin receptor. The receptor may be somatostatin receptor 2. The receptor may be a gastrin-releasing peptide receptor. The receptor may be a neurokinin receptor. The may be neurokinin 1 receptor, also known as tachykinin 1 receptor. The receptor may be a melanocortin receptor. The receptor may be melanocortin 1 receptor. The receptor may be a neurotensin receptor. The receptor may be a neuropeptide Y receptor. The neuropeptide Y receptor (NPYR) may be selected from NPY1R, NPY2R, PPYR1 and NPY5R.

Y may bind an antigen or cell surface marker on a cell. The antigen or cell surface marker may comprise cluster of differentiation protein. The differentiation protein may comprise CD38.

Y may bind an adhesion molecule. The adhesion molecule may be CLL-1.

Y may bind an integrin. The integrin may be an av integrin. The integrin may be avB3 integrin.

Y may bind a prostate specific membrane antigen (PSMA). Y may comprise DUPA. Y may consist essentially of DUPA.

Y may be a G protein coupled receptor agonist. Y may be a G protein coupled receptor antagonist. Y may be a cholecystokinin (CCK) receptor agonist. Y may be a cholecystokinin (CCK) receptor antagonist. Y may be a cholecystokinin A receptor agonist. Y may be a cholecystokinin A receptor antagonist. Y may be a cholecystokinin B receptor agonist. Y may be a cholecystokinin B receptor antagonist. The cholecystokinin B receptor antagonist may be pentagastrin.

Y may comprise a hormone. Y may comprise a hormonal ligand. Y may comprise a hormone receptor agonist. Y may comprise a hormone receptor antagonist. Y may comprise gonadotropin releasing hormone. Y may be a melanocortin receptor ligand. Y may comprise α-melanocyte-stimulating hormone, afamelanotide, BMS-470,539, bremelanotide, melanotan II or agouti signaling peptide.

Y comprise a neuropeptide. Y may comprise a tachykinin. Y may comprise a neurokinin receptor ligand. Y may comprise substance P. Y may comprise a neurokinin. The neurokinin may be neurokinin A. The neuropeptide may comprise neuropeptide Y. Y may comprise a neuropeptide Y receptor agonist or a neuropeptide Y receptor antagonist. The neuropeptide Y receptor agonist may be selected from peptide YY and pancreatic polypeptide. The neuropeptide Y receptor antagonist may be selected from BIBP-3226, Lu AA-33810, BIIE-0246 and UR-AK49. The neuropeptide may comprise a neurotensin receptor ligand. The neurotensin receptor ligand may be a neurotensin receptor agonist. The neurotensin receptor agonist may be selected from beta-lactotensin, JMV-449, neurotensin, neuromedin N, PD-149,163 and non-peptide partial agonists derived from SR-48692. The neurotensin receptor ligand may comprise a neurotensin receptor antagonist. The neurotensin receptor antagonist may be selected from Levocabastine ($NTS_2$ selective, also $H_1$ histamine antagonist), SR-48692 ($NTS_1$ selective), or SR-142,948.

Y may comprise a peptide hormone. The peptide hormone may be a somatostatin, or growth hormone inhibiting hormone or somatotropin release-inhibiting factor or somatotropin release-inhibiting hormone. Y may comprise a somatostatin analog. Y may comprise octreotide. Y may comprise octreotate. The octreotate may be DOTA labeled for $^{68}$Ga PET imaging and $^{177}$Lu radio therapy.

Y may comprise a peptide. Y may comprise a small peptide. Y may comprise a small peptide ligand. Y may comprise a cyclic peptide. Y may comprise an Arginine-Glycine-Aspartatic Acid (RGD) sequence. Y may comprise an RGD-containing ligand for an integrin. Y may comprise cRGD. Y may comprise cilengitide. The small peptide may comprise a ligand for a gastrin-releasing peptide receptor. The small peptide may comprise a ligand for a bombesin receptor selected from BBR1, BBR2 and BBR3. The ligand for a gastrin-releasing peptide receptor may comprise bombesin, neuromedin B, gastrin-releasing peptide. The ligand for the gastrin-releasing peptide receptor may comprise bombesin.

The targeting agent antibody conjugate may comprise a radiolabeled isotope. The targeting agent antibody conjugate may comprise a chelating agent for a radiolabeled isotope. The targeting agent may comprise a radiolabeled isotope. The targeting agent may comprise a chelating agent for a radiolabeled isotope. Y may comprise a chelating agent for a radiolabeled isotope. Y may comprise a (1,4,7,10-tetraaza-cyclododecane-1,4,7,10-tetraacetic acid) DOTA. The radiolabeled isotope may comprise Yttrium. The radiolabeled isotope may be $^{90}$Y. DOTA may comprise DOTATOC. DOTA may comprise DOTA-TATE.

Y may comprise at least a portion of a sequence selected from SEQ ID NOs: 3-40. Y may comprise a sequence that is at least 50% identical to a sequence selected from SEQ ID NOs: 3-40. Y may comprise a sequence that is at least 60% identical to a sequence selected from SEQ ID NOs: 3-40. Y may comprise a sequence that is at least 70% identical to a sequence selected from SEQ ID NOs: 3-40. Y may comprise a sequence that is at least 80% identical to a sequence selected from SEQ ID NOs: 3-40. Y may comprise a sequence that is at least 50% identical to a sequence selected from SEQ ID NOs: 3-40. Y may comprise a sequence that is at least 85% identical to a sequence selected from SEQ ID NOs: 3-40. Y may comprise a sequence that is at least 90% identical to a sequence selected from SEQ ID NOs: 3-40. Y may comprise a sequence that is at least 95% identical to a sequence selected from SEQ ID NOs: 3-40. Y may comprise a sequence that is at least 97% identical to a sequence selected from SEQ ID NOs: 3-40.

Y may comprise a sequence comprising five or more amino acids based on or derived from a sequence selected from SEQ ID NOs: 3-40. Y may comprise a sequence comprising 6, 7, 8, 9, 10 or more amino acids based on or derived from a sequence selected from SEQ ID NOs: 3-40. Y may comprise a sequence comprising 15, 16, 17, 18, 19, 20 or more amino acids based on or derived from a sequence selected from SEQ ID NOs: 3-40. Y may comprise a sequence comprising 25, 30, 35, 40, 45, 50 or more amino acids based on or derived from a sequence selected from SEQ ID NOs: 3-40. Y may comprise a sequence comprising 55, 60, 65, 70, 75, 80, 85, 90, 95, 100 or more amino acids based on or derived from a sequence selected from SEQ ID NOs: 3-40. The amino acids may be consecutive. The amino acids may be non-consecutive.

Y may comprise a peptide sequence that differs from a peptide sequence based on or derived from one or more targeting agents by less than or equal to about 20, 17, 15, 12, 10, 8, 6, 5, 4 or fewer amino acids. Y may comprise a peptide sequence that differs from a peptide sequence based on or derived from one or more targeting agents by less than or equal to 4 or fewer amino acids. Y may comprise a peptide sequence that differs from a peptide sequence based on or derived from one or more targeting agents by less than or equal to about 3 or fewer amino acids. Y may comprise a peptide sequence that differs from a peptide sequence based on or derived from one or more targeting agents by less than or equal to about 2 or fewer amino acids. Y may comprise a peptide sequence that differs from a peptide sequence based on or derived from one or more targeting agents by less than or equal to about 1 or fewer amino acids. The amino acids may be consecutive, nonconsecutive, or a combination thereof. For example, Y may comprise a peptide sequence that differs from a peptide sequence based on or derived from one or more targeting agents by less than about 3 consecutive amino acids. Alternatively, or additionally, Y may comprise a peptide sequence that differs from a peptide sequence based on or derived from one or more targeting agents by less than about 2 non-consecutive amino acids. In another example, Y may comprise a peptide sequence that differs from a peptide sequence based on or derived from one or more targeting agents by less than about 5 amino acids, wherein 2 of the amino acids are consecutive and 2 of the amino acids are non-consecutive.

Y may comprise a protein or peptide based on a nucleotide sequence that differs from a nucleotide sequence based on or derived from one or more targeting agents by less than or equal to about 30, 25, 20, 19, 18, 17, 16, 15, 14, 13, 12, 11, 10, 9, 8, 7, 6, 5, 4 or fewer nucleotides or base pairs. Y may comprise a protein or peptide based on a nucleotide sequence that differs from a nucleotide sequence based on or derived from one or more targeting agents by less than or equal to about 15 or fewer nucleotides or base pairs. Y may comprise protein or peptide based on a nucleotide sequence that differs from a nucleotide sequence based on or derived from one or more targeting agents by less than or equal to about 12 or fewer nucleotides or base pairs. Y may comprise a protein or peptide based on a nucleotide sequence that differs from a nucleotide sequence based on or derived from one or more targeting agents by less than or equal to about 9 or fewer nucleotides or base pairs. Y may comprise a protein or peptide based on a nucleotide sequence that differs from a nucleotide sequence based on or derived from one or more targeting agents by less than or equal to about 6 or fewer nucleotides or base pairs. Y may comprise a protein or peptide based on a nucleotide sequence that differs from a nucleotide sequence based on or derived from one or more targeting agents by less than or equal to about 4 or fewer nucleotides or base pairs. Y may comprise a protein or peptide based on a nucleotide sequence that differs from a nucleotide sequence based on or derived from one or more targeting agents by less than or equal to about 3 or fewer nucleotides or base pairs. Y may comprise a protein or peptide based on a nucleotide sequence that differs from a nucleotide sequence based on or derived from one or more targeting agents by less than or equal to about 2 or fewer nucleotides or base pairs. Y may comprise a protein or peptide based on a nucleotide sequence that differs from a nucleotide sequence based on or derived from one or more targeting agents by less than or equal to about 1 or fewer nucleotides or base pairs. The nucleotides or base pairs may be consecutive, nonconsecutive, or a combination thereof. For example, Y may comprise a protein or peptide based on a nucleotide sequence that differs from a nucleotide sequence based on or derived from one or more targeting agents by less than about 3 consecutive nucleotides or base pairs. Alternatively, or additionally, Y may comprise a protein or peptide based on a nucleotide sequence that differs from a nucleotide sequence based on or derived from one or more targeting agents by less than about 2 non-consecutive nucleotides or base pairs. In another example, Y may comprise a protein or peptide based on a nucleotide sequence that differs from a nucleotide sequence based on or derived from one or more targeting agents by less than about 5 nucleotides or base pairs, wherein 2 of the nucleotides or base pairs are consecutive and 2 of the nucleotides or base pairs are non-consecutive.

The peptide sequence of Y may differ from the peptide sequence of the targeting agents that it is based on and/or derived from by one or more amino acid substitutions. The peptide sequence of Y may differ from the peptide sequence of the targeting agents that it is based on and/or derived from by two or more amino acid substitutions. The peptide sequence of Y may differ from the peptide sequence of the targeting agents that it is based on and/or derived from by three or more amino acid substitutions. The peptide sequence of Y may differ from the peptide sequence of the targeting agents that it is based on and/or derived from by four or more amino acid substitutions. The peptide sequence of Y may differ from the peptide sequence of the targeting agents that it is based on and/or derived from by five or more amino acid substitutions. The peptide sequence of Y may differ from the peptide sequence of the targeting agents that it is based on and/or derived from by six or more amino acid substitutions. The peptide sequence of Y may differ from the peptide sequence of the targeting agents that it is based on and/or derived from by 1, 2, 3, 4, 5, 6, 7, 8, 9, 10, 12, 14, 15, 17, 20, 25 or more amino acid substitutions.

The nucleotide sequence of Y may differ from the nucleotide sequence of the targeting agent that it is based on and/or derived from by one or more nucleotide and/or base pair substitutions. The nucleotide sequence of Y may differ from the nucleotide sequence of the targeting agent that it is based on and/or derived from by two or more nucleotide and/or base pair substitutions. The nucleotide sequence of Y may differ from the nucleotide sequence of the targeting agent that it is based on and/or derived from by three or more nucleotide and/or base pair substitutions. The nucleotide sequence of Y may differ from the nucleotide sequence of the targeting agent that it is based on and/or derived from by four or more nucleotide and/or base pair substitutions. The nucleotide sequence of Y may differ from the nucleotide sequence of the targeting agent that it is based on and/or derived from by five or more nucleotide and/or base pair substitutions. The nucleotide sequence of Y may differ from the nucleotide sequence of the targeting agent that it is based on and/or derived from by six or more nucleotide and/or base pair substitutions. The nucleotide sequence of Y may differ from the nucleotide sequence of the targeting agent that it is based on and/or derived from by nine or more nucleotide and/or base pair substitutions. The nucleotide sequence of Y may differ from the nucleotide sequence of the targeting agent that it is based on and/or derived from by twelve or more nucleotide and/or base pair substitutions. The nucleotide sequence of Y may differ from the nucleotide sequence of the targeting agent that it is based on and/or derived from by fifteen or more nucleotide and/or base pair substitutions. The nucleotide sequence of Y may differ from the nucleotide sequence of the targeting agent that it is based on and/or derived from by eighteen or more nucleotide and/or base pair substitutions. The nucleotide sequence of Y may differ from the nucleotide sequence of the targeting agent that it is based on and/or derived from by 20, 22, 24, 25, 27, 30 or more nucleotide and/or base pair substitutions.

Y may comprise one or more unnatural amino acids. Y may comprise two or more unnatural amino acids. Y may comprise three or more unnatural amino acids. Y may comprise four or more unnatural amino acids. Y may comprise 5, 6, 7, 8, 9, 10 or more unnatural amino acids.

Y may be coupled to one or more linkers. Y may be linked to X by one or more linkers. Y may be linked to X by two or more linkers. Y may be linked to X by three or more linkers.

The distance between X and Y may be between about 1 angstroms (Å) to about 120 angstroms (Å). The distance between X and Y may be between about 5 angstroms (Å) to about 105 angstroms (Å). The distance between X and Y may be between about 10 angstroms (Å) to about 100 angstroms (Å). The distance between X and Y may be between about 10 angstroms (Å) to about 90 angstroms (Å). The distance between X and Y may be between about 10 angstroms (Å) to about 80 angstroms (Å). The distance between X and Y may be between about 10 angstroms (Å) to about 70 angstroms (Å). The distance between X and Y may be between about 15 angstroms (Å) to about 45 angstroms (Å). The distance between X and Y may be equal to or greater than about 4, 5, 6, 7, 8, 9, 10, 11, 12, 13, 14, 15, 16, 17, 18, 19, 20, 25, 27, 30 or more angstroms. The distance between X and Y may be equal to or greater than about 10 angstroms. The distance between X and Y may be equal to or greater than about 15 angstroms. The distance between X and Y may be equal to or greater than about 20 angstroms. The distance between X and Y may be equal to or less than about 110, 100, 90, 85, 80, 75, 70, 65, 60, 55, 50, 45, 43, 42, 41, 40, 39, 38, 37, 36, 35, 34, 33, 32, 31, 30 or fewer angstroms. The distance between X and Y may be equal to or less than about 100 angstroms. The distance between X and Y may be equal to or less than about 80 angstroms. The distance between X and Y may be equal to or less than about 60 angstroms. The distance between X and Y may be equal to or less than about 40 angstroms.

II. Linkers

The targeting agent antibody conjugates disclosed herein may comprise one or more linkers (e.g., L1, L2). The targeting agent antibody conjugates disclosed herein may comprise two or more linkers. The targeting agent antibody conjugates disclosed herein may comprise three or more linkers. The targeting agent antibody conjugates disclosed herein may comprise 4, 5, 6, 7 or more linkers.

The linker may comprise a chemical bond. The linker may comprise a functional group. The linker may comprise an amino acid. The linker may comprise a peptide. The linker may comprise a polymer. The polymer may be a polyethylene glycol.

The one or more linkers may comprise one or more reactive functional groups that may react with a complementary reactive functional group on a coupling partner. The linker may be bifunctional. The bifunctional linker may be heterobifunctional. The linker may comprise ethylene glycol. The linker may be a bifunctional ethylene glycol linker.

One or more linkers may be formed by reaction of an amino acid on X with a linker already attached to Y. One or more linkers may be formed by reaction of an amino acid or another reactive functional group on Y with a linker already attached to X. One or more linkers may be formed by reaction of a linker already attached to X with another linker already attached to Y. In order to form a linker already attached to X or Y, a bifunctional linker, with two orthogonally reactive functional groups, may be coupled to X or Y, such that one remaining reactive functional group is available for subsequent coupling.

The linker may be the product of a bioorthogonal reaction, non-limiting examples of which are reviewed in Kim et al., Curr Opin Chem Bio 17:412-419 (2013). The linker may comprise an oxime, a tetrazole, a Diels Alder adduct, a hetero Diels Alder adduct, an aromatic substitution reaction product, a nucleophilic substitution reaction product, an ester, an amide, a carbamate, an ether, a thioether, or a Michael reaction product. The linker may be a cycloaddition product, a metathesis reaction product, a metal-mediated cross-coupling reaction product, a radical polymerization product, an oxidative coupling product, an acyl-transfer reaction product, or a photo click reaction product. The cycloaddition may be a Huisgen-cycloaddition. The cycloaddition may be a copper-free [3+2] Huisgen-cycloaddition. The cycloaddition may be a Diels-Alder reaction. The cycloaddition may be a hetero Diels-Alder reaction. The linker may be the product of an enzyme-mediated reaction. The linker may be a product of a transglutaminase-mediated reaction, non-limiting examples of which are described in Lin et al., J. Am. Chem. Soc. 128:4542-4543 (2006) and WO 2013/093809. The linker may comprise a disulfide bridge that connects two cysteine residues, such as ThioBridge™ technology by PolyTherics. The linker may comprise a maleimide bridge that connects two amino acid residues. The linker may comprise a maleimide bridge that connects two cysteine residues.

Each of the one or more linkers may comprise one or more ethylene glycols. Each of the one or more linkers may comprise at least one reactive functional group selected from alkoxy-amine, hydrazine, aryl/alkyl azide, alkyne, alkene, tetrazine, dichlorotriazine, tresylate, succinimidyl carbonate, benzotriazole carbonate, nitrophenyl carbonate, trichlorophenyl carbonate, carbonylimidazole, succinimidyl succinate, maleimide, vinylsulfone, haloacetamide, and disulfide. The alkene may be selected from norbornene, trans-cyclooctene, and cyclopropene. Each of the one or more linkers may comprise at least one alkoxy amine. Each of the one or more linkers may comprise at least one azide. Each of the one or more linkers may comprise at least one cyclooctyne. Each of the one or more linkers may comprise at least one tetrazine.

The linker may couple with one or more natural amino acids on X or Y. The linker may couple with one or more unnatural amino acids on X or Y. The linker may couple with an amino acid which is the product of site-specific mutagenesis. The linker may couple with a cysteine which is the product of site-specific mutagenesis. The linker (e.g., substituted maleimide) may couple with a cysteine which is the product of site-specific mutagenesis, as well as a native cysteine residue. Two linkers, each with complementary reactive functional groups, may couple with one another.

The one or more linkers may comprise a cleavable linker. The one or more linkers may comprise a non-cleavable linker. The one or more linkers may comprise a flexible linker. The one or more linkers may comprise an inflexible linker.

The ethylene glycol linker may comprise about 1, about 2, about 3, about 4, about 5, about 6, about 7, about 8, about 9, about 10, about 11, about 12, about 13, about 14, about 15, about 16, about 17, about 18, about 19 or about 20 ethylene glycol subunits. The one or more linkers may comprise a 1,4-dicarboxylic moiety. The one or more linkers may comprise a 1,3-dinitro substituted phenyl moiety. The one or more linkers may comprise The one or more linkers may comprise an alkoxy-amine (or aminooxy) group, azide group and/or cyclooctyne group at one or more termini. The one or more linkers may comprise an alkoxy-amine at one terminus and an azide group at the other terminus. The one or more linkers may comprise an alkoxy-amine at one terminus and a cyclooctyne group at the other terminus. The alkoxy-amine may form a stable oxime with a ketone group on an amino acid.

The alkoxy-amine may form a stable oxime with a ketone group on an unnatural amino acid. The ketone group may be on a p-acetyl phenylalanine (pAcF).

The one or more linkers may be coupled to X, Y, or a combination thereof. The one or more linkers may be coupled to X and/or Y to form one or more intermediates of the Formula III: L1-X, Formula IIIA: X-L1, Formula IV: L1-Y or Formula IVA: Y-L1. The one or more linkers may be coupled to X and/or Y by an oxime. The one or more linkers may be coupled to X and/or Y by a cyclooctyne, cyclopropene, arly/alkyl azides, trans-cyclooctene, norborene, tetrazine, or a combination thereof. The one or more linkers may be coupled to X and/or Y by a covalent bond, non-covalent bond, ionic bond, or a combination thereof.

The two or more linkers may be linked. The two or more linkers may be linked through one or more copper-free reactions. The two or more linkers may be linked through one or more cycloadditions. The two or more linkers may be linked through one or more Huisgen-cycloadditions. The two or more linkers may be linked through one or more copper-free [3+2] Huisgen-cycloadditions. The two or more linkers may be linked through one or more copper-containing reactions. The two or more linkers may be linked through one or more Diels Alder reactions. The two or more linkers may be linked through one or more hetero Diels Alder reactions.

Targeting agent antibody conjugates may be optimized by adjusting linker length. Linkers may be relatively short. Linkers may be relatively long. The one or more linkers may be between about 1 angstroms (Å) to about 120 angstroms (Å) in length. The one or more linkers may be between about 5 angstroms (Å) to about 105 angstroms (Å) in length. The one or more linkers may be between about 10 angstroms (Å) to about 100 angstroms (Å) in length. The one or more linkers may be between about 10 angstroms (Å) to about 90 angstroms (Å) in length. The one or more linkers may be between about 10 angstroms (Å) to about 80 angstroms (Å) in length. The one or more linkers may be between about 10 angstroms (Å) to about 70 angstroms (Å) in length. The one or more linkers may be between about 15 angstroms (Å) to about 45 angstroms (Å) in length. The one or more linkers may be equal to or greater than about 4, 5, 6, 7, 8, 9, 10, 11, 12, 13, 14, 15, 16, 17, 18, 19, 20, 25, 27, 30 or more angstroms in length. The one or more linkers may be equal to or greater than about 10 angstroms in length. The one or more linkers may be equal to or greater than about 15 angstroms in length. The one or more linkers may be equal to or greater than about 20 angstroms in length. The one or more linkers may be equal to or less than about 110, 100, 90, 85, 80, 75, 70, 65, 60, 55, 50, 45, 43, 42, 41, 40, 39, 38, 37, 36, 35, 34, 33, 32, 31, 30 or fewer angstroms in length. The one or more linkers may be equal to or less than about 100 angstroms in length. The one or more linkers may be equal to or less than about 80 angstroms in length. The one or more linkers may be equal to or less than about 60 angstroms in length. The one or more linkers may be equal to or less than about 40 angstroms in length.

The total length of the linkers may be between about 1 angstroms (Å) to about 120 angstroms (Å). The total length of the linkers may be between about 5 angstroms (Å) to about 105 angstroms (Å). The total length of the linkers may be between about 10 angstroms (Å) to about 100 angstroms (Å). The total length of the linkers may be between about 10 angstroms (Å) to about 90 angstroms (Å). The total length of the linkers may be between about 10 angstroms (Å) to about 80 angstroms (Å). The total length of the linkers may be between about 10 angstroms (Å) to about 70 angstroms (Å). The total length of the linkers may be between about 15 angstroms (Å) to about 45 angstroms (Å). The total length of the linkers may be equal to or greater than about 4, 5, 6, 7, 8, 9, 10, 11, 12, 13, 14, 15, 16, 17, 18, 19, 20, 25, 27, 30 or more angstroms. The total length of the linkers may be equal to or greater than about 10 angstroms. The total length of the linkers may be equal to or greater than about 15 angstroms. The total length of the linkers may be equal to or greater than about 20 angstroms. The total length of the linkers may be equal to or less than about 110, 100, 90, 85, 80, 75, 70, 65, 60, 55, 50, 45, 43, 42, 41, 40, 39, 38, 37, 36, 35, 34, 33, 32, 31, 30 or fewer angstroms. The total length of the linkers may be equal to or less than about 100 angstroms. The total length of the linkers may be equal to or less than about 80 angstroms. The total length of the linkers may be equal to or less than about 60 angstroms. The total length of the linkers may be equal to or less than about 40 angstroms. Prostate Specific Membrane Antigen Binding Small Molecule Antibody Conjugate (PSMA C)

The targeting agent antibody conjugate may comprise an anti-CD3 Fab; one or more DUPA molecules; and one or more linkers, wherein the antibody or antibody fragment is linked to the one or more targeting agents by the one or more linkers. The anti-CD3 Fab may comprise one or more unnatural amino acids. A first unnatural amino acid and a second unnatural amino acid may replace a natural amino acid of the anti-CD3 Fab. The first DUPA molecule and the second DUPA molecule may be site-specifically linked to a first unnatural amino acid and a second unnatural amino acid of the anti-CD3 Fab. The natural amino acid may be selected from alanine (Ala), lysine (Lys), serine (Ser) and/or threonine (Thr) residue of X and/or Y. The natural amino acid that is replaced may be selected from Lysine 138 (Lys 138) of a heavy chain of the anti-CD3 Fab, Alanine 123 (Ala 123) of a heavy chain of the anti-CD3 Fab, Threonine 109 (Thr 109) of a heavy chain of the anti-CD3 Fab and Serine 202 (Ser 202) of a heavy chain of the anti-CD3 Fab. The targeting agent antibody conjugate may be of Formula I: X-L1-Y or Formula IA: Y-L1-X, wherein: X comprises the anti-CD3 Fab; L1 comprises the one or more linkers; and Y comprises one or more DUPA molecules. The targeting agent antibody conjugate may comprise a compound selected from the compounds of Formula V, Formula VI, Formula VII and Formula VIII:

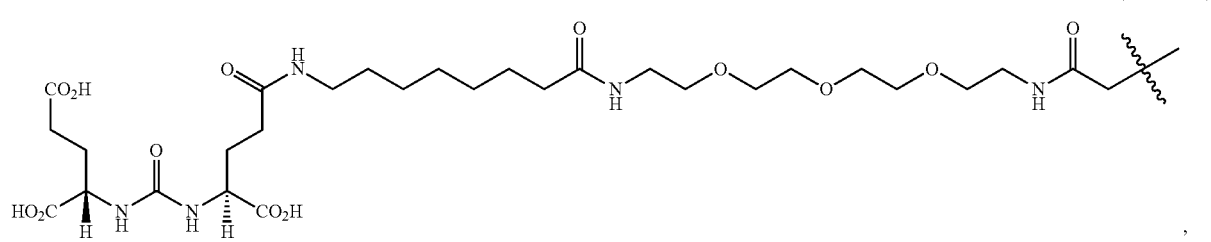

(Formula V)

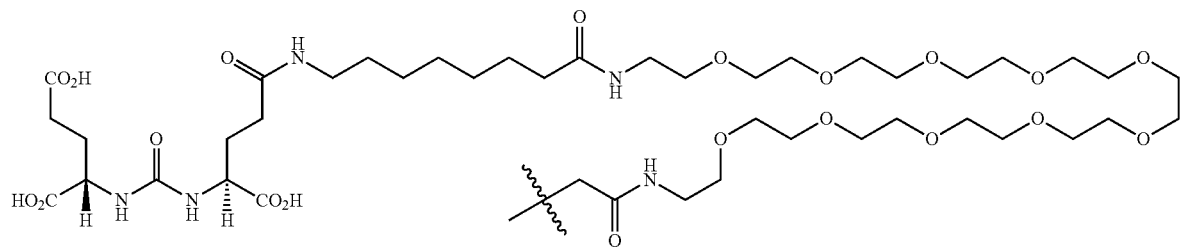
(Formula VI)
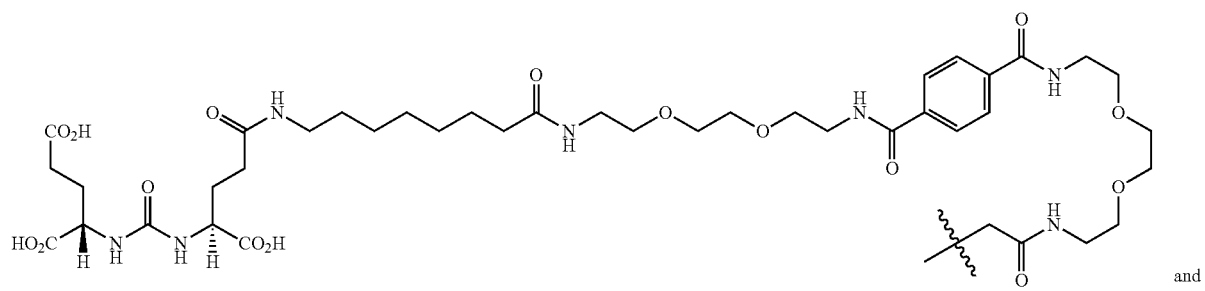
(Formula VII)
and
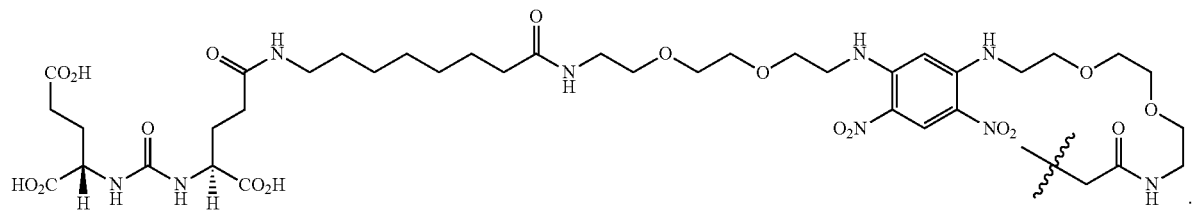
(Formula VIII)
The targeting agent antibody conjugate may comprise a compound of Formula IX:
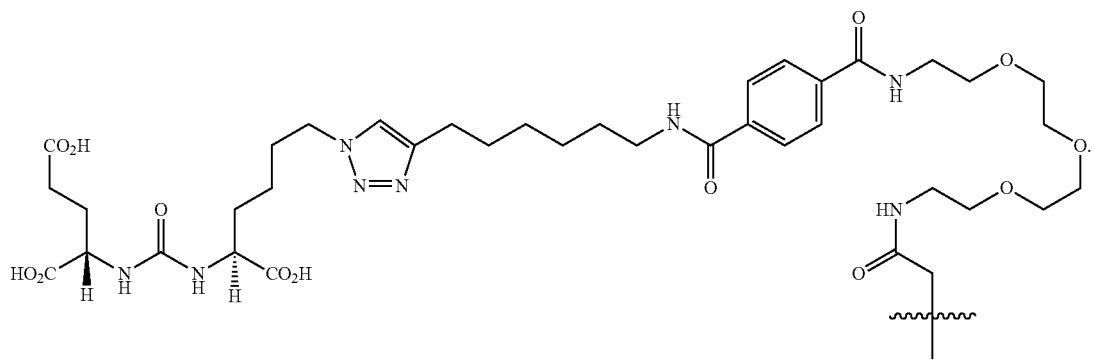
(Formula IX)

The targeting agent antibody conjugate may comprise a compound of Formula X:

(Formula X)

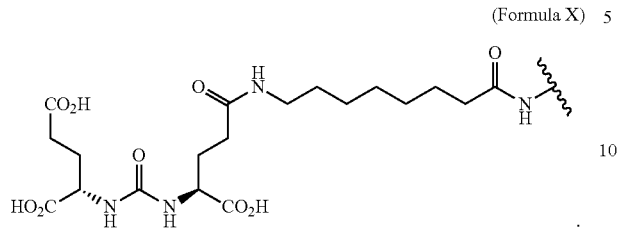

The targeting agent antibody conjugate may comprise a compound of Formula XI:

(Formula XI)

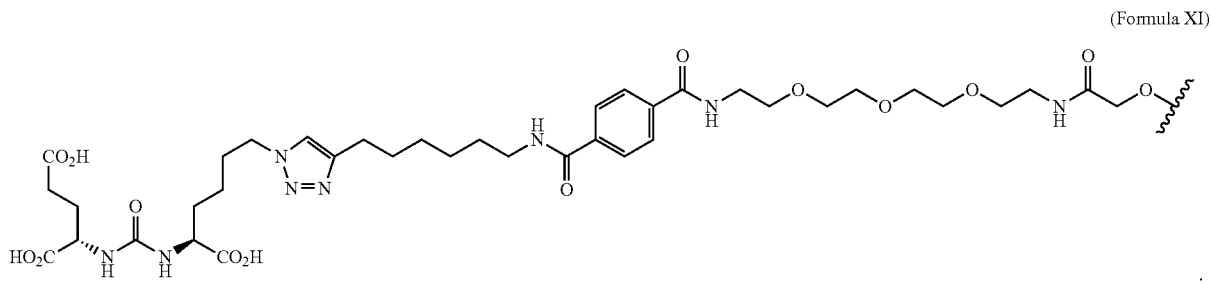 [SMILES: *OCC(=O)NCCOCCOCCOCCNC(=O)c1ccc(C(=O)NCCCCCCc2cn(CCCC[C@H](NC(=O)N[C@@H](CCC(=O)O)C(=O)O)C(=O)O)nn2)cc1 ; "."]

In another aspect, provided herein are compounds of Formula XII:

Y-L-A$^1$-L$^1$-A$^2$-L$^2$-A$^3$-L$^3$-X$^2$ (Formula XII)

wherein:

Y is a ligand of prostate specific membrane antigen (PSMA);

L is

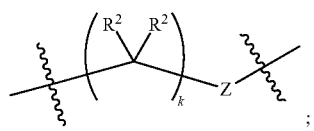

A$^1$ is selected from the group consisting of an aryl, a 5- to 6-membered heteroaryl, —C(O)—, —N(R$^1$)—, —O—, —C(O)N(R$^1$)—, —N(R$^1$)C(O)—, —S(O)$_{1,2}$N(R$^1$)—, and —N(R$^1$)S(O)$_{1,2}$—;

L$^1$ is

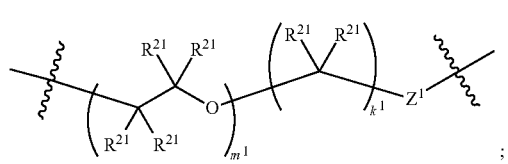

A$^2$ is selected from the group consisting of a bond, —C(O)—, —N(R$^1$)—, —O—, —C(O)N(R$^1$)—, —N(R$^1$)C(O)—, —S(O)$_{1,2}$N(R$^1$)—, and —N(R$^1$)S(O)$_{1,2}$—;

L$^2$ is

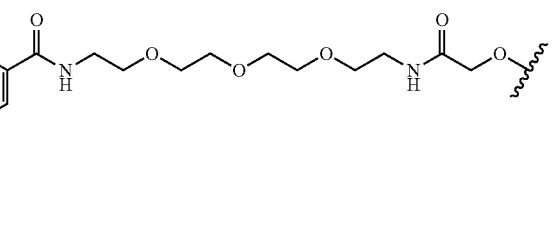

A$^3$ is a bond,

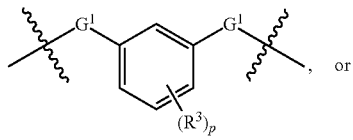

, or

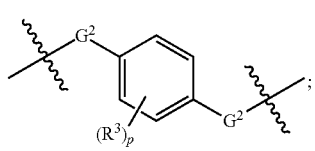

;

L$^3$ is

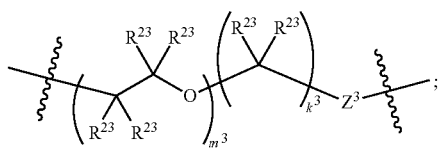

;

X$^2$ is a linker bound to a functional group that reacts with an amino acid, or a linker bound to a modified amino acid, wherein the modified amino acid is part of X, wherein X is a modified therapeutic peptide, protein, or antibody;

each R$^1$ is independently selected from H, alkyl, or haloalkyl;

each R$^2$, R$^{21}$, R$^{22}$, and R$^{23}$ is independently selected from H, halo, —OR$^1$, —CN, —SR$^1$, alkyl, cycloalkyl, haloalkyl, arylalkyl, or heteroarylalkyl;

each $R^3$ is independently selected from halo, —$OR^1$, —CN, —$SR^1$, alkyl, cycloalkyl, haloalkyl, arylalkyl, or heteroarylalkyl, —$NO_2$, and $NR^1R^1$;

each $G^1$ and $G^2$ is independently selected from the group consisting of a bond, —C(O)—, —N($R^1$)—, —O—, —C(O)N($R^1$)—, —N($R^1$)C(O)—, —S(O)$_{1,2}$N($R^1$)—, and —N($R^1$)S(O)$_{1,2}$—;

each Z, $Z^1$, $Z^2$, and $Z^3$ is independently selected from the group consisting of a bond, —O—, and —N($R^1$)—;

k, $k^1$, $k^2$ and $k^3$ are each independently selected from 0, 1, 2, 3, 4, 5, 6, 7, 8, 9, and 10;

$m^1$, $m^2$ and $m^3$ are each independently selected from 0, 1, 2, 3, 4, 5, 6, 7, 8, 9, and 10; and p is 0, 1, 2, 3 or 4;

or a stereoisomer thereof.

In some embodiments described above or below of a compound of Formula XII, the compound is of Formula XIIa:

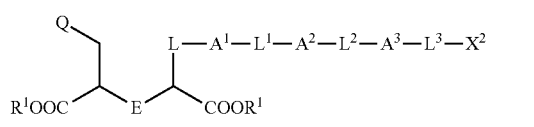

(Formula XIIa)

wherein:
Q is selected from the group consisting of:

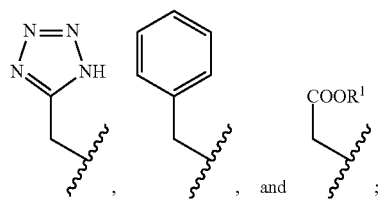

and

E is selected from the group consisting of:

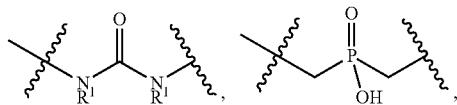

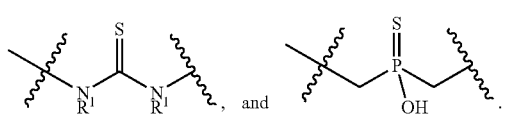

, and

In some embodiments described above or below of a compound of Formula XII, the compound is of Formula XIIb:

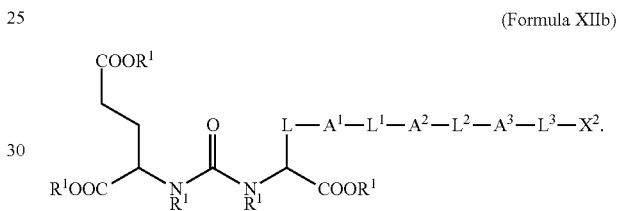

(Formula XIIb)

In further embodiments described above or below of a compound of Formula XII, the compound is of Formula XIIc:

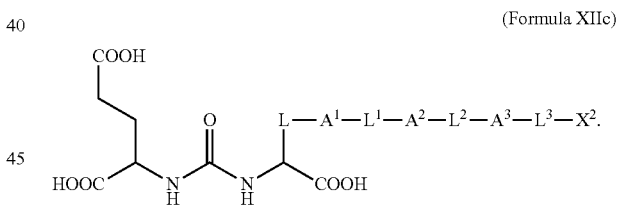

(Formula XIIc)

In some embodiments described above or below of a compound of Formula XII, the compound is of Formula XIId:

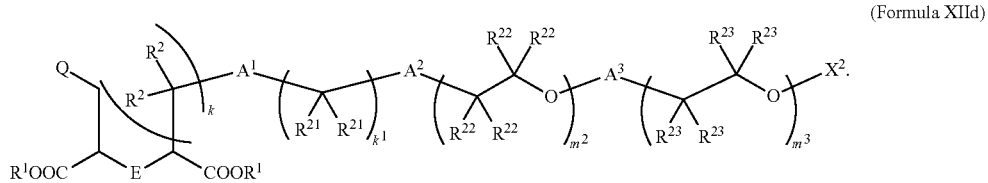

(Formula XIId)

In further embodiments described above or below of a compound of Formula XII, the compound is of Formula XIIe:

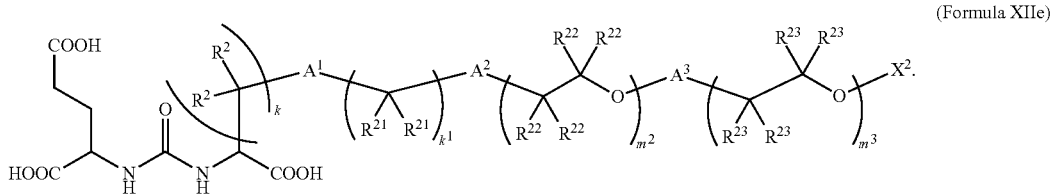
(Formula XIIe)

In still further embodiments described above or below of a compound of Formula XII, the compound is of Formula XIIf:

(Formula XIIf)

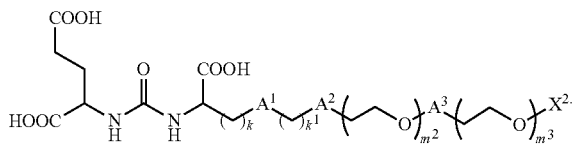

In some embodiments described above or below of a compound of Formula XII, $A^1$ is —C(O)N(H)—. In some embodiments described above or below of a compound of Formula XII, $A^1$ is

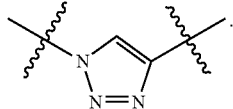 [SMILES: *c1cn(*)nn1]

In some embodiments described above or below of a compound of Formula XII, $A^3$ is

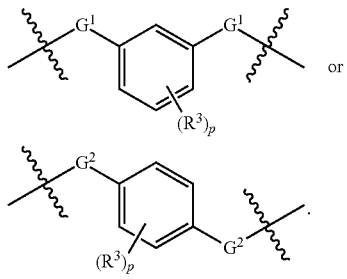
or

In further embodiments described above or below of a compound of Formula XII, $A^3$ is

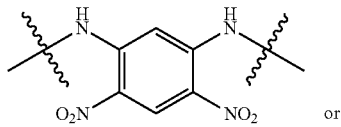
or

-continued

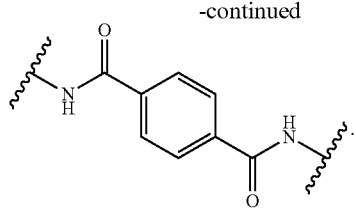

In some embodiments described above or below of a compound of Formula XII, each $R^2$, $R^{21}$, $R^{22}$, $R^{23}$, and $R^{24}$ is independently selected from H, F, —CH$_3$, or —CF$_3$. In some embodiments described above or below of a compound of Formula XII, each $R^2$, $R^{21}$, $R^{22}$, $R^{23}$, and $R^{24}$ is H.

In some embodiments described above or below of a compound of Formula XII, $X^2$ is

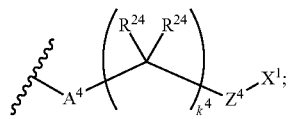

wherein:
$A^4$ is selected from the group consisting of a bond, —C(O)—, —N(R$^1$)—, —O—, —C(O)N(R$^1$)—, —N(R$^1$)C(O)—, —S(O)$_{1,2}$N(R$^1$)—, and —N(R$^1$)S(O)$_{1,2}$—;
each $R^{24}$ is independently selected from H, halo, —OR$^1$, —CN, —SR$^1$, alkyl, cycloalkyl, haloalkyl, arylalkyl, or heteroarylalkyl;
$k^4$ is selected from 0, 1, 2, 3, 4, 5, 6, 7, 8, 9, and 10;
$Z^4$ is selected from a bond, aryl, and a 5- to 6-membered heteroaryl; and
$X^1$ is —ONH$_2$,

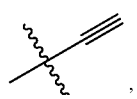 [SMILES: *C#C]

—N$_3$,

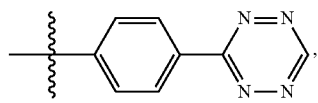 [SMILES: *c1ccc(-c2nncnn2)cc1]

—N(H)NH$_2$, or —SH.

In some embodiments described above or below of a compound of Formula XII, $X^2$ is

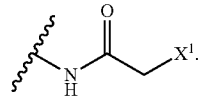

In further embodiments described above or below of a compound of Formula XII, $X^2$ is

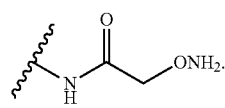

In some embodiments described above or below of a compound of Formula XII, the compound is selected from:

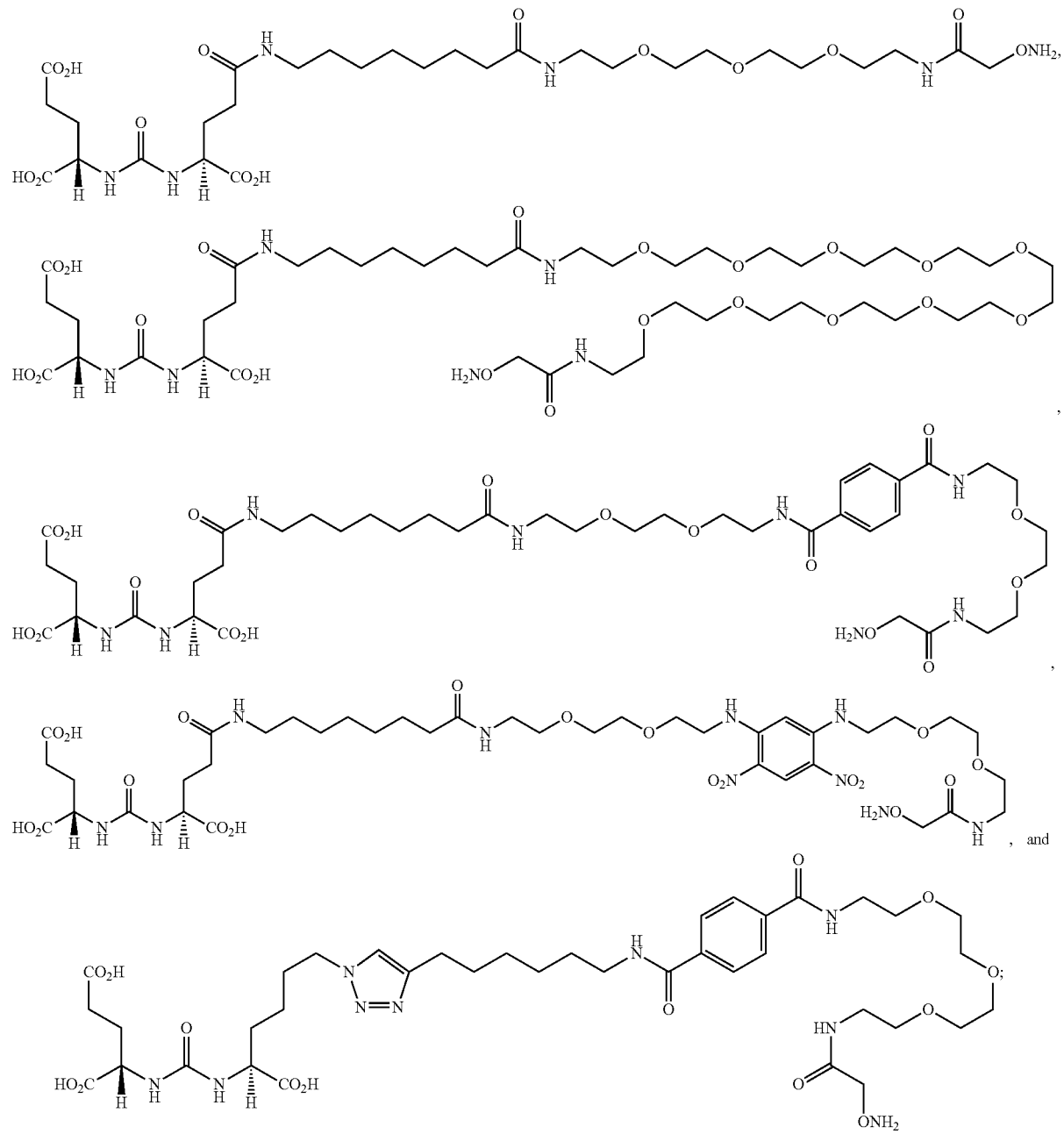

or a stereoisomer thereof.

In some embodiments described above or below of a compound of Formula XII, $X^2$ is

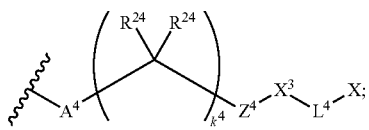

wherein:
 $A^4$ is selected from the group consisting of a bond, —C(O)—, —N(R$^1$)—, —O—, —C(O)N(R$^1$)—, —N(R$^1$)C(O)—, —S(O)$_{1,2}$N(R$^1$)—, and —N(R$^1$)S(O)$_{1,2}$—;
 each $R^{24}$ is independently selected from H, halo, —OR$^1$, —CN, —SR$^1$, alkyl, cycloalkyl, haloalkyl, arylalkyl, or heteroarylalkyl;
 $k^4$ is selected from 0, 1, 2, 3, 4, 5, 6, 7, 8, 9, and 10;
 $Z^4$ is selected from a bond, aryl, and a 5- to 6-membered heteroaryl; and

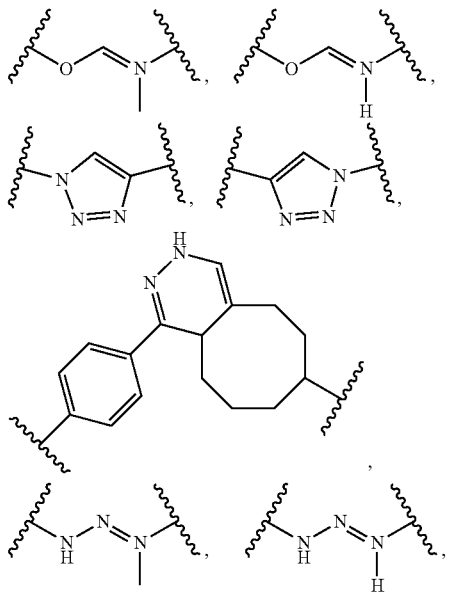

H or —S—;
 X is a modified therapeutic peptide, protein, or antibody;
 $L^4$ is a bond directly attached to a modified amino acid, or a linker bound to a modified amino acid, wherein the modified amino acid is part of X.
In some embodiments described above or below of a compound of Formula XII, the amino acid is an unnatural amino acid.

In some embodiments described above or below of a compound of Formula XII, k is 1, 2, or 3; and Z is a bond.

In some embodiments described above or below of a compound of Formula XII, $A^1$ is —C(O)N(R$^1$)—, 6-membered aryl, or 5-membered heteroaryl.

In some embodiments described above or below of a compound of Formula XII, $m^1$ is 0; $k^1$ is 6 or 7; and $Z^1$ is a bond.

In some embodiments described above or below of a compound of Formula XII, $A^2$ is a bond; $m^2$ and $k^2$ are 0; and $Z^2$ is a bond.

In some embodiments described above or below of a compound of Formula XII, $A^2$ is —C(O)N(H)—; $m^2$ is 2; $k^2$ is 2; and $Z^2$ is a bond. In some embodiments described above or below of a compound of Formula XII, $A^2$ is —C(O)N(H)—; $m^2$ is 3; $k^2$ is 2; and $Z^2$ is a bond. In some embodiments described above or below of a compound of Formula XII, $A^2$ is —C(O)N(H)—; $m^2$ is 10; $k^2$ is 2; and $Z^2$ is a bond.

In some embodiments described above or below of a compound of Formula XII, $R^3$ is —NO$_2$; and p is 2.

In some embodiments described above or below of a compound of Formula XII, each GX$^1$ and GX$^2$ are independently selected from the group consisting of —N(H)—, —C(O)N(H)—, and —N(H)C(O)—.

In some embodiments described above or below of a compound of Formula XII, $m^3$ is 3; $k^3$ is 2; and $Z^3$ is a bond. In some embodiments described above or below of a compound of Formula XII, $m^3$ is 2; $k^3$ is 2; and $Z^3$ is a bond.

In some embodiments described above or below of a compound of Formula XII, $A^3$ is a bond; $m^3$ and $k^3$ are 0; and $Z^3$ is a bond.

III. Unnatural Amino Acids

The targeting agent antibody conjugates disclosed herein may comprise one or more unnatural amino acids. As used herein, the terms "unnatural amino acid" and "non-natural amino acid" refer to non-proteinogenic amino acids that either occur naturally or are chemically synthesized. The targeting agent antibody conjugates disclosed herein may comprise X, wherein X comprises one or more unnatural amino acids. The targeting agent antibody conjugates disclosed herein may comprise Y, wherein Y comprises one or more unnatural amino acids. The antibodies disclosed herein may comprise 2, 3, 4, 5, 6, 7, 8, 9, 10 or more unnatural amino acids. The unnatural amino acid may react with the linker to create a chemical bond.

The one or more unnatural amino acids may be incorporated into an antibody (e.g., antibody of Formula I, IA, II, and IIA); intermediate (e.g., intermediate of Formula III, IIIA, IV, IVA); X antibody or antibody fragment; Y (e.g. peptide); or a combination thereof. The one or more unnatural amino acids may be site-specifically incorporated into an antibody (e.g., antibody of Formula I, IA, II, and IIA); intermediate (e.g., intermediate of Formula III, IIIA, IV, IVA); X antibody or antibody fragment; Y peptide; or a combination thereof. The one or more unnatural amino acids may be incorporated into an antibody fragment of an antibody (e.g., antibody of Formula I, IA, II, and IIA); intermediate (e.g., intermediate of Formula III, IIIA, IV, IVA); X antibody or antibody fragment; Y peptide; or a combination thereof.

The one or more unnatural amino acids may be incorporated into a heavy chain, light chain, variable region, constant region, Fab fragment of an antibody (e.g., antibody of Formula I, IA, II, and IIA); intermediate (e.g., intermediate of Formula III, IIIA, IV, IVA); X antibody or antibody fragment; Y peptide; or a combination thereof.

The one or more unnatural amino acids may be inserted between two naturally occurring amino acids in the antibody or antibody fragment. The one or more unnatural amino acids may replace one or more naturally occurring amino acids in the antibody or antibody fragment. The one or more unnatural amino acids may be incorporated at the N terminus of the antibody or antibody fragment. The one or more unnatural amino acids may be incorporated at the C terminus of the antibody or antibody fragment. The unnatural amino acid may be incorporated distal to the binding region of the antibody or antibody fragment. The unnatural amino acid may be incorporated near the binding region of the antibody or antibody fragment. The unnatural amino acid may be incorporated in the binding region of the antibody or antibody fragment.

The one or more unnatural amino acids may be inserted between two naturally occurring amino acids in the targeting agent. The one or more unnatural amino acids may replace one or more naturally occurring amino acids in the targeting agent. The one or more unnatural amino acids may be incorporated at the N terminus of the targeting agent. The one or more unnatural amino acids may be incorporated at the C terminus of the targeting agent. The unnatural amino acid may be incorporated distal to the binding region of the targeting agent. The unnatural amino acid may be incorporated near the binding region of the targeting agent. The unnatural amino acid may be incorporated in the binding region of the targeting agent.

The one or more unnatural amino acids may be encoded by a codon that does not code for one of the twenty natural amino acids. The one or more unnatural amino acids may be encoded by a nonsense codon (stop codon). The stop codon may be an amber codon. The amber codon may comprise a UAG sequence. The stop codon may be an ochre codon. The ochre codon may comprise a UAA sequence. The stop codon may be an opal or umber codon. The opal or umber codon may comprise a UGA sequence. The one or more unnatural amino acids may be encoded by a four-base codon.

The one or more unnatural amino acids may be p-acetylphenylalanine (pAcF or pAcPhe). The one or more unnatural amino acids may be selenocysteine. The one or more unnatural amino cids may be p-fluorophenylalanine (pFPhe). The one or more unnatural amino acids may be selected from the group comprising p-azidophenylalanine (pAzF), p-benzoylphenylalanine (pBpF), p-propargyloxy-phenylalanine (pPrF), p-iodophenylalanine (pIF), p-cyanophenylalanine (pCNF), p-carboxylmethylphenylalanine (pCmF), 3-(2-naphthyl)alanine (NapA), p-boronophenylalanine (pBoF), o-nitrophenylalanine (oNiF), (8-hydroxyquinolin-3-yl)alanine (HQA), selenocysteine, and (2,2'-bipyridin-5-yl)alanine (BipyA).

The one or more unnatural amino acids may be j3-amino acids (j33 and 32), homo-amino acids, proline and pyruvic acid derivatives, 3-substituted alanine derivatives, glycine derivatives, ring-substituted phenylalanine and tyrosine derivatives, linear core amino acids, diamino acids, D-amino acids, N-methyl amino acids, or a combination thereof.

Additional examples of unnatural amino acids include, but are not limited to, 1) various substituted tyrosine and phenylalanine analogues such as O-methyl-L-tyrosine, p-amino-L-phenylalanine, 3-nitro-L-tyrosine, p-nitro-L-phenylalanine, m-methoxy-L-phenylalanine and p-isopropyl-L-phenylalanine; 2) amino acids with aryl azide and benzophenone groups that may be photo-cross-linked; 3) amino acids that have unique chemical reactivity including acetyl-L-phenylalanine and m-acetyl-L-phenylalanine, O-allyl-L-tyrosine, O-(2-propynyl)-L-tyrosine, p-ethylthiocarbonyl-L-phenylalanine and p-(3-oxobutanoyl)-L-phenylalanine; 4) heavy-atom-containing amino acids for phasing in X-ray crystallography including p-iodo and p-bromo-L-phenylalanine; 5) the redox-active amino acid dihydroxy-L-phenylalanine; 6) glycosylated amino acids including b-N-acetylglucosamine-O-serine and a-N-acetylgalactosamine-O-threonine; 7) fluorescent amino acids with naphthyl, dansyl, and 7-aminocoumarin side chains; 8) photocleavable and photoisomerizable amino acids with azobenzene and nitrobenzyl Cys, Ser, and Tyr side chains; 9) the phosphotyrosine mimetic p-carboxymethyl-L-phenylalanine; 10) the glutamine homologue homoglutamine; and 11) 2-aminooctanoic acid. The unnatural amino acid may be modified to incorporate a chemical group. The unnatural amino acid may be modified to incorporate a ketone group.

The one or more unnatural amino acids may comprise at least one oxime, carbonyl, dicarbonyl, hydroxylamine group or a combination thereof. The one or more unnatural amino acids may comprise at least one carbonyl, dicarbonyl, alkoxy-amine, hydrazine, acyclic alkene, acyclic alkyne, cyclooctyne, aryl/alkyl azide, norbornene, cyclopropene, trans-cyclooctene, or tetrazine functional group or a combination thereof.

The one or more unnatural amino acids may be incorporated into X and/or Y by methods known in the art. Cell-based or cell-free systems may be used to alter the genetic sequence of X and/or Y, thereby producing X and/or Y with one or more unnatural amino acids. Auxotrophic strains may be used in place of engineered tRNA and synthetase. The one or more unnatural amino acids may be produced through selective reaction of one or more natural amino acids. The selective reaction may be mediated by one or more enzymes. In one non-limiting example, the selective reaction of one or more cysteines with formylglycine generating enzyme (FGE) may produce one or more formylglycines as described in Rabuka et al., Nature Protocols 7:1052-1067 (2012).

The one or more unnatural amino acids may take part in a chemical reaction to form a linker. The chemical reaction to form the linker may be a bioorthogonal reaction. The chemical reaction to form the linker may be click chemistry.

Additional unnatural amino acids are disclosed in Liu et al. (Annu Rev Biochem, 79:413-44, 2010), Wang et al. (Angew Chem Int Ed, 44:34-66, 2005) and PCT application numbers PCT/US2012/039472, PCT/US2012/039468, PCT/US2007/088009, PCT/US2009/058668, PCT/US2007/089142, PCT/US2007/088011, PCT/US2007/001485, PCT/US2006/049397, PCT/US2006/047822 and PCT/US2006/044682, all of which are incorporated by reference in their entireties.

IV. Targeting Agent Antibody Conjugate Compositions

Disclosed herein are compositions comprising one or more targeting agent antibody conjugates disclosed herein. The compositions may comprise a targeting agent antibody conjugate comprising (a) an antibody or antibody fragment comprising one or more unnatural amino acids; (b) one or more linkers; and (c) a targeting agent, wherein the one or more linkers links the antibody or antibody fragment to the targeting agent. The one or more linkers links the antibody or antibody fragment to the targeting agent site-specifically. The antibody or antibody fragment may comprise one or more unnatural amino acids. The targeting agent may comprise one or more unnatural amino acids. The composition may further comprise one or more pharmaceutically acceptable excipients. The composition may further comprise one or more solvents or diluents. The composition may further comprise one or more pharmaceutical carriers.

The composition may comprise a targeting agent antibody conjugate of Formula I: X-L1-Y, wherein (i) X comprises an antibody or antibody fragment; (ii) L1 comprises one or more linkers; and (iii) Y comprises a targeting agent. The antibody or antibody fragment and the targeting agent may be site-specifically linked by the one or more linkers. The antibody, antibody fragment and/or targeting agent may comprise one or more unnatural amino acids. The antibody or antibody fragment and the targeting agent may be linked at the site of the one or more unnatural amino acids. The composition may further comprise one or more pharmaceutically acceptable excipients. The composition may further comprise one or more solvents or diluents. The composition may further comprise one or more pharmaceutical carriers.

The composition may comprise a targeting agent antibody conjugate of Formula IA: Y-L1-X, wherein (i) X comprises an antibody or antibody fragment; (ii) L1 comprises one or more linkers; and (iii) Y comprises a targeting agent. The antibody or antibody fragment and the targeting agent may be site-specifically linked by the one or more linkers. The antibody, antibody fragment and/or targeting agent may comprise one or more unnatural amino acids. The antibody or antibody fragment and the targeting agent may be linked at the site of the one or more unnatural amino acids. The composition may further comprise one or more pharmaceutically acceptable excipients. The composition may further comprise one or more solvents or diluents. The composition may further comprise one or more pharmaceutical carriers.

The composition may comprise a targeting agent antibody conjugate of Formula II: X-$L^1$-$L^2$-Y, wherein (i) X comprises an antibody or antibody fragment; (ii) L1 and L2 comprise one or more linkers; and (iii) Y comprises a targeting agent. The antibody or antibody fragment and the targeting agent may be site-specifically linked by the one or more linkers. The antibody, antibody fragment and/or targeting agent may comprise one or more unnatural amino acids. The antibody or antibody fragment and the targeting agent may be linked at the site of the one or more unnatural amino acids. The composition may further comprise one or more pharmaceutically acceptable excipients. The composition may further comprise one or more solvents or diluents. The composition may further comprise one or more pharmaceutical carriers.

The composition may comprise a targeting agent antibody conjugate of Formula IIA: Y-L2-L1-X, wherein (i) X comprises an antibody or antibody fragment; (ii) L1 and L2 comprise one or more linkers; and (iii) Y comprises a targeting agent. The antibody or antibody fragment and the targeting agent may be site-specifically linked by the one or more linkers. The antibody, antibody fragment and/or targeting agent may comprise one or more unnatural amino acids. The antibody or antibody fragment and the targeting agent may be linked at the site of the one or more unnatural amino acids. The composition may further comprise one or more pharmaceutically acceptable excipients. The composition may further comprise one or more solvents or diluents. The composition may further comprise one or more pharmaceutical carriers.

The term "pharmaceutically acceptable" as used herein, refers to a material that does not abrogate the biological activity or properties of the agents described herein, and is relatively nontoxic (i.e., the toxicity of the material significantly outweighs the benefit of the material). In some instances, a pharmaceutically acceptable material may be administered to an individual without causing significant undesirable biological effects or significantly interacting in a deleterious manner with any of the components of the composition in which it is contained.

Pharmaceutical compositions herein may be formulated using one or more physiologically acceptable carriers including excipients and auxiliaries which facilitate processing of the active agents into preparations which are used pharmaceutically. Proper formulation is dependent upon the route of administration chosen. A summary of pharmaceutical compositions is found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins, 1999).

A pharmaceutical composition disclosed herein may further comprise a pharmaceutically acceptable diluent(s), excipient(s), or carrier(s). The pharmaceutical compositions may include other medicinal or pharmaceutical agents, carriers, adjuvants, such as preserving, stabilizing, wetting or emulsifying agents, solution promoters, salts for regulating the osmotic pressure, and/or buffers. In addition, the pharmaceutical compositions also contain other therapeutically valuable substances.

A pharmaceutical composition disclosed herein may be administered to a subject by any suitable administration route, including but not limited to, parenteral (intravenous, subcutaneous, intraperitoneal, intramuscular, intravascular, intrathecal, intravitreal, infusion, or local), topical, oral, or nasal administration. A suitable administration route may comprise a microneedle device.

Formulations suitable for intramuscular, subcutaneous, peritumoral, or intravenous injection may include physiologically acceptable sterile aqueous or non-aqueous solutions, dispersions, suspensions or emulsions, and sterile powders for reconstitution into sterile injectable solutions or dispersions. Examples of suitable aqueous and non-aqueous carriers, diluents, solvents, or vehicles including water, ethanol, polyols (propyleneglycol, polyethylene-glycol, glycerol, cremophor and the like), suitable mixtures thereof, vegetable oils (such as olive oil) and injectable organic esters such as ethyl oleate. Proper fluidity is maintained, for example, by the use of a coating such as lecithin, by the maintenance of the required particle size in the case of dispersions, and by the use of surfactants. Formulations suitable for subcutaneous injection also contain optional additives such as preserving, wetting, emulsifying, and dispensing agents.

For intravenous injections, an active agent may be optionally formulated in aqueous solutions, preferably in physiologically compatible buffers such as Hank's solution, Ringer's solution, or physiological saline buffer.

Parenteral injections optionally involve bolus injection or continuous infusion. Formulations for injection are optionally presented in unit dosage form, e.g., in ampoules or in multi dose containers, with an added preservative. The pharmaceutical composition described herein may be in a form suitable for parenteral injection as a sterile suspensions, solutions or emulsions in oily or aqueous vehicles, and contain formulatory agents such as suspending, stabilizing and/or dispersing agents. Pharmaceutical formulations for parenteral administration include aqueous solutions of an active agent in water soluble form. Additionally, suspensions are optionally prepared as appropriate oily injection suspensions.

The pharmaceutical composition described herein may be in unit dosage forms suitable for single administration of precise dosages. In unit dosage form, the formulation may be divided into unit doses containing appropriate quantities of an active agent disclosed herein. The unit dosage may be in the form of a package containing discrete quantities of the formulation. Non-limiting examples are packaged tablets or capsules, and powders in vials or ampoules. Aqueous suspension compositions may be packaged in single-dose non-reclosable containers. Alternatively, multiple-dose reclosable containers are used, in which case it is typical to include a preservative in the composition. By way of example only, formulations for parenteral injection are presented in unit dosage form, which include, but are not limited to ampoules, or in multi dose containers, with an added preservative.

The pharmaceutical composition may be administered at a dosage of about 0.1 mg/kg, 0.2 mg/kg, 0.3 mg/kg, 0.4 mg/kg, 0.5 mg/kg, 0.6 mg/kg, 0.7 mg/kg, 0.8 mg/kg, 0.9 mg/kg, 1 mg/kg, 1.1 mg/kg, 1.2 mg/kg, 1.3 mg/kg, 1.4 mg/kg, about 1.5 mg/kg, 1.6 mg/kg, 1.7 mg/kg, 1.8 mg/kg, 1.9 mg/kg, 2.0 mg/kg, 2.1 mg/kg, 2.2 mg/kg, 2.3 mg/kg, 2.4 mg/kg, 2.5 mg/kg, 2.6 mg/kg, 2.7 mg/kg, 2.8 mg/kg, 2.9 mg/kg or about 3.0 mg/kg. The pharmaceutical composition may be administered at a dosage of about 3.5 mg/kg, 4.0 mg/kg, 4.5 mg/kg, 5.0 mg/kg, 6.0 mg/kg, 7.0 mg/kg, 8.0 mg/kg, 9.0 mg/kg or about 10 mg/kg.

The pharmaceutical composition may be administered once daily, twice daily, three times daily or more. The pharmaceutical composition may be administered once weekly, twice weekly, three times weekly or more. The pharmaceutical composition may be administered bi-weekly. The pharmaceutical composition may be administered monthly. The pharmaceutical composition may be administered as needed.

The pharmaceutical composition may be co-administered with a therapeutic treatment. The therapeutic treatment may comprise an anti-inflammatory treatment. The anti-inflammatory treatment may comprise a steroid. The anti-inflammatory treatment may comprise a non-steroid. The therapeutic treatment may comprise an antibiotic. The therapeutic treatment may comprise anti-viral drug. The therapeutic treatment may comprise a chemotherapy. The therapeutic treatment may comprise a radiation. The therapeutic treatment may comprise a bi-specific antibody. The therapeutic treatment may comprise an additional targeting agent antibody conjugate.

V. Targeting Agent Antibody Conjugate Production Methods

Disclosed herein are methods of producing targeting agent antibody conjugate of Formula I: X-L1-Y or Formula IA: Y-L1-X. The method may comprise coupling one or more linkers to Y, wherein Y comprises the targeting agent, to produce an intermediate Y-L1 or L1-Y; and conjugating the intermediate to X, wherein X comprises at least a portion of an antibody or antibody fragment, thereby producing the targeting agent antibody conjugate. The method may further comprise conjugating the intermediate to X and/or Y site-specifically. The method may further comprise incorporating one or more unnatural amino acids into X and/or Y. Alternatively, the method may comprise coupling one or more linkers to the antibody or antibody fragment to produce a an intermediate X-L1 or L1X, and conjugating the intermediate to Y, wherein Y comprises a targeting agent, thereby producing the targeting agent antibody conjugate . . . Conjugating the intermediate X-L1 or L1X to the targeting agent may comprise forming an oxime. Forming an oxime may require acidic conditions. The method may further comprise conjugating the intermediate to X and/or Y site-specifically. The method may further comprise incorporating one or more unnatural amino acids into X and/or Y.

Further disclosed herein is a method of producing the targeting agent antibody conjugate of Formula II: X-L1-L2-Y, comprising (a) incorporating one or more unnatural amino acids into X and/or Y, wherein (i) X comprises at least a portion of an antibody or antibody fragment; and (ii) Y comprises at least a portion of a peptide or protein; (b) coupling L1 to X to produce a first intermediate of Formula III: X-L1 and coupling L2 to Y to produce a second intermediate of Formula IV: L2-Y; and (c) linking the first intermediate of Formula III to the second intermediate of Formula IV, thereby producing the targeting agent antibody conjugate of Formula II.

The method of producing the targeting agent antibody conjugate may further comprise engineering a nucleic acid encoding the antibody or antibody fragment. The method may further comprise incorporating a non-sense codon into the nucleic acid. The non-sense codon may be an amber codon. The method may further comprise incorporating an unnatural amino acid into the nucleic acid site-specifically. The method may further comprise incorporating an unnatural amino acid into the nucleic acid at the non-sense codon. The method may further comprise expressing the nucleic acid in a cell. The method may further comprise co-expressing an orthogonal tRNA/tyrosyl-tRNA synthetase pair. The orthogonal tRNA/tyrosyl-tRNA synthetase pair may incorporate the unnatural amino acid selectively in response to the non-sense codon.

VA. Incorporation of Unnatural Amino Acids

Incorporating one or more unnatural amino acids into the antibody or antibody fragment may comprise modifying one or more amino acid residues in the antibody or antibody fragment. Modifying the one or more amino acid residues in the antibody or antibody fragment may comprise mutating one or more nucleotides in the nucleotide sequence encoding the targeting agent. Mutating the one or more nucleotides in the nucleotide sequence encoding the targeting agent may comprise altering a codon encoding an amino acid to a nonsense codon.

Incorporating one or more unnatural amino acids into the antibody or antibody fragment may comprise modifying one or more amino acid residues in the antibody or antibody fragment to produce one or more amber codons in the antibody or antibody fragment.

The one or more unnatural amino acids may be incorporated into the antibody or antibody fragment in response to an amber codon. The one or more unnatural amino acids may be site-specifically incorporated into the antibody or antibody fragment.

Incorporating one or more unnatural amino acids into the antibody or antibody fragment may comprise use of one or more genetically encoded unnatural amino acids with orthogonal chemical reactivity relative to the canonical twenty amino acids to site-specifically modify the targeting agent. Incorporating the one or more unnatural amino acids may comprise use of an evolved tRNA/aminoacyl-tRNA synthetase pair to site-specifically incorporate one or more unnatural amino acids at defined sites in the targeting agent in response to one or more amber nonsense codon.

Incorporating one or more unnatural amino acids into a targeting agent may comprise modifying one or more amino acid residues in a targeting agent. Modifying the one or more amino acid residues in a targeting agent may comprise mutating one or more nucleotides in the nucleotide sequence encoding the targeting agent. Mutating the one or more nucleotides in the nucleotide sequence encoding the targeting agent may comprise altering a codon encoding an amino acid to a nonsense codon.

Incorporating one or more unnatural amino acids into a targeting agent may comprise modifying one or more amino acid residues in a targeting agent to produce one or more amber codons in a targeting agent.

The one or more unnatural amino acids may be incorporated into a targeting agent in response to an amber codon. The one or more unnatural amino acids may be site-specifically incorporated into a targeting agent.

Incorporating one or more unnatural amino acids into a targeting agent may comprise use of one or more genetically encoded unnatural amino acids with orthogonal chemical reactivity relative to the canonical twenty amino acids to site-specifically modify the targeting agent. Incorporating the one or more unnatural amino acids may comprise use of an evolved tRNA/aminoacyl-tRNA synthetase pair to site-specifically incorporate one or more unnatural amino acids at defined sites in the targeting agent in response to one or more amber nonsense codon.

Additional methods for incorporating unnatural amino acids include, but are not limited to, methods disclosed in Chatterjee et al. (A Versatile Platform for Single- and Multiple-Unnatural Amino Acid Mutagenesis in *Escherichia coli*, Biochemistry, 2013), Kazane et al. (*J Am Chem Soc*, 135(1):340-6, 2013), Kim et al. (*J Am Chem Soc*, 134(24): 9918-21, 2012), Johnson et al. (*Nat Chem Biol*, 7(11):779-86, 2011) and Hutchins et al. (*J Mol Biol*, 406(4):595-603, 2011).

VB. Coupling of Linkers

The methods disclosed herein may comprise coupling one or more linkers to one or more antibodies, antibody fragments, targeting agents, or combinations thereof to produce one or more intermediates such as an antibody-linker intermediate, an antibody fragment-linker intermediate and/or a targeting agent antibody conjugate-linker intermediate. The methods may comprise coupling a first linker to an antibody or antibody fragment to produce an antibody-linker intermediate or antibody fragment-linker intermediate. The methods may comprise coupling a linker to a targeting agent to produce a targeting agent-linker intermediate.

Coupling of the one or more linkers to the antibody, antibody fragment, or targeting agent may occur simultaneously. Coupling of the one or more linkers to the antibody, antibody fragment, or targeting molecule may occur sequentially. Coupling of the one or more linkers to the antibody, antibody fragment, or targeting molecule may occur in a single reaction volume. Coupling of the one or more linkers to the antibody, antibody fragment, or targeting molecule may occur in two or more reaction volumes.

Coupling one or more linkers to the antibody, antibody fragment and/or targeting molecule may comprise forming one or more oximes between the linker and the antibody, antibody fragment or targeting molecule. Coupling one or more linkers to the antibody, antibody fragment and/or targeting agent may comprise forming one or more stable bonds between linker and the antibody, antibody fragment or targeting agent. Coupling one or more linkers to the antibody, antibody fragment and/or targeting agent may comprise forming one or more covalent bonds between linker and the antibody, antibody fragment or targeting agent. Coupling one or more linkers to the antibody, antibody fragment and/or targeting agent may comprise forming one or more non-covalent bonds between linker and the antibody, antibody fragment or targeting agent. Coupling one or more linkers to the antibody, antibody fragment and/or ligand may comprise forming one or more ionic bonds between linker and the antibody, antibody fragment or targeting agent.

Coupling one or more linkers to the antibody or antibody fragment may comprise site specifically coupling one or more linkers to the antibody or antibody fragment. Site-specific coupling may comprise linking the one or more linkers to the unnatural amino acid of the antibody or antibody fragment. Linking the one or more linkers to the unnatural amino acid of the antibody or antibody fragment may comprise formation of an oxime. Linking the one or more linkers to the unnatural amino acid of the antibody or antibody fragment may comprise, by way of non-limiting example, reacting a hydroxylamine of the one or more linkers with an aldehyde or ketone of a amino acid. The amino acid may be an unnatural amino acid.

VC. Linking Antibodies, Antibody Fragments, and/or Targeting Agents

The methods may comprise linking the antibody, antibody fragment, targeting agent or intermediates thereof to produce a targeting agent antibody conjugate comprising (a) an antibody or antibody fragment; (b) one or more linkers; and (c) a targeting agent, wherein the one or more linkers link the first antibody or antibody fragment to the targeting agent. The method may further comprise conjugating the one or more linkers to a targeting agent to produce a targeting agent-linker intermediate (Y-L1 or L1-Y) and coupling the targeting agent-linker intermediate to the antibody or antibody fragment. The method may further comprise conjugating the one or more linkers to the antibody or antibody fragment to produce an antibody-linker intermediate or antibody fragment-linker intermediate (X-L1 or L1-X) and coupling the antibody-linker intermediate or antibody-fragment-linker intermediate to the targeting agent. Coupling an intermediate to an antibody, antibody fragment or targeting agent may comprise formation of an oxime. Coupling an intermediate to an antibody, antibody fragment or targeting agent may comprise formation of the oxime in an acidic solution. Coupling an intermediate to an antibody, antibody fragment or targeting agent may comprise formation of the oxime in a slightly acidic solution. Coupling an intermediate to an antibody, antibody fragment or targeting agent may comprise formation of the oxime in a slightly neutral solution. The antibody or antibody fragment may comprise an unnatural amino acid. Linking the antibody or antibody fragment to the targeting agent-linker intermediate may comprise forming an oxime between the unnatural amino acid and the targeting agent-linker intermediate. The targeting agent may comprise an unnatural amino acid. Linking the targeting agent to the antibody-linker intermediate or antibody fragment-linker intermediate may comprise forming an oxime between the unnatural amino acid and the antibody-linker intermediate or the antibody fragment-linker intermediate. The method of producing a targeting agent antibody conjugate may comprise (a) conjugating a first linker (L1) to the antibody or antibody fragment to produce an antibody-linker intermediate or antibody fragment-linker intermediate (X-L1 or L1-X); (b) conjugating a second linker (L2) to the targeting agent to produce a targeting agent-linker intermediate (Y-L2 or L2-Y); and (c) linking the two intermediates together to produce the targeting agent antibody conjugate, X-L1-L2-Y or Y-L2-L-X. Conjugating the linker to the antibody, antibody fragment or targeting agent may comprise production of an ionic bond, a covalent bond, a non-covalent bond or a combination thereof between the linker and the antibody, antibody fragment or targeting agent. Conjugating the linker to the antibody, antibody fragment or targeting agent may be performed as described in Roberts et al., Advanced Drug Delivery Reviews 54:459-476 (2002). L1 and/or L2 may comprise a linker selected from a bifunctional linker, a cleavable linker, a non-cleavable linker, an ethylene glycol linker, a bifunctional ethylene glycol linker, a flexible linker, or an inflexible linker. L1 and/or L2 may comprise a linker selected from the group comprising cyclooctyne, cyclopropene, arly/alkyl azides, trans-cyclooctene, norborene, and tetrazines. A terminus of L1 and/or a terminus of L2 may comprise an alkoxy-amine. A terminus of L1 and/or a terminus of L2 may comprise an azide or cyclooctyne group. X may be coupled to L1 by a chemical group selected from a cyclooctyne, cyclopropene, arly/alkyl azide, trans-cyclooctene, norborene, and tetrazine. Linking the antibody-linker intermediate or antibody fragment-linker intermediate (X-L$^1$ or L$^1$-X) and targeting agent-linker intermediate (Y-L2 or L2-Y) may comprise conducting one or more copper-free reactions. Linking the antibody-linker intermediate or antibody fragment-linker intermediate (X-L1 or L1-X) and targeting agent-linker intermediate (Y-L2 or L2-Y) may comprise conducting one or more copper-containing reactions. Linking the antibody-linker intermediate or antibody fragment-linker intermediate (X-L1 or L1-X) and targeting agent-linker intermediate (Y-L2 or L2-Y) may comprise one or more cycloadditions. Linking the antibody-linker intermediate or antibody fragment-linker intermediate (X-L1 or L1-X) and targeting agent-linker intermediate (Y-L2 or L2-Y) may comprise one or more Huisgen-cycloadditions. Linking the antibody-linker intermediate or antibody fragment-linker intermediate (X-L1 or L1-X) and targeting agent-linker intermediate (Y-L2 or L2-Y) may comprise one or more Diels Alder reactions. Linking the antibody-linker intermediate or antibody fragment-linker intermediate (X-L1 or L1-X) and targeting agent-linker intermediate (Y-L2 or L2-Y) may comprise one or more Hetero Diels Alder reaction.

VD. Purification of Antibodies

The methods may further comprise purifying the targeting agent antibody conjugate comprising (a) an antibody or antibody fragment comprising one or more unnatural amino acids; (b) a targeting agent; and (c) one or more linkers, wherein the one or more linkers link the antibody or antibody fragment to the targeting agent. The methods may further comprise purifying one or more intermediates of the antibody, antibody fragment or targeting agent (e.g., antibody-linker, antibody fragment-linker, or ligand-linker molecule). Purifying the antibody or intermediates may comprise removal of excess linkers, non-linked antibodies, non-linked antibody fragments or non-linked ligands. Purifying the antibody or intermediates may comprise use of one or more concentrator columns, electrophoresis, filtration, centrifugation, chromatography or a combination thereof. Chromatography may comprise size-exclusion chromatography. Additional chromatography methods include, but are not limited to, hydrophobic interaction chromatography, ion exchange chromatography, affinity chromatography, metal binding, immunoaffinity chromatography, and high performance liquid chromatography or high pressure liquid chromatography. Electrophoresis may comprise denaturing electrophoresis or non-denaturing electrophoresis.

Antibodies, antibody fragments, targeting agents or intermediates may comprise one or more tags. The linkers may comprise one or more tags. The tags may be used to purify the antibodies, antibody fragments, targeting agents or intermediates. The one or more tags may be cleaved by one or more proteases. Examples of tags include, but are not limited to, polyhistidine, FLAG, HA, c-myc, V5, chitin binding protein (CBP), maltose binding protein (MBP), and glutathione-S-transferase (GST).

The methods may further comprise lyophilization or ultracentrifugation of the antibodies, antibody fragments, targeting agents or intermediates.

The purity of the antibody or antibody fragment may be equal to or greater than 50%, 55%, 60%, 65%, 70%, 75%, 80%, 85%, 90%, 91%, 92%, 93%, 94%, 95%, 96%, 97%, 98%, 99% or more. The purity of the antibody may be equal to or greater than 85%. The purity of the antibody or antibody fragment may be equal to or greater than 90%. The purity of the antibody or antibody fragment may be equal to or greater than 95%. The purity of the antibody or antibody fragment may be equal to or greater than 97%.

The purity of the intermediate (e.g., antibody-linker, antibody fragment-linker, targeting agent-linker) may be equal to or greater than 50%, 55%, 60%, 65%, 70%, 75%, 80%, 85%, 90%, 91%, 92%, 93%, 94%, 95%, 96%, 97%, 98%, 99% or more. The purity of the intermediate may be equal to or greater than 85%. The purity of the intermediate may be equal to or greater than 90%. The purity of the intermediate may be equal to or greater than 95%. The purity of the intermediate may be equal to or greater than 97%.

The purity of the targeting agent may be equal to or greater than 50%, 55%, 60%, 65%, 70%, 75%, 80%, 85%, 90%, 91%, 92%, 93%, 94%, 95%, 96%, 97%, 98%, 99% or more. The purity of the targeting agent may be equal to or greater than 85%. The purity of the targeting agent may be equal to or greater than 90%. The purity of the targeting agent may be equal to or greater than 95%. The purity of the targeting agent may be equal to or greater than 97%.

The homogeneity of the antibody or antibody fragment may be equal to or greater than 50%, 55%, 60%, 65%, 70%, 75%, 80%, 85%, 90%, 91%, 92%, 93%, 94%, 95%, 96%, 97%, 98%, 99% or more. The homogeneity of the antibody or antibody fragment may be equal to or greater than 85%. The homogeneity of the antibody or antibody fragment may be equal to or greater than 90%. The homogeneity of the antibody or antibody fragment may be equal to or greater than 95%. The homogeneity of the antibody or antibody fragment may be equal to or greater than 97%.

The homogeneity of the intermediate (e.g., antibody-linker, antibody fragment-linker, targeting agent-linker) may be equal to or greater than 50%, 55%, 60%, 65%, 70%, 75%, 80%, 85%, 90%, 91%, 92%, 93%, 94%, 95%, 96%, 97%, 98%, 99% or more. The homogeneity of the antibody may be equal to or greater than 85%. The homogeneity of the antibody may be equal to or greater than 90%. The homogeneity of the antibody may be equal to or greater than 95%. The homogeneity of the antibody may be equal to or greater than 97%.

The homogeneity of the targeting agent may be equal to or greater than 50%, 55%, 60%, 65%, 70%, 75%, 80%, 85%, 90%, 91%, 92%, 93%, 94%, 95%, 96%, 97%, 98%, 99% or more. The homogeneity of the targeting agent may be equal to or greater than 85%. The homogeneity of the targeting agent may be equal to or greater than 90%. The homogeneity of the targeting agent may be equal to or greater than 95%. The homogeneity of the targeting agent may be equal to or greater than 97%.

VI. Cells

The targeting agent antibody conjugates disclosed herein may bind to one or more receptors, co-receptors, antigens, or cell markers on one or more cells. The targeting agent antibody conjugates disclosed herein may comprise (a) an antibody or antibody fragment and (b) a targeting agent, wherein (i) the antibody or antibody fragment binds to or interacts with a receptor, co-receptor, antigen or cell marker on a first cell; (ii) the targeting agent binds to or interacts with a receptor, co-receptor, antigen or cell marker on a second cell; or (iii) a combination of (i) and (ii), and wherein (iv) the antibody or antibody fragment comprises one or more unnatural amino acids; (v) the targeting agent comprises one or more unnatural amino acids; or (vi) a combination of (iv) and (v). The first cell may be a cytotoxic effector cell. The second cell may be a target cell. Generally, binding of the cytotoxic effector cell and the target cell to the targeting agent antibody construct brings the target cell into a proximity with the cytotoxic effector cell that is sufficiently close for an activity of the cytotoxic effector cell to have an effect on the target cell. For example, when the cytotoxic effector cell and the target cell are bound to the targeting agent antibody conjugate, the cytotoxic effector cell may release cytokines that bind to cytokine receptors on the target cell.

The cytotoxic effector cell may a cytotoxic cell. The cytotoxic cell may be a hematopoietic cell. The hematopoietic cell may be a macrophage, a neutrophil, an eosinophil, a NK cell, a B-cell, or a T-cell. The hematopoietic cell may be a T cell. The T cell may be a cytotoxic T cell. The T cell may be a natural killer T cell.

The target cell may be a cancerous cell. The target cell may be a tumor cell. The target cell may be a leukemic cell. The target cell may be a lymphomic cell. The target cell may be a metastatic cell. The target cell may be genetically modified. The target cell may comprise a genetic mutation. The genetic mutation may comprise an oncogenic mutation. The genetic mutation may be a mutation of a tumor suppressor gene. The genetic mutation may be a mutation of a protooncogene. The target cell may be an inflammatory cell. The target cell may be an infected cell. The target cell may be a pathogenic cell.

The first cell and the second cell may be the same type of cell. The first cell and the second cell may be different cell types. Alternatively, the first cell and the second cell may be the same cell. The targeting agent antibody conjugate may bind to or interact with a receptor, co-receptor, antigen or cell marker on more than two different cell types. The antibody or antibody fragment may bind to or interact with a receptor, co-receptor, antigen or cell marker on two or more different cell types. The targeting agent may bind to or interact with a receptor, co-receptor, antigen or cell marker on two or more different cell types. The different cell types may differ by their cell lineage. The different cell types may differ by their function. The different cell types may differ by the expression of one or more proteins. The different cell types may differ by their morphology. The different cell types may differ by their locations. The different cell types may differ by their genotype. The different cell types may differ by a single genetic mutation. The different cell types may differ by a more than one genetic mutation.

The one or more cells may comprise hematopoietic cells. Hematopoietic cells include, but are not limited to, basophilic myelocytes, basophils, B-cells, burst forming unit erythroid (BFU-E), burst forming unit megakaryocytes (BFU-Mk), colony forming unit basophils (CFU-Bas), colony forming unit erythroid (CFU-E), colonly forming unit eosinophils (CFU-Eo), colony forming unit granulocytes (CFU-G), colony forming unit granulocyte erythrocyte monocyte maccrophage (CFU-GEMM), colony forming unit granulocyte maccrophage (CFU-GM), colony forming unite megakaryocyte (CFU-Mk, CFU-MEG), common dendritic progenitor, common lymphoid progenitor cells, common myeloerythroid progenitors, common myeloid progenitors, common myelolymphoid progenitors, double negative 1 (DN1) cells, DN2 cells, DN3 cells, DN4 cells, double-positive cells (DP cells), eosinophilic myelocytes, eosinophils, erythrocytes, lymphoid stem cells, lymphoid-related dendritic cells, macrophages, mast cells, megakaryocytes, memory B-cells, memory cells, memory T-cells, monoblasts, monocytes, myeloblasts, myeloid stem cells, myeloid-related dendritic cells, neutrophilic myelocytes, neutrophils, natural killer cells (NK-cells), natural killer T-cells (NKT-cells), platelets, pro-B1-cells, pro-B-2-cells, pro-B-cells, proerythroblasts, promonocytes, regulatory T-cells (Tregs), T-cells, T-helper (Th) cells, Th0 cells, Th1 cells, Th2 cells, Th3 cells, Th17 cells. BFU-E or CFU-E may refer to erythroid precursor cells that may differentiate into erythrocytes. CFU-E cells may be more developed than BFU-E cells. CFU-Eo may refer to developmental type of blood-forming cells that may develop into eosinophils. CFU-G may refer to a developmental type of blood-forming cells that may be a precursor of granulocytes. CFU-GEMM may refer to a pluripotent type of precursor cell in the lineage of blood-forming cells that may differentiate into granulocytes, erythrocytes, monocytes and/or macrophages. CFU-GM may refer to a pluropotent type of precursor cell in the lineage of blood-forming cells that may differentiate into granuloctyes and/or macrophages. BFU-Mk, CFU-Mk or CFU-MEG may refer to precursor cells that may differentiate into megakaryocytes. CFU-Mk or CFU-MEG cells may be more developed than BFU-Mk cells.

The one or more cells may be from an organ or tissue. The organ may be a gland organ. The organ may be an organ of the digestive or endocrine system. The organ may be both an endocrine gland and a digestive organ. The organ may be derived from endoderm, ectoderm, primitive endoderm, or mesoderm. The organ may be an adrenal gland. In some cases, the adrenal gland comprises chromaffin cells or ganglion cells. Alternatively, the organ is an appendix, bladder, or brain. In some cases, the brain comprises neurons (e.g., nerve cells) or glial cells. Glial cells include, but are not limited to, astrocytes, oligodendrocytes, and ependymal cells. In some instances, the organ is an ear, esophagus, eye, or gallbladder. The gallbladder comprises cholecystocytes. The organ may be a kidney. The kidney may comprise a kidney glomerulus parietal cell, kidney glomerululs podocyte, kidney proximal tubule brush border cell, Loop of Henle thin segment cell, thick ascending limb cell, kidney distal tubule cell, kidney collecting ductal cell, or interstitial kidney cell. In some instances, the organ is a large intestine and the large intestine may comprise enterocytes, goblet cells, caveolated tuft cells, enteroendocrine cells, or ganglion neurons. The organ may be a liver. The liver may comprise parenchymal or non-parenchymal cells. Examples of parenchymal cells comprise hepatocytes. Non-parenchymal cells include, but are not limited to, sinusoidal endothelial cells, kupffer cells and hepatic stellate cells. In some instances, the organ is a lung, mouth, nose, parathyroid gland, pineal gland, pituitary gland, skin, small intestine, stomach, spleen, thymus, thyroid gland, trachea, uterus, or vermiform appendix. In some instances, the organ may be a heart. In some instances, the heart comprises cardiomyocytes. In some instances, the organ is a muscle (e.g., heart muscle, skeletal muscle, smooth muscle, etc.). The muscle may comprise myocytes.

In some cases, the cells are from a tissue. The tissue may be a connective tissue, epithelial tissue, muscular tissue, or nervous tissue. Alternatively, the tissue is a bone, tendon (both referred to as musculoskeletal grafts), cornea, skin, heart valve, or vein.

Connective tissue may be a fibrous tissue and is often found throughout the body. Examples of connective tissues include, but are not limited to, connective tissue, fat tissue, dense fibrous tissue, cartilage, bone, blood, and lymph. Generally, connective tissue has three main components: cells, fibers, and extracellular matrix, which may be embedded in the body fluids. Fibroblasts are often the cells responsible for the production of connective tissue. The interaction of the fibers, the extracellular matrix and the water, together, may form the pliable connective tissue as a whole. Connective tissue may make up a variety of physical structures including tendons and the connective framework of fibers in muscles, capsules and ligaments around joints, cartilage, bone, adipose tissue, blood and lymphatic tissue. Connective tissue (CT) may be classified into three subtypes: embryonic CT, proper CT, and special CT. The proper CT subtype may include dense regular CT, dense irregular CT, and loose CT. The special CT subtype may include cartilage, bone, adipose tissue, blood, hematopoietic tissue and lymphatic tissue.

Often connective tissues have distinct functions, characteristics, and compositions. The functions of connective tissue may include storage of energy, protection of organs, providing structural framework for the body, and connection of body tissues. The connective tissue may be characterized by cells that are spread through an extracellular fluid. In some instances, the connective tissue may comprise a ground substance, which is often a clear, colorless, and viscous fluid containing glycosaminoglycans and proteoglycans. The ground substance may fix the bodywater and the collagen fibers in the intercellular spaces. Ground substance may also slow the spread of pathogens.

The connective tissue may be fibrous and the fibrous tissue may comprise distinct compositions and be localized to specific areas of the body. For example, collagenous fibers often contain alpha polypeptide chains and may be primarily localized to a tendon, ligament, skin, cornea, cartilage, bone, blood vessels, gut, and intervertebral disc. In another example, elastic fibers may comprise elastic microfibrill and elastin and may be primarily localized to an extracellular matrix. Reticular fibers are another example of fibrous tissue and may be localized to the liver, bone marrow, or lymphatic organs.

However, not all types of connective tissues are fibrous. Examples of non-fibrous connective tissues are adipose tissue and blood. Adipose tissue may provide a "mechanical cushioning" to our body. Although there is often no dense collagen network in adipose tissue, groups of adipose cells may be kept together by collagen fibers and collagen sheets in order to keep fat tissue under compression in place (for example the sole of the foot).

Epithelia are tissues that may consist of closely apposed cells without intervening intercellular substances. Epithelia are often avascular, but epithelia may "grow" on an underlying layer of vascular connective tissue. The connective tissue and the epithelium may be separated by a basement membrane. Epithelium may cover all free surfaces of the body. Epithelium may also line the large internal body cavities, where it is termed mesothelium. Furthermore, the internal surfaces of blood and lymph vessels may be lined by epithelium, here called endothelium. Epithelia are often classified on the basis of the number of cell layers and the shape of the cells in the surface layer. If there is only one layer of cells in the epithelium, it is designated simple. If there are two or more layers of cells, it is termed stratified. Cells in the surface layer may be described according to their height as squamous (scale- or plate-like), cuboidal or columnar.

Different types of epithelial tissues may have specialized functions and locations within the body. For example, pseudostratified columnar may function to remove dust and particles from airways and may have cilia. The pseudostratified columnar may line the respiratory passageways. The simple columnar may be involved in absorption and often line the uterus and most organs of the digestive tract. The simple cuboidal may be involved in secretion and absorption and may be localized to glands, kidney tubules, and ovaries. The simple squamous may play a role in diffusion and filtration and may be localized to lungs, walls of capillaries and vessels. The stratified squamous may protect underlying cells and is often localized to the skin, throat, vagina, and mouth. The stratified cuboidal may be involved in protection and may line ducts of the mammary glands, sweat glands, and pancreas. The stratified columnar may be involved in protection and secretion and may be localized to the male urethra and vas deferens, and parts of the pharynx.

Muscular tissue is often a contractile tissue and may be derived from the mesodermal layer of embryonic germ cells. Muscle cells may contain contractile filaments that move past each other and change the size of the cell. They are classified as skeletal, cardiac, or smooth muscles. Skeletal muscle or "voluntary muscle" may be anchored by tendons (or by aponeuroses at a few places) to bone and may be used to effect skeletal movement such as locomotion and in maintaining posture. Smooth muscle or "involuntary muscle" is often found within the walls of organs and structures such as the esophagus, stomach, intestines, bronchi, uterus, urethra, bladder, blood vessels, and the arrector pill in the skin (in which it controls erection of body hair). Cardiac muscle is also an "involuntary muscle" but may be more structurally similar to skeletal muscle, and is often found in the heart.

Cardiac and skeletal muscles are often "striated" in that they contain sarcomeres and are packed into highly regular arrangements of bundles. While skeletal muscles may be arranged in regular, parallel bundles, cardiac muscle often connects at branching, irregular angles (called intercalated discs). Striated muscle may contract and relax in short, intense bursts, whereas smooth muscle may sustain longer or even near-permanent contractions.

Skeletal muscle may be divided into several subtypes. Type I, slow oxidative, slow twitch, or "red" muscle is often dense with capillaries and may be rich in mitochondria and myoglobin, giving the muscle tissue its characteristic red color. It may carry more oxygen and sustain aerobic activity. Type II, fast twitch muscle, has three major kinds, Type IIa, Type IIx, and Type IIb. Type IIa is often aerobic and may be rich in mitochondria and capillaries and may appear red. Type IIx (also known as type IId), which is often less dense in mitochondria and myoglobin. Type IIb, which may be anaerobic, glycolytic, "white" muscle that is often even less dense in mitochondria and myoglobin.

Nervous tissue is one of four major classes of tissue. Nervous tissue is often the main component of the nervous system, the brain, spinal cord, and nerves, which may regulate and control body functions. Nervous tissue is often composed of neurons and the neuroglia cells. Neurons may transmit impulses. Neuroglial cells may assist in propagation of the nerve impulse as well as provide nutrients to the neuron. Nervous tissue is often made of nerve cells that may come in many varieties, all of which may be distinctly characterized by the axon or long stem like part of the cell that sends action potential signals to the next cell.

Functions of the nervous system may include sensory input, integration, controls of muscles and glands, homeostasis, and mental activity. Nervous tissue may react to stimuli and may conduct impulses to various organs in the body which often bring about a response to the stimulus. Nerve tissue (as in the brain, spinal cord and peripheral nerves that branch throughout the body) are often made up of specialized nerve cells called neurons. Neurons are easily stimulated and transmit impulses very rapidly. A nerve often comprises many nerve cell fibers (neurons) bound together by connective tissue. A sheath of dense connective tissue, the epineurium may surround the nerve. This sheath penetrates the nerve to form the perineurium which surrounds bundles of nerve fibers. Blood vessels of various sizes may be seen in the epineurium. The endoneurium, which consists of a thin layer of loose connective tissue, surrounds the individual nerve fibers.

The cell body may be enclosed by a cell (plasma) membrane and may have a central nucleus. Granules called Nissl bodies are often found in the cytoplasm of the cell body. Within the cell body, extremely fine neurofibrils may extend from the dendrites into the axon. The axon is often surrounded by the myelin sheath, which forms a whitish, non-cellular, fatty layer around the axon. Outside the myelin sheath may be a cellular layer called the neurilemma or sheath of Schwann cells. The myelin sheath together with the neurilemma is also known as the medullary sheath. This medullary sheath may be interrupted at intervals by the nodes of Ranvier.

Neurons may be classified both structurally and functionally. Structural classification may group neurons according to the number of processes extending from their cell body. Three major neuron groups often make up this classification: multipolar (polar=end, pole), bipolar and unipolar neurons. Multipolar neurons often have three or more processes. These are the most common neuron type in humans (more than 99% of neurons belong to this class) and the major neuron type in the CNS. Bipolar neurons are often spindle-shaped, with a dendrite at one end and an axon at the other. An example may be found in the light-sensitive retina of the eye. Unipolar neurons often comprise sensory neurons. Sensory neurons normally have only a single process or fibre which divides close to the cell body into two main branches (axon and dendrite).

The cells may also comprise hair follicles, hair cells, ear hair cells, ear hair stem cells, or cochlear cells. Hair cells are often the sensory receptors of both the auditory system and the vestibular system. The auditory hair cells may be located within the organ of Corti on a thin basilar membrane in the cochlea of the inner ear. Cochlear hair cells may come in two anatomically and functionally distinct types: the outer and inner hair cells.

The one or more cells may be a pathogenic cell. Pathogenic cells include, but are not limited to, bacteria, viruses, fungi, and protozoans. Examples of pathogens may include, but are not limited to, the bacteria, viruses, fungi, and protozoans disclosed herein.

VII. Receptors, Co-Receptors, Antigens and Cell Markers

The targeting agent antibody conjugates disclosed herein may bind to one or more receptors, co-receptors, antigens, or cell markers on one or more cells. The targeting agent antibody conjugates disclosed herein may comprise (a) an antibody or antibody fragment and (b) targeting agent, wherein (i) the antibody or antibody fragment binds to or interacts with a receptor, co-receptor, antigen or cell marker on a first cell; (ii) the targeting agent binds to or interacts with a receptor, co-receptor, antigen or cell marker on a second cell; or (iii) a combination of (i) and (ii), and wherein (iv) the antibody or antibody fragment comprises one or more unnatural amino acids; (v) the targeting agent comprises one or more unnatural amino acids; or (vi) a combination of (iv) and (v). The first cell and the second cell may be the same type of cell. The first cell and the second cell may be different cell types. Alternatively, the first cell and the second cell may be the same cell.

For example, for a targeting agent antibody conjugate of Formula I, IA, II, and/or IIA, X comprises an antibody or antibody fragment that may binds to a receptor, co-receptor, antigen, trans-membrane protein or cell marker. Alternatively, or additionally, for a targeting agent antibody conjugate of Formula I, IA, II, and/or IIA, Y comprises a targeting agent that may bind to a receptor, co-receptor, antigen or cell marker.

Examples of receptors, co-receptors, antigens or cell markers may include, but are not limited to, a receptor, co-receptor, antigen or cell marker on a hematopoietic cell, tissue cell, epithelial cell, mesothelial cell, dermal cell, endothelial cell, dendritic cell, vascular cell, stromal cell, neuron, cancer cell, bacteria, fungus, or virus. The receptors, co-receptors, antigens or cell markers may be selected from the group comprising MUC16, GPNMB, Cripto, ED-8, TMEFF2, EphB2, EphA2, FAP, mesothelin, TAG-72, GD2, CAIX, and 5T4.

The receptor, co-receptor, antigen or cell marker may be overexpressed on a prostate cancer cell. The receptors, co-receptors, antigens or cell markers may comprise an endothelin. The receptor, co-receptor, antigen or cell marker may be PSMA.

The receptor may be a G-protein coupled receptor (GPCR). The receptor may be a tyrosine kinase receptor. The receptor may be a cytokine receptor. The receptor may be a chemokine receptor. The receptor may be a growth factor receptor. The growth factor receptor may be an epidermal growth factor receptor (EGFR), platelet derived growth factor receptor (PDGFR) or fibroblast growth factor receptor (FGFR). The EGFR may be EGFR1. The EGFR may be Her2. The receptor may be a cholecystokinin B receptor. The receptor may be a gonadotropin-releasing hormone receptor. The receptor may be a somatostatin receptor. The receptor may be somatostatin receptor 2. The receptor may be a gastrin-releasing peptide receptor. The receptor may be a neurokinin receptor. The may be neurokinin 1 receptor, also known as tachykinin 1 receptor. The receptor may be a melanocortin receptor. The receptor may be melanocortin 1 receptor. The receptor may be a neurotensin receptor. The receptor may be a neuropeptide Y receptor. The receptor may be an integrin. The integrin may be an av integrin. The integrin may be avB3 integrin.

The receptor, co-receptor, antigen or cell surface marker may comprise a cluster of differentiation protein. The cluster of differentiation protein may be selected from CD19, CD20, CD22, CD25, CD30, CD40, CD56, CD64, CD70, CD74, CD79, CD105, CD138, CD174, CD205, CD227, CD326, CD340, The differentiation protein may comprise CD38.

The trans-membrane protein may comprise a glycoprotein. The glycoprotein may be C-type lectin-like molecule-1 (CLL-1).

The receptor, co-receptor, antigen, trans-membrane protein or cell marker may be a cell adhesion molecule. The cell adhesion molecule may bind a cell. The cell adhesion molecule may bind extracellular matrix. The receptor, co-receptor, antigen or cell surface marker may comprise a gap junction protein.

An antigen may evoke the production of one or more antibodies. An antigen may refer to a molecule or molecular fragment that may be bound by a major histocompatiblity complex (MHC) and presented to a T-cell receptor. The term "antigen" may also refer to an immunogen. An immunogen may provoke an adaptive immune response if injected on its own into a subject. An immunogen may induce an immune response by itself. An antigen may also refer to a hapten. A hapten may be a targeting agent. Generally, a hapten may induce an immune response when attached to a larger carrier molecule, such as a protein. Antigens may be proteins or polysaccharides. Antigens may comprise parts (e.g., coats, capsules, cell walls, flagella, fimbrae, and toxins) of bacteria, viruses, and other microorganisms. Lipids and nucleic acids may be antigenic when combined with proteins and polysaccharides. Antigens may include superantigens, T-dependent antigens and T-independent antigens.

Antigens may be exogenous antigens or endogeneous antigens. Exogenous antigens are typically antigens that have entered the body from the outside, for example by inhalation, ingestion, or injection. Some antigens may start out as exogenous antigens, and later become endogenous (for example, intracellular viruses). Intracellular antigens may be released back into circulation upon the destruction of the infected cell, again. Endogenous antigens may be antigens that have been generated within previously-normal cells as a result of normal cell metabolism, or because of viral or intracellular bacterial infection.

Antigens may also include autoantigens. An autoantigen may be a normal protein or complex of proteins (and sometimes DNA or RNA) that is recognized by the immune system of patients suffering from a specific autoimmune disease. These antigens should, under normal conditions, not be the target of the immune system, but, due to mainly genetic and environmental factors, the normal immunological tolerance for such an antigen has been lost in these patients.

Antigens may include tumor antigens. Tumor antigens or neoantigens may be antigens that are presented by MHC I or MHC II molecules on the surface of tumor cells. These antigens may sometimes be presented by tumor cells and never by the normal ones. In this case, they are called tumor-specific antigens (TSAs) and, in general, result from a tumor-specific mutation. More common are antigens that are presented by tumor cells and normal cells, and they are called tumor-associated antigens (TAAs). Cytotoxic T lymphocytes that recognize these antigens may be able to destroy the tumor cells before they proliferate or metastasize. Tumor antigens may also be on the surface of the tumor in the form of, for example, a mutated receptor, in which case they may be recognized by B cells.

VIII. Indications

The targeting agent antibody conjugates and compositions disclosed herein may be used to treat one or more diseases or conditions in a subject in need thereof. The method may comprise administering a targeting agent antibody conjugate to a subject in need thereof. The targeting agent antibody conjugate may comprise (a) a first region comprising an antibody or antibody fragment that interacts with a surface marker on a first cell; and (b) a second region comprising a non-antibody region that interacts with a surface marker on a second cell. The antibody or antibody fragment may comprise an anti-CD3 antibody. The non-antibody region may interact with a PSMA on the second cell. The non-antibody region may comprise DUPA. The targeting agent antibody conjugate may further comprise one or more linkers. The one or more linkers may connect the first region and the second region. The one or more diseases or conditions may be a cancer, a pathogenic infection, autoimmune disease, inflammatory disease, or genetic disorder.

In some instances, the one or more diseases comprises a cancer. The cancer may comprise a recurrent and/or refractory cancer. Examples of cancers include, but are not limited to, sarcomas, carcinomas, lymphomas or leukemias.

The cancer may comprise a neuroendocrine cancer. The cancer may comprise a pancreatic cancer. The cancer may comprise an exocrine pancreatic cancer. The cancer may comprise a thyroid cancer. The thyroid cancer may comprise a medullary thyroid cancer.

The cancer may comprise a prostate cancer. The prostate cancer may be a PSMA-positive prostate cancer. PSMA expression may be highly upregulated and restricted to cancer cells in some or all stages of the prostate cancer. The cancer may be hormone-refractory prostate cancer.

The cancer may comprise an epithelial cancer. The cancer may comprise a breast cancer. The cancer may comprise an endometrial cancer. The cancer may comprise an ovarian cancer. The ovarian cancer may comprise a stromal ovarian cancer. The cancer may comprise a cervical cancer.

The cancer may comprise a skin cancer. The skin cancer may comprise a neo-angiogenic skin cancer. The skin cancer may comprise a melanoma.

The cancer may comprise a kidney cancer.

The cancer may comprise a lung cancer. The lung cancer may comprise a small cell lung cancer. The lung cancer may comprise a non-small cell lung cancer.

The cancer may comprise a colorectal cancer. The cancer may comprise a gastric cancer. The cancer may comprise a colon cancer.

The cancer may comprise a brain cancer. The brain cancer may comprise a brain tumor. The cancer may comprise a glioblastoma. The cancer may comprise an astrocytoma.

The cancer may comprise a blood cancer. The blood cancer may comprise a leukemia. The leukemia may comprise a myeloid leukemia. The cancer may comprise a lymphoma. The lymphoma may comprise a non-Hodgkin's lymphoma.

The cancer may comprise a sarcoma. The sarcoma may comprise an Ewing's sarcoma.

Sarcomas are cancers of the bone, cartilage, fat, muscle, blood vessels, or other connective or supportive tissue. Sarcomas include, but are not limited to, bone cancer, fibrosarcoma, chondrosarcoma, Ewing's sarcoma, malignant hemangioendothelioma, malignant schwannoma, bilateral vestibular schwannoma, osteosarcoma, soft tissue sarcomas (e.g. alveolar soft part sarcoma, angiosarcoma, cystosarcoma phylloides, dermatofibrosarcoma, desmoid tumor, epithelioid sarcoma, extraskeletal osteosarcoma, fibrosarcoma, hemangiopericytoma, hemangiosarcoma, Kaposi's sarcoma, leiomyosarcoma, liposarcoma, lymphangiosarcoma, lymphosarcoma, malignant fibrous histiocytoma, neurofibrosarcoma, rhabdomyosarcoma, and synovial sarcoma).

Carcinomas are cancers that begin in the epithelial cells, which are cells that cover the surface of the body, produce hormones, and make up glands. By way of non-limiting example, carcinomas include breast cancer, pancreatic cancer, lung cancer, colon cancer, colorectal cancer, rectal cancer, kidney cancer, bladder cancer, stomach cancer, prostate cancer, liver cancer, ovarian cancer, brain cancer, vaginal cancer, vulvar cancer, uterine cancer, oral cancer, penile cancer, testicular cancer, esophageal cancer, skin cancer, cancer of the fallopian tubes, head and neck cancer, gastrointestinal stromal cancer, adenocarcinoma, cutaneous or intraocular melanoma, cancer of the anal region, cancer of the small intestine, cancer of the endocrine system, cancer of the thyroid gland, cancer of the parathyroid gland, cancer of the adrenal gland, cancer of the urethra, cancer of the renal pelvis, cancer of the ureter, cancer of the endometrium, cancer of the cervix, cancer of the pituitary gland, neoplasms of the central nervous system (CNS), primary CNS lymphoma, brain stem glioma, and spinal axis tumors. In some instances, the cancer is a skin cancer, such as a basal cell carcinoma, squamous, melanoma, nonmelanoma, or actinic (solar) keratosis.

In some instances, the cancer is a lung cancer. Lung cancer may start in the airways that branch off the trachea to supply the lungs (bronchi) or the small air sacs of the lung (the alveoli). Lung cancers include non-small cell lung carcinoma (NSCLC), small cell lung carcinoma, and mesothelioma. Examples of NSCLC include squamous cell carcinoma, adenocarcinoma, and large cell carcinoma. The mesothelioma may be a cancerous tumor of the lining of the lung and chest cavity (pleura) or lining of the abdomen (peritoneum). The mesothelioma may be due to asbestos exposure. The cancer may be a brain cancer, such as a glioblastoma.

Alternatively, the cancer may be a central nervous system (CNS) tumor. CNS tumors may be classified as gliomas or nongliomas. The glioma may be malignant glioma, high grade glioma, diffuse intrinsic pontine glioma. Examples of gliomas include astrocytomas, oligodendrogliomas (or mixtures of oligodendroglioma and astocytoma elements), and ependymomas. Astrocytomas include, but are not limited to, low-grade astrocytomas, anaplastic astrocytomas, glioblastoma multiforme, pilocytic astrocytoma, pleomorphic xanthoastrocytoma, and subependymal giant cell astrocytoma. Oligodendrogliomas include low-grade oligodendrogliomas (or oligoastrocytomas) and anaplastic oligodendriogliomas. Nongliomas include meningiomas, pituitary adenomas, primary CNS lymphomas, and medulloblastomas. In some instances, the cancer is a meningioma.

The leukemia may be an acute lymphocytic leukemia, acute myelocytic leukemia, chronic lymphocytic leukemia, or chronic myelocytic leukemia. Additional types of leukemias include hairy cell leukemia, chronic myelomonocytic leukemia, and juvenile myelomonocytic leukemia.

Lymphomas are cancers of the lymphocytes and may develop from either B or T lymphocytes. The two major types of lymphoma are Hodgkin's lymphoma, previously known as Hodgkin's disease, and non-Hodgkin's lymphoma. Hodgkin's lymphoma is marked by the presence of the Reed-Sternberg cell. Non-Hodgkin's lymphomas are all lymphomas which are not Hodgkin's lymphoma. Non-Hodgkin lymphomas may be indolent lymphomas and aggressive lymphomas. Non-Hodgkin's lymphomas include, but are not limited to, diffuse large B cell lymphoma, follicular lymphoma, mucosa-associated lymphatic tissue lymphoma (MALT), small cell lymphocytic lymphoma, mantle cell lymphoma, Burkitt's lymphoma, mediastinal large B cell lymphoma, Waldenström macroglobulinemia, nodal marginal zone B cell lymphoma (NMZL), splenic marginal zone lymphoma (SMZL), extranodal marginal zone B cell lymphoma, intravascular large B cell lymphoma, primary effusion lymphoma, and lymphomatoid granulomatosis.

The one or more diseases or conditions may be a pathogenic infection. Pathogenic infections may be caused by one or more pathogens. In some instances, the pathogen is a bacterium, fungi, virus, or protozoan.

Exemplary pathogens include but are not limited to: *Bordetella, Borrelia, Brucella, Campylobacter, Chlamydia, Chlamydophila, Clostridium, Corynebacterium, Enterococcus, Escherichia, Francisella, Haemophilus, Helicobacter, Legionella, Leptospira, Listeria, Mycobacterium, Mycoplasma, Neisseria, Pseudomonas, Rickettsia, Salmonella, Shigella, Staphylococcus, Streptococcus, Treponema, Vibrio*, or *Yersinia*. In some cases, the disease or condition caused by the pathogen is tuberculosis and the heterogeneous sample comprises foreign molecules derived from the bacterium *Mycobacterium tuberculosis* and molecules derived from the subject. In some instances, the disease or condition is caused by a bacterium is tuberculosis, pneumonia, which may be caused by bacteria such as *Streptococcus* and *Pseudomonas*, a foodborne illness, which may be caused by bacteria such as *Shigella, Campylobacter* and *Salmonella*, and an infection such as tetanus, typhoid fever, diphtheria, syphilis and leprosy. The disease or condition may be bacterial vaginosis, a disease of the vagina caused by an imbalance of naturally occurring bacterial flora. Alternatively, the disease or condition is a bacterial meningitis, a bacterial inflammation of the meninges (e.g., the protective membranes covering the brain and spinal cord). Other diseases or conditions caused by bacteria include, but are not limited to, bacterial pneumonia, a urinary tract infection, bacterial gastroenteritis, and bacterial skin infection. Examples of bacterial skin infections include, but are not limited to, impetigo which may be caused by *Staphylococcus aureus* or *Streptococcus pyogenes*; erysipelas which may be caused by a *streptococcus* bacterial infection of the deep epidermis with lymphatic spread; and cellulitis which may be caused by normal skin flora or by exogenous bacteria.

The pathogen may be a fungus, such as, *Candida, Aspergillus, Cryptococcus, Histoplasma, Pneumocystis*, and *Stachybotrys*. Examples of diseases or conditions caused by a fungus include, but are not limited to, jock itch, yeast infection, ringworm, and athlete's foot.

The pathogen may be a virus. Examples of viruses include, but are not limited to, adenovirus, coxsackievirus, Epstein-Barr virus, Hepatitis virus (e.g., Hepatitis A, B, and C), herpes simplex virus (type 1 and 2), cytomegalovirus, herpes virus, HIV, influenza virus, measles virus, mumps virus, papillomavirus, parainfluenza virus, poliovirus, respiratory syncytial virus, rubella virus, and varicella-zoster virus. Examples of diseases or conditions caused by viruses include, but are not limited to, cold, flu, hepatitis, AIDS, chicken pox, rubella, mumps, measles, warts, and poliomyelitis.

The pathogen may be a protozoan, such as *Acanthamoeba* (e.g., *A. astronyxis, A. castellanii, A. culbertsoni, A. hatchetti, A. polyphaga, A. rhysodes, A. healyi, A. divionensis*), *Brachiola* (e.g., *B. connori, B. vesicularum*), *Cryptosporidium* (e.g., *C. parvum*), *Cyclospora* (e.g., *C. cayetanensis*), *Encephalitozoon* (e.g., *E. cuniculi, E. hellem, E. intestinalis*), *Entamoeba* (e.g., *E. histolytica*), *Enterocytozoon* (e.g., *E. bieneusi*), *Giardia* (e.g., *G. lamblia*), *Isospora* (e.g., *I. belli*), *Microsporidium* (e.g., *M. africanum, M. ceylonensis*), *Naegleria* (e.g., *N. fowleri*), *Nosema* (e.g., *N. algerae, N. ocularum*), *Pleistophora, Trachipleistophora* (e.g., *T. anthropophthera, T. hominis*), and *Vittaforma* (e.g., *V. corneae*).

The disease or condition may be an autoimmune disease or autoimmune related disease. An autoimmune disorder may be a malfunction of the body's immune system that causes the body to attack its own tissues. Examples of autoimmune diseases and autoimmune related diseases include, but are not limited to, Addison's disease, alopecia areata, ankylosing spondylitis, antiphospholipid syndrome (APS), autoimmune aplastic anemia, autoimmune hemolytic anemia, autoimmune hepatitis, autoimmune myocarditis, Behcet's disease, celiac sprue, Crohn's disease, dermatomyositis, eosinophilic fasciitis, erythema nodosum, giant cell arteritis (temporal arteritis), Goodpasture's syndrome, Graves' disease, Hashimoto's disease, idiopathic thrombocytopenic purpura (ITP), IgA nephropathy, juvenile arthritis, diabetes, juvenile diabetes, Kawasaki syndrome, Lambert- Eaton syndrome, lupus (SLE), mixed connective tissue disease (MCTD), multiple sclerosis, myasthenia gravis, pemphigus, polyarteritis nodosa, type I, II, & III autoimmune polyglandular syndromes, polymyalgia rheumatica, polymyositis, psoriasis, psoriatic arthritis, Reiter's syndrome, relapsing polychondritis, rheumatoid arthritis, sarcoidosis, scleroderma, Sjogren's syndrome, sperm & testicular autoimmunity, stiff person syndrome, Takayasu's arteritis, temporal arteritis/giant cell arteritis, ulcerative colitis, uveitis, vasculitis, vitiligo, and Wegener's granulomatosis.

The disease or condition may be an inflammatory disease. Examples of inflammatory diseases include, but are not limited to, alveolitis, amyloidosis, angiitis, ankylosing spondylitis, avascular necrosis, Basedow's disease, Bell's palsy, bursitis, carpal tunnel syndrome, celiac disease, cholangitis, chondromalacia patella, chronic active hepatitis, chronic fatigue syndrome, Cogan's syndrome, congenital hip dysplasia, costochondritis, Crohn's Disease, cystic fibrosis, De Quervain's tendinitis, diabetes associated arthritis, diffuse idiopathic skeletal hyperostosis, discoid lupus, Ehlers-Danlos syndrome, familial mediterranean fever, fascitis, fibrositis/fibromyalgia, frozen shoulder, ganglion cysts, giant cell arteritis, gout, Graves' Disease, HIV-associated rheumatic disease syndromes, hyperparathyroid associated arthritis, infectious arthritis, inflammatory bowel syndrome/irritable bowel syndrome, juvenile rheumatoid arthritis, lyme disease, Marfan's Syndrome, Mikulicz's Disease, mixed connective tissue disease, multiple sclerosis, myofascial pain syndrome, osteoarthritis, osteomalacia, osteoporosis and corticosteroid-induced osteoporosis, Paget's Disease, palindromic rheumatism, Parkinson's Disease, Plummer's Disease, polymyalgia rheumatica, polymyositis, pseudogout, psoriatic arthritis, Raynaud's Phenomenon/Syndrome, Reiter's Syndrome, rheumatic fever, rheumatoid arthritis, sarcoidosis, sciatica (lumbar radiculopathy), scleroderma, scurvy, sickle cell arthritis, Sjogren's Syndrome, spinal stenosis, spondyloisthesis, Still's Disease, systemic lupus erythematosis, Takayasu's (Pulseless) Disease, Tendinitis, tennis elbow/golf elbow, thyroid associated arthritis, trigger finger, ulcerative colitis, Wegener's Granulomatosis, and Whipple's Disease.

Further disclosed herein are uses of the targeting agent antibody conjugate disclosed herein to treat a disease or condition. Disclosed herein is the use of a targeting agent antibody conjugate to treat a cancer in a subject in need thereof, wherein the targeting agent antibody conjugate comprises (a) a first region comprising an antibody or antibody fragment that interacts with an immune cell; and (b) a second region comprising a non-antibody portion that interacts with a target cell. The targeting agent antibody conjugate may further comprise one or more linkers. The one or more linkers may connect the first region and the second region of the targeting agent antibody conjugate. The non-antibody portion may interact with PSMA on the target cell. The non-antibody portion may comprise DUPA. The antibody or antibody fragment may comprise an anti-CD3 antibody. The cancer may be a prostate cancer.

IX. Immune Modulation

The targeting agent antibody conjugates disclosed herein may be used to modulate an immune response. Modulation of an immune response may comprise stimulating, activating, increasing, enhancing, or up-regulating an immune response. Modulation of an immune response may comprise suppressing, inhibiting, preventing, reducing, or downregulating an immune response. For example, the antibodies may comprise an antibody or antibody fragment that may bind to a first cell and a targeting agent that may bind to a second cell. Binding of the antibody to the first and second cell may result in modulation of an immune response. The first cell may be an immune cell. The immune cell may be a hematopoietic cell. The second cell may be an immune cell, healthy cell, cancer cell, bacteria, or virally-infected.

Methods of modulating an immune response may comprise (a) contacting an immune cell with a targeting agent antibody conjugate to produce an immune cell-targeting agent antibody conjugate complex; and (b) contacting a target cell with the immune cell-targeting agent antibody conjugate complex, thereby modulating an immune response from the immune cell.

Alternatively, the method may comprise (a) contacting a target cell with a targeting agent antibody conjugate to produce a target cell-targeting agent antibody conjugate complex; and (b) contacting an immune cell with the target cell-targeting agent antibody conjugate complex, thereby modulating an immune response from the immune cell. The targeting agent antibody conjugate may comprise an antibody or fragment thereof that interacts with a cell surface marker on the immune cell. The cell surface marker on the immune may be a receptor or co-receptor. The cell surface marker may be a CD3 T cell co-receptor. The cell surface marker on the immune cell may be a protein, glycoprotein, or steroid. The immune cell may be a T cell. The targeting agent antibody conjugate may comprise a non-antibody portion that interacts with a cell surface marker on a target cell. The targeting agent antibody conjugate may connect the immune cell to the target cell. The target cell may be a cancerous cell. The target cell may be a virally infected cell. The target cell may be an immune cell. The immune cell may be a T cell. The immune cell may be a macrophage. The immune cell may be a B cell. The cell surface marker on the target cell may be a receptor, co-receptor, surface protein, glycoprotein, or steroid. The non-antibody portion of the targeting antibody conjugate may comprise a ligand, cytokine, toxin, or small molecule. Methods of modulating the immune response may further comprise administering one or more additional targeting agent antibody conjugates to the subject. The one or more additional targeting agent antibody conjugates may interact with one or more additional immune cells. The one or more additional immune cells may be the same type of immune cell as the previous immune cell. For example, a first targeting agent antibody conjugate may interact at with a T cell and a second targeting agent antibody conjugate may also interact with a T cell. Alternatively, or additionally, the one or more additional immune cells may be a different type of immune cell as the previous immune cell. For example, a first targeting agent antibody conjugate may interact with an antigen presenting cell and a second targeting agent antibody conjugate may interact with a T cell. The one or more additional targeting agent antibody conjugates may interact with one or more additional cells. The one or more additional cells may be of the same cell type as the immune cell or the target cell. For example, a first targeting agent antibody conjugate may interact with a virally infected cell and a second targeting agent antibody conjugate may interact with a virally infected cell. Alternatively, or additionally, the one or more additional cells may be different from the immune cell or target cell. For example, a first targeting agent antibody conjugate may interact with a bacterial cell and a second targeting agent antibody conjugate may interact with a virally infected cell.

In another alternative, the method may comprise (a) contacting a sample comprising a target cell and an immune cell with targeting agent antibody conjugate; and (b) connecting the target cell and the immune cell via the targeting agent antibody conjugate, thereby modulating an immune response from the immune cell. The targeting agent antibody conjugate may comprise an antibody or fragment thereof that interacts with a cell surface marker on the immune cell. The cell surface marker on the immune may be a receptor or co-receptor. The cell surface marker may be a CD3 T cell co-receptor. The cell surface marker on the immune cell may be a protein, glycoprotein, or steroid. The immune cell may be a T cell. The targeting agent antibody conjugate may comprise a non-antibody portion that interacts with a cell surface marker on a target cell. The targeting agent antibody conjugate may connect the immune cell to the target cell. The target cell may be a cancerous cell. The target cell may be a virally infected cell. The target cell may be an immune cell. The immune cell may be a T cell. The immune cell may be a macrophage. The immune cell may be a B cell. The cell surface marker on the target cell may be a receptor, co-receptor, surface protein, glycoprotein, or steroid. The non-antibody portion of the targeting antibody conjugate may comprise a ligand, cytokine, toxin, or small molecule. Methods of modulating the immune response may further comprise administering one or more additional targeting agent antibody conjugates to the subject. The one or more additional targeting agent antibody conjugates may interact with one or more additional immune cells. The one or more additional immune cells may be the same type of immune cell as the previous immune cell. For example, a first targeting agent antibody conjugate may interact at with a T cell and a second targeting agent antibody conjugate may also interact with a T cell. Alternatively, or additionally, the one or more additional immune cells may be a different type of immune cell as the previous immune cell. For example, a first targeting agent antibody conjugate may interact with an antigen presenting cell and a second targeting agent antibody conjugate may interact with a T cell. The one or more additional targeting agent antibody conjugates may interact with one or more additional cells. The one or more additional cells may be of the same cell type as the immune cell or the target cell. For example, a first targeting agent antibody conjugate may interact with a virally infected cell and a second targeting agent antibody conjugate may interact with a virally infected cell. Alternatively, or additionally, the one or more additional cells may be different from the immune cell or target cell. For example, a first targeting agent antibody conjugate may interact with a bacterial cell and a second targeting agent antibody conjugate may interact with a virally infected cell.

Methods of modulating an immune response may comprise administering a composition comprising a targeting agent antibody conjugate to a subject in need thereof, wherein the targeting agent antibody conjugate comprises an antibody or antibody fragment that interacts with a cell surface marker on an immune cell. The cell surface marker on the immune may be a receptor or co-receptor. The cell surface marker may be a CD3 T cell co-receptor. The cell surface marker on the immune cell may be a protein, glycoprotein, or steroid. The immune cell may be a T cell. The targeting agent antibody conjugate may comprise a non-antibody portion that interacts with a cell surface marker on a second cell. The targeting agent antibody conjugate may connect the immune cell to the second cell. The second cell may be a cancerous cell. The second cell may be a virally infected cell. The second cell may be an immune cell. The immune cell may be a T cell. The immune cell may be a macrophage. The immune cell may be a B cell. The cell surface marker on the second cell may be a receptor, co-receptor, surface protein, glycoprotein, or steroid. The non-antibody portion of the targeting antibody conjugate may comprise a ligand, cytokine, toxin, or small molecule. Methods of modulating the immune response may further comprise administering one or more additional targeting agent antibody conjugates to the subject. The one or more additional targeting agent antibody conjugates may interact with one or more additional immune cells. The one or more additional immune cells may be the same type of immune cell as the previous immune cell. For example, a first targeting agent antibody conjugate may interact at with a T cell and a second targeting agent antibody conjugate may also interact with a T cell. Alternatively, or additionally, the one or more additional immune cells may be a different type of immune cell as the previous immune cell. For example, a first targeting agent antibody conjugate may interact with an antigen presenting cell and a second targeting agent antibody conjugate may interact with a T cell. The one or more additional targeting agent antibody conjugates may interact with one or more additional cells. The one or more additional cells may be of the same cell type as the immune cell or the second cell. For example, a first targeting agent antibody conjugate may interact with a virally infected cell and a second targeting agent antibody conjugate may interact with a virally infected cell. Alternatively, or additionally, the one or more additional cells may be different from the immune cell or second cell. For example, a first targeting agent antibody conjugate may interact with a bacterial cell and a second targeting agent antibody conjugate may interact with a virally infected cell.

X. Additional Applications

Further disclosed herein are methods of connecting two or more cells. The method may comprise contacting a sample comprising two or more cells with a targeting agent antibody conjugate. The targeting agent antibody conjugate may comprise (a) a first region comprising an antibody or antibody fragment; and (b) a second region comprising a non-antibody portion. The antibody or antibody fragment may interact with a surface marker on a first cell. The non-antibody portion may interact with a surface marker on a second cell. The first and second cells may be the same type of cell. The first and second cells may be different types of cells. The surface markers may be a receptor, co-receptor, protein, glycoprotein, antigen, polysaccharide, or steroid. The method may further comprise contacting the sample with one or more additional targeting agent antibody conjugates. The one or more additional targeting agent antibody conjugates may comprise (a) a first region comprising an antibody or antibody fragment; and (b) a second region comprising a non-antibody portion. The antibody or antibody fragment of the one or more additional targeting agent antibody conjugates may interact with a surface marker on the first cell, the second cell, or a third cell. The non-antibody portion of the one or more additional targeting agent antibody conjugates may interact with a surface marker on the first cell, the second cell, or a fourth cell. The first, second, third, and/or fourth cells may be the same cell type. The first, second, third, and/or fourth cells may be different cell types.

The targeting agent antibody conjugates may be used to connect multiple cells. As such, multi-cell complexes may be formed by the attachment of the targeting agent antibody conjugates to the cells. Cell scaffolds and/or cell matrices may be formed by the attachment of the targeting agent antibody conjugates to the cells.

The first region and second region of the targeting agent antibody conjugates may be connected by one or more linkers. The linkers may be biodegradable. The linkers may be cleavable. As such, temporary cell-cell complexes, scaffolds or matrices may be formed by using targeting agent antibody conjugates comprising biodegradable, cleavable or otherwise degradable linkers to connect two or more cells. Alternatively, or additionally, the linkers may be resistant to cleavage or degradation. As such, permanent or semi-permanent cell-cell complexes, scaffolds or matrices may be formed by using targeting agent antibody conjugates comprising cleavage or degradation-resistant linkers to connect two or more cells. The targeting agent antibody conjugates may comprise a mixture of degradable and non-degradable linkers to create flexible cell-cell complexes.

The use of the targeting agent antibody conjugates may enable analysis of cell-cell interactions and signal transduction pathways. The cells may further be isolated and expression profiling of the cells may be performed. These type of analyses may be used in the diagnosis, prognosis, and/or treatment of a disease or condition in a subject in need thereof.

EXAMPLES

Figure 9:
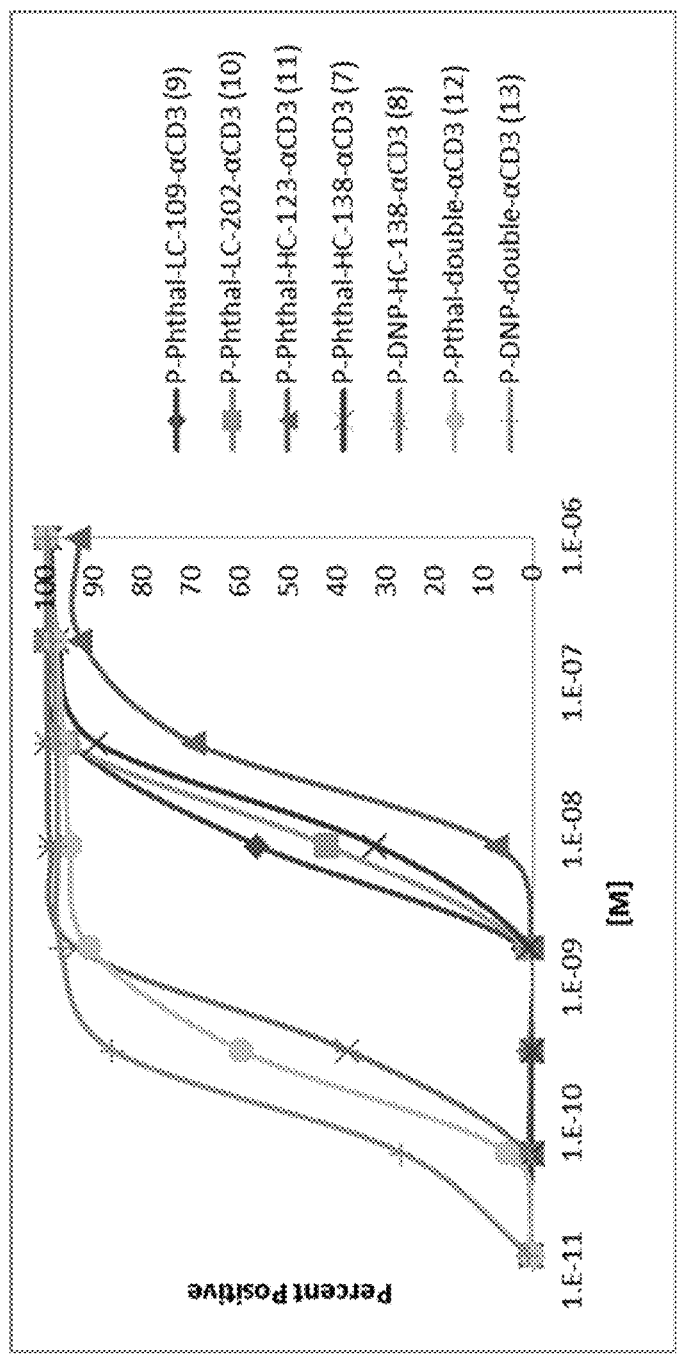
FIG. 9 depicts High-throughput FACS analysis of the binding of different P-anti-CD3 conjugates to PSMA-positive C4-2 cells at various concentrations. P-Phthal-double conjugate shows significantly improved affinity compared to the corresponding monoconjugates.

Example 1: Flow Cytometry Analysis: DUPA-Phthal-Double-αCD3 Binding to C4-2 Cells In this example, we conjugated two DUPA ligands to an anti-CD3 Fab such that the bivalent ligand may simultaneously bind each subunit of the PSMA homodimer with high avidity. To synthesize a bivalent Fab, we introduced TAG codons at two different positions (light chain S202 and heavy chain K138), and the double mutant was expressed and purified as described above. Notably, the expression levels were comparable to other single mutants and the wild type antibody that were previously expressed. The double mutant antibody was conjugated with P-Phthal (3) or P-DNP (4) as described above; LC-MS analysis revealed that the reaction was complete (>95% efficiency) within 48 hours, yielding the bivalent conjugates, P-Phthal-double-αCD3 (12) and P-DNP-double-αCD3 (13). After purification, the structures were confirmed by SDS-PAGE and LC-MS (the reaction yields after purifications are >90%). Binding of the bivalent conjugates to C4-2 cells was then assessed (together with monovalent conjugates) using flow cytometry (FIG. 9, Table 1). A significant improvement was observed in binding affinity (>60-fold) for the bivalent P-Phthal-double-αCD3 (12) compared to the monovalent P-Phthal-HK138-αCD3 (7). Interestingly, P-DNP-double-αCD3 (13) did not show significant improvement over its monovalent equivalent P-DNP-HK138-αCD3 (8), which already had high affinity. The enhanced binding affinity of P-Phthal-double-αCD3 (12) was particularly encouraging because despite the high affinity of the DNP group, its known high immunogenicity might limit its use in vivo.

TABLE 1

FACS analysis of the binding of different P-anti-CD3 conjugates to PSMA-positive C4-2 cells at various concentrations.

| | Percent Positive | | | | | | |
|---|---|---|---|---|---|---|---|
| [M] | P-Phthal-LC-109 | P-Phthal-LC-202 | P-Phthal-HC-123 | P-Phthal-HC-138 | P-DNP-HC | P-Pthal-double | P-DNP-double |
| 0.000001 | 100 | 99.9 | 93.2 | 99 | 99.9 | 99.8 | 99.6 |
| 2E−07 | 99.4 | 99.8 | 92.8 | 97.5 | 100 | 98 | 98.7 |
| 4E−08 | 95.2 | 95.6 | 69.7 | 89.5 | 99.5 | 96.2 | 97.7 |
| 8E−09 | 56.7 | 42.5 | 7.6 | 32.4 | 99 | 95.1 | 97.5 |
| 1.6E−09 | 1.94 | 1.37 | 0.42 | 0.82 | 93.7 | 91 | 96.9 |
| 3.2E−10 | 0.49 | 0.47 | 0.76 | 0.079 | 38.2 | 60 | 86.3 |
| 6.4E−11 | 0.88 | 0.38 | 0.29 | 0.08 | 1.44 | 5.46 | 27.1 |
| 1.28E−11 | 0 | 0.66 | 0.52 | 0.43 | 0.13 | 0.4 | 0.81 |

Example 2: In Vitro Cytotoxicity of DUPA/Anti-CD3 Conjugates

Figure 10:
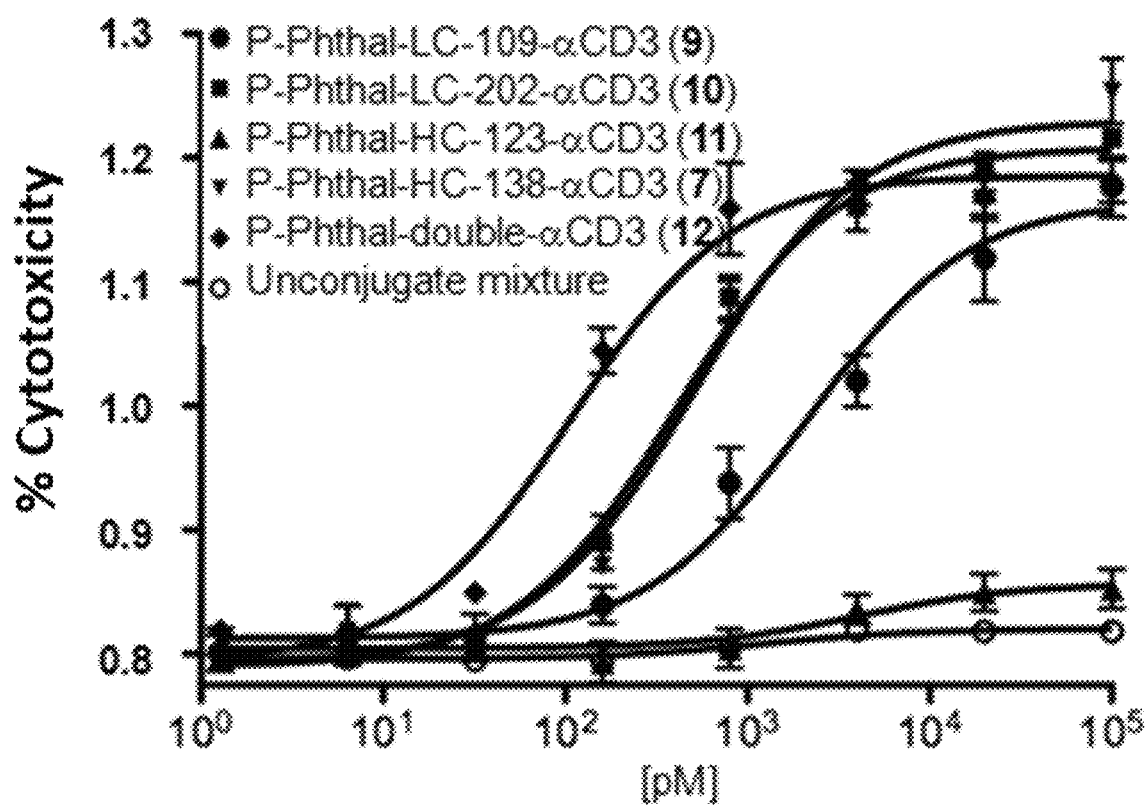
FIG. 10 depicts In vitro cytotoxicity of target cells in the presence of freshly purified unactivated hPBMCs (T:E=1:10). Conjugates show dose-dependent activity on PSMA-positive C4-2 cells with different $EC_{50}$ values whereas the unconjugated mixture shows no activity.

We next compared the in vitro cytotoxicity of various DUPA/αCD3 conjugates. Freshly purified human peripheral blood mononuclear cells (hPBMCs) were mixed with C4-2 (PSMA+) cells at a 10:1 ratio (100,000 and 10,000 cells, respectively), and incubated with each conjugate for 24 hours. A 1:1 mixture of wild-type UCHT1 Fab and the DUPA-linker conjugate (P-DNP, 4) was used as a negative control. Cytotoxicity was determined by measuring lactose dehydrogenase (LDH) released from lysed target cells. As shown in FIG. 10 and Table 2, each of the conjugates, with the exception of P-Phthal-HC-123-αCD3 (11) which poorly bound C4-2 cells in the previous assay, showed dose dependent cytotoxicity. P-Phthal-LC-109-αCD3 (9) showed reduced cytotoxicity ($EC_{50}$~4.1 nM) compared to P-Phthal-LC-202-αCD3 (10, $EC_{50}$~0.4 nM) and P-Phthal-HC-138-αCD3 (7, $EC_{50}$ 0.5 nM), although all had similar affinities in the binding studies. Finally, P-Phthal-doubleα-CD3 (12) showed the highest cytotoxicity ($EC_{50}$~0.1 nM) compared to the monovalent constructs. No cytotoxicity was observed even at the highest concentration measured with the unconjugated DUPA-linker and UCHT1 Fab mixtures. Taken together, these results indicate that not only the affinity but also the geometry of the bispecific significantly affects cytotoxicity. Based on the binding and in vitro cytotoxicity assays, we chose the P-Phthal-double-αCD3 (12) (also referred to as PSMA-targeting Small Molecule Antibody Conjugate, P-targeting agent antibody conjugate) conjugate for further characterization.

TABLE 2

In vitro cytotoxicity of target cells

| [pM] | T109 | | | S202 | | | A123 | | |
|---|---|---|---|---|---|---|---|---|---|
| 0 | −6.31405 | −1.15703 | 8.561983 | −3.33884 | 0.628099 | 1.619835 | −1.91715 | 4.861349 | 3.218076 |
| 1.28 | −5.52066 | 2.016529 | 3.801653 | −2.34711 | 2.809917 | −1.95041 | −2.12256 | 3.834303 | 4.450531 |
| 6.4 | −6.5124 | 7.570248 | 7.966942 | −2.94215 | 3.206612 | 4.198347 | −0.27388 | 0.342349 | 2.191031 |
| 32 | −4.92562 | 6.578512 | 6.380165 | −2.94215 | 4.198347 | 3.404959 | 0.342349 | 3.012667 | 6.710031 |
| 160 | 2.214876 | 9.752066 | 11.73554 | 10.54545 | 25.61983 | 17.8843 | −3.97124 | −5.40911 | 5.272167 |
| 800 | 16.29752 | 35.33884 | 30.97521 | 52 | 63.70248 | 56.95868 | −3.97124 | −0.06847 | 6.710031 |
| 4000 | 35.73554 | 47.83471 | 48.6281 | 64.29752 | 75.80165 | 76.3967 | 5.272167 | 4.450531 | 11.84526 |
| 20000 | 51.20661 | 65.09091 | 75.20661 | 72.42975 | 83.1405 | 77.58678 | 8.764122 | 5.477576 | 15.54262 |
| 100000 | 66.47934 | 76.19835 | 83.33884 | 83.1405 | 83.73553 | 82.54546 | 9.996576 | 5.272167 | 16.15885 |

| [pM] | K138 | | | phthal double | | | unconj | | |
|---|---|---|---|---|---|---|---|---|---|
| 0 | −3.14961 | −2.9442 | −0.06847 | −5.89878 | 7.504363 | 3.73473 | 0 | 0 | 0 |
| 1.28 | −1.71174 | −0.06847 | 1.163985 | 2.268761 | 5.410122 | 3.73473 | 0 | 0.230681 | 0.230947 |
| 6.4 | −2.53338 | 1.369394 | 12.05067 | −1.08202 | 3.525306 | 4.991274 | −0.92593 | −0.46136 | −0.57737 |
| 32 | −2.12256 | 1.780212 | 4.245121 | 6.876091 | 11.90227 | 10.85515 | −0.61728 | −0.69204 | −1.61663 |
| 160 | 16.15885 | 12.05067 | 14.31017 | 42.26876 | 49.5986 | 54.83421 | −1.64609 | −0.92272 | −1.15473 |
| 800 | 51.0784 | 56.82985 | 62.58131 | 59.86038 | 70.12216 | 85.41013 | 0.514403 | 1.845444 | 0.577367 |
| 4000 | 78.1924 | 77.16535 | 74.70045 | 69.49389 | 78.49913 | 77.452 | 4.526749 | 3.921569 | 3.117783 |
| 20000 | 70.59226 | 82.30058 | 76.13831 | 66.56196 | 75.56719 | 78.70855 | 2.777778 | 3.921569 | 4.157044 |
| 100000 | 84.9709 | 85.99795 | 101.1982 | 74.52007 | 82.68761 | 71.37871 | 2.469136 | 5.536332 | 3.00231 |

Figure 11:
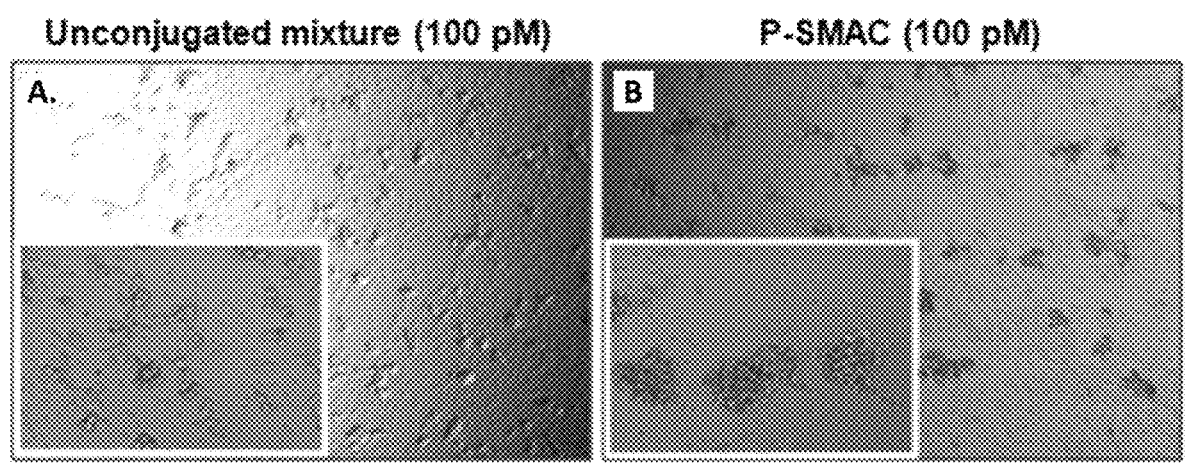
FIG. 11 depicts Microscope images of the 100 pM wells, where cell clusters may be observed only on C4-2 cells in the presence of the P-targeting agent antibody conjugate conjugate. Unconjugated anti-CD3 and P-Phthal mixture had no effect on cell clustering.

Finally, the rosette morphology that is evident upon synapse formation was clearly observed only in the presence of the P-targeting agent antibody conjugate with C4-2 cells (FIG. 11).

Example 3: In Vivo PK and Antitumor Activity

We first evaluated the pharmacokinetics of the P-targeting agent antibody conjugate. Male Sprague Dawley rats (Charles River) were injected intravenously at time zero at 1 and 5 mg/kg for P-targeting agent antibody conjugate or 0.5 mg/kg for the unconjugated UCHT1 Fab. Blood was collected at regular intervals to 32 hours and processed to measure drug concentrations using a sandwich-ELISA. Interestingly, the P-targeting agent antibody conjugate showed significantly improved circulating half-life (~5-6 hours) compared to the unconjugated Fab (~1 hour) perhaps due to the increased overall hydrophobicity of the DUPA-linker moiety after conjugation. Of note, P-targeting agent antibody conjugate has an improved serum half-life relative to small bispecific scFvs such as BiTEs (Bispecific T cell Engager, ~2 hour half-life in human) despite their similar molecular weight (~50,000 Da). The enhanced serum half-life of P-targeting agent antibody conjugate translates into a human half-life of >1x/day dosing. Also, the small size of P-targeting agent antibody conjugate may be advantageous for penetrating solid tumors.

Figure 12:
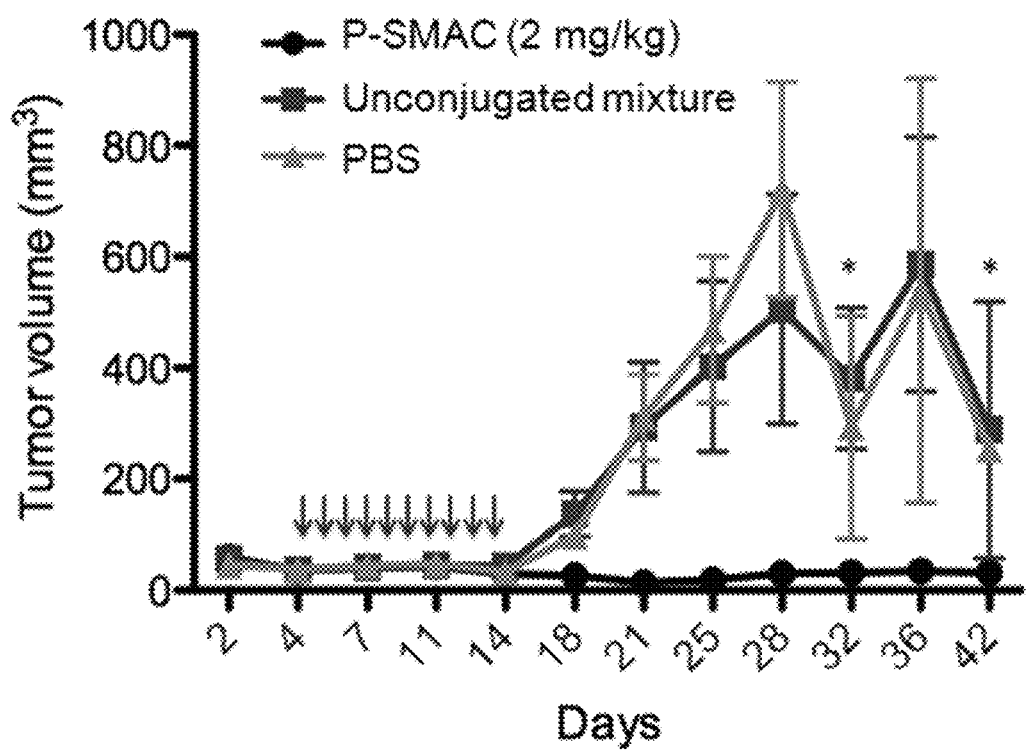
FIG. 12 depicts in vivo efficacy studies of P-targeting agent antibody conjugate. In the prophylactic model, $1 \times 10^6$ C4-2 cells were mixed with $2 \times 10^6$ PBMCs (1:2 ratio) in Matrigel and injected SC into the right shoulder of male NOD-SCID mice. P-targeting agent antibody conjugate, unconjugated Fab, or PBS (n=6) were administered at 2 mg/kg everyday for 10 days by IV starting on Day 4. Tumors were monitored by external caliper measurements for regular intervals for 6 weeks. P-targeting agent antibody conjugate suppressed tumor growth (p<0.0001) while the control groups developed rapid tumors. * indicates that mice with large tumors (>1000 mm$^3$) were sacrificed before these days.

We next established a mouse xenograft model to evaluate the in vivo efficacy of P-targeting agent antibody conjugate. Immunodeficient NOD/SCID mice were subcutaneously injected with a mixture of 1×10$^6$ C4-2 cells and 2×10$^6$ hPBMCs in matrigel (BD Bioscience). After 4 days, treatment was initiated by injecting 2 mg/kg of drug via the tail vein and continued for 10 days (n=6). In a control group, mice were injected with an unconjugated mixture of P-Phthal (3) and UCHT1 wild-type Fab, and another group of mice was injected with vehicle alone (n=6). Tumor growth was monitored by external caliper measurement. The mixture and vehicle group showed tumor outgrowth approximately two weeks after implantation. However, the treatment group did not develop any palpable tumors for up to 6 weeks (when all of the mice in the other two groups had to be sacrificed due to the large sizes of the tumors) (FIG. 12, Table 3). Histology also confirmed the formation of solid tumors in mice from the control groups (PBS and mixture group) while no solid tumors were detected in the treatment group. After confirming the prophylactic efficacy of P-targeting agent antibody conjugate, we carried a xenograft model in which we delayed treatment until we observed the formation of a palpable tumor. In this treatment study, we used NOD/scid gamma (NSG, Jackson Laboratory) mice, which are known to be more suitable for immune reconstitution with human-derived cells. On day zero, 1×10$^6$ C4-2 cells in matrigel were subcutaneously injected and, after three days, 20×10$^6$ hPBMCs were separately injected into the peritoneal cavity. This separate injection of hPBMCs further allows assessing the capability of P-targeting agent antibody conjugate to redirect T cells form the periphery to the site of tumor. Palpable solid tumors (~150 mm$^3$) were formed in mice approximately two weeks after tumor implantation, at which time we started treatment via tail vein injection with 1 mg/kg P-targeting agent antibody conjugate for 10 days (n=7). On the first and fourth day of treatment, we co-injected 10×10$^6$ of ex vivo expanded T cells from the same donor via tail vein into all groups to supplement more cytotoxic effector cells. After treatment was started, immediate tumor shrinkage was observed in the treatment group, whereas the vehicle group (n=7) again showed rapid tumor outgrowth.

TABLE 3

In-vivo efficacy studies of P-targeting agent antibody conjugate

| Day | Tumor Volume [mm³] | | | | | |
|---|---|---|---|---|---|---|
| P-targeting agent antibody conjugate | | | | | | |
| 2 | 37.888 | 113.4 | 61.32 | 48.618 | 46.08 | 52.022 |
| 4 | 35.77 | 37.23 | 35.52 | 37.765 | 31.098 | 36.72 |
| 7 | 31.968 | 21.78 | 44.376 | 60.04 | 43.2 | 43.8 |
| 11 | 29.127 | 42.282 | 43.092 | 74.646 | 29.07 | 37.422 |
| 14 | 27.269 | 27.72 | 25.2405 | 38.766 | 29.106 | 29.106 |
| 18 | 13.8355 | 36.686 | 20.8035 | 27.255 | 28.44 | 28.116 |
| 21 | 18.63 | 22.62 | 0 | 19.7945 | 0 | 20.475 |
| 25 | 18.009 | 26.18 | 23.79 | 22.32 | 11.088 | 10.962 |
| 28 | 14.413 | 40.95 | 21.168 | 37.026 | 28.49 | 39.368 |
| 32 | 45.2965 | 74.493 | 0 | 24.36 | 28.86 | 14.64 |
| 36 | 36.6825 | 96.148 | 34.02 | 22.01 | 0 | 16.896 |
| 42 | 23.94 | 74.8 | 30.016 | 41.616 | 0 | 16.775 |
| Unconjugated mixture | | | | | | |
| 2 | 46.512 | 52.65 | 65.934 | 51.714 | 51.205 | 67.068 |
| 4 | 37.185 | 26.88 | 36.96 | 39.347 | 38.08 | 37.488 |
| 7 | 35.644 | 44.968 | 40.32 | 39.9 | 45.54 | 43.2 |
| 11 | 54.32 | 37.422 | 54 | 43.12 | 44.968 | 34.125 |
| 14 | 41.208 | 30.66 | 51.264 | 49.217 | 55.48 | 34.684 |
| 18 | 36.92 | 44.156 | 227.476 | 203.463 | 250.908 | 58.32 |
| 21 | 44.625 | 25.3125 | 601.965 | 563.64 | 494.125 | 26.04 |
| 25 | 169.32 | 38.25 | 686.28 | 944.58 | 532.35 | 44.064 |
| 28 | 180.5 | 63.882 | 757.68 | 1387.2 | 513.188 | 131.648 |
| 32 | 360.47 | 73.44 | | | 697.6375 | 393.12 |
| 36 | 356.16 | 91.047 | | | 1130.96 | 766.233 |
| 42 | 519.294 | 57.646 | | | | |
| PBS | | | | | | |
| 2 | 40.052 | 49.928 | 36.4 | 45.369 | 58.8 | 44.384 |
| 4 | 37.8 | 25.62 | 39.69 | 34.6385 | 62.123 | 25.56 |
| 7 | 32.319 | 36.652 | 33.744 | 43.911 | 67.716 | 51.128 |
| 11 | 27.702 | 39.36 | 40.664 | 63.121 | 54.614 | 57.4275 |
| 14 | 35.6655 | 35.438 | 18.4 | 41.7075 | 37.296 | 30.03 |
| 18 | 143.64 | 156.8 | 54.648 | 92.4 | 104.4 | 37.31 |
| 21 | 379.008 | 157.32 | 375.417 | 597.1875 | 297.54 | 54.1875 |
| 25 | 427.68 | 121.968 | 701.22 | 702.1 | 810.16 | 48.048 |
| 28 | 842.996 | 209.088 | 1163.986 | 1098.2 | 963.746 | 48.96 |
| 32 | | 493.476 | | | | 92.4 |
| 36 | | 921.6 | | | | 157.32 |
| 42 | | | | | | 253.376 |

Example 4: Synthesis of Second Generation P-Linker Compounds

In this example, we have designed and synthesized a second generation P-linker compound, which showed significantly improved activity compared to the first generation P-linkers in the PSMA enzyme inhibition assay. The in vitro and in vivo efficacy and PK of the second generation P-linker compound is evaluated as described above.

An orthotopic prostate cancer xenograft model in immunodeficient mice (NOD/SCID gamma) allows us monitor the migration and penetration of adoptively transferred human T-cells into tumors in the prostate gland. An isograft prostate cancer model in immunocompetent mice to is also utilized to further examine the in vivo activity and safety of targeting agent antibody conjugate. For that purpose, a mouse prostate cancer cell line, RM-1-hPSMA, which is syngeneic in B6 mice is used. To recruit mouse T-cells, a mouse specific αCD3 Fab (2C11) is conjugated with P-linkers as described above. Importantly, mPSMA strongly binds DUPA (the parent enzyme inhibitor of P-linkers) which enables assessment of efficacy and safety in mice. The pharmacokinetics and safety of P-targeting agent antibody conjugate is evaluated in a non-human primate, cynomolgus macaque (cyno) model. In previous reports, glutamate carboxy peptidase activity of cynoPSMA was efficiently inhibited by substrate analogue inhibitors (such as DUPA) and therefore should have high affinity to our DUPA-linker. A cynomolgus monkey/human cross reactive targeting agent antibody conjugate is prepared by the conjugation of DUPA-linker to a high affinity human/cynomolgus cross-reactive αCD3 Fab (SP34). The goal of these studies is to provide the requisite information to guide a Phase I dose escalating study in humans.

Figure 13:
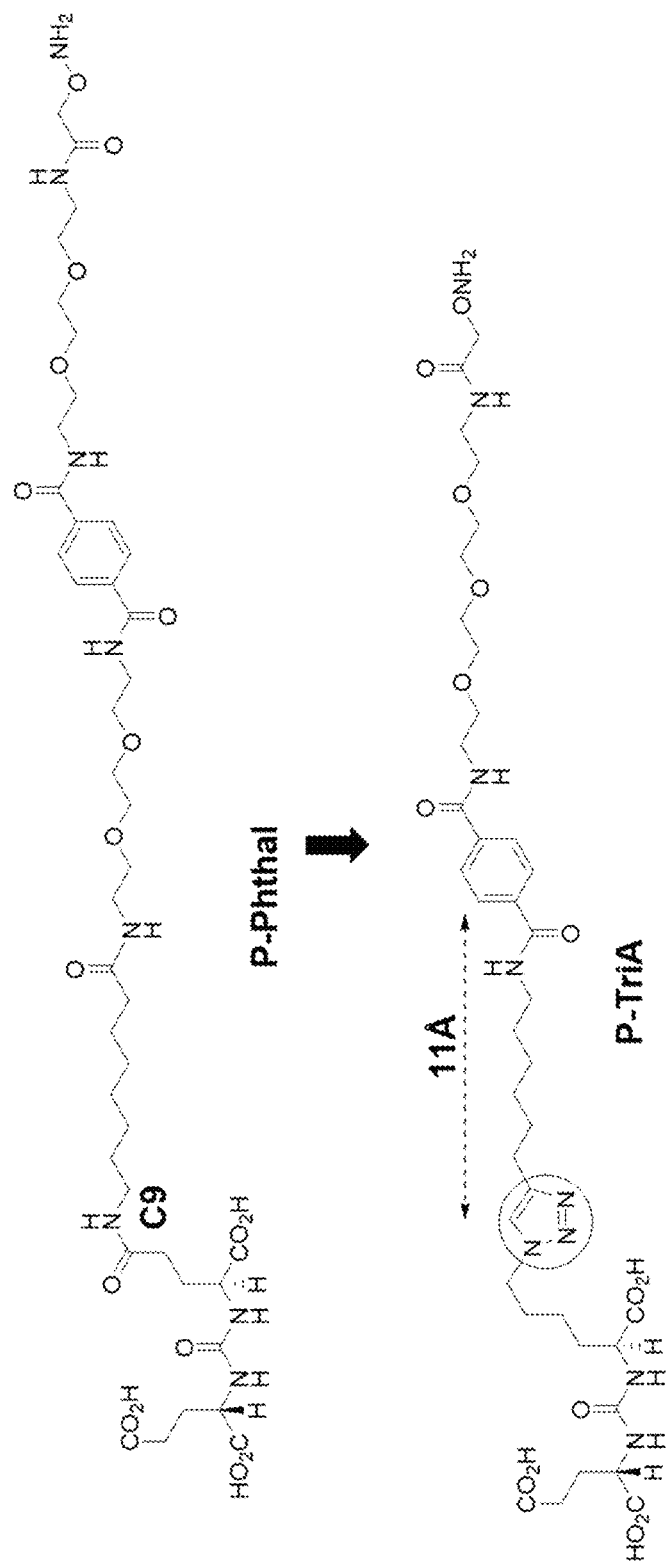
FIG. 13 depicts the design of the second-generation PSMA targeting compound, P-TriA. The amide group at C-9 position in P-Phthal was changed to a triazole group to increase the affinity with a hydrophobic pocket near the PSMA enzyme active site. Based on the distance between the first and second hydrophobic binding pocket (~11 Å) in the crystal structure, shorter hydrocarbon linker was introduced before the phthalimide group.
Figure 14:
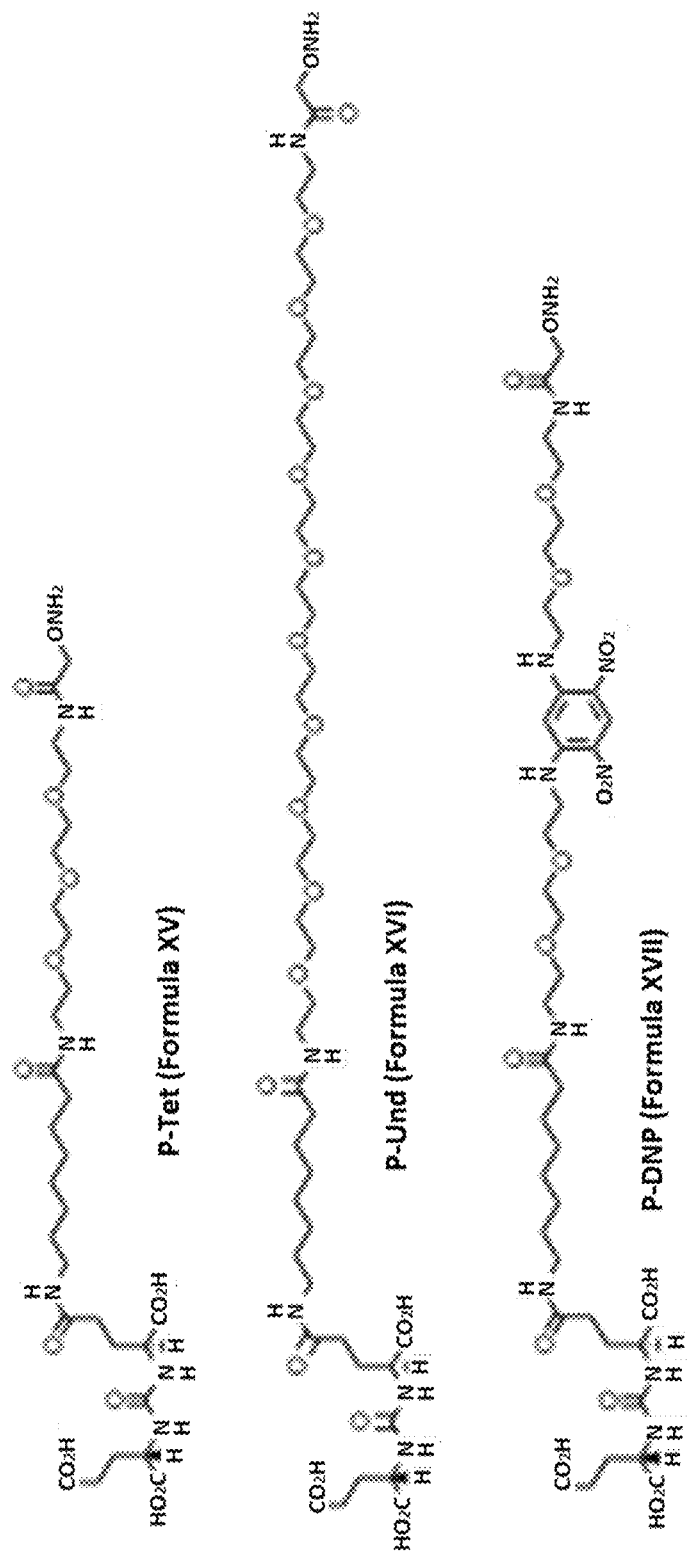
FIG. 14 depicts the chemical structures of P-Tet, P-Und, and P-DNP.

Example 5: Complete Structure-Activity Relationship Study to Determine Optimal Targeting Agent Antibody Conjugate Candidate We have found that the affinity of P-linker compounds significantly affects target cell binding of the resulting P-targeting agent antibody conjugates, which in turn affect their cytotoxic activity in cell-based assays. To further improve the affinity of P-linker, we re-examined previous structure-activity relationship (SAR) data and the co-crystal structures of PSMA-inhibitor complexes. Based on the analysis, we designed a second generation P-linker candidate, P-TriA (FIG. 15J Compound 14), in which the C-9 amide group in P-Phthal is substituted with a triazole linkage, and a shorter linear hydrocarbon linker was used to connect two hydrophobic aromatic groups, triazole and phthalimide groups (FIG. 13).

PSMA Inhibition Assay

A 10 mM solution of N-acetyl-aspartyl-glutamate (NAAG) in 40 mM NaOH was diluted to 40 μM in Reaction Buffer (0.1 M Tris-HCl, pH=7.5), and the solution was added to a 384 well plate (10 μL per well). For $K_M$ measurements and $K_M$ negative controls (absence of PSMA), the NAAG solution was serially diluted 2-fold to obtain final NAAG concentrations ranging 40 μL-312.5 nM. For $IC_{50}$ measurements, the targeting agent PSMA inhibitors in Reaction Buffer containing 40 NM NAAG solution was serially diluted 5-fold to obtain final inhibitor concentrations ranging 100 μL-51.2 pM. To initiate reactions, 10 μL of rhPSMA (20 M in Reaction Buffer, R&D research) was added to each well. Reaction Buffer (10 μL) was added to the $K_M$ control series. The plate was incubated at 37° C. for 30 min, and then heated to 95° C. for 3 min. Levels of glutamic acid were quantified using Amplex® Red Glutamic Acid/Glutamate Oxidase Assay Kit (Invitrogen). Fluorescence intensities were measured using a SpectraMax Gemini EM microplate reader (GMI) with excitation and emission filters of 545 and 590 nm, respectively. Ki values were calculated using the Cheng-Prusoff equation from $IC_{50}$ and $K_M$ values and these values were calculated using GraphPad Prism software. $K_M$ value (0.288 μM) is consistent with that reported in the literature (Humblet, V.; Misra, P.; Bhushan, K. R.; Nasr, K.; Ko, Y.-S.; Tsukamoto, T.; Pannier, N.; Frangioni, J. V.; Maison, W. *J. Med. Chem.* 2009, 52, 544-550). All reported data represent the mean of triplicate experiments.

Figure 16A:
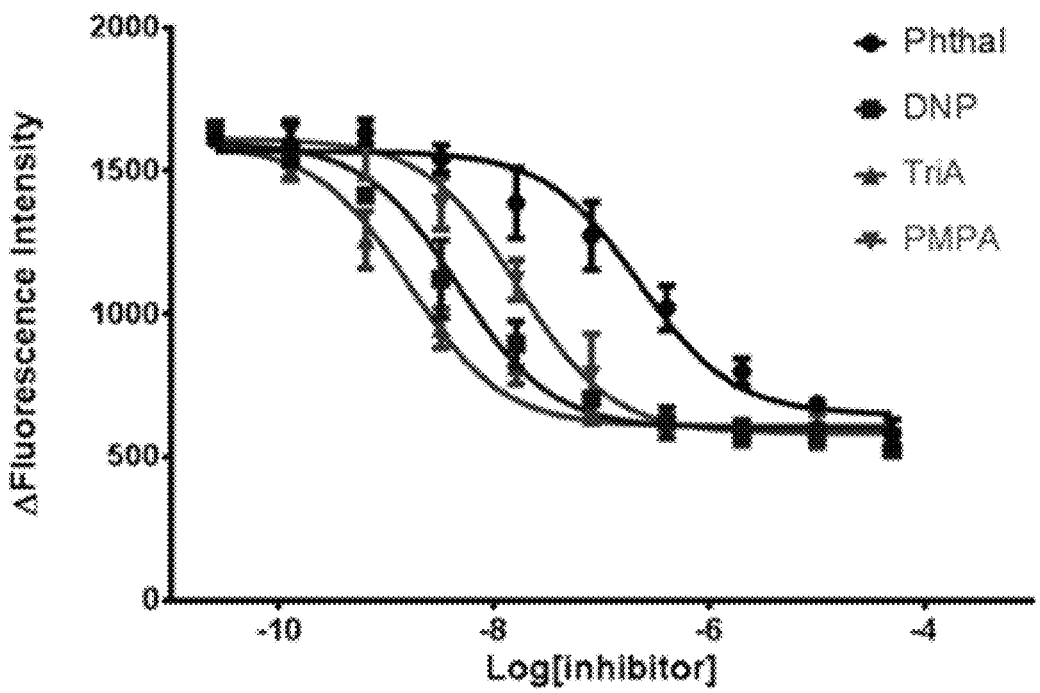
FIG. 16A-B depict the results of a PSMA inhibition assay. (A) depicts representative PSMA inhibition curves by different inhibitors. (B) depicts a Km curve obtained from PSMA inhibition assay.

FIG. 16A and Table 4 depict a representative PSMA inhibition curve by different inhibitors (P-Pthal, P-DNP, and P-TriA). The known PSMA inhibitor PMPA was used as a control for the experiment.

TABLE 4

PSMA Inhibition Assay

| [μM] | Relative Fluorescence Units | | | |
|---|---|---|---|---|
| | Phthal | DNP | TriA | PMPA |
| 50 | 581.035 | 525.6755 | 559.8246667 | 549.6583333 |
| 10 | 688.1815 | 581.8336667 | 599.969 | 567.78 |
| 2 | 798.8586667 | 586.843 | 562.8576667 | 599.2116667 |
| 0.4 | 1021.402333 | 622.7463333 | 586.721 | 651.3216667 |
| 0.08 | 1273.804667 | 704.2426667 | 664.949 | 787.839 |
| 0.016 | 1387.603 | 896.7893333 | 817.1303333 | 1118.747667 |
| 0.0032 | 1542.606 | 1123.0625 | 950.487 | 1386.251333 |
| 0.00064 | 1633.913 | 1413.9875 | 1259.409667 | 1575.243667 |
| 0.000128 | 1592.5445 | 1558.430667 | 1499.6145 | 1633.926333 |
| 0.0000256 | 1608.653333 | 1650.519 | 1618.877333 | 1622.5365 |

Figure 16B:
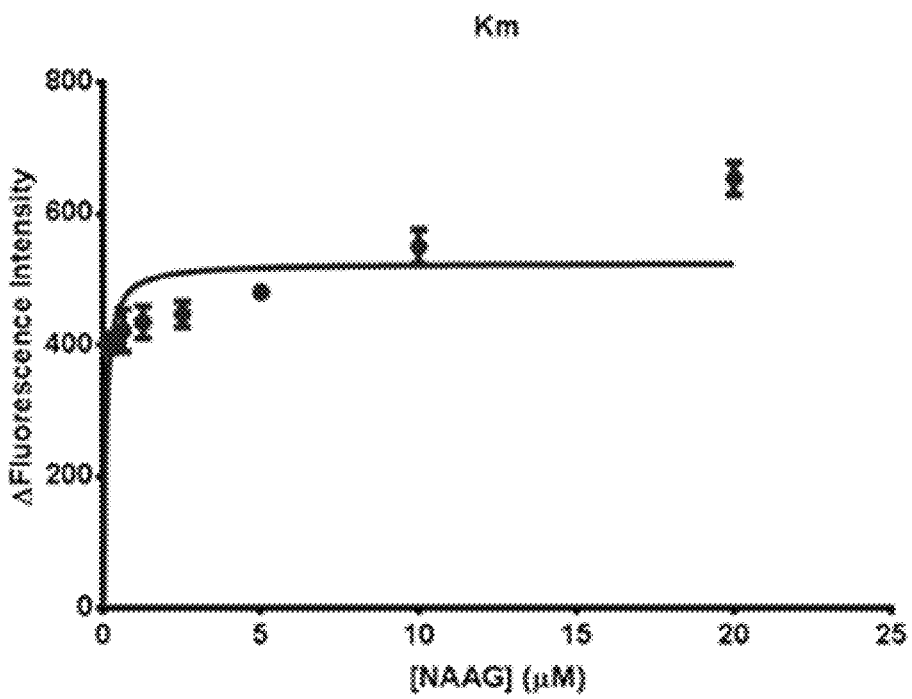

FIG. 16B and Table 5 depict Km curve obtained from the same experiment described in FIG. 16A and Table 4.

TABLE 5

$K_M$ measurement

| NAAG [μM] | RFU |
|---|---|
| 20 | 653.474 |
| 10 | 549.5883333 |
| 5 | 480.622 |
| 2.5 | 446.9936667 |
| 1.25 | 434.8145 |
| 0.625 | 422.2223333 |
| 0.3125 | 400.6455 |
| 0.15625 | 403.0393333 |

As shown in Table 6, the enzyme-based inhibition assay revealed more than 400-fold enhanced affinity for the P-TriA (average Ki=4.8 pM) compared to P-Phthal (average Ki=2 nM).

TABLE 6

| Trial | Phthal $IC_{50}$ (Ki) | DNP $IC_{50}$ (Ki) | TriA $IC_{50}$ (Ki) | PMPA $IC_{50}$ (Ki) | Km |
|---|---|---|---|---|---|
| 1 | $2.08 \times 10^{-7}$M ($2.95 \times 10^{-9}$M) | $7.28 \times 10^{-9}$M ($2.95 \times 10^{-10}$M) | $1.62 \times 10^{-10}$M ($2.30 \times 10^{-12}$M) | $1.11 \times 10^{-8}$M ($1.58 \times 10^{-10}$M) | $2.88 \times 10^{-7}$M |
| 2 | $3.97 \times 10^{-7}$M ($2.15 \times 10^{-9}$M) | $4.46 \times 10^{-9}$M ($2.42 \times 10^{-11}$M) | $1.09 \times 10^{-9}$M ($5.91 \times 10^{-12}$M) | $2.48 \times 10^{-8}$M ($1.34 \times 10^{-10}$M) | $1.09 \times 10^{-7}$M |
| 3 | $2.23 \times 10^{-7}$M ($8.39 \times 10^{-10}$M) | $4.58 \times 10^{-9}$M ($1.72 \times 10^{-11}$M) | $1.63 \times 10^{-9}$M ($6.13 \times 10^{-12}$M) | $1.66 \times 10^{-8}$M ($6.24 \times 10^{-11}$M) | $7.55 \times 10^{-7}$M |
| Average Ki | $1.98 \times 10^{-9}$M | $4.82 \times 10^{-11}$M | $4.78 \times 10^{-12}$M | $1.18 \times 10^{-10}$M | |

In Vitro Cytotoxicity Assays

Peripheral blood mononuclear cells (PBMCs) were purified from fresh healthy human donor blood by conventional Ficoll-Hypaque gradient centrifugation. Purified PBMCs were washed and incubated in flasks in RPMI media with 10% FBS for 1 hours to remove any adherent cells. C4-2 (PSMA+) cells (target cells) were dissociated with 0.05% tryspin/EDTA solution (HyClone) and washed with RPMI with 10% FBS. $1 \times 10^4$ target cells were mixed with PBMCs at 1:10 ratio in 100 mL, and incubated with different concentrations of conjugated and unconjugated Fabs (10 mL in PBS) for 24 and 48 hours at 37° C. Cytotoxicity of each well was measured for LDH (lactate dehydrogenase) levels in supernatant using Cytotox-96 non-radioactive cytotoxicity assay kit (Promega). Lysis solution (10 mL, provided in the same kit) was added to wells with only target cells to get the maximum killing, and spontaneous killing was measured from wells with effector and target cells treated with vehicle (10 mL PBS). The absorbance at 490 nm was recorded using SpectraMax 250 plate reader (Molecular Devices Corp.). Percent cytotoxicity was calculated by:

$$\% \text{ Cytotoxicity} = (\text{Absorbance}_{expt} - \text{Absorbance}_{spontaneous\ average}) / (\text{Absorbance}_{max\ killing\ average} - \text{Absorbance}_{spontaneous\ average}) \times 100$$

Figure 17A:
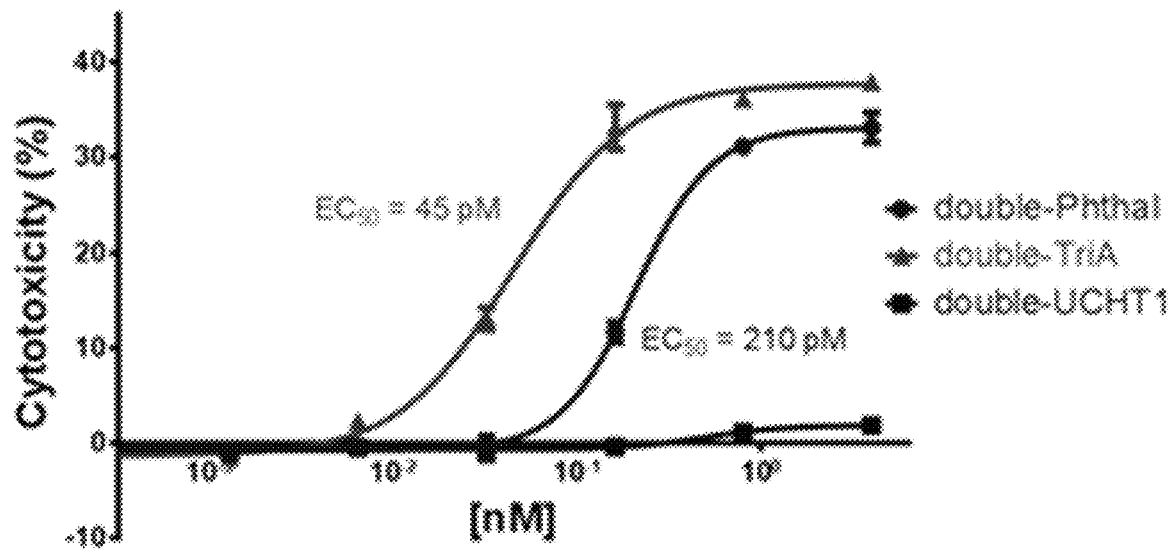
FIG. 17A-B depict the results of in vitro cytotoxicity assays in C4-2 cells at 24 hours and 48 hours.
Figure 17B:
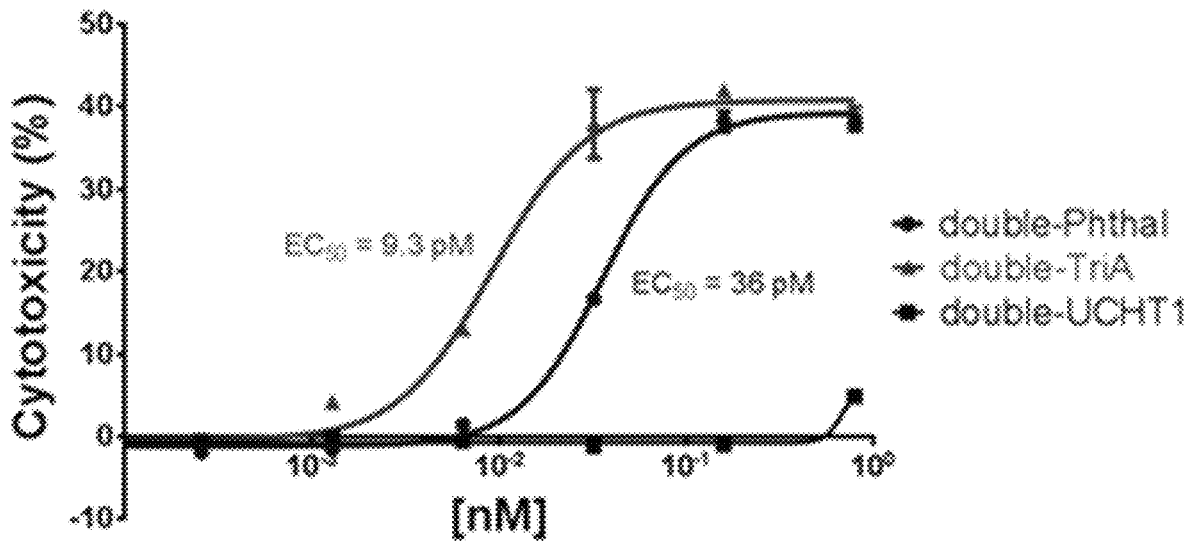
Figure 18A:
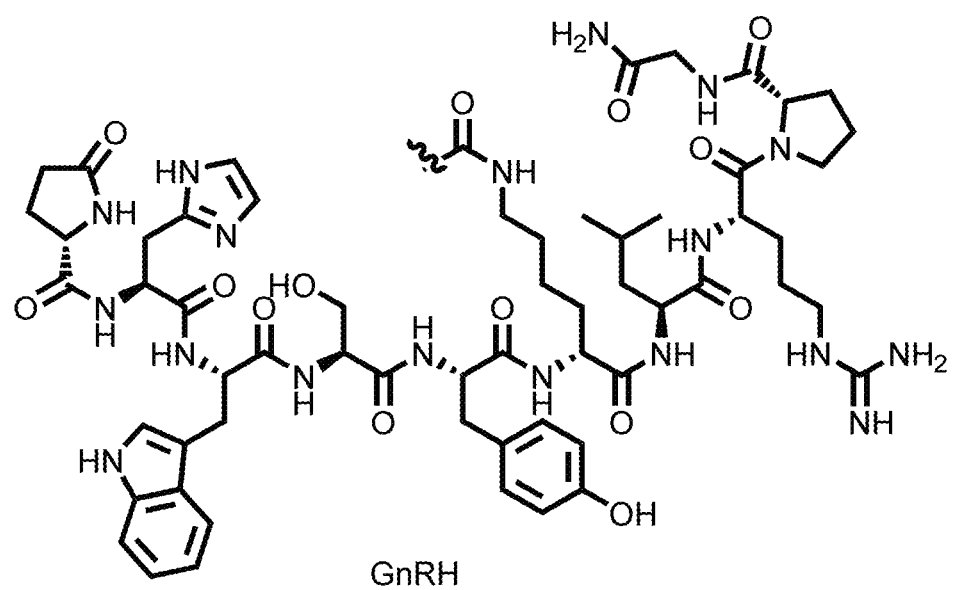
FIG. 18A-F depict structures of exemplary targeting agents.
Figure 18B:
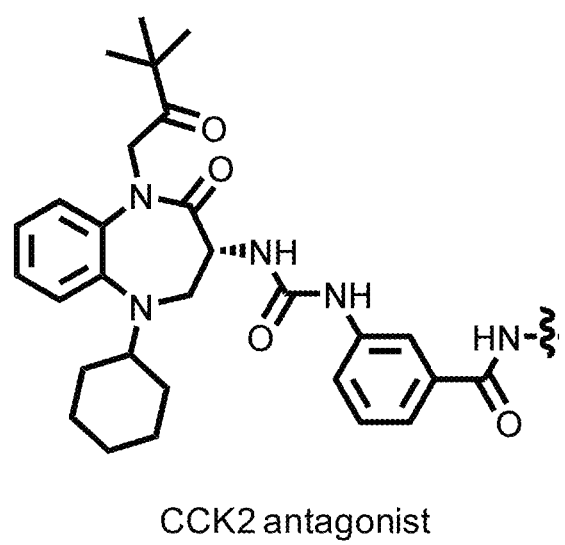
Figure 18C:
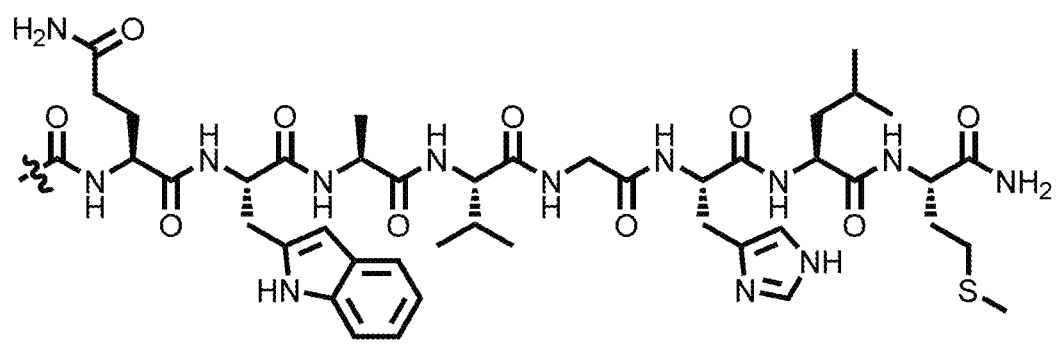
Figure 18D:
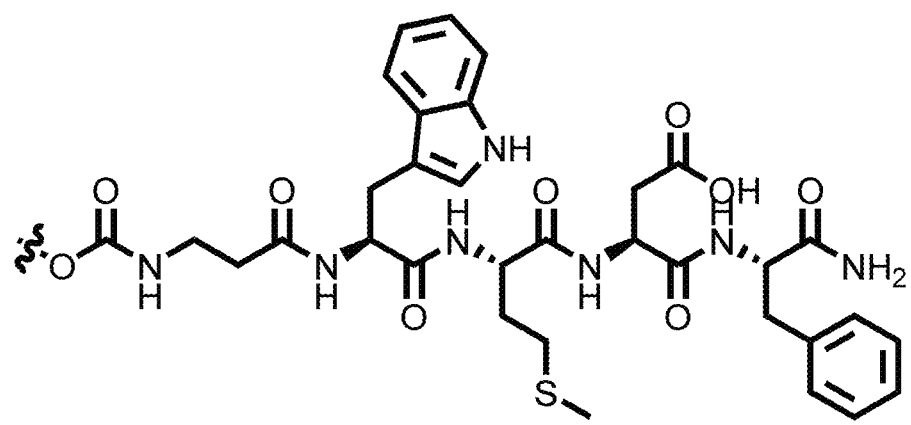
Figure 18E:
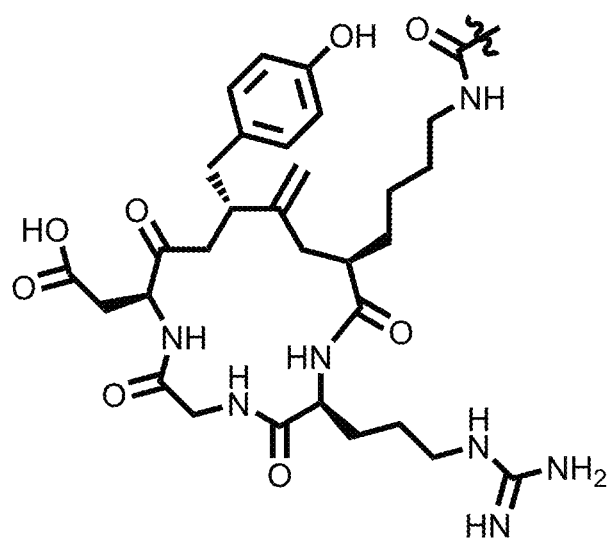
Figure 18F:
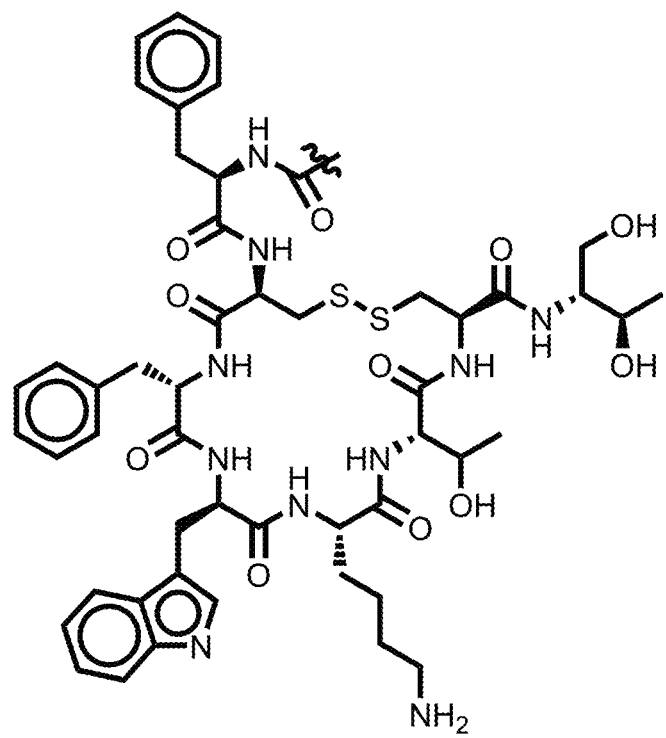

FIG. 17A-B shows the cytotoxicity at 24 hours and 48 hours, respectively. Table 7 shows the numerical values of the graphs depicted in FIG. 17A-B.

TABLE 7

In vitro cytotoxicity assay

| | % Cytotoxicity | | |
|---|---|---|---|
| [pM] | double-Phthal conjugate | double-TriA conjugate | wt-UCHT1 |
| | 24 h | | |
| 0 | 0 | 0 | 0 |
| 0.0512 | −0.892388451 | −1.319308255 | −0.175284838 |
| 0.256 | −0.699912511 | −1.604564093 | −0.876424189 |
| 1.28 | −0.699912511 | −1.497593154 | −0.911481157 |
| 6.4 | −0.31496063 | 2.31770369 | −0.473269062 |
| 32 | −0.472440945 | 13.06828312 | −0.753724803 |
| 160 | 11.65354331 | 33.17881975 | −0.403155127 |
| 800 | 31.14610674 | 36.14726333 | 1.191936897 |
| 4000 | 33.14085739 | 37.93902656 | 1.858019281 |
| | 48 h | | |
| 0 | 0 | 0 | 0 |
| 0.01024 | −1.277711965 | −1.636828645 | −0.608963949 |
| 0.0512 | −0.913860213 | −1.227621483 | −1.023059435 |
| 0.256 | −1.827720426 | −1.585677749 | −0.519649237 |
| 1.28 | −1.523100355 | 4.228473998 | −0.081195193 |
| 6.4 | 1.455407006 | 13.04347826 | −0.487171159 |
| 32 | 16.68641056 | 37.92838875 | −1.104254628 |
| 160 | 38.26366559 | 42.01193521 | −0.941864242 |
| 800 | 38.09443222 | 38.72122762 | 4.871711595 |

In another experiment, P-TriA is conjugate to αCD Fab to generate a second generation P-targeting agent antibody conjugate. The in vitro activity and in vivo PK and efficacy of the second generation P-targeting agent antibody conjugate is compared with the first generation P-targeting agent antibody conjugate. The in vitro efficacy of the targeting agent antibody conjugate using other human PSMA-positive prostate cancer cell lines including 22Rv1 and PC-3-huPSMA is also evaluated. In addition, the activity of the targeting agent antibody conjugate is also tested in patient-derived prostate cancer tissue. The published tissue-specificity of the P-linker moiety using a corresponding fluorescein isothiocyanate (FITC) conjugate and frozen tissue microarray (Asterand) may also be confirmed. In addition to the subcutaneous xenograft model described above, the optimal P-targeting agent antibody conjugate construct in an orthotopic prostate cancer model, which more closely mimics the specific tumor microenvironment of the prostate gland, may also be determined. In order to determine the optimal P-targeting agent antibody conjugate construct, a luciferized prostate cancer cell line (LNCaP-Luc) is used to monitor tumor growth and regression by bioluminescence imaging. On day 0, cancer cells ($1.0 \times 10^6$ cells) are injected in the posterior prostatic lobe in 6-week old NSG mice. After two weeks, freshly purified hPBMCs are intraperitoneally injected. Tumor growth is monitored twice per week and increases in tumor bioluminescence are expected to be observed around 4-week post tumor implantation. Prior to starting treatment, mice are bled and correct immune reconstitution is assessed by detecting human T cells in periphery using FACS. During treatment, 0.2-1 mg/kg of P-targeting agent antibody conjugate is intravenously administered daily for up to 10 days. Tumor growth is monitored up to 8 weeks. IHC studies are performed to detect infiltrated T-cells in the prostate gland.

Example 6: Safety and Efficacy Studies in Immunocompetent Mice

In order to accurately assess drugs and to optimize the treatment protocol, a mouse surrogate P-targeting agent antibody conjugate that may recognize mouse T cells is generated. A hamster monoclonal 145-2C11 that binds mouse CD3 (this antibody also binds epsilon subunit as UCHT1 does) is used in the generation of the mouse surrogate P-targeting agent antibody conjugate. The variable region sequence of 145-2C11 was obtained from the literature, and the synthetic gene is cloned into the pBAD expression vector to express pAcF-containing Fab in E. coli. We are confirming the binding of m-P-targeting agent antibody conjugate using FACS and its in vitro activity is measured using purified mPBMCs. Our P-linker moieties are based on the hPSMA enzyme inhibitors, which have shown similar activity against various PSMAs from different origins including mouse, rat, dog, and monkey. Therefore the optimized DUPA-linker compound we developed in previous studies may be directly conjugated to an anti-m-CD3 antibody to quickly generate the mouse surrogate version of P-targeting agent antibody conjugate (mP-targeting agent antibody conjugate). However, unlike human, the expression levels of mPSMA in normal mouse prostate tissues are very low, and over-expression in known mouse prostate cancer cell lines is controversial. To mimic the human PSMA expression levels, therefore, we are using the mouse prostate cancer cell line RM-1 that is stably transduced with human PSMA (RM-1-hPSMA). The parent RM-1 cell line is MHC 1-deficient and syngeneic in C57BL/6 (B6) mice and it is known that RM-1-hPSMA also grows well in immunocompetent B6 mice. We may first confirm the in vitro activity of mP-targeting agent antibody conjugate against RM-1-hPSMA in the presence of mPBMCs. We may then measure the pharmacokinetic parameters, which together with the in vitro activity experiments determine the dosing paradigm for the efficacy studies. For in vivo studies, we are orthotopically injecting $0.5 \times 10^6$ RM-1-hPSMA cells into B6 mice. At ~day 10, when the tumors reach ~200 mm³, mice are treated by intravenously injecting mP-targeting agent antibody conjugate. We determine the minimal efficacious dose, optimal dosing frequency, and maximum tolerated dose. We also assess the immuno-toxicity of mP-targeting agent antibody conjugate in B6 mice in various organs (e.g., brain, liver, heart, kidneys, spleen, lung, etc.). Of note, although there has been no direct comparison, some reports suggest that there are significant amounts of mPSMA expressions in mouse kidney compared with human, which should be considered during the assessment of kidney toxicity. Body weight, elevated cytokine levels (TNF-α, IFN-γ, IL-6, IL-2 etc.), and activation status of T-cells (CD69 and CD25-positive) are measured during the treatment to monitor the dose-related side effects such as cytokine release syndrome in mice. We believe the dose dependent efficacy data together with the maximum tolerated dose and pharmacokinetic parameters determined in this study provides guidance for a safe starting dose in the non-human primate study, as well as a better estimate of the efficacious dose in man.

Example 7. Generation of a Human/Cynomolgus Monkey Cross-Reactive P-Targeting Agent Antibody Conjugate and Safety Studies in Non-Human Primates We are evaluating the pharmacokinetics and safety of P-targeting agent antibody conjugate in a non-human primate, cynomolgus macaque (cyno) model. Unfortunately, we have determined that the UCHT1 is not sufficiently cyno cross-reactive to allow safety assessment in NHPs. Therefore a human/cynomolgus monkey cross-reactive P-targeting agent antibody conjugate (cyP-targeting agent antibody conjugate) is prepared by the conjugation of the P-linker to human/cynomolgus cross-reactive αCD3 Fab (SP34), which also binds the CD3 epsilon chain with high affinity (Kd=4 nM). As SP34 is originally derived from mouse, we are making a chimeric or humanized version of SP34. As discussed above, our P-linker compound should have similar affinity with cyno-PSMAs. We confirm the binding with CHO cells transfected with cynoPSMA. In vitro cytotoxicity against C4-2 cells is measured in the presence of cyPBMCs. We also perform similar in vitro cytotoxicity assays using purified human and cyno T-cells, and compare their responses (magnitude of target cell lysis, efficacy, T-cell activation status, and cytokine release). We also assess the efficacy of the bispecific in the rodent C4-2 xenograft model and carry out PK, dose escalation and dose frequency studies as described above.

For the in vivo NHP PK studies, male cynomolgus monkeys intravenously receive vehicle control or cyP-targeting agent antibody conjugate. Blood samples be collected at regular time points to determine PK parameters. We are using the cyno PK data together with the rodent PK, safety and efficacy study data to design an ascending dose cyno safety study, where groups of three male cynomolgus monkey intravenously receive different amounts of cyP-targeting agent antibody conjugate up to three weeks (with Charles River, SNBL, or Covance). During the safety study, animals are observed for mortality or moribundity as well as clinical signs or reactions to treatment. Other analyses are conducted including body temperature, ophthalmology, body weight, food consumption, cardiovascular function, hematology, coagulation, serum chemistry, urine analysis, lymphocyte subtyping (FACS), cytokine release, and toxicokinetics. Serum is also prepared for measuring serum concentration levels of cyP-targeting agent antibody conjugate and for immunogenicity evaluation. After treatment, tissues and organs from animals are subjected to a thorough macroscopic assessment as well as histopathological examination. The goal of these studies and the rodent studies is to provide the requisite data for a Phase I dose escalating study in humans.

Example 8: Targeting Agent Antibody Conjugate Production Optimization, Stability Tests, and Development of Bioanalytical Methods In this example, we are developing an optimized protocol for the production of P-targeting agent antibody conjugate to provide enough material for the studies disclosed herein. The humanized SP34 sequence is sub-cloned into different types of fermentation vectors to screen for optimal inducible systems. We also optimize *E. coli* cell strains as well as other fermentation parameters and determine the stability of the expression system. Antibodies from fermentation batches are compared with ones from previous small-batch expression to ensure their purity and activity. Targeting agent conjugation conditions (temperature, pH, concentrations, and ligand-to-antibody ratio) are optimized for large-scale reactions. Alternative purification methods are tested to readily remove excess targeting agents after the large-scale conjugation. We test the serum stability of P-targeting agent antibody conjugate by incubation in pooled human serum at 37° C. under sterile conditions. Aliquots are analyzed at timed intervals for the concentration of intact P-targeting agent antibody conjugate and degradation products (e.g., free DUPA-linkers) by LS-MS. In vitro cytotoxicity is also performed to determine the concentrations of functionally active P-targeting agent antibody conjugate in serum. The thermal stability profile is assessed by differential scanning calorimetry (DSC) to determine the $T_m$ of the P-targeting agent antibody conjugate compared with the parent SP34. Long-term stability is tested at 4° C. over at least 2 months at different concentrations (1-50 mg/ml) in various pre-formulation buffers. We are also developing bioanalytical methods to more accurately determine pharmacokinetic parameters of P-targeting agent antibody conjugate. In pharmacokinetic studies, to only detect functionally intact P-targeting agent antibody conjugate s, huPSMA-coated ELISA plates are used to capture P-targeting agent antibody conjugate in serum followed by incubation with purified CD3 epsilon chain with hexahistidine tag (His-tag) (SEQ ID NO: 41). After incubation with secondary αHis-Tag antibodies conjugated with horse radish peroxidase, signals are visualized using a chemiluminescent kit. For immunogenicity studies, P-targeting agent antibody conjugate is covalently immobilized to a sensor chip, and serum antibody responses against P-targeting agent antibody conjugate is analyzed by surface plasmon resonance (SPR) detection. The specificity of binding to P-targeting agent antibody conjugate observed in serum samples is confirmed by competition experiments using free P-targeting agent antibody conjugate.

Example 9: Synthesis of (S)-2-(3-((S)-5-(4-(6-(4-(1-(aminooxy)-2-oxo-6,9,12-trioxa-3-azatetradecan-14-ylcarbamoyl)benzamido)hexyl)-1H-1,2,3-triazol-1-yl)-1-carboxypentyl)ureido)pentanedioic acid (P-TriA)

Synthesis of (10S,14S)-tri-tert-butyl 2,2-dimethyl-4,12-dioxo-3-oxa-5,11,13-triazahexadecane-10,14,16-tricarboxylate As shown in the reaction scheme depicted in FIG. 15A, to a solution of 1 (5.83 g, 19.7 mmol) in $CH_2Cl_2$ (150 mL) was added triphosgene (2.92 g, 9.85 mmol). The reaction mixture was cooled to −78° C. and slowly added Et$_3$N (27.5 mL, 0.197 mol). After the reaction mixture was stirred for 1 h at ambient temperature, a solution of 2 (Maindron, N.; Poupart, S.; Hamon, M.; Langlois, J.-B.; Ple, N.; Jean, L.; Romieu, A.; Renard, P.-Y. *Org. Biomol. Chem.*, 2011, 9, 2357-2370) in CH$_2$Cl$_2$ (10 mL) added. After stirring for 14 h at ambient temperature, the reaction mixture was quenched with saturated aq. NH$_4$Cl. The aqueous layer was extracted with CH$_2$Cl$_2$ and the combined organic layers were dried over MgSO$_4$ and concentrated in vacuo. The residue was purified by flash column chromatography on silica gel (EtOAc:n-hexane=1:3) to afford 11.2 g (97%) of 3 as a pale yellow oil: R 0.5 (EtOAc:n-hexane=1:2); $^1$H NMR (400 MHz, CDCl$_3$) δ 5.50 (d, 1H, J=8.3 Hz), 5.46 (d, 1H, J=8.0 Hz), 5.01 (s, 1H), 4.31 (m, 2H), 3.04 (m, 2H), 2.26 (m, 2H), 2.03 (m, 1H), 1.83 (m, 1H), 1.70 (m, 1H), 1.58 (m, 1H), 1.41 (s, 9H), 1.40 (s, 9H), 1.39 (s, 9H), 1.38 (s, 9H), 1.32 (m, 4H); LR-MS (ESI+) m/z 588 (M+H$^+$).

Figure 15A:
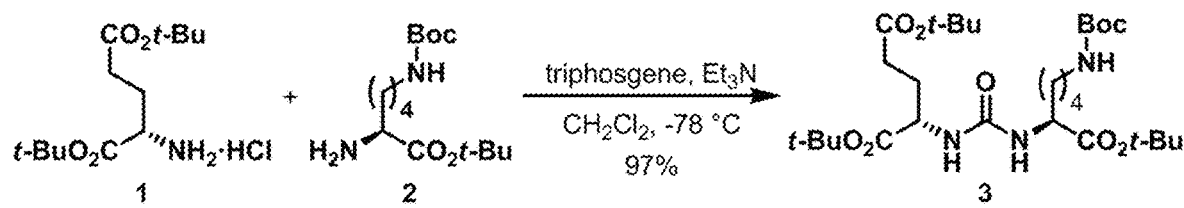
FIG. 15A-J depict reaction schemes for the synthesis of (S)-2-(3-((S)-5-(4-(6-(4-(1-(aminooxy)-2-oxo-6,9,12-trioxa-3-azatetradecan-14-ylcarbamoyl)benzamido)hexyl)-1H-1,2,3-triazol-1-yl)-1-carboxypentyl)ureido)pentanedioic acid (P-TriA).
Figure 15B:
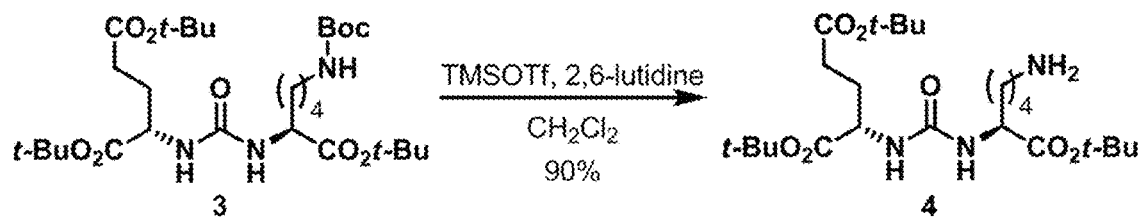

Synthesis of (S)-di-tert-butyl 2-(3-((S)-6-amino-1-tert-butoxy-1-oxohexan-2-yl)ureido)pentanedioate As shown in the reaction scheme depicted in FIG. 15B, to a solution of 3 (10.8 g, 18.4 mmol) in CH$_2$Cl$_2$ (100 mL) were added 2,6-lutidine (4.29 mL, 36.8 mmol) and TMSOTf (5.00 mL, 27.6 mmol) at 0° C. After stirring for 30 min at ambient temperature, the reaction mixture was quenched with MeOH and concentrated in vacuo. The residue was purified by flash column chromatography on silica gel (EtOAc:n-hexane=3:1 to MeOH:EtOAc=1:10) to afford 8.09 g (90%) of 4 as an yellow oil: R$_f$0.4 (MeOH:EtOAc=1:10); LR-MS (ESI+) m/z 488 (M+H$^+$).

Figure 15C:
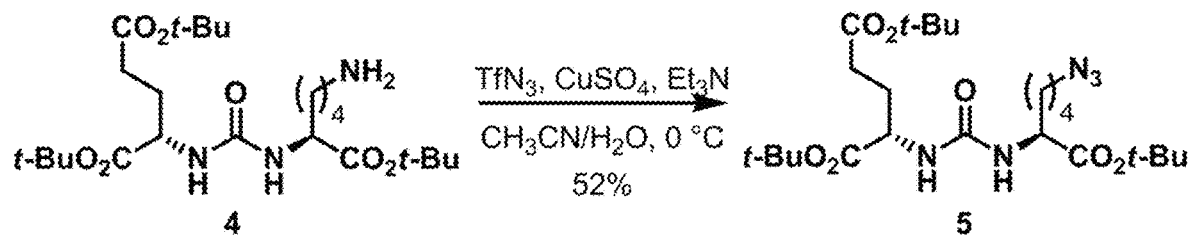

Synthesis of (S)-di-tert-butyl 2-(3-((S)-6-azido-1-tert-butoxy-1-oxohexan-2-yl)ureido)pentanedioate As shown in the reaction scheme depicted in FIG. 15C, to a solution of sodium azide (1.55 g, 23.8 mmol) in CH$_3$CN (30 mL) was added dropwise Tf$_2$O (3.20 mL, 19.0 mmol) at 0° C. After 1 h, to a solution of 4 (5.80 g, 11.9 mmol), Et$_3$N (4.98 mL, 35.7 mL) and CuSO$_4$ (38.0 mg, 0.238 mmol) in CH$_3$CN (mL) was added dropwise above the triflic azide solution at 0° C. After stirring for 14 h at ambient temperature, the reaction mixture was quenched with saturated aq. NH$_4$Cl. The aqueous layer was extracted with EtOAc and the combined organic layers were dried over MgSO$_4$ and concentrated in vacuo. The residue was purified by flash column chromatography on silica gel (EtOAc:n-hexane=1:3) to afford 3.20 g (52%) of 5 as white solid: R$_f$0.3 (EtOAc:n-hexane=1:2); $^1$H NMR (400 MHz, CDCl$_3$) δ 6.33 (s, 2H), 5.22 (m, 2H), 4.28 (m, 2H), 3.26 (t, 2H, J=6.8 Hz), 2.28 (m, 2H), 2.02 (m, 1H), 1.86 (m, 1H), 1.77 (m, 1H), 1.61 (m, 3H), 1.46 (s, 18H), 1.43 (s, 9H); LR-MS (ESI+) m/z 514 (M+H$^+$).

Synthesis of tert-butyl oct-7-ynylcarbamate

Figure 15D:
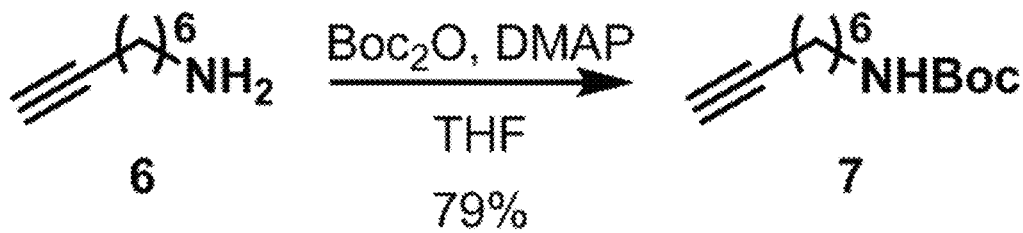

As shown in the reaction scheme depicted in FIG. 15D, to a solution of 6 (Coutrot, F.; Romuald, C.; Busseron, E. *Org. Lett.*, 2008, 10, 3741-3744) (101 mg, 0.807 mmol) in THF/H$_2$O (4/4 mL) were added NaHCO$_3$ (102 mg, 1.21 mmol) and Boc$_2$O (0.210 mL, 0.968 mmol). After stirring for 14 h at ambient temperature, the reaction mixture was quenched with saturated aq. NH$_4$Cl. The aqueous layer was extracted with EtOAc and the combined organic layers were dried over MgSO$_4$ and concentrated in vacuo. The residue was purified by flash column chromatography on silica gel (EtOAc:n-hexane=1:7) to afford 144 mg (79%) of 7 as a pale yellow oil: R$_f$0.5 (EtOAc:n-hexane=1:7); LR-MS (ESI+) m/z 226 (M+H$^+$).

Figure 15E:
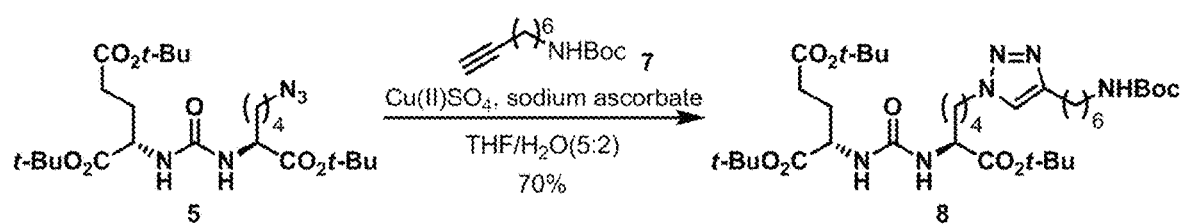

Synthesis of (S)-di-tert-butyl 2-(3-((S)-1-tert-butoxy-6-(4-(6-(tert-butoxycarbonylamino)hexyl)-1H-1,2,3-triazol-1-yl)-1-oxohexan-2-yl)ureido)pentanedioate As shown in the reaction scheme depicted in FIG. 15E, to a solution of 5 (770 mg, 1.25 mmol), 7 (309 mg, 1.37 mmol) and sodium ascorbate (99.1 mg, 0.500 mmol) in THF (20 mL) was added a solution of CuSO$_4$*H$_2$O (62.4 mg, 0.250 mmol) in H$_2$O (3.2 mL). After stirring for 30 min at ambient temperature, the aqueous layer was extracted with EtOAc and the combined organic layers were dried over MgSO$_4$ and concentrated in vacuo. The residue was purified by flash column chromatography on silica gel (EtOAc:n-hexane=2:1) to afford 644 mg (70%) of 8 as white solid: R$_f$0.3 (EtOAc:n-hexane=2:1); $^1$H NMR (400 MHz, CDCl$_3$) δ 5.28 (m, 2H), 4.57 (s, 1H), 4.30 (m, 4H), 3.08 (m, 2H), 2.67 (t, 2H, J=7.7 Hz), 2.30 (m, 2H), 2.04 (m, 2H), 1.89 (m, 2H), 1.78 (m, 2H), 1.64 (m, 3H), 1.44 (s, 9H), 1.41 (s, 27H), 1.37 (m, 8H); LR-MS (ESI+) m/z 739 (M+H$^+$).

Figure 15F:
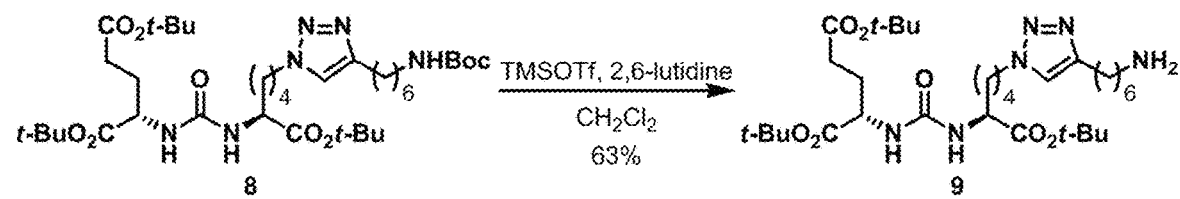

Synthesis of (S)-di-tert-butyl 2-(3-((S)-6-(4-(6-aminohexyl)-1H-1,2,3-triazol-1-yl)-1-tert-butoxy-1-oxohexan-2-yl)ureido)pentanedioate As shown in the reaction scheme depicted in FIG. 15F, to a solution of 8 (644 mg, 0.872 mmol) in CH$_2$Cl$_2$ (10 mL) were added 2,6-lutidine (0.200 mL, 1.74 mmol) and TMSOTf (0.240 mL, 1.31 mmol) at 0° C. After stirring for 30 min at ambient temperature, the reaction mixture was quenched with MeOH and concentrated in vacuo. The residue was purified by flash column chromatography on silica gel (EtOAc:n-hexane=3:1 to MeOH:EtOAc=1:10) to afford 351 mg (63%) of 9 as an yellow oil: R$_f$0.2 (MeOH:EtOAc=1:10); LR-MS (ESI+) m/z 639 (M+H$^+$).

Figure 15G:
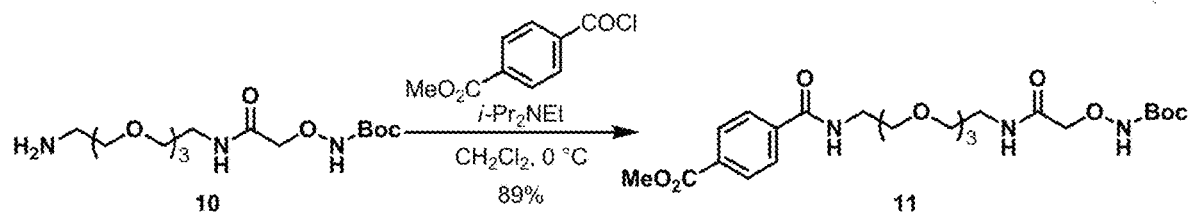

Synthesis of methyl 4-(2,2-dimethyl-4,8-dioxo-3,6,12,15,18-pentaoxa-5,9-diazaicosan-20-ylcarbamoyl)benzoate As shown in the reaction scheme depicted in FIG. 15G, to a solution of 10 (Hagemeyer, C; Peter, K.; Johnston, A. P. R.; Owen, D. PCT Int. Appl. WO 2012142659 A1, 2012) (74.5 mg, 0.209 mmol) in CH$_2$Cl$_2$ (5 mL) were added i-PrNEt (54.7 μL, 0.314 mmol) and 4-(chlorocarbonyl)benzoic acid methyl ester (125 mg, 0.627 mmol) at 0° C. After stirring for 12 h at ambient temperature, the reaction mixture was quenched with saturated aq. NH$_4$Cl. The aqueous layer was extracted with CH$_2$Cl$_2$ and the combined organic layers were dried over MgSO$_4$ and concentrated in vacuo. The residue was purified by flash column chromatography on silica gel (MeOH:EtOAc=1:20) to afford 98.1 mg (89%) of 11 as a pale yellow oil: R$_f$0.4 (MeOH:EtOAc=1:10); LR-MS (ESI+) m/z 550 (M+Na$^+$).

Figure 15H:
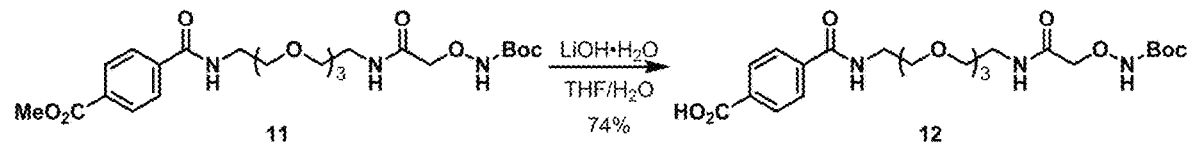

Synthesis of 4-(2,2-dimethyl-4,8-dioxo-3,6,12,15,18-pentaoxa-5,9-diazaicosan-20-ylcarbamoyl)benzoic acid As shown in the reaction scheme depicted in FIG. 15H, to a solution of 11 (200 mg, 0.379 mmol) in THF/H$_2$O (5/5 mL) was added LiOH.H$_2$O (23.9 mg, 0.569 mmol). After stirring for 4 h at ambient temperature, the reaction mixture was acidified with 2N HCl. The aqueous layer was extracted with EtOAc and the combined organic layers were dried over MgSO$_4$ and concentrated in vacuo. The residue was purified by flash column chromatography on silica gel (MeOH:EtOAc=1:7) to afford 118 mg (74%) of 12 as a pale yellow oil: R$_f$0.2 (MeOH:EtOAc=1:7); LR-MS (ESI+) m/z 536 (M+Na$^+$).

Figure 15I:
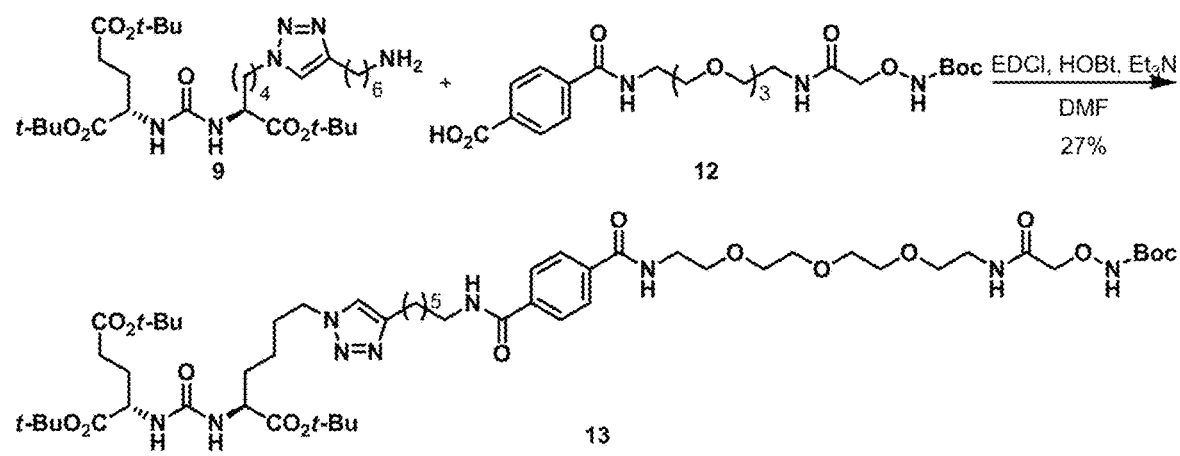

Synthesis of (S)-di-tert-butyl 2-(3-((S)-1-tert-bu-toxy-6-(4-(6-(4-(2,2-dimethyl-4,8-dioxo-3,6,12,15,18-pentaoxa-5,9-diazaicosan-20-ylcarbamoyl)ben-zamido)hexyl)-1H-1,2,3-triazol-1-yl)-1-oxohexan-2-yl)ureido)pentanedioate As shown in the reaction scheme depicted in FIG. 15I, to a solution of 9 (45.8 mg, 71.7 μmol) and 12 (43.8 mg, 71.7 μmol) in DMF (5 mL) were added EDCI (41.2 mg, 0.215 mmol), HOBt (29.1 mg, 0.215 mmol) and Et$_3$N (30.0 μL, 0.215 mmol) at 0° C. After stirring for 14 h at ambient temperature, the reaction mixture was quenched with saturated aq. NH$_4$Cl. The aqueous layer was extracted with EtOAc and the combined organic layers were dried over MgSO$_4$ and concentrated in vacuo. The residue was purified by flash column chromatography on silica gel (MeOH:EtOAc=1:15) to afford 22.0 mg (27%) of 13 as a pale yellow oil: LR-MS (ESI+) m/z 1134 (M+H$^+$).

Synthesis of (S)-2-(3-((S)-5-(4-(6-(4-(1-(aminooxy)-2-oxo-6,9,12-trioxa-3-azatetradecan-14-ylcarbam-oyl)benzamido)hexyl)-1H-1,2,3-triazol-1-yl)-1-car-boxypentyl)ureido)pentanedioic acid (P-TriA)

Figure 15J:
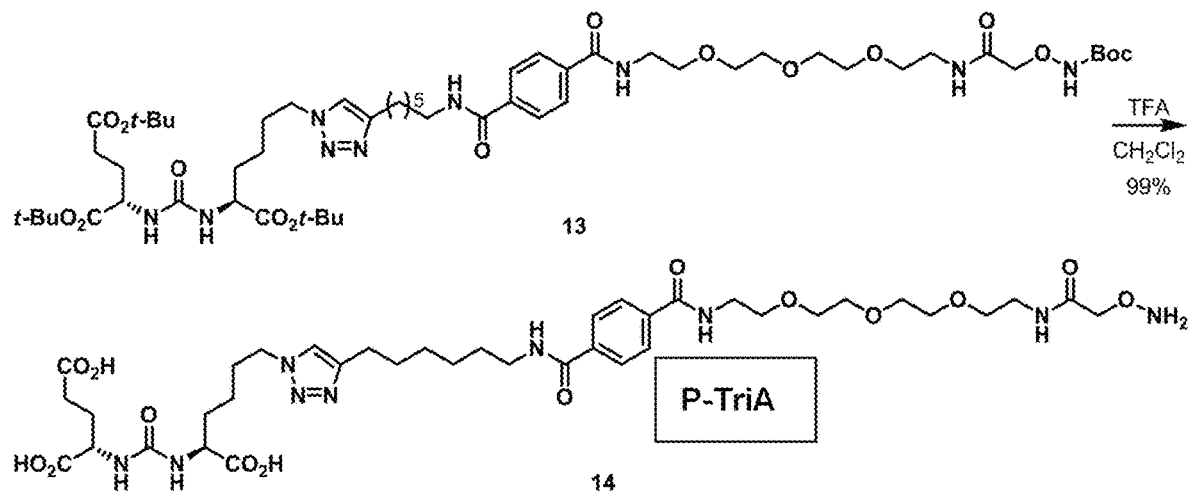
Figure 15K:
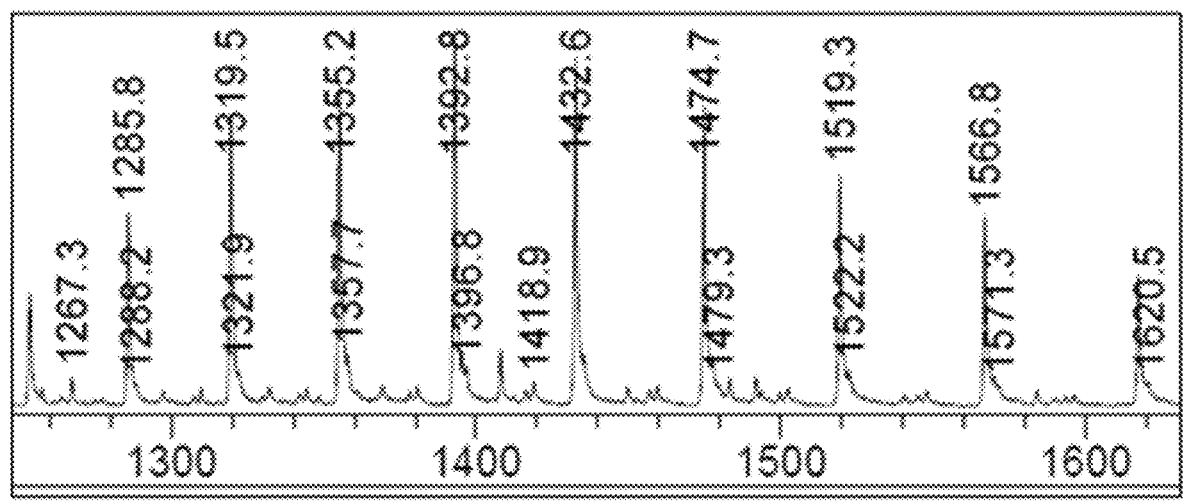
FIG. 15K depicts the ESI-MS analysis P-TriA conjugated to an anti-CD3 Fab.
Figure 15L:
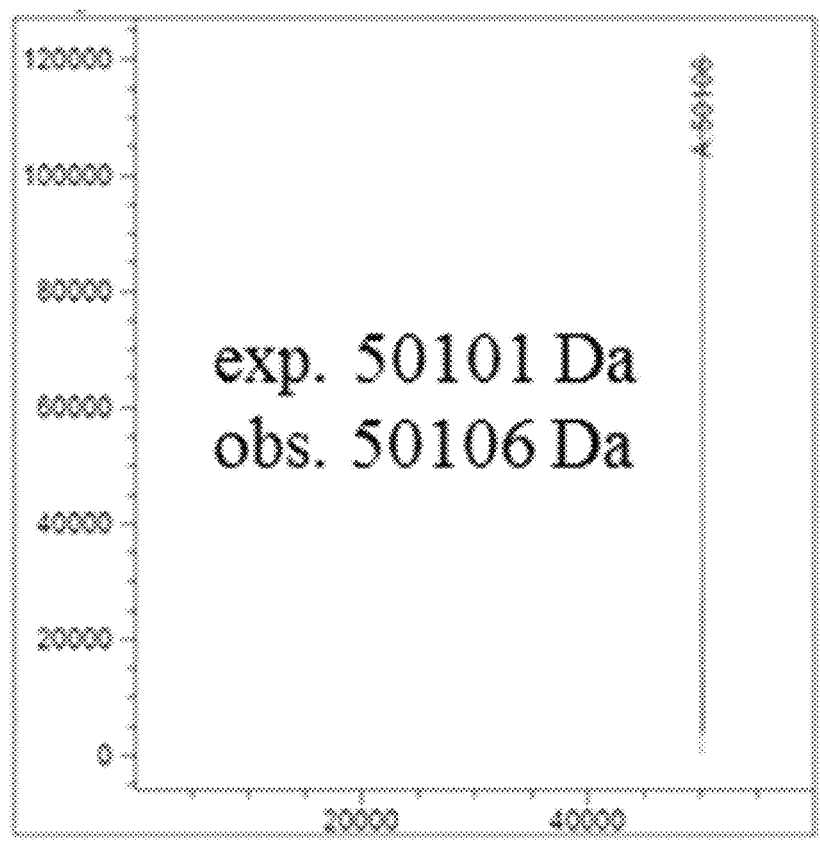
FIG. 15L depicts the deconvoluted mass spectrum of P-TriA conjugated to an anti-CD3 Fab

As shown in the reaction scheme depicted in FIG. 15J, to a solution of 13 (26.6 mg, 23.4 μmol) in CH$_2$Cl$_2$ (1.5 mL) was added TFA (1.5 mL). After stirring for 14 h at ambient temperature, the reaction mixture was concentrated in vacuo. The residue was purified by flash column chromatography on silica gel (MeOH:EtOAc=1:15) to afford 20.1 mg (99%) of 14 as a pale yellow oil: LR-MS (ESI+) m/z 866 (M+H$^+$). The ESI-MS analysis and deconvoluted mass spectrum of P-TriaA (compound 14) conjugated to an anti-CD3 Fab (UCHT1) pAcF mutant (LC-202X/HC-138X) are depicted in FIGS. 15K and 15L, respectively.

TABLE 8

Sequences of antibodies, antibody fragments or targeting agents (sites for UCHT1 unnatural amino acid incorporation are underlined)

| | Description | SEQUENCE |
|---|---|---|
| 1 | Light chain of an anti-CD3 clone of UCHT1 | ATGAAAAAGAATATCGCATTTCTTCTTGCTAGC ATGTTCGTTTTTTCTATTGCTACAAACGCATAC GCTGACATCCAGATGACCCAGTCTCCATCCTCC CTGTCTGCATCTGTAGGAGACAGAGTCACCAT CACTTGCCGGGCAAGTCAGGACATCCGTAATT ATCTGAACTGGTATCAGCAGAAACCAGGGAAA GCCCCTAAGCTCCTGATCTATTATACCTCCCGC CTGGAGTCTGGGGTCCCATCAAGGTTCAGTGG CTCTGGATCTGGGACAGATTACACTCTGACCAT CAGCAGTCTGCAACCTGAAGATTTTGCAACTT ACTACTGTCAACAGGGTAATACTCTGCCGTGG ACGTTCGGCCAAGGTACCAAGGTGGAGATCAA ACGAACTGTGGCTGCACCATCTGTCTTCATCTT CCCGCCATCTGATGAGCAGTTGAAATCTGGAA CTGCCTCTGTCGTGTGCCTGCTGAATAACTTCT ATCCCAGAGAGGCCAAAGTACAGTGGAAGGTG GATAACGCCCTCCAATCGGGTAACTCCCAGGA GAGTGTCACAGAGCAGGACAGCAAGGACAGC ACCTACAGCCTCAGCAGCACCCTGACGCTGAG CAAAGCAGACTACGAGAAACACAAAGTCTACG CCTGCGAAGTCACCCATCAGGGCCTGTCCTCG CCCGTCACAAAGAGCTTCAACAGGGGAGAGTG T |
| 2 | Hevy chain of an anti-CD3 clone of UCHT1 | ATGAAAAAGAATATCGCATTTCTTCTTGCATCT ATGTTCGTTTTTTCTATTGCTACAAACGCGTAC GCTGAGGTGCAGCTGGTGGAGTCTGGAGGAGG CTTGGTCCAGCCTGGGGGGTCCCTGAGACTCTC CTGTGCAGCCTCTGGGTACTCCTTTACCGGCTA CACTATGAACTGGGTCCGCCAGGCTCCAGGGA AGGGGCTGGAGTGGGTCGCACTGATTAATCCT TATAAAGGTGTTTCCACCTATAACCAGAAATTC AAGGATCGATTCACCATCTCCGTAGATAAATC CAAAAACACGGCGTATCTTCAAATGAACAGCC TGAGAGCCGAGGACACGGCCGTGTATTACTGT GCTAGAAGCGGATACTACGGCGATAGTGACTG GTATTTTGACGTCTGGGGCCAAGGAACCCTGG TCACCGTCTCCTCAGCCTCCACCAAGGGCCCA TCGGTCTTCCCCCTGGCACCCTCCTCCAAGAGC ACCTCTGGGGGCACAGCGGCCCTGGGCTGCCT GGTCAAGGACTACTTCCCCGAACCGGTGACGG TGTCGTGGAACTCAGGCGCCCTGACCAGCGGC GTGCACACCTTCCCGGCTGTCCTACAGTCCTCA |

TABLE 8-continued

Sequences of antibodies, antibody fragments or targeting agents (sites for UCHT1 unnatural amino acid incorporation are underlined)

| | Description | SEQUENCE |
|---|---|---|
| | | GGACTCTACTCCCTCAGCAGCGTGGTGACTGT GCCCTCTAGCAGCTTGGGCACCCAGACCTACA TCTGCAACGTGAATCACAAGCCCAGCAACACC AAGGTGGACAAGAAAGTTGAGCCCAAATCTTG TGACAAAACTCACACA |
| 3 | SS-14 (somatostatin analog) | Ala-Gly-cyclo(Cys-Lys-Asn-Phe-Phe-Trp-Lys-Thr-Phe-Thr-Ser-Cys) |
| 4 | OC (somatostatin analog) | D-Phe1-cyclo(Cys2-Phe3-D-Trp4-Lys5-Thr6-Cys7)Thr(ol)8 |
| 5 | TOC (somatostatin analog) | D-Phe1-cyclo(Cys2-Tyr3-D-Trp4-Lys5-Thr6-Cys7)Thr(ol)8 |
| 6 | TATE (somatostatin analog) | D-Phe1-cyclo(Cys2-Tyr3-D-Trp4-Lys5-Thr6-Cys7)Thr8 |
| 7 | NOC (somatostatin analog) | D-Phe1-cyclo(Cys2-1-NaI3-D-Trp4-Lys5-Thr6-Cys7)Thr(ol)8 |
| 8 | NOC-ATE (somatostatin analog) | D-Phe1-cyclo(Cys2-1-NaI3-D-Trp4-Lys5-Thr6-Cys7)Thr8 |
| 9 | BOC (somatostatin analog) | D-Phe1-cyclo(Cys2-BzThi3-D-Trp4-Lys5-Thr6-Cys7)Thr(ol)8 |
| 10 | BOC-ATE (somatostatin analog) | D-Phe1-cyclo(Cys2-BzThi3-D-Trp4-Lys5-Thr6-Cys7)Thr8 |
| 11 | KE108 (somatostatin analog) | Tyr-cyclo(DAB-Arg-Phe-Phe-D-Trp-Lys-Thr-Phe) |
| 12 | LM3 (somatostatin analog) | p-Cl-Phe-cyclo(D-Cys-Tyr-D-Aph(Cbm)-LysThr-Cys)D-Tyr-NH2 |
| 13 | BN (bombesin analog) | pGlu1-Gln2-Arg3-Leu4-Gly5-Asn6-Gln7-Trp8-Ala9-Val10-Gly11-His12-Leu13-Met14-NH2 |
| 14 | RP527 (bombesin analog) | N35-Gly-5-Ava-[Gln7-Trp8-Ala9-Val10-Gly11-His12-Leu13-Met14-NH2] |
| 15 | Demobesin 1 (bombesin analog) | N40-1-bzlg0[D-Phe6-Gln7-Trp8-Ala9-Val10-Gly11-His12-Leu-NHEt13] |
| 16 | Demobesin 4 (bombesin analog) | N4-[Pro1-Gln2-Arg3-Tyr4-Gly5-Asn6-Gln7-Trp8-Ala9-Val10-Gly11-His12-Leu13-Nle14-NH2] |
| 17 | BBS-38 (bombesin analog) | (NαHis)Ac-β-Ala-β-Ala-[Gln7-Trp8-Ala9-Val10-Gly11-His12-Cha13-Nle14-NH2] |
| 18 | BAY 86-4367 (bombesin analog) | 3-cyano-4-trimethylammonium-benzoyl-Ala(SO3H)-Ala(SO3H)-Ava-[Gln7-Trp8-Ala9-Val10-NMeGly11-His12-Sta13-Leu14-NH2] |
| 19 | MG (minigastrin analog) | Leu1-Glu2-Glu3-Glu4-Glu5-Glu6-Ala7-Tyr8-Gly9-Trp10-Met11-Asp12-Phe13-NH2 |

TABLE 8-continued

Sequences of antibodies, antibody fragments or targeting agents (sites for UCHT1 unnatural amino acid incorporation are underlined)

| | Description | SEQUENCE |
|---|---|---|
| 20 | MG0 (minigastrin analog) | D-Glu1-Glu2-Glu3-Glu4-Glu5-Glu6-Ala7-Tyr8-Gly9-Trp10-Met11-Asp12-Phe13-NH2 |
| 21 | MG11 (minigastrin analog) | D-Glu-Ala-Tyr-Gly-Trp-Met-Asp-Phe-NH2 |
| 22 | H2-Met (minigastrin analog) | His-His-Glu-Ala-Tyr-Gly-Trp-Met-Asp-Phe-NH2 |
| 23 | H2-Nle (minigastrin analog) | His-His-Glu-Ala-Tyr-Gly-Trp-Nle-Asp-Phe-NH2 |
| 24 | Demogastrin (minigastrin analog) | N4-D-Glu-(Glu)5-Ala-Tyr-Gly-Trp-Met-Asp-Phe-NH2 |
| 25 | Cyclo-MG1 (minigastrin analog) | c(γ-D-Glu-Ala-Tyr-D-Lys)-Trp-Met-Asp-Phe-NH2 |
| 26 | MGD5 (minigastrin analog) | Gly-Ser-Cys(succinimidopropionyl-Glu-Ala-Tyr-Gly-Trp-Nle-Asp-Phe-NH2)-Glu-Ala-Tyr-Gly-Trp-Nle-Asp-Phe-NH2 |
| 27 | Buserelin (GnRH analog) | pGlu1-His2-Trp3-Ser4-Tyr5-D-Ser(tBu)6-Leu7-Arg8-Pro9-NHC2H5 |
| 28 | Goserelin (GnRH analog) | pGlu1-His2-Trp3-Ser4-Tyr5-D-Ser(tBu)6-Leu7-Arg8-Pro9-AzGly10-NH2 |
| 29 | Leuprolide (GnRH analog) | pGlu1-His2-Trp3-Ser4-Tyr5-D-Leu6-Leu7-Arg8-Pro9-NHC2H5 |
| 30 | Nafarelin (GnRH analog) | pGlu1-His2-Trp3-Ser4-Tyr5-D-Nal(2)6-Leu7-Arg8-Pro9-NHC2H5 |
| 31 | Triptorelin (GnRH analog) | pGlu1-His2-Trp3-Ser4-Tyr5-D-Trp6-Leu7-Arg8-Pro9-Gly10-NH2 |
| 32 | Abarelix (GnRH analog) | Ac-D-Ala1-D-Cpa2-D-Ala3-Ser4-Tyr5-D-Asp6-Leu7-Ilys8-Pro9-D-Ala10-NH2 |
| 33 | Acyline (GnRH analog) | Ac-D-Nal1-D-Cpa2-D-Pal3-Ser4-Aph(Ac)5-D-Aph(Ac)6-Leu7-Ilys8-Pro9-D-Ala10-NH2 |
| 34 | Antarelix (GnRH analog) | Ac-D-Nal1-D-Cpa2-D-Pal3-Ser4-Tyr5-D-Hci6-Leu7-Ilys8-Pro9-D-Ala10-NH2 |
| 35 | Antide (GnRH analog) | Ac-D-Nal1-D-Cpa2-D-Pal3-Ser4-Lys(Nic)5-D-Lys(Nic)6-Leu7-Ilys8-Pro9-D-Ala10-NH2 |
| 36 | Azaline B (GnRH analog) | Ac-D-Nal1-D-Cpa2-D-Pal3-Ser4-Aph(Atz)5-D-Aph(Atz)6-Leu7-Ilys8-Pro9-D-Ala10-NH2 |
| 37 | Cetrorelix (GnRH analog) | Ac-D-Nal1-D-Cpa2-D-Pal3-Ser4-Tyr5-D-Cit6-Leu7-Arg8-Pro9-D-Ala10-NH2 |
| 38 | Degarelix (GnRH analog) | Ac-D-Nal1-D-Cpa2-D-Pal3-Ser4-Aph(L-hydroorotyl)5-D-Aph(carbamoyl)6-Leu7-Ilys8-Pro9-D-Ala10-NH2 |
| 39 | Ganirelix (GnRH analog) | Ac-D-Nal1-D-Cpa2-D-Pal3-Ser4-Tyr5-D-hArg(Et2)6-Leu7-hArg(Et2)8-Pro9-D-Ala10-NH2 |
| 40 | Ozarelix (GnRH analog) | Ac-D-Nal1-D-Cpa2-D-Pal3-Ser4-N-MeTyr5-D-hCit6-Nle7-Arg8-Pro9-D-Ala10-NH2 |

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of the present invention is embodied by the appended claims.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

---

That which is claimed is:
1. A compound comprising:
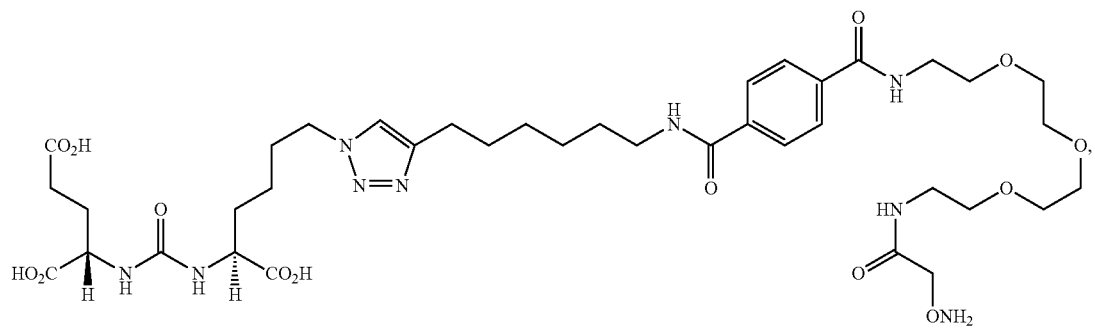
or a stereoisomer thereof.
* * * * *

SEQUENCE LISTING

<160> NUMBER OF SEQ ID NOS: 41

<210> SEQ ID NO 1
<211> LENGTH: 711
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1

```
atgaaaaaga atatcgcatt tcttcttgct agcatgttcg ttttttctat tgctacaaac      60
gcatacgctg acatccagat gacccagtct ccatcctccc tgtctgcatc tgtaggagac     120
agagtcacca tcacttgccg ggcaagtcag gacatccgta attatctgaa ctggtatcag     180
cagaaaccag ggaaagcccc taagctcctg atctattata cctcccgcct ggagtctggg     240
gtcccatcaa ggttcagtgg ctctggatct gggacagatt acactctgac catcagcagt     300
ctgcaacctg aagattttgc aacttactac tgtcaacagg gtaatactct gccgtggacg     360
ttcggccaag gtaccaaggt ggagatcaaa cgaactgtgg ctgcaccatc tgtcttcatc     420
ttcccgccat ctgatgagca gttgaaatct ggaactgcct ctgtcgtgtg cctgctgaat     480
aacttctatc ccagagaggc caaagtacag tggaaggtgg ataacgccct ccaatcgggt     540
aactcccagg agagtgtcac agagcaggac agcaaggaca gcacctacag cctcagcagc     600
accctgacgc tgagcaaagc agactacgag aaacacaaag tctacgcctg cgaagtcacc     660
catcagggcc tgtcctcgcc cgtcacaaag agcttcaaca ggggagagtg t             711
```

<210> SEQ ID NO 2
<211> LENGTH: 759
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 2

```
atgaaaaaga atatcgcatt tcttcttgca tctatgttcg ttttttctat tgctacaaac      60
gcgtacgctg aggtgcagct ggtggagtct ggaggaggct tggtccagcc tgggggtcc     120 ctgagactct cctgtgcagc ctctgggtac tcctttaccg gctacactat gaactgggtc     180
cgccaggctc agggaaggg gctggagtgg gtcgactga ttaatcctta taaggtgtt      240 tccacctata accagaaatt caaggatcga ttcaccatct ccgtagataa atccaaaaac     300
```

```
acggcgtatc ttcaaatgaa cagcctgaga gccgaggaca cggccgtgta ttactgtgct      360
agaagcggat actacggcga tagtgactgg tattttgacg tctggggcca aggaaccctg      420
gtcaccgtct cctcagcctc caccaagggc ccatcggtct tccccctggc accctcctcc      480
aagagcacct ctgggggcac agcggccctg gctgcctgg tcaaggacta cttccccgaa       540
ccggtgacgg tgtcgtggaa ctcaggcgcc ctgaccagcg gcgtgcacac cttcccggct      600
gtcctacagt cctcaggact ctactccctc agcagcgtgg tgactgtgcc ctctagcagc      660
ttgggcaccc agacctacat ctgcaacgtg aatcacaagc ccagcaacac caaggtggac      720
aagaaagttg agcccaaatc ttgtgacaaa actcacaca                             759
```

<210> SEQ ID NO 3
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (3)..(14)
<223> OTHER INFORMATION: Cyclic

<400> SEQUENCE: 3

Ala Gly Cys Lys Asn Phe Phe Trp Lys Thr Phe Thr Ser Cys
1               5                   10

<210> SEQ ID NO 4
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-amino acid
<220> FEATURE:
<221> NAME/KEY: misc_feature
<222> LOCATION: (2)..(7)
<223> OTHER INFORMATION: Cyclic
<220> FEATURE:
<221> NAME/KEY: MOD_RES
<222> LOCATION: (4)..(4)
<223> OTHER INFORMATION: D-amino acid
<220> FEATURE:
<221> NAME/KEY: MOD_RES
<222> LOCATION: (8)..(8)
<223> OTHER INFORMATION: Thr(ol)

<400> SEQUENCE: 4

Phe Cys Phe Trp Lys Thr Cys Thr
1               5

<210> SEQ ID NO 5
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-amino acid
<220> FEATURE:
<221> NAME/KEY: misc_feature

```
<222> LOCATION: (2)..(7)
<223> OTHER INFORMATION: Cyclic
<220> FEATURE:
<221> NAME/KEY: MOD_RES
<222> LOCATION: (4)..(4)
<223> OTHER INFORMATION: D-amino acid
<220> FEATURE:
<221> NAME/KEY: MOD_RES
<222> LOCATION: (8)..(8)
<223> OTHER INFORMATION: Thr(ol)

<400> SEQUENCE: 5

Phe Cys Tyr Trp Lys Thr Cys Thr
1               5

<210> SEQ ID NO 6
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-amino acid
<220> FEATURE:
<221> NAME/KEY: misc_feature
<222> LOCATION: (2)..(7)
<223> OTHER INFORMATION: Cyclic
<220> FEATURE:
<221> NAME/KEY: MOD_RES
<222> LOCATION: (4)..(4)
<223> OTHER INFORMATION: D-amino acid

<400> SEQUENCE: 6

Phe Cys Tyr Trp Lys Thr Cys Thr
1               5

<210> SEQ ID NO 7
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-amino acid
<220> FEATURE:
<221> NAME/KEY: misc_feature
<222> LOCATION: (2)..(7)
<223> OTHER INFORMATION: Cyclic
<220> FEATURE:
<221> NAME/KEY: MOD_RES
<222> LOCATION: (3)..(3)
<223> OTHER INFORMATION: 1-Nal
<220> FEATURE:
<221> NAME/KEY: MOD_RES
<222> LOCATION: (4)..(4)
<223> OTHER INFORMATION: D-amino acid
<220> FEATURE:
<221> NAME/KEY: MOD_RES
<222> LOCATION: (8)..(8)
<223> OTHER INFORMATION: Thr(ol)

<400> SEQUENCE: 7

Phe Cys Ala Trp Lys Thr Cys Thr
1               5

<210> SEQ ID NO 8
<211> LENGTH: 8
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-amino acid
<220> FEATURE:
<221> NAME/KEY: misc_feature
<222> LOCATION: (2)..(7)
<223> OTHER INFORMATION: Cyclic
<220> FEATURE:
<221> NAME/KEY: MOD_RES
<222> LOCATION: (3)..(3)
<223> OTHER INFORMATION: 1-Nal
<220> FEATURE:
<221> NAME/KEY: MOD_RES
<222> LOCATION: (4)..(4)
<223> OTHER INFORMATION: D-amino acid

<400> SEQUENCE: 8

Phe Cys Ala Trp Lys Thr Cys Thr
1               5

<210> SEQ ID NO 9
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-amino acid
<220> FEATURE:
<221> NAME/KEY: misc_feature
<222> LOCATION: (2)..(7)
<223> OTHER INFORMATION: Cyclic
<220> FEATURE:
<221> NAME/KEY: MOD_RES
<222> LOCATION: (3)..(3)
<223> OTHER INFORMATION: BzThi
<220> FEATURE:
<221> NAME/KEY: MOD_RES
<222> LOCATION: (4)..(4)
<223> OTHER INFORMATION: D-amino acid
<220> FEATURE:
<221> NAME/KEY: MOD_RES
<222> LOCATION: (8)..(8)
<223> OTHER INFORMATION: Thr(ol)

<400> SEQUENCE: 9

Phe Cys Xaa Trp Lys Thr Cys Thr
1               5

<210> SEQ ID NO 10
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-amino acid
<220> FEATURE:
<221> NAME/KEY: misc_feature
<222> LOCATION: (2)..(7)
<223> OTHER INFORMATION: Cyclic
<220> FEATURE:
<221> NAME/KEY: MOD_RES
```

```
<222> LOCATION: (3)..(3)
<223> OTHER INFORMATION: BzThi
<220> FEATURE:
<221> NAME/KEY: MOD_RES
<222> LOCATION: (4)..(4)
<223> OTHER INFORMATION: D-amino acid

<400> SEQUENCE: 10

Phe Cys Xaa Trp Lys Thr Cys Thr
1               5

<210> SEQ ID NO 11
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: DAB
<220> FEATURE:
<221> NAME/KEY: misc_feature
<222> LOCATION: (2)..(9)
<223> OTHER INFORMATION: Cyclic
<220> FEATURE:
<221> NAME/KEY: MOD_RES
<222> LOCATION: (6)..(6)
<223> OTHER INFORMATION: D-amino acid

<400> SEQUENCE: 11

Tyr Xaa Arg Phe Phe Trp Lys Thr Phe
1               5

<210> SEQ ID NO 12
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: p-Cl-Phe
<220> FEATURE:
<221> NAME/KEY: MOD_RES
<222> LOCATION: (2)..(2)
<223> OTHER INFORMATION: D-amino acid
<220> FEATURE:
<221> NAME/KEY: misc_feature
<222> LOCATION: (2)..(7)
<223> OTHER INFORMATION: Cyclic
<220> FEATURE:
<221> NAME/KEY: MOD_RES
<222> LOCATION: (4)..(4)
<223> OTHER INFORMATION: D-Aph(Cbm)
<220> FEATURE:
<221> NAME/KEY: MOD_RES
<222> LOCATION: (8)..(8)
<223> OTHER INFORMATION: D-amino acid
<220> FEATURE:
<223> OTHER INFORMATION: C-term NH2

<400> SEQUENCE: 12

Phe Cys Tyr Xaa Lys Thr Cys Tyr
1               5

<210> SEQ ID NO 13
<211> LENGTH: 14
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: pGlu
<220> FEATURE:
<223> OTHER INFORMATION: C-term NH2

<400> SEQUENCE: 13

Glu Gln Arg Leu Gly Asn Gln Trp Ala Val Gly His Leu Met
1               5                   10

<210> SEQ ID NO 14
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: N,N-dimethyl-Gly
<220> FEATURE:
<221> NAME/KEY: MOD_RES
<222> LOCATION: (3)..(3)
<223> OTHER INFORMATION: Cys(acm)
<220> FEATURE:
<221> NAME/KEY: misc_feature
<222> LOCATION: (1)..(3)
<223> OTHER INFORMATION: N3S
<220> FEATURE:
<221> NAME/KEY: MOD_RES
<222> LOCATION: (5)..(5)
<223> OTHER INFORMATION: Ava
<220> FEATURE:
<223> OTHER INFORMATION: C-term NH2

<400> SEQUENCE: 14

Gly Ser Cys Gly Xaa Gln Trp Ala Val Gly His Leu Met
1               5                   10

<210> SEQ ID NO 15
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term N40-1-bzlg0
<220> FEATURE:
<221> NAME/KEY: MOD_RES
<222> LOCATION: (1)..(1)
<223> OTHER INFORMATION: D-amino acid
<220> FEATURE:
<223> OTHER INFORMATION: C-term NHEt13

<400> SEQUENCE: 15

Phe Gln Trp Ala Val Gly His Leu
1               5

<210> SEQ ID NO 16
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term N4
```

```
<220> FEATURE:
<221> NAME/KEY: MOD_RES
<222> LOCATION: (14)..(14)
<223> OTHER INFORMATION: Nle
<220> FEATURE:
<223> OTHER INFORMATION: C-term NH2

<400> SEQUENCE: 16

Pro Gln Arg Tyr Gly Asn Gln Trp Ala Val Gly His Leu Leu
1               5                   10

<210> SEQ ID NO 17
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: (N-alphaHis)Ac
<220> FEATURE:
<221> NAME/KEY: MOD_RES
<222> LOCATION: (2)..(3)
<223> OTHER INFORMATION: Beta-Ala
<220> FEATURE:
<221> NAME/KEY: MOD_RES
<222> LOCATION: (10)..(10)
<223> OTHER INFORMATION: Cha
<220> FEATURE:
<221> NAME/KEY: MOD_RES
<222> LOCATION: (11)..(11)
<223> OTHER INFORMATION: Nle
<220> FEATURE:
<223> OTHER INFORMATION: C-term NH2

<400> SEQUENCE: 17

His Ala Ala Gln Trp Ala Val Gly His Ala Leu
1               5                   10

<210> SEQ ID NO 18
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 3-cyano-4-trimethylammonium-benzoyl
<220> FEATURE:
<221> NAME/KEY: MOD_RES
<222> LOCATION: (1)..(2)
<223> OTHER INFORMATION: Ala(SO3H)
<220> FEATURE:
<221> NAME/KEY: MOD_RES
<222> LOCATION: (3)..(3)
<223> OTHER INFORMATION: Ava
<220> FEATURE:
<221> NAME/KEY: MOD_RES
<222> LOCATION: (8)..(8)
<223> OTHER INFORMATION: NMeGly
<220> FEATURE:
<221> NAME/KEY: MOD_RES
<222> LOCATION: (10)..(10)
<223> OTHER INFORMATION: Sta
<220> FEATURE:
<223> OTHER INFORMATION: C-term NH2

<400> SEQUENCE: 18

Ala Ala Xaa Gln Trp Ala Val Gly His Xaa Leu
1               5                   10
```

```
<210> SEQ ID NO 19
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term NH2

<400> SEQUENCE: 19

Leu Glu Glu Glu Glu Glu Ala Tyr Gly Trp Met Asp Phe
1               5                   10

<210> SEQ ID NO 20
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-amino acid
<220> FEATURE:
<223> OTHER INFORMATION: C-term NH2

<400> SEQUENCE: 20

Glu Glu Glu Glu Glu Glu Ala Tyr Gly Trp Met Asp Phe
1               5                   10

<210> SEQ ID NO 21
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-amino acid
<220> FEATURE:
<223> OTHER INFORMATION: C-term NH2

<400> SEQUENCE: 21

Glu Ala Tyr Gly Trp Met Asp Phe
1               5

<210> SEQ ID NO 22
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term NH2

<400> SEQUENCE: 22

His His Glu Ala Tyr Gly Trp Met Asp Phe
1               5                   10

<210> SEQ ID NO 23
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<221> NAME/KEY: MOD_RES
<222> LOCATION: (8)..(8)
<223> OTHER INFORMATION: Nle
<220> FEATURE:
<223> OTHER INFORMATION: C-term NH2

<400> SEQUENCE: 23

His His Glu Ala Tyr Gly Trp Leu Asp Phe
1               5                   10

<210> SEQ ID NO 24
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term N4
<220> FEATURE:
<221> NAME/KEY: MOD_RES
<222> LOCATION: (1)..(1)
<223> OTHER INFORMATION: D-amino acid
<220> FEATURE:
<223> OTHER INFORMATION: C-term NH2

<400> SEQUENCE: 24

Glu Glu Glu Glu Glu Glu Ala Tyr Gly Trp Met Asp Phe
1               5                   10

<210> SEQ ID NO 25
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: gamma-D-Glu
<220> FEATURE:
<221> NAME/KEY: misc_feature
<222> LOCATION: (1)..(4)
<223> OTHER INFORMATION: Cyclic
<220> FEATURE:
<221> NAME/KEY: MOD_RES
<222> LOCATION: (4)..(4)
<223> OTHER INFORMATION: D-amino acid
<220> FEATURE:
<223> OTHER INFORMATION: C-term NH2

<400> SEQUENCE: 25

Glu Ala Tyr Lys Trp Met Asp Phe
1               5

<210> SEQ ID NO 26
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (3)..(3)
<223> OTHER INFORMATION: Cys modified with a unique side chain
<220> FEATURE:
<221> NAME/KEY: MOD_RES
<222> LOCATION: (9)..(9)
<223> OTHER INFORMATION: Nle
<220> FEATURE:
```

```
<223> OTHER INFORMATION: C-term NH2
<220> FEATURE:
<223> OTHER INFORMATION: see specification as filed for detailed
      description of substitutions and preferred embodiments

<400> SEQUENCE: 26

Gly Ser Cys Glu Ala Tyr Gly Trp Leu Asp Phe
1               5                   10

<210> SEQ ID NO 27
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: pGlu
<220> FEATURE:
<221> NAME/KEY: MOD_RES
<222> LOCATION: (6)..(6)
<223> OTHER INFORMATION: D-Ser(tBu)
<220> FEATURE:
<223> OTHER INFORMATION: C-term NHC2H5

<400> SEQUENCE: 27

Glu His Trp Ser Tyr Ser Leu Arg Pro
1               5

<210> SEQ ID NO 28
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: pGlu
<220> FEATURE:
<221> NAME/KEY: MOD_RES
<222> LOCATION: (6)..(6)
<223> OTHER INFORMATION: D-Ser(tBu)
<220> FEATURE:
<221> NAME/KEY: MOD_RES
<222> LOCATION: (10)..(10)
<223> OTHER INFORMATION: AzGly
<220> FEATURE:
<223> OTHER INFORMATION: C-term NH2

<400> SEQUENCE: 28

Glu His Trp Ser Tyr Ser Leu Arg Pro Gly
1               5                   10

<210> SEQ ID NO 29
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: pGlu
<220> FEATURE:
<221> NAME/KEY: MOD_RES
<222> LOCATION: (6)..(6)
<223> OTHER INFORMATION: D-amino acid
<220> FEATURE:
```

```
<223> OTHER INFORMATION: C-term NHC2H5

<400> SEQUENCE: 29

Glu His Trp Ser Tyr Leu Leu Arg Pro
1               5

<210> SEQ ID NO 30
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: pGlu
<220> FEATURE:
<221> NAME/KEY: MOD_RES
<222> LOCATION: (6)..(6)
<223> OTHER INFORMATION: D-Nal(2)
<220> FEATURE:
<223> OTHER INFORMATION: C-term NHC2H5

<400> SEQUENCE: 30

Glu His Trp Ser Tyr Ala Leu Arg Pro
1               5

<210> SEQ ID NO 31
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: pGlu
<220> FEATURE:
<221> NAME/KEY: MOD_RES
<222> LOCATION: (6)..(6)
<223> OTHER INFORMATION: D-amino acid
<220> FEATURE:
<223> OTHER INFORMATION: C-term NH2

<400> SEQUENCE: 31

Glu His Trp Ser Tyr Trp Leu Arg Pro Gly
1               5                   10

<210> SEQ ID NO 32
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: D-amino acid
<220> FEATURE:
<221> NAME/KEY: MOD_RES
<222> LOCATION: (2)..(2)
<223> OTHER INFORMATION: D-Cpa
<220> FEATURE:
<221> NAME/KEY: MOD_RES
<222> LOCATION: (3)..(3)
<223> OTHER INFORMATION: D-amino acid
<220> FEATURE:
<221> NAME/KEY: MOD_RES
```

```
<222> LOCATION: (6)..(6)
<223> OTHER INFORMATION: D-amino acid
<220> FEATURE:
<221> NAME/KEY: MOD_RES
<222> LOCATION: (8)..(8)
<223> OTHER INFORMATION: I-Lys
<220> FEATURE:
<221> NAME/KEY: MOD_RES
<222> LOCATION: (10)..(10)
<223> OTHER INFORMATION: D-amino acid
<220> FEATURE:
<223> OTHER INFORMATION: C-term NH2

<400> SEQUENCE: 32

Ala Xaa Ala Ser Tyr Asp Leu Lys Pro Ala
1               5                   10

<210> SEQ ID NO 33
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: D-Nal
<220> FEATURE:
<221> NAME/KEY: MOD_RES
<222> LOCATION: (2)..(2)
<223> OTHER INFORMATION: D-Cpa
<220> FEATURE:
<221> NAME/KEY: MOD_RES
<222> LOCATION: (3)..(3)
<223> OTHER INFORMATION: D-Pal
<220> FEATURE:
<221> NAME/KEY: MOD_RES
<222> LOCATION: (5)..(5)
<223> OTHER INFORMATION: Aph(Ac)
<220> FEATURE:
<221> NAME/KEY: MOD_RES
<222> LOCATION: (6)..(6)
<223> OTHER INFORMATION: D-Aph(Ac)
<220> FEATURE:
<221> NAME/KEY: MOD_RES
<222> LOCATION: (8)..(8)
<223> OTHER INFORMATION: I-Lys
<220> FEATURE:
<221> NAME/KEY: MOD_RES
<222> LOCATION: (10)..(10)
<223> OTHER INFORMATION: D-amino acid
<220> FEATURE:
<223> OTHER INFORMATION: C-term NH2

<400> SEQUENCE: 33

Ala Xaa Xaa Ser Phe Phe Leu Lys Pro Ala
1               5                   10

<210> SEQ ID NO 34
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: D-Nal
<220> FEATURE:
```

```
<221> NAME/KEY: MOD_RES
<222> LOCATION: (2)..(2)
<223> OTHER INFORMATION: D-Cpa
<220> FEATURE:
<221> NAME/KEY: MOD_RES
<222> LOCATION: (3)..(3)
<223> OTHER INFORMATION: D-Pal
<220> FEATURE:
<221> NAME/KEY: MOD_RES
<222> LOCATION: (6)..(6)
<223> OTHER INFORMATION: D-Hci
<220> FEATURE:
<221> NAME/KEY: MOD_RES
<222> LOCATION: (8)..(8)
<223> OTHER INFORMATION: I-Lys
<220> FEATURE:
<221> NAME/KEY: MOD_RES
<222> LOCATION: (10)..(10)
<223> OTHER INFORMATION: D-amino acid
<220> FEATURE:
<223> OTHER INFORMATION: C-term NH2

<400> SEQUENCE: 34

Ala Xaa Xaa Ser Tyr Xaa Leu Lys Pro Ala
1               5                   10

<210> SEQ ID NO 35
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: D-Nal
<220> FEATURE:
<221> NAME/KEY: MOD_RES
<222> LOCATION: (2)..(2)
<223> OTHER INFORMATION: D-Cpa
<220> FEATURE:
<221> NAME/KEY: MOD_RES
<222> LOCATION: (3)..(3)
<223> OTHER INFORMATION: D-Pal
<220> FEATURE:
<221> NAME/KEY: MOD_RES
<222> LOCATION: (5)..(5)
<223> OTHER INFORMATION: Lys(Nic)
<220> FEATURE:
<221> NAME/KEY: MOD_RES
<222> LOCATION: (6)..(6)
<223> OTHER INFORMATION: D-Lys(Nic)
<220> FEATURE:
<221> NAME/KEY: MOD_RES
<222> LOCATION: (8)..(8)
<223> OTHER INFORMATION: I-Lys
<220> FEATURE:
<221> NAME/KEY: MOD_RES
<222> LOCATION: (10)..(10)
<223> OTHER INFORMATION: D-amino acid
<220> FEATURE:
<223> OTHER INFORMATION: C-term NH2

<400> SEQUENCE: 35

Ala Xaa Xaa Ser Lys Lys Leu Lys Pro Ala
1               5                   10

<210> SEQ ID NO 36
<211> LENGTH: 10
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: D-Nal
<220> FEATURE:
<221> NAME/KEY: MOD_RES
<222> LOCATION: (2)..(2)
<223> OTHER INFORMATION: D-Cpa
<220> FEATURE:
<221> NAME/KEY: MOD_RES
<222> LOCATION: (3)..(3)
<223> OTHER INFORMATION: D-Pal
<220> FEATURE:
<221> NAME/KEY: MOD_RES
<222> LOCATION: (5)..(5)
<223> OTHER INFORMATION: Aph(Atz)
<220> FEATURE:
<221> NAME/KEY: MOD_RES
<222> LOCATION: (6)..(6)
<223> OTHER INFORMATION: D-Aph(Atz)
<220> FEATURE:
<221> NAME/KEY: MOD_RES
<222> LOCATION: (8)..(8)
<223> OTHER INFORMATION: I-Lys
<220> FEATURE:
<221> NAME/KEY: MOD_RES
<222> LOCATION: (10)..(10)
<223> OTHER INFORMATION: D-amino acid
<220> FEATURE:
<223> OTHER INFORMATION: C-term NH2

<400> SEQUENCE: 36

Ala Xaa Xaa Ser Phe Phe Leu Lys Pro Ala
1               5                   10

<210> SEQ ID NO 37
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: D-Nal
<220> FEATURE:
<221> NAME/KEY: MOD_RES
<222> LOCATION: (2)..(2)
<223> OTHER INFORMATION: D-Cpa
<220> FEATURE:
<221> NAME/KEY: MOD_RES
<222> LOCATION: (3)..(3)
<223> OTHER INFORMATION: D-Pal
<220> FEATURE:
<221> NAME/KEY: MOD_RES
<222> LOCATION: (6)..(6)
<223> OTHER INFORMATION: D-Cit
<220> FEATURE:
<221> NAME/KEY: MOD_RES
<222> LOCATION: (10)..(10)
<223> OTHER INFORMATION: D-amino acid
<220> FEATURE:
<223> OTHER INFORMATION: C-term NH2

<400> SEQUENCE: 37

Ala Xaa Xaa Ser Tyr Xaa Leu Arg Pro Ala
1               5                   10
```

```
<210> SEQ ID NO 38
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: D-Nal
<220> FEATURE:
<221> NAME/KEY: MOD_RES
<222> LOCATION: (2)..(2)
<223> OTHER INFORMATION: D-Cpa
<220> FEATURE:
<221> NAME/KEY: MOD_RES
<222> LOCATION: (3)..(3)
<223> OTHER INFORMATION: D-Pal
<220> FEATURE:
<221> NAME/KEY: MOD_RES
<222> LOCATION: (5)..(5)
<223> OTHER INFORMATION: Aph(L-hydroorotyl)
<220> FEATURE:
<221> NAME/KEY: MOD_RES
<222> LOCATION: (6)..(6)
<223> OTHER INFORMATION: D-Aph(carbamoyl)
<220> FEATURE:
<221> NAME/KEY: MOD_RES
<222> LOCATION: (8)..(8)
<223> OTHER INFORMATION: I-Lys
<220> FEATURE:
<221> NAME/KEY: MOD_RES
<222> LOCATION: (10)..(10)
<223> OTHER INFORMATION: D-amino acid
<220> FEATURE:
<223> OTHER INFORMATION: C-term NH2

<400> SEQUENCE: 38

Ala Xaa Xaa Ser Phe Phe Leu Lys Pro Ala
1               5                   10

<210> SEQ ID NO 39
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: D-Nal
<220> FEATURE:
<221> NAME/KEY: MOD_RES
<222> LOCATION: (2)..(2)
<223> OTHER INFORMATION: D-Cpa
<220> FEATURE:
<221> NAME/KEY: MOD_RES
<222> LOCATION: (3)..(3)
<223> OTHER INFORMATION: D-Pal
<220> FEATURE:
<221> NAME/KEY: MOD_RES
<222> LOCATION: (6)..(6)
<223> OTHER INFORMATION: D-hArg(Et2)
<220> FEATURE:
<221> NAME/KEY: MOD_RES
<222> LOCATION: (8)..(8)
<223> OTHER INFORMATION: hArg(Et2)
<220> FEATURE:
<221> NAME/KEY: MOD_RES
<222> LOCATION: (10)..(10)
<223> OTHER INFORMATION: D-amino acid
```

```
<220> FEATURE:
<223> OTHER INFORMATION: C-term NH2

<400> SEQUENCE: 39

Ala Xaa Xaa Ser Tyr Arg Leu Arg Pro Ala
1               5                   10

<210> SEQ ID NO 40
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: D-Nal
<220> FEATURE:
<221> NAME/KEY: MOD_RES
<222> LOCATION: (2)..(2)
<223> OTHER INFORMATION: D-Cpa
<220> FEATURE:
<221> NAME/KEY: MOD_RES
<222> LOCATION: (3)..(3)
<223> OTHER INFORMATION: D-Pal
<220> FEATURE:
<221> NAME/KEY: MOD_RES
<222> LOCATION: (5)..(5)
<223> OTHER INFORMATION: N-MeTyr
<220> FEATURE:
<221> NAME/KEY: MOD_RES
<222> LOCATION: (6)..(6)
<223> OTHER INFORMATION: D-hCit
<220> FEATURE:
<221> NAME/KEY: MOD_RES
<222> LOCATION: (7)..(7)
<223> OTHER INFORMATION: Nle
<220> FEATURE:
<221> NAME/KEY: MOD_RES
<222> LOCATION: (10)..(10)
<223> OTHER INFORMATION: D-amino acid
<220> FEATURE:
<223> OTHER INFORMATION: C-term NH2

<400> SEQUENCE: 40

Ala Xaa Xaa Ser Tyr Xaa Leu Arg Pro Ala
1               5                   10

<210> SEQ ID NO 41
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 41

His His His His His His
1               5
```